(12) United States Patent
Drmanac et al.

(10) Patent No.: US 9,499,863 B2
(45) Date of Patent: Nov. 22, 2016

(54) REDUCING GC BIAS IN DNA SEQUENCING USING NUCLEOTIDE ANALOGS

(71) Applicant: Complete Genomics, Inc., Mountain View, CA (US)

(72) Inventors: Radoje Drmanac, Los Altos Hills, CA (US); Brock A. Peters, San Francisco, CA (US); Andrei Alexeev, Woodland, CA (US); Peter Hong, Castro Valley, CA (US)

(73) Assignee: Complete Genomics, Inc., Mountain View, CA (US)

( * ) Notice: Subject to any disclaimer, the term of this patent is extended or adjusted under 35 U.S.C. 154(b) by 228 days.

(21) Appl. No.: 14/028,319

(22) Filed: Sep. 16, 2013

(65) Prior Publication Data

US 2014/0005056 A1 Jan. 2, 2014

Related U.S. Application Data

(60) Division of application No. 12/816,365, filed on Jun. 15, 2010, now Pat. No. 8,592,150, which is a continuation-in-part of application No. 12/329,365, filed on Dec. 5, 2008, now Pat. No. 8,415,099.

(60) Provisional application No. 61/187,162, filed on Jun. 15, 2009, provisional application No. 60/992,485, filed on Dec. 5, 2007, provisional application No. 61/026,337, filed on Feb. 5, 2008, provisional application No. 61/035,914, filed on Mar. 12, 2008, provisional application No. 61/061,134, filed on Jun. 13, 2008, provisional application No. 61/116,193, filed on Nov. 19, 2008, provisional application No. 61/102,586, filed on Oct. 3, 2008.

(51) Int. Cl.
C12Q 1/68 (2006.01)
C12P 19/34 (2006.01)

(52) U.S. Cl.
CPC ............. *C12Q 1/6874* (2013.01); *C12P 19/34* (2013.01); *C12Q 1/6869* (2013.01)

(58) Field of Classification Search
None
See application file for complete search history.

(56) References Cited

U.S. PATENT DOCUMENTS

| | | | |
|---|---|---|---|
| 4,719,179 A | 1/1988 | Barany | 435/172.1 |
| 4,883,750 A | 11/1989 | Whiteley | 435/6 |
| 5,091,302 A | 2/1992 | Newman | 435/6 |
| 5,124,246 A | 6/1992 | Urdea | 435/6 |
| 5,143,854 A | 9/1992 | Pirrung | 436/518 |
| 5,202,231 A | 4/1993 | Drmanac | 435/6 |
| 5,354,668 A | 10/1994 | Auerbach | 435/91.1 |
| 5,403,708 A | 4/1995 | Brennan | 435/6 |
| 5,426,180 A | 6/1995 | Kool | 536/25.3 |
| 5,427,930 A | 6/1995 | Birkenmeyer | 435/91.52 |
| 5,474,796 A | 12/1995 | Brennan | 427/2.13 |
| 5,492,806 A | 2/1996 | Drmanac et al. | |
| 5,508,169 A | 4/1996 | Deugau | 435/6 |
| 5,525,464 A | 6/1996 | Drmanac | 435/6 |
| 5,632,957 A | 5/1997 | Heller | 422/68.1 |
| 5,641,658 A | 6/1997 | Adams | 435/91.2 |
| 5,648,245 A | 7/1997 | Fire | 435/91.1 |
| 5,710,000 A | 1/1998 | Sapolsky | 435/6 |
| 5,714,320 A | 2/1998 | Kool | 435/6 |
| 5,728,524 A | 3/1998 | Sibson | 435/6 |
| 5,744,305 A | 4/1998 | Fodor | 435/6 |
| 5,800,992 A | 9/1998 | Fodor | 435/6 |
| 5,854,033 A | 12/1998 | Lizardi | 435/91.2 |
| 5,866,337 A | 2/1999 | Schon | 435/6 |
| 5,871,921 A | 2/1999 | Landegren | 435/66 |
| 5,888,737 A | 3/1999 | DuBridge | 435/6 |
| 5,994,068 A | 11/1999 | Guilfoyle | 435/6 |
| 6,004,755 A | 12/1999 | Wang | 435/6 |
| 6,013,445 A | 1/2000 | Albrecht | 435/6 |
| 6,045,994 A | 4/2000 | Zabeau | 435/6 |
| 6,046,039 A * | 4/2000 | Wong | C12N 15/10 435/5 |
| 6,077,668 A | 6/2000 | Kool | 435/6 |
| 6,096,880 A | 8/2000 | Kool | 536/25.3 |
| 6,124,120 A | 9/2000 | Lizardi | 435/91.2 |
| 6,136,537 A | 10/2000 | Macevicz | 435/6 |
| 6,143,495 A | 11/2000 | Lizardi | 435/6 |
| 6,143,527 A | 11/2000 | Pachuk | 435/91.1 |
| 6,210,891 B1 | 4/2001 | Nyren | 435/6 |
| 6,210,894 B1 | 4/2001 | Brennan | 435/6 |

(Continued)

FOREIGN PATENT DOCUMENTS

| | | |
|---|---|---|
| JP | 4-262799 | 9/1992 |
| JP | 4-304900 | 10/1992 |
| WO | WO 95/09248 | 4/1995 |
| WO | WO 01/09384 | 2/2001 |
| WO | WO 01/62982 | 8/2001 |

(Continued)

OTHER PUBLICATIONS

Baskaran et al. Genome Research (1997) 6: 633-638.*
Final Office Action in U.S. Appl. No. 13/448,279 mailed Nov. 27, 2013.
Wolf et al., "A genotyping strategy based on incorporation and cleavage of chemically modified nucleotides" PNAS (Aug. 2002) vol. 99 No. 17 pp. 11073-11078.

(Continued)

*Primary Examiner* — Angela M Bertagna
(74) *Attorney, Agent, or Firm* — Kilpatrick Townsend & Stockton LLP

(57) ABSTRACT

The present invention is directed to methods and compositions for long fragment read sequencing. The present invention encompasses methods and compositions for preparing long fragments of genomic DNA, for processing genomic DNA for long fragment read sequencing methods, as well as software and algorithms for processing and analyzing sequence data.

24 Claims, 27 Drawing Sheets

(56) References Cited

U.S. PATENT DOCUMENTS

| | | | |
|---|---|---|---|
| 6,218,152 B1 | 4/2001 | Auerbach | 435/91.2 |
| 6,221,603 B1 | 4/2001 | Mahtani | 435/6 |
| 6,255,469 B1 | 7/2001 | Seeman | 536/23.1 |
| 6,258,539 B1 | 7/2001 | Hunkapiller | 435/6 |
| 6,261,808 B1 | 7/2001 | Auerbach | 435/91.1 |
| 6,270,961 B1 | 8/2001 | Drmanac | 435/6 |
| 6,274,320 B1 | 8/2001 | Rothberg | 435/6 |
| 6,274,351 B1 | 8/2001 | Peponnet | 435/91.1 |
| 6,284,497 B1 | 9/2001 | Sabanayagam | 435/91.2 |
| 6,287,824 B1 | 9/2001 | Lizardi | 435/91.2 |
| 6,291,183 B1 | 9/2001 | Pirrung | 435/6 |
| 6,297,006 B1 | 10/2001 | Drmanac | 435/6 |
| 6,297,016 B1 | 10/2001 | Egholm | 435/6 |
| 6,306,597 B1 | 10/2001 | Macevicz | 435/6 |
| 6,309,824 B1 | 10/2001 | Drmanac | 435/6 |
| 6,316,229 B1 | 11/2001 | Lizardi | 435/91.1 |
| 6,329,150 B1 | 12/2001 | Lizardi | 435/6 |
| 6,344,329 B1 | 2/2002 | Lizardi | 435/6 |
| 6,346,413 B1 | 2/2002 | Fodor | 435/287.2 |
| 6,355,419 B1 | 3/2002 | Alfenito | |
| 6,355,432 B1 | 3/2002 | Fodor | 435/6 |
| 6,401,267 B1 | 6/2002 | Drmanac | 435/6 |
| 6,403,320 B1 | 6/2002 | Read | 435/6 |
| 6,413,722 B1 | 7/2002 | Arnold | 435/6 |
| 6,432,360 B1 | 8/2002 | Church | 422/68.1 |
| 6,472,156 B1 | 10/2002 | Wittwer | 435/6 |
| 6,491,871 B1 | 12/2002 | Fodor | 422/63 |
| 6,500,620 B2 | 12/2002 | Yu | 435/6 |
| 6,514,768 B1 | 2/2003 | Guire | 436/518 |
| 6,534,293 B1 | 3/2003 | Barany | 435/91.2 |
| 6,558,928 B1 | 5/2003 | Landegren | 435/91.1 |
| 6,573,369 B2 | 6/2003 | Henderson | 536/23.1 |
| 6,576,448 B2 | 6/2003 | Weissman | 435/91.2 |
| 6,589,726 B1 | 7/2003 | Butler | 435/4 |
| 6,610,481 B2 | 8/2003 | Koch | 435/6 |
| 6,610,492 B1 | 8/2003 | Stanton, Jr. et al. | |
| 6,620,584 B1 | 9/2003 | Chee | 435/6 |
| 6,632,609 B2 | 10/2003 | Lizardi | 435/6 |
| 6,653,077 B1 | 11/2003 | Brenner | 435/6 |
| 6,660,229 B2 | 12/2003 | Cantor et al. | |
| 6,783,943 B2 | 8/2004 | Christian | 435/6 |
| 6,787,308 B2 | 9/2004 | Balasubramanian | 435/6 |
| 6,812,005 B2 | 11/2004 | Fan | 435/91.2 |
| 6,828,100 B1 | 12/2004 | Ronaghi | 435/6 |
| 6,833,246 B2 | 12/2004 | Balasubramanian | 435/6 |
| 6,864,052 B1 | 3/2005 | Drmanac | 435/6 |
| 6,890,741 B2 | 5/2005 | Fan | 435/91.2 |
| 6,913,884 B2 | 7/2005 | Stuelpnagel | 435/6 |
| 6,975,943 B2 | 12/2005 | Gibbs | |
| 6,977,153 B2 | 12/2005 | Kumar | 435/6 |
| 6,998,228 B2 | 2/2006 | Henderson | 435/4 |
| 7,011,945 B2 | 3/2006 | Qiao | 435/6 |
| 7,064,197 B1 | 6/2006 | Rabbani | 536/24.3 |
| 7,074,600 B2 | 7/2006 | Dean et al. | |
| 7,083,929 B2 | 8/2006 | Wong | |
| 7,232,656 B2 | 6/2007 | Balasubramanian et al. | |
| 7,244,559 B2 | 7/2007 | Rothberg | 435/6 |
| 7,264,929 B2 | 9/2007 | Rothberg | 435/6 |
| 7,276,720 B2 | 10/2007 | Ulmer | 356/246 |
| 7,297,778 B2 | 11/2007 | Matsuzaki et al. | |
| 7,384,737 B2 | 6/2008 | Barnes | 435/6 |
| 7,544,473 B2 | 6/2009 | Brenner | 435/6 |
| 7,565,346 B2 | 7/2009 | Fan et al. | |
| 7,709,197 B2 | 5/2010 | Drmanac | |
| 7,807,375 B2 | 10/2010 | Cantor et al. | |
| 7,897,344 B2 | 3/2011 | Dahl et al. | |
| 7,901,891 B2 | 3/2011 | Drmanac | |
| 8,592,150 B2 | 11/2013 | Drmanac et al. | |
| 8,614,073 B2 | 12/2013 | van Eijk et al. | |
| 8,673,562 B2 | 3/2014 | Drmanac et al. | |
| 8,765,375 B2 | 7/2014 | Drmanac et al. | |
| 8,765,379 B2 | 7/2014 | Drmanac et al. | |
| 8,765,382 B2 | 7/2014 | Drmanac et al. | |
| 8,771,957 B2 | 7/2014 | Drmanac et al. | |
| 8,771,958 B2 | 7/2014 | Drmanac et al. | |
| 2002/0004204 A1 | 1/2002 | O'Keefe | 435/6 |
| 2002/0012930 A1 | 1/2002 | Rothberg et al. | |
| 2002/0012939 A1 | 1/2002 | Palsson | |
| 2002/0025532 A1 | 2/2002 | Huang et al. | |
| 2002/0055100 A1 | 5/2002 | Kawashima | 435/6 |
| 2002/0076716 A1 | 6/2002 | Sabanayagam | 435/6 |
| 2002/0197621 A1 | 12/2002 | Drmanac | 435/6 |
| 2003/0068629 A1 | 4/2003 | Rothberg | 435/6 |
| 2003/0092007 A1 | 5/2003 | Gibbs et al. | |
| 2003/0100006 A1 | 5/2003 | Senapathy | |
| 2003/0148313 A1 | 8/2003 | Strathmann | |
| 2004/0002090 A1 | 1/2004 | Mayer | 435/6 |
| 2004/0005614 A1* | 1/2004 | Kurn | C12Q 1/68 506/4 |
| 2004/0029165 A1 | 2/2004 | Wong | |
| 2004/0229221 A1 | 11/2004 | Schon | 435/6 |
| 2004/0248144 A1 | 12/2004 | Mir | 435/6 |
| 2004/0248161 A1 | 12/2004 | Rothberg | 435/6 |
| 2004/0259118 A1 | 12/2004 | Macevicz | |
| 2005/0019776 A1 | 1/2005 | Callow | 435/6 |
| 2005/0037356 A1 | 2/2005 | Gullberg | 435/6 |
| 2005/0042633 A1 | 2/2005 | Williams | |
| 2005/0042649 A1 | 2/2005 | Balasubramanian | 435/6 |
| 2005/0100939 A1 | 5/2005 | Namsaraev | 435/6 |
| 2005/0130173 A1 | 6/2005 | Leamon et al. | |
| 2005/0191656 A1 | 9/2005 | Drmanac | 435/6 |
| 2005/0202489 A1 | 9/2005 | Cho et al. | |
| 2005/0208538 A1* | 9/2005 | Kurn | C12P 19/34 435/6.12 |
| 2005/0214840 A1 | 9/2005 | Chen | 435/6 |
| 2005/0244863 A1 | 11/2005 | Mir | 435/6 |
| 2006/0012793 A1 | 1/2006 | Harris | 356/436 |
| 2006/0024681 A1 | 2/2006 | Smith | 435/6 |
| 2006/0024711 A1 | 2/2006 | Lapidus | 435/6 |
| 2006/0073506 A1 | 4/2006 | Christians et al. | |
| 2006/0223097 A1 | 10/2006 | Sapolsky | 435/6 |
| 2006/0223122 A1 | 10/2006 | Fogo et al. | |
| 2006/0234234 A1 | 10/2006 | Van Dongen et al. | |
| 2006/0246453 A1 | 11/2006 | Kato et al. | |
| 2007/0015182 A1 | 1/2007 | Abarzua | 435/6 |
| 2007/0037152 A1 | 2/2007 | Drmanac | 435/6 |
| 2007/0037197 A1 | 2/2007 | Young | 435/6 |
| 2007/0042401 A1 | 2/2007 | Morgan et al. | |
| 2007/0054311 A1 | 3/2007 | Kamberov et al. | |
| 2007/0072208 A1 | 3/2007 | Drmanac | 435/6 |
| 2007/0099208 A1 | 5/2007 | Drmanac | 435/6 |
| 2008/0051294 A1 | 2/2008 | Gormley et al. | |
| 2008/0234136 A1 | 9/2008 | Drmanac | 506/3 |
| 2008/0318796 A1 | 12/2008 | Drmanac | 506/3 |
| 2009/0005252 A1 | 1/2009 | Drmanac | 506/3 |
| 2009/0005259 A1 | 1/2009 | Drmanac | 506/3 |
| 2009/0011416 A1 | 1/2009 | Drmanac | 435/6 |
| 2009/0011943 A1 | 1/2009 | Drmanac | 506/4 |
| 2009/0036316 A1 | 2/2009 | Drmanac | 506/4 |
| 2009/0099041 A1 | 4/2009 | Church | 506/26 |
| 2009/0118488 A1 | 5/2009 | Drmanac | 536/24.2 |
| 2009/0137404 A1 | 5/2009 | Drmanac | 506/3 |
| 2009/0137414 A1 | 5/2009 | Drmanac | 506/9 |
| 2009/0155781 A1 | 6/2009 | Drmanac | 435/6 |
| 2009/0264299 A1 | 10/2009 | Drmanac | 506/3 |
| 2010/0199155 A1 | 8/2010 | Kermani et al. | |
| 2011/0033854 A1 | 2/2011 | Drmanac et al. | |
| 2011/0319281 A1 | 12/2011 | Drmanac | |
| 2013/0059740 A1 | 3/2013 | Drmanac et al. | |
| 2013/0124100 A1 | 5/2013 | Drmanac et al. | |

FOREIGN PATENT DOCUMENTS

| | | |
|---|---|---|
| WO | 02/061143 A2 | 8/2002 |
| WO | WO 02/074988 | 9/2002 |
| WO | 02/103046 A2 | 12/2002 |
| WO | WO 03/012119 | 2/2003 |
| WO | WO 03/040391 | 5/2003 |
| WO | 03/102231 A1 | 12/2003 |
| WO | WO 2004/072294 | 8/2004 |
| WO | WO 2004/076683 | 9/2004 |
| WO | WO 2005/040425 | 5/2005 |
| WO | WO 2005/047523 | 5/2005 |
| WO | WO 2005/078130 | 8/2005 |

(56) References Cited

FOREIGN PATENT DOCUMENTS

| | | | |
|---|---|---|---|
| WO | WO 2005/080605 | 9/2005 | |
| WO | WO 2005/082098 | 9/2005 | |
| WO | WO 2005/093094 | 10/2005 | |
| WO | WO 2005/116262 | 12/2005 | |
| WO | WO 2006/007207 | 1/2006 | |
| WO | WO 2006/040549 | 4/2006 | |
| WO | WO 2006/055521 | 5/2006 | |
| WO | WO 2006/073504 | 7/2006 | |
| WO | WO 2006/084132 | 8/2006 | |
| WO | WO 2006/138257 | 12/2006 | |
| WO | WO 2007/014397 | 2/2007 | |
| WO | WO 2007/025124 | 3/2007 | |
| WO | 2007/037678 A2 | 4/2007 | |
| WO | 2007/044245 A2 | 4/2007 | |
| WO | WO 2007/061425 | 5/2007 | |
| WO | WO 2007/062160 | 5/2007 | |
| WO | WO 2007091077 A1 * | 8/2007 | .......... C12Q 1/6874 |
| WO | WO 2007/106509 | 9/2007 | |
| WO | WO 2007/120208 | 10/2007 | |
| WO | WO 2007/121489 | 10/2007 | |
| WO | 2007/133710 A2 | 11/2007 | |
| WO | WO 2007/133710 A2 | 11/2007 | |

OTHER PUBLICATIONS

Kelly et al., "Miniaturizing chemistry and biology in microdroplets" Chemical Communications (2007) 18: pp. 1773-1788.
International Preliminary Report on Patentability for PCT Application No. PCT/US2010/038741, mailed Dec. 29, 2011, 14 pages.
"Phasing Analysis Service for Whole Human Genome Sequencing," Illumina Genome Network, Data Sheet: Genome Network Services, downloaded on Mar. 18, 2015 from http://www.illumina.com, 4 pages.
Batzoglou et al., "ARACHNE: A Whole-Genome Shotgun Assembler," Genome Research, 12:177-189 (2002).
Burgtorf et al., "Clone-Based Systematic Haplotyping (CSH): A Procedure for Physical Haplotyping of Whole Genomes," Genome Research, 13(12):2717-2724 (2003).
Cheung et al., "Whole Genome Amplification using a Degenerate Oligonucleotide Primer Allows Hundreds of Genotypes to be Performed on Less Than One Nanogram of Genomic DNA," Proceedings of the National Academy of Sciences, 93:14676-14679 (1996).
Cui et al, "Determination of Gene Organization in Individual Haplotypes by Analyzing Single DNA Fragments from a Single Spermatozoa," Proceedings of the National Academy of Sciences, 95:10791-10796 (1998).
Dear et al., "A High-Resolution Metric HAPPY Map of Human Chromosome 14," Genomics, 48:232-241 (1998).
Dear et al., "Happy Mapping: Linkage Mapping using a Physical Analogue of Meiosis," Nucleic Acids Research, 21:13-20 (1993).
Delius et al., "Separation of Complementary Strands of Plasmid DNA using the Biotin-Avidin System and its Application to Heteroduplex Formation and RNA/DNA Hybridizations in Electron Microscopy," Nucleic Acids Research, 13:5457-5469 (1985).
Drmanac et al., "Human Genome Sequencing using Unchained Base Reads on Self-Assembly DNA Nanoarrays," Science, 327(78):78-81 (2010).
Drmanac et al., "Sequencing by Hybridization (SBH): Advantages, Achievements, and Opportunities," Advances in Biochemical Engineering/Biotechnology, 77:75-101 (2002).
Havlak et al., "The Atlas Genome Assembly System," Genome Research, 14:721-732 (2004).
Hubbell, "Multiplex Sequencing by Hybridization," Journal of Computational Biology, 8(2):141-149 (2001).
Jiang et al., "Old Can Be New Again: HAPPY Whole Genome Sequencing, Mapping and Assembly," International Journal of Biological Science, 5:298-303 (2009).
Kandpal et al., "Selective Enrichment of a Large Size Genomic DNA Fragment by Affinity Capture: An Approach for Genome Mapping," Nucleic Acids Research, 18:1789-1795 (1990).

Lander et al., "Genomic Mapping by Fingerprinting Random Clones: A Mathematical Analysis," Genomics, 2:231-239 (1988).
Li et al., "Estimating the Repeat Structure and Length of DNA Sequences using L-Tuples," Genome Research, 13:1916-1922 (2003).
Mitra et al., "Digital Genotyping and Haplotyping with Polymerase Colonies," Proceedings of the National Academy of Sciences, 100:5926-5931 (2003).
Pevzner et al., "An Eulerian Path Approach to DNA Fragment Assembly," Proceedings of the National Academy of Sciences, 98:9748-9753 (2001).
Ramsay et al., "Intimate Association of Microsatellite Repeats with Retrotransposons and Other Dispersed Repetitive Elements in Barley," The Plant Journal, 17(4):415-425 (1999).
Vogelstein et al., "Digital PCR," Proceedings of the National Academy of Sciences, 96:9236-9241 (1999).
Waterston et al., "On the Sequencing of the Human Genome," Proceedings of the National Academy of Sciences, 99:3712-3716 (2002).
Prodromou et al. "DNA Fragmentation-Based Combinatorial Approaches to Soluble Protein Expression," *Drug Discovery Today*, 12(21-22):931-938 (Nov. 2007).
Williams Richard et al., "Amplification of Complex Gene Libraries by Emulsion PCR," *Nature Methods*, 3(7):545-550 (Jun. 21, 2006).
Blanco et al., "High efficient DNA synthesis by the phage phi 29 DNA polymerase," J. Biol. Chem., v. 264, issue 15, p. 8935-8940 (1989).
Brenner et al, "Gene Expression Analysis by Massivly Parallel Signature Sequencing (MPSS) on Microbead Arrays," Nature Biotechnology, v. 18, p. 630-634 (2000).
Callow, Matthew J., et al. "Selective DNA amplification from complex genomes using universal double-sided adapters," Nucleic Acids Research, vol. 32, No. 2, e21, p. 1-6, (Jan. 2004).
Chen et al., "A Homogeneous, Ligase-Mediated DNA Diagnostic Test", Genome Research, vol. 8, No. 5, May 1998, pp. 549-556.
Collins et al, "Directional cloning of DNA fragments at a large distance from an initial probe: A circularization method," Proc. Natl. Acad. Sci., 81: 6812-6816 (1984).
Cowie et al, "Identification of APC gene mutations in colorectal cancer using universal microarray-based combinatorial sequencing-by-hybridization," Human Mutation, 24:261-271 (2004).
Dahl et al, "Multiplex amplification enabled by selective circularization of large sets of genomic DNA fragments," Nucleic Acids Research, 33(8): e71 (2005).
Henke, W. et al., "Betaine Improves the PCR Amplification of GC-Rich DNA Sequences," Nucleic Acids Research, v. 25, No. 19, p. 3957-3958, (Jan. 1, 1997).
Ladner, D.P. et al., "Multiplex detection of hotspot mutations by rolling circl-enabled universal microarrays," Laboratory Investigation, US and CA Academy of Pa;thology, vol. 81, No. 8, p. 1079-1086 (Aug. 1, 2001).
Li, M. et al., "BEAMing up for detection and quantification of rare sequence variants," Nature Methods, vol. 3, pp. 95-97 (2006).
Metzker, "Emerging Technologies in DNA Sequencing," Genome Research, 15: 1767-1776 (2005).
Paul, P., et al., "Single-Molecule Dilution and Multiple Displacement Amplification for Molecular Haplotyping," Biotechniques, v. 38, No. 4, p. 553-559 (Apr. 4, 2005).
Reich, S., et al., "Combinatorial Domain Hunting: An Effective Approach for the Identification of Soluble Protein Domains Adaptable to High-Throughput Applications," Protein Science, v. 15, No. 10, p. 2357, (Oct. 2006).
Shendure et al, "Accurate multiplex polony sequencing of an evolved bacterial genome," Science, 309: 1728-1732 (2005).
Shendure et al, "Advanced Sequencing Technologies: Methods and Goals," Nature Reviews Genetics, vol. 5, pp. 335-344 (2004).
Smirnov et al, "Method of manufacturing whole-genome microarrays by rolling circle amplification," Genes, Chromosomes & Cancer, 40: 72-77 (2004).
Tringe et al, "Metagenomics: DNA Sequencing of Environmental Samples," Nature Reviews Genetics, vol. 6, pp. 805-814 (2005.

(56) References Cited

OTHER PUBLICATIONS

Vingron et al., "Sequence Alignment and Penalty Choice Review of Concepts, Case Studies and Implications," J. Mol. Biol, vol. 235, issue 1, pp. 1-12 (1994).

Voss, H. et al., "Efficient Low Redundancy Large-Scale DNA Sequencing at EMBL," J. of Biotechn., v. 41, No. 2, (1995).

Documents on file in U.S. Appl. No. 11/451,692 (now issues as U.S. Pat. No. 7,910,354): Non-Final Office Action (Jun. 5, 2008); Response (Dec. 5, 2008); Ex Parte Quayle Action Apr. 17, 2009); Response (Jun. 17, 2009.

Documents on file in U.S. Appl. No. 12/335,168 (now issued as U.S. Pat. No. 7,901,891): Non-Final Office Action (Nov. 19, 2009); Supplemental Non-Final Office Action (Dec. 1, 2009); Response (Mar. 31, 2010); Final Office Action (Aug. 11, 2010); Response (Oct. 11, 2010).

Documents on file in U.S. Appl. No. 13/017,244: Non-Final Office Action (Aug. 1, 2012); Response (Feb. 1, 2013); Supplemental Response (Feb. 4, 2013); Interview Summary (Feb. 25, 2013); Supplemental Response (Apr. 4, 2013); Interview Summary (Jul. 22, 2013); Final Office Action (Oct. 2, 2013).

Documents on file in Canadian Application No. 2,611,743, Office Action (Oct. 16, 2012); Response (Apr. 16, 2013).

Documents on file in European Application No. 06760745.7: European Search Report and Search Opinion (Sep. 17, 2009); Office Action (Jan. 11, 2010); Response (Jan. 13, 2010); Office Action (Sep. 2, 2010); Response (Mar. 14, 2011); Office Action (Jul. 18, 2012); Response (May 15, 2013); Office Action (Jul. 15, 2013).

Documents on file in European Application No. 12150825.3; European Search Report and Search Opinion (Jul. 17, 2012); Office Action (Jun. 27, 2013).

Documents on file in International Application No. PCT/US2006/022950: International Search Report (Dec. 13, 2007); International Preliminary Report on Patentability (Dec. 17, 2007).

Documents on file in U.S. Appl. No. 12/816,365: Non-Final Office Action (Mar. 29, 2012); Response (Oct. 1, 2012); Final Office Action (Jan. 4, 2013); Interview Summary (Jun. 3, 2013); Notice of Appeal (Jun. 4, 2013); Response (Jul. 10, 2013).

Documents on file in Chinese Application No. 201080036235.6: Office Action (Nov. 5, 2012); Response (May 20, 2013; Office Action (Sep. 16, 2013).

Documents on file in European Application No. 10725582.0: Office Action (Dec. 10, 2012); Response (Jun. 20, 2013); Office Action (Jul. 3, 2013); Response (Sep. 16, 2013).

Documents on filed in International Application No. PCT/US2010/038741: International Search Report (Jul. 21, 2011); International Preliminary Report on Patentability (Dec. 16, 2011).

Documents on file in U.S. Appl. No. 13/448,279: Non-Final Office Action (Mar. 28, 2013); Interview Summary (Aug. 21, 2013); Interview Summary (Aug. 23, 2013); Response (Aug. 27, 2013); Interview Summary (Aug. 28, 2013); Supplemental Response (Sep. 23, 2013).

Ansorge, Next-generation DNA sequencing techniques, New Biotechnology, vol. 25, Issue 4, Apr. 2009, pp. 195-203.

Kozarewa et al., Amplification-free Illumina sequencing-library preparation facilitates improved mapping and assembly of (G=C)-biased genomes, Nat Methods., vol. 6, Issue 4, Apr. 2009, pp. 291-296.

Shendure et al., Next-generation DNA sequencing, Nature, vol. 26, No. 10, Oct. 2008, pp. 1135-1145.

\* cited by examiner

Figure 4A
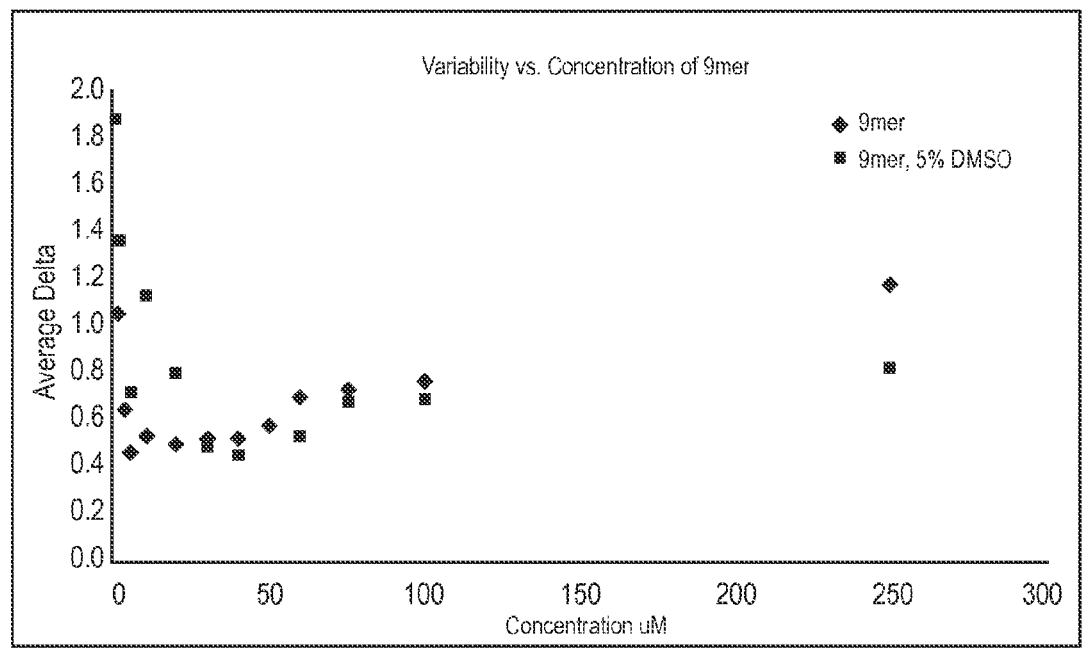
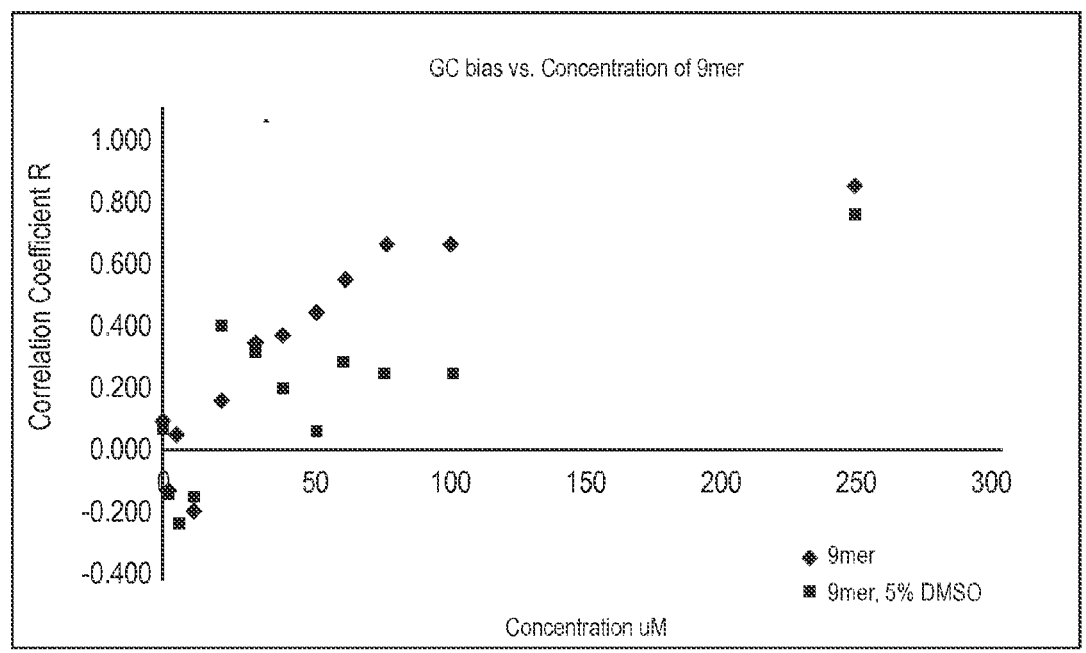
Figure 4B

Schematic of Adaptor ⟋1000

```
          ┌─1001              ┌─1002                    ┌─1003
|----------5_Arm------|-binding_region-|----------3_Arm----------|
|T|<EcoP15-|                                        |-EcoP15>|T|
 └1004  └1005                                        1005┘ 1004┘
```

Schematic of 5' Adaptor Arm ⟋1010

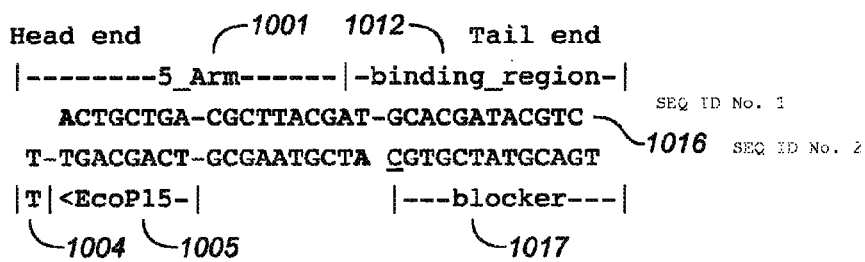

Schematic of 3' Adaptor Arm ⟋1020

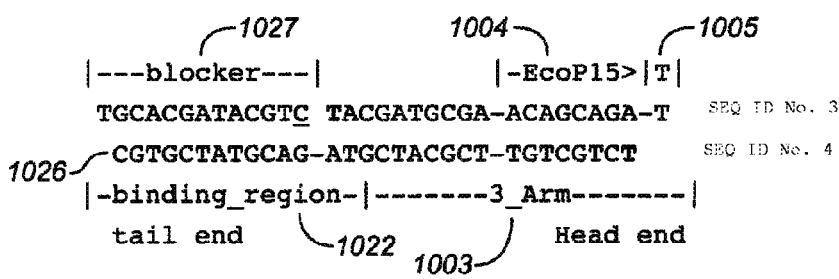

Schematic of Final Adaptor ⟋1030

```
413333331           2              2         133333314
AACTGCTGANNNNNNNNNNNGNNNNNNNNNNCNNNNNNNNNNNNACAGCAGAT   SEQ ID No. 5
AACTGCTGACGCTTACGATGCACGATACGTCTACGATGCGAACAGCAGA       SEQ ID No. 6
   TGACGACTGCGAATGCTACGTGCTATGCAGATGCTACGCTTGTCGTCTA    SEQ ID No. 7
```

```
                         ┌─2512                      ┌─2511
SEQ ID No. 8  ...BBBBBBBBBBBBBBBBBBBBGATCATCGTCAGCAGTCGCGTAGCTAG ─┐─2501
                                                                  ─2502
                                    2503─┐ SEQ ID No. 14  TCGTCAGCGCATCGATC ─┘
                         ┌─2512          ↓  SEQ ID No. 14  TCGTCAGCGCATCGATC  ─2504
SEQ ID No. 3  ...BBBBBBBBBBBBBBBBBBBBGATCATCGTCAGCAGTCGCGTAGCTAG
           SEQ ID No. 15    2506─┐ NNNNNCTAGTAGCAG ─2505  ╲─2511
                                 ↓                    ┌─2513
              SEQ ID No. 16     NNNNNCTAGTAGCAGTCGTCAGCGCATCGATC  ─2507
SEQ ID No. 6  ...BBBBBBBBBBBBBBBBBBBBGATCATCGTCAGCAGTCGCGTAGCTAG
                                                              ╲─2511
                    ┌ NNNANNNN
               2508┤  NNNTNNNN    ├─2509
                   │  NNNGNNNN
               2514─└ NNNCNNNN              2513
SEQ ID No. 17        NNNANNNNNNNNCTAGTAGCAGTCGTCAGCGCATCGATC  ─2510
SEQ ID No. 18 ...BBBBBBBBBBBTBBBBBBBBBGATCATCGTCAGCAGTCGCGTAGCTAG
                ╲─2512          FIG. 25              ╲─2511
```

FIG. 26

```
...BBBBBBBBBBBBBBBBBBBBAGCAGTCGCGTAGCTAG ─2601  SEQ ID No. 19
                                              ─2602
           2603─┐       TCGTCAGCGCATCGATC ─┘ SEQ ID No. 14
                ↓
   SEQ ID No. 14   TCGTCAGCGCATCGATC  ─2604
...BBBBBBBBBBBBBBBBBBBBAGCAGTCGCGTAGCTAG  SEQ ID No. 19
           2606─┐ NNNNNNN ─2605
                ↓
   SEQ ID No. 20    NNNNNNNTCGTCAGCGCATCGATC  ─2607
...BBBBBBBBBBBBBBBBBBBBAGCAGTCGCGTAGCTAG  SEQ ID No. 19
            ┌ NNNANN
       2608┤  NNNTNN    ├─2609
           │  NNNGNN
           └ NNNCNN

SEQ ID No. 21  NNNANNNNNNNNCTAGTAGCAGTCGTCAGCGCATCGATC  ─2610
...BBBBBBBBBBBTBBBBBBBBBGATCATCGTCAGCAGTCGCGTAGCTAG  SEQ ID No. 18
                         FIG. 26
```

REDUCING GC BIAS IN DNA SEQUENCING USING NUCLEOTIDE ANALOGS

CROSS REFERENCE TO RELATED APPLICATIONS

This application is a divisional application of U.S. patent application Ser. No. 12/816,365, filed Jun. 15, 2010 and issued as U.S. Pat. No. 8,592,150, which claims the benefit of priority to U.S. Patent Application No. 61/187,162, filed Jun. 15, 2009, and is a continuation-in-part of U.S. patent application Ser. No. 12/329,365, filed Dec. 5, 2008 and issued as U.S. Pat. No. 8,415,009, which claims the benefit of priority of 60/992,485, filed Dec. 5, 2007; 61/026,337, filed Feb. 5, 2008; 61/035,914, filed Mar. 12, 2008; 61/061,134, filed Jun. 13, 2008; 61/116,193, filed Nov. 19, 2008; 61/102,586, and filed on Oct. 3, 2008. The aforelisted priority applications, along with U.S. patent application Ser. No. 12/265,593, filed Nov. 5, 2008; and Ser. No. 12/266,385, filed Nov. 6, 2008; is each hereby incorporated herein by reference in its entirety for all purposes.

BACKGROUND OF THE INVENTION

Large-scale genomic sequence analysis is a key step toward understanding a wide range of biological phenomena. The need for low-cost, high-throughput sequencing and re-sequencing has led to the development of new approaches to sequencing that employ parallel analysis of multiple nucleic acid targets simultaneously.

Conventional methods of sequencing are generally restricted to determining a few tens of nucleotides before signals become significantly degraded, thus placing a significant limit on overall sequencing efficiency. Conventional methods of sequencing are also often limited by signal-to-noise ratios that render such methods unsuitable for single-molecule sequencing.

It would be advantageous for the field if methods and compositions could be designed to increase the efficiency of sequencing reactions as well as the efficiency of assembling complete sequences from shorter read lengths.

SUMMARY OF THE INVENTION

Accordingly, the present invention provides methods and compositions for sequencing reactions.

In an exemplary embodiment, the present invention provides a method of fragmenting a double-stranded target nucleic acid. This method includes (a) providing genomic DNA; (b) dividing DNA into a number of separate aliquots; (c) amplifying the DNA in the separate aliquots in the presence of a population of dNTPs that includes dNTP analogs, such that a number of nucleotides in the DNA are replaced by dNTP analogs; (d) removing the dNTP analogs to form gapped DNA; (e) treating the gapped DNA to translate the gaps until gaps on opposite strands converge, thereby creating blunt-ended DNA fragments. In a further embodiment, substantially every fragment in a separate mixture is non-overlapping with every other fragment of the same aliquot.

In a further embodiment and in accordance with any of the above, the present invention provides a method for fragmenting nucleic acids that includes the steps of: (a) providing at least two genome-equivalents of DNA for at least one genome; (b) dividing the DNA into a first tier of separate mixtures; (c) amplifying the DNA in the separate mixtures, wherein the amplifying is conducted with a population of dNTPs that comprises a predetermined ratio of dUTP to dTTP, such that a number of thymines in said DNA are replaced by uracils, and a predetermined ratio of 5-methyl dCTP to dCTP, such that a number of cytosines are replaced by 5-methyl cytosines; (d) removing the uracils and the 5-methyl cytosines to form gapped DNA; (e) treating the gapped DNA to translate said gaps until gaps on opposite strands converge, thereby creating blunt-ended DNA fragments, where the blunt-ended fragments have less GC bias and less coverage bias as compared to fragments generated in the absence of 5-methyl cytosine.

In a further embodiment, the present invention provides a method of fragmenting a double-stranded target nucleic acid that includes the steps of: (a) providing genomic DNA; (b) dividing the DNA into separate aliquots; (c) amplifying the DNA in the separate aliquots to form a plurality of amplicons, where the amplifying is conducted with a population of dNTPs that comprises dNTP analogs, such that a number of nucleotides in the amplicons are replaced by the dNTP analogs; and wherein the amplifying is conducted in the presence of an additive selected from glycogen, DMSO, ET SSB, betaine, and any combination thereof; (c) removing the dNTP analogs from the amplicons to form gapped DNA; (d) treating the gapped DNA to translate said gaps until gaps on opposite strands converge, thereby creating blunt-ended DNA fragments, wherein the blunt-ended fragments have less GC bias as compared to fragments generated in the absence of the additive.

In a further embodiment, the present invention provides a method of obtaining sequence information from a genome that includes the steps: (a) providing a population of first fragments of said genome; (b) preparing emulsion droplets of the first fragments, such that each emulsion droplet comprises a subset of the population of first fragments; (c) obtaining a population of second fragments within each emulsion droplet, such that the second fragments are shorter than the first fragments from which they are derived; (d) combining the emulsion droplets of the second fragments with emulsion droplets of adaptor tags; (e) ligating the second fragments with the adaptor tags to form tagged fragments; (f) combining the tagged fragments into a single mixture; (g) obtaining sequence reads from the tagged fragments, where the sequence reads include sequence information from the adaptor tags and the fragments to identify fragments from the same emulsion droplet, thereby providing sequence information for the genome.

BRIEF DESCRIPTION OF THE DRAWINGS

FIG. 4 shows the effect of DMSO and primer concentration on variability (FIG. 4A) and GC bias (FIG. 4B) in MDA reactions.

FIG. 10 is a schematic illustration of components of adaptors that are useful for controlling the way such adaptors are inserted into a target nucleic acid.

FIG. 11 is a schematic illustration of an embodiment of an arm-by-arm ligation process for inserting adaptors into target nucleic acids.

FIG. 25 is a schematic illustration of one embodiment of a combinatorial probe anchor ligation method.

FIG. 26 is a schematic illustration of one embodiment of a combinatorial probe anchor ligation method.

DETAILED DESCRIPTION OF THE INVENTION

Figure 1:
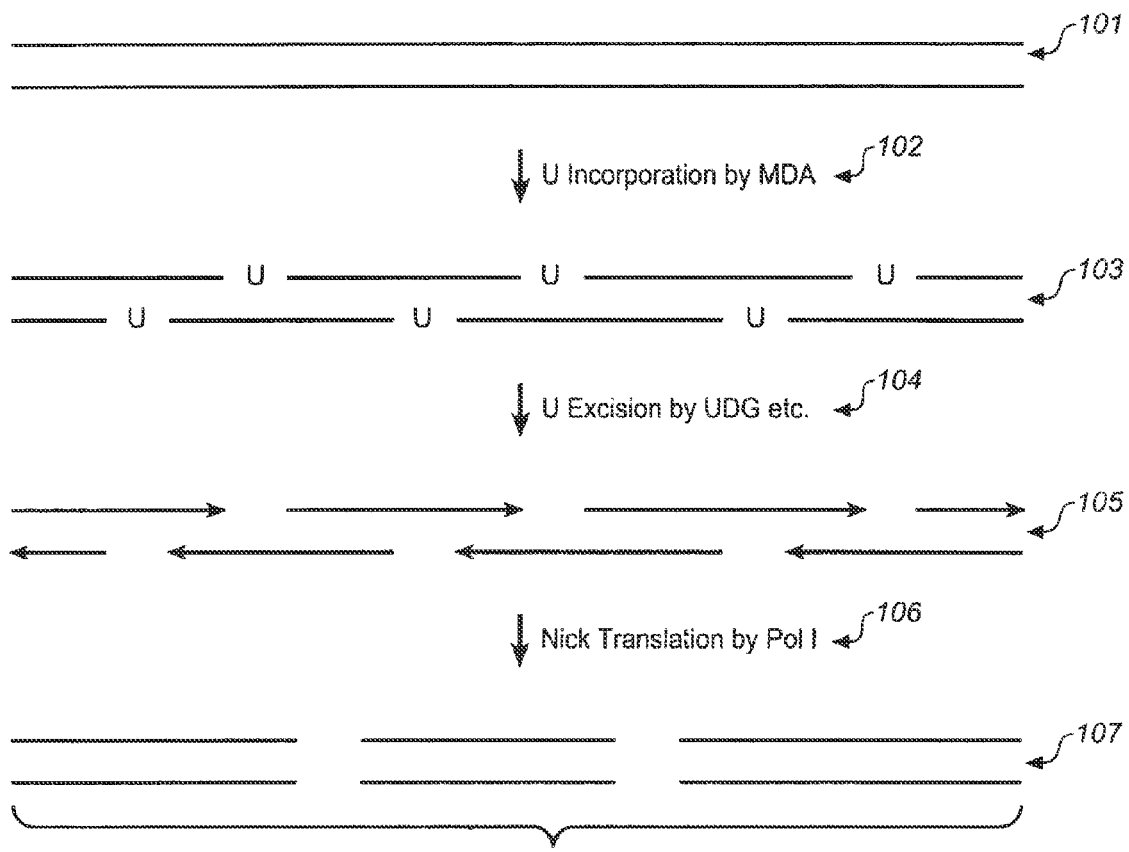
FIG. 1 is a schematic illustration of an embodiment of a method for fragmenting nucleic acids.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L, (1995) *Biochemistry* (4th Ed.) Freeman, New York, Gait, *"Oligonucleotide Synthesis: A Practical Approach"* 1984, IRL Press, London, Nelson and Cox (2000), *Lehninger, Principles of Biochemistry* $3^{rd}$ Ed., W. H. Freeman Pub. New York, N.Y. and Berg et al. (2002) *Biochemistry,* $5^{th}$ Ed., W. H. Freeman Pub. New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Although the present invention is described primarily with reference to specific embodiments, it is also envisioned that other embodiments will become apparent to those skilled in the art upon reading the present disclosure, and it is intended that such embodiments be contained within the present inventive methods.

I. Overview

The present invention is directed to compositions and methods for nucleic acid identification and detection, which find use in a wide variety of applications as described herein. Such applications include sequencing of whole genomes, sequencing of multiple whole genomes, and detecting specific target sequences, including single nucleotide polymorphisms (SNPs) and gene targets of interest.

The present invention provides compositions and methods for isolating and fragmenting nucleic acids from a sample. For some applications, fragments are produced using a Controlled Random Enzymatic (CoRE) approach. In general, the CoRE fragmentation method involves replacing a number of nucleotides in target nucleic acids with modified nucleotides or nucleotide analogs. The modified/analog nucleotides are then removed by enzymatic treatment to produce gapped nucleic acids. Further enzymatic treatment translates those gaps along the nucleic acid until gaps on opposite strands converge, resulting in blunt-ended nucleic acid fragments. Fragments produced in accordance with the present invention can be reproducibly controlled for length, bias and coverage.

One method by which nucleotides are replaced in target nucleic acids in accordance with the CoRE fragmentation approach is through amplification of the original population of target nucleic acids. This amplification is generally conducted in the presence of a population of dNTPs, where that population includes a predetermined ratio of dNTP analogs to naturally-occurring nucleotides. For example, in CoRE methods in which thymines are replaced by deoxyuracils, the target nucleic acids are amplified using a population of dNTPs that contains a predetermined ratio of dUTPs to dTTPs. The number of thymines that are replaced (and thus the length of the resultant fragments) can be controlled by manipulating the ratio of dUTPs to dTTPs. Similarly, CoRE methods that replace cytosines with 5-methyl cytosines or that replace adenines with inosine would utilize populations of dNTPs doped with a predetermined proportion of 5-methyl cytosines or inosines. As will be appreciated, CoRE methods can also utilize any combination of deoxyuracils, 5-methyl cytosines, and inosines to replace multiple nucleotides within the nucleic acid.

Methods of amplification used for CoRE or to amplify any nucleic acid construct described herein can include a large number of amplification methods known in the art. In some applications, Multiple Displacement Amplification (MDA) is used to amplify nucleic acids for use in sequencing and other applications described in further detail herein. The present invention provides compositions and methods for MDA that reduce the GC bias that is inherent to many amplification methods, particularly whole genome amplification methods. In some applications, methods of the present invention include MDA methods that utilize additives such as betaine, glycerol, and single strand binding proteins to prevent or ameliorate GC bias.

Nucleic acids, including nucleic acid fragments produced in accordance with the present invention, can be used in a number of sequencing applications. In certain applications, sequence information is obtained from nucleic acid fragments using Long Fragment Read (LFR) sequencing. Such methods include physical separation of long genomic DNA fragments across many different aliquots such that the probability of any given region of the genome of both the maternal and paternal component in the same aliquot is very rare. By placing a unique identifier in each aliquot and analyzing many aliquot in the aggregate, long fragments of DNA can be assembled into a diploid genome, e.g. the sequence of each parental chromosome can be obtained. In certain LFR applications, emulsion droplets are used in which each droplet contains a small number of fragments, and all the emulsion droplets together contain fragments representing one or more copies or equivalents of an entire genome. Emulsion droplets containing nucleic acid fragments are combined with emulsion droplets containing adaptors. The combined droplets provide an enclosed space for ligation of adaptors to fragments, such that different combined droplets contain fragments tagged with different adaptors. In some applications, two or more adaptor tag components are contained in the adaptor droplets, such that upon combination with a droplet containing nucleic acid fragments, unique combinatorial tags are ligated to the fragments. In applications utilizing droplets, reagents such as ligase and buffers can be included in the emulsion droplets containing the nucleic acid fragments, the droplets containing the adaptors, or in separate droplets that are then combined with the fragment and adaptor droplets. An advantage of using emulsion droplets is that reduction of reaction volumes to picoliter levels provides a reduction in the costs and time associated with producing LFR libraries. Aliquots of nucleic acids can also be distributed among different containers or vessels, such as different wells in a multiwell microtiter plate for LFR sequencing.

Regardless of the method by which different LFR aliquot libraries are produced and tagged, the resultant nucleic acids can then be sequenced using methods known in the art and described in further detail herein. Sequence reads from individual fragments can be assembled using sequence information from their associated tag adaptors to identify fragments from the same aliquot.

II. Preparation of Nucleic Acids

The present invention includes methods and compositions for isolating nucleic acids from samples. By "nucleic acid" or "oligonucleotide" or "polynucleotide" or grammatical equivalents herein means at least two nucleotides covalently linked together. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. As used herein, the term "nucleotide" encompasses both nucleotides and nucleosides as well as nucleoside and nucleotide analogs, and modified nucleotides such as amino modified nucleotides. In addition, "nucleotide" includes non-naturally occurring analog structures. Thus, for example, the individual units of a peptide nucleic acid, each containing a base, may be referred to herein as a nucleotide.

In the present invention, as is further discussed herein, nucleotide analogs are used in many embodiments. Nucleotide analogs include any nucleotide that can be incorporated into genomic DNA that allows subsequent cleavage, either enzymatically or chemically. Thus dUTP is considered a nucleotide analog, because uracil is not normally in the deoxy state. Inosine, and 5-methyl cytosine are also considered modified nucleotides or nucleotide analogs. In addition, as further described below, several bases of RNA can be incorporated into genomic DNA to allow subsequent cleavage by RNAse H, and thus in these embodiments, those RNA bases would be considered analogs for the purposes of the present invention. Nucleotide analogs may also include abasic residues, such as 2'-deoxyribosylformamide, 2'-deoxyribose, 1'2'-dideoxy ribofuranose or propanediol.

A nucleic acid of the present invention will generally contain phosphodiester bonds, although in some cases, as outlined below (for example in the construction of primers and probes such as label probes), nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid (also referred to herein as "PNA") backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids (also referred to herein as "LNA"), Koshkin et al., J. Am. Chem. Soc. 120:13252 3 (1998); positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev, (1995) pp 169 176). Several nucleic acid analogs are described in Rawls, C & E News Jun. 2, 1997 page 35. "Locked nucleic acids" (LNA™) are also included within the definition of nucleic acid analogs. LNAs are a class of nucleic acid analogues in which the ribose ring is "locked" by a methylene bridge connecting the 2'-O atom with the 4'-C atom. All of these references are hereby expressly incorporated by reference in their entirety for all purposes and in particular for all teachings related to nucleic acids. These modifications of the ribose-phosphate backbone may be done to increase the stability and half-life of such molecules in physiological environments. For example, PNA:DNA and LNA-DNA hybrids can exhibit higher stability and thus may be used in some embodiments.

Target nucleic acids can be obtained from a sample using methods known in the art. The term "target nucleic acid" refers to a nucleic acid of interest and unless otherwise specified is used interchangeably with the terms "nucleic acid" and "polynucleotide". As will be appreciated, the sample may comprise any number of substances, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); biological warfare agent samples; research samples (i.e. in the case of nucleic acids, the sample may be the products of an amplification reaction, including both target and signal amplification as is generally described in PCT/US99/01705, such as PCR amplification reaction); purified samples, such as purified genomic DNA, RNA, proteins, etc.; raw samples (bacteria, virus, genomic DNA, etc.); as will be appreciated by those in the art, virtually any experimental manipulation may have been done on the sample. In one aspect, the nucleic acid constructs of the invention are formed from genomic DNA. In certain embodiments, the genomic DNA is obtained from whole blood or cell preparations from blood or cell cultures.

In one aspect, target nucleic acids of the invention are genomic nucleic acids, although other target nucleic acids can be used, including mRNA (and corresponding cDNAs, etc.). Target nucleic acids include naturally occurring or genetically altered or synthetically prepared nucleic acids (such as genomic DNA from a mammalian disease model). Target nucleic acids can be obtained from virtually any source and can be prepared using methods known in the art. For example, target nucleic acids can be directly isolated without amplification, isolated by amplification using methods known in the art, including without limitation polymerase chain reaction (PCR), multiple displacement amplification (MDA) (which encompasses and is used interchangeably with the term strand displacement amplification (SDA)), rolling circle amplification (RCA) (which encompasses and is used interchangeably with the term rolling circle replication (RCR)) and other amplification methodologies. Target nucleic acids may also be obtained through cloning, including but not limited to cloning into vehicles such as plasmids, yeast, and bacterial artificial chromosomes.

In some aspects, the target nucleic acids comprise mRNAs or cDNAs. In certain embodiments, the target DNA is created using isolated transcripts from a biological sample. Isolated mRNA may be reverse transcribed into cDNAs using conventional techniques, again as described in *Genome Analysis: A Laboratory Manual Series* (Vols. I-IV) or *Molecular Cloning: A Laboratory Manual.*

Target nucleic acids may be single stranded or double stranded, as specified, or contain portions of both double stranded or single stranded sequence. Depending on the application, the nucleic acids may be DNA (including genomic and cDNA), RNA (including mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

In some embodiments the target nucleic acids are genomic DNA, in many embodiments mammalian genomic DNA and in particular human genomic DNA. In some cases, the genomic DNA may be obtained from normal somatic tissue, germinal tissue, or in some cases from diseased tissue, such as tumor tissue. In many embodiments, as outlined herein, a number of genome equivalents are used, generally from 1 to 30, with from 5 to 20 being useful in many embodiments. Many embodiments utilize 10 genome equivalents. Genome equivalents can comprise complete genomes from one or more cells or can comprise an amount of DNA that covers the genome of one or more cells (i.e., a single diploid cell has 2 genome equivalents of DNA). In some embodiments, at least two genome equivalents are used in methods of the invention in order to fully cover a diploid genome.

In an exemplary embodiment, genomic DNA is isolated from a target organism. By "target organism" is meant an organism of interest and as will be appreciated, this term encompasses any organism from which nucleic acids can be obtained, particularly from mammals, including humans, although in some embodiments, the target organism is a pathogen (for example for the detection of bacterial or viral infections). Methods of obtaining nucleic acids from target organisms are well known in the art. Samples comprising genomic DNA of humans find use in many aspects and embodiments of the present invention. In some aspects such as whole genome sequencing, about 1 to about 100 or more genome equivalents of DNA are preferably obtained to ensure that the population of target DNA fragments sufficiently covers the entire genome. The number of genome equivalents obtained may depend in part on the methods used to further prepare fragments of the genomic DNA for use in accordance with the present invention. For example, in the long fragment read methods described further below, about 1 to about 50 genome equivalents are generally utilized. In further embodiments, about 2-40, 3-30, 4-20, and 5-10 genome equivalents are used in methods of the invention. In still further embodiments, about 1, 2, 3, 4, 5, 6, 7, 8, 9, 10, 11, 12, 13, 14, 15, 16, 17, 18, 19 or 20 genome equivalents are used. For certain methods, about 1000 to about 100,000 genome equivalents are generally utilized. For some methods in which no amplification is used prior to fragmenting, about 100,000 to about 1,000,000 genome equivalents are used.

Libraries containing nucleic acid constructs or fragments generated from a population containing one or more genome equivalents will comprise target nucleic acids whose sequences, once identified and assembled, will provide most or all of the sequence of an entire genome.

Target nucleic acids are isolated using conventional techniques, for example as disclosed in Sambrook and Russell, *Molecular Cloning: A Laboratory Manual*, cited supra.

In some embodiments, target nucleic acids are treated to protect them during subsequent chemical or mechanical manipulations. For example, in certain embodiments, target nucleic acids are isolated in the presence of (or combined after isolation) with spermidine or polyvinylpyrrolidone 40 (PVP40) to protect them from shearing during mechanical manipulations such as pipetting. Such protection is of particular use for applications that utilize long nucleic acid fragments, such as the LFR methods described in further detail below. In some cases, it is advantageous to provide carrier DNA, e.g. unrelated circular synthetic double-stranded DNA, to be mixed and used with the sample DNA whenever only small amounts of sample DNA are available and there is danger of losses through nonspecific binding, e.g. to container walls and the like.

II.A. Fragmenting Target Nucleic Acids

In some aspects of the present invention, target nucleic acids are fragmented. Fragment sizes of the target nucleic acid can vary depending on the source target nucleic acid and the library construction methods used. For certain applications, longer fragments are of use in the invention. Such longer fragments may range in size from about 100,000 to about 1,000,000 nucleotides in length. In further embodiments, longer fragments are about 50,000; 100,000; 150,000; 200,000; 250,000; 300,000; 350,000; 400,000; 450,000; 500,000; 700,000; 900,000; 1,000,000; 1,500,000 nucleotides in length. In yet further embodiments, longer fragments range from about 150,000-950,000; 200,000-900,000; 250,000-850,000; 300,000-800,000; 350,000-750,000; 400,000-700,000; 450,000-650,000; and 500,000-600,000 nucleotides in length. For certain applications, fragments in the range of from about 50 to about 600 nucleotides in length are used in methods of the present invention. In further embodiments, these fragments are about 100, 200, 300, 400, 500, 600, 700, 800, 900, 1000, 1200, 1400, 1600, 1800, and 2000 nucleotides in length. In yet further embodiments, the fragments are 10-100, 50-100, 50-300, 100-200, 200-300, 50-400, 100-400, 200-400, 300-400, 400-500, 400-600, 500-600, 50-1000, 100-1000, 200-1000, 300-1000, 400-1000, 500-1000, 600-1000, 700-1000, 700-900, 700-800, 800-1000, 900-1000, 1500-2000, 1750-2000, and 50-2000 nucleotides in length.

Many mechanical and enzymatic fragmentation methods are well known in the art. In many embodiments, shear forces created during lysis and extraction will mechanically generate fragments in the desired range. Further mechanical fragmentation methods include sonication and nebulization. Mechanical fragmentation methods have the advantage of producing fragments of a particular size range in a predictable manner. However, mechanical fragmentation approaches typically require large (>2 μg) or volumes (>200 μL) of input nucleic acid. Thus, mechanical fragmentation approaches are only used in single sample processing.

Enzymatic fragmentation methods can also be used to generate nucleic acid fragments, particularly shorter fragments of 1-5 kb in size. Enzymatic fragmentation methods include the use of endonucleases. Enzymatic methods can be used with modest quantities and volumes of nucleic acids and are more amenable than mechanical fragmentation methods to multi-sample processing. However, enzymatic fragmentation methods are inherently prone to variability in the degree of fragmentation, because to achieve consistent fragment size distributions in such methods requires extremely careful control of enzyme activity, substrate amounts and concentrations, and digestion time.

In some embodiments, fragments of a particular size or in a particular range of sizes are isolated. Such methods are well known in the art. For example, gel fractionation can be used to produce a population of fragments of a particular size within a range of basepairs, for example for 500 base pairs±50 base pairs.

In some cases, particularly when it is desired to isolate long fragments (such as fragments from about 150 to about 750 kilobases in length), the present invention provides methods in which cells are lysed and the intact nucleic are pelleted with a gentle centrifugation step. The nucleic acid, usually genomic DNA, is released through enzymatic digestion, using for example proteinase K and RNase digestion over several hours. The resultant material is then dialyzed overnight or diluted directly to lower the concentration of remaining cellular waste. Since such methods of isolating the nucleic acid does not involve many disruptive processes (such as ethanol precipitation, centrifugation, and vortexing), the genomic nucleic acid remains largely intact, yielding a majority of fragments in excess of 100 kilobases.

II.A.1. CoRE Fragmentation

As discussed above, methods of fragmentation for use in the present invention include both mechanical and enzymatic fragmentation methods, as well as combinations of enzymatic and fragmentation methods. In one aspect, the present invention provides a method of fragmentation referred to herein as Controlled Random Enzymatic (CoRE) fragmentation. The CoRE fragmentation methods described herein can be used alone or in combination with other mechanical and enzymatic fragmentation methods known in the art.

In general, the CoRE fragmentation method involves replacing a number of nucleotides in target nucleic acids with nucleotide analogs. The nucleic acids containing the nucleotide analogs are then treated enzymatically or chemically to produce gapped nucleic acids. In certain embodiments, the enzymatic/chemical treatment excises the nucleotide analogs from the nucleic acids to form gapped nucleic acids. In certain embodiments, the enzymatic/chemical treatment produces a nick either immediately 3' or 5' to the nucleotide analogs to form the gapped nucleic acids. "Gapped nucleic acids" are generally double stranded nucleic acids containing nicks or gaps of a single nucleotide or multiple nucleotides in at least one strand.

Further enzymatic treatment of the gapped nucleic acids translates those gaps along the nucleic acid until gaps on opposite strands converge, resulting in blunt-ended nucleic acid fragments. Fragments produced in accordance with the present invention can be reproducibly controlled for length, bias and coverage. CoRE fragmentation has the advantages of enzymatic fragmentation (such as the ability to use low amounts and/or volumes of DNA) without many of its drawbacks (including sensitivity to variation in substrate or enzyme concentration and sensitivity to digestion time).

In further embodiments, nucleotide analogs are introduced into nucleic acids by amplifying the nucleic acids in the presence of dNTPs that include a predetermined ratio of nucleotide analogs to naturally occurring nucleotides. Amplification with this mixed population of nucleotides and nucleotide analogs results in amplicons in which a number of the naturally occurring nucleotides are replaced by a nucleotide analog. The number of nucleotides replaced by the analogs are controlled by controlling the predetermined ratio of analog to naturally occurring nucleotides in the dNTPs used in the amplification process. This "predetermined ratio" is the proportion of analog to natural nucleotide that is needed to produce fragments of the desired length. For example, if the starting nucleic acids are about 100,000 bases in length, the predetermined ratio of analog to nucleotide ratio can be adjusted to replace the desired number of nucleotides to eventually produce (in a non-limiting example) fragments of 10,000 bases in length (after treatment to produce gapped nucleic acids and then further treatment to produce double stranded fragments).

The number of nucleotides that are replaced in the amplicons by nucleotide analogs is controlled by manipulating the ratio of nucleotide analogs to naturally occurring nucleotides in the population of dNTPs used in the amplification process. In some embodiments, the population of dNTPs used in the amplification process to produce amplicons with nucleotides replaced by nucleotide analogs comprises about 0.05% to about 30% nucleotide analogs. In further embodiments, the population of dNTPs comprises about 0.1%-0.5%, 0.5%-0.7%, 1%-25%, 5%-20%, 10%-15% nucleotide analogs. In still further embodiments, the population of dNTPs comprises at least about 0.5%, 0.75%, 1%, 2%, 3%, 4%, 5%, 6%, 7%, 8%, 9%, 10%, 11%, 12%, 13%, 14%, 15% nucleotide analogs.

In some embodiments, about 0.01-5% of one or more species of nucleotides (A, C, G and/or T) are replaced by a nucleotide analog in accordance with the methods described herein. In further embodiments, about 0.05%-4%, 0.1%-3%, 0.2%-2%, 0.3%-1%, 0.4%-0.9%, 0.5%-0.8%, and 0.6%-0.7% of one or more species of nucleotides are replaced by a nucleotide analog in accordance with the above-described methods. In still further embodiments, at least about 0.1%, 0.2%, 0.25%, 0.3%, 0.4%, 0.5%, 0.6%, 0.7%, 0.75%, 0.8%, 0.9%, 1%, 2%, 3%, 4%, and 5% of one or more species of nucleotides are replaced by a nucleotide analog in accordance with the above-described methods.

After the nucleic acids are amplified in the presence of dNTPs containing a predetermined ratio of nucleotide analogs, the resultant amplicons have some naturally occurring nucleotides replaced by nucleotide analogs. The amplicons are then treated chemically or with one or more enzymes to either remove the nucleotide analogs or to produce a nick in the amplicon either 5' or 3' to the nucleotide analog to produce gapped nucleic acids. The gapped nucleic acids are then treated with an enzyme, generally a polymerase, to translate the gaps along the length of the nucleic acids until gaps on opposite strands converge. This results in a population of blunt-ended double stranded fragments.

In some embodiments, the present invention provides CoRE methods in which thymines are replaced by uracils or deoxyuracils, the target nucleic acids are amplified using a population of dNTPs that contains a predetermined ratio of dUTPs to dTTPs. As discussed above, the number of thymines that are replaced (and thus the length of the resultant fragments) can be controlled by manipulating the ratio of dUTPs to dTTPs—for example, a higher proportion of dUTPs in comparison to dTTPs will result in a greater number of thymines in the target nucleic acid substituted with uracil. The subsequent treatment to remove the dUTPs (or create nicks either 3' or 5' of the dUTPs) will then result in shorter fragments, because the substitutions will have occurred with greater frequency along the nucleic acid. Similarly, CoRE methods that replace cytosines with 5-methyl cytosines or that replace adenines with inosine would utilize populations of dNTPs doped with a predetermined proportion of 5-methyl cytosines or inosines. As will be appreciated, CoRE methods in accordance with the present invention can utilize any combination of deoxyuracils, 5-methyl cytosines, and inosines to replace multiple species of nucleotides along the nucleic acid with analogs.

In further embodiments, a dNTP population comprising 4% dUTP with respect to dTTP is used to amplify nucleic acids to produce amplicons in which a proportion of the thymines are replaced with deoxyuracil. Such a concentration of dUTP will generally result in an incorporation of approximately 0.05%-0.1% of the thymines in the resultant amplicons being replaced with deoxyuracil. As discussed above, the amount of deoxyuracil incorporated into the amplicons can be tuned by the proportion of dUTP to dTTP included in the dNTPs used to amplify the nucleic acids. In certain embodiments, the population of dUTPs with respect to dTTPs comprises about 0.1%-0.5%, 0.5%-0.8%, 1%-25%, 5%-20%, 10%-15% dUTPs. In still further embodiments, the population of dNTPs comprises at least about 0.5%, 0.75% 1%, 2%, 3%, 4%, 5%, 6%, 7%, 8%, 9%, 10%, 11%, 12%, 13%, 14%, 15% dUTPs.

In some embodiments, a combination of nucleotide analogs is used in the amplification step of the CoRE method, such that two different species of nucleotides are replaced by nucleotide analogs in the resultant amplicons. For example, in some embodiments, both thymines and cytosines are replaced with nucleotide analogs. In further embodiments, thymines are replaced by deoxyuracils and cytosines are replaced by 5-methyl cytosines. As discussed above, a range of proportions of the analogs to the naturally occurring nucleotides can be used to control the size of the fragments that result when the amplicons are treated to form gapped nucleic acids and then the gapped nucleic acids are treated to form double stranded fragments. In certain embodiments, the same proportion of dUTP and 5-methyl cytosine is used with respect to the naturally occurring nucleotides. In other words, a dNTP population comprising about 0.05%-25% dUTP with respect to dTTP and 0.05%-25% 5-methyl cytosine with respect to cytosine is used to create amplicons in which a proportion of the thymines and cytosines are replaced by the corresponding analogs. In still further embodiments, the dNTP population comprises about 4-5% 5-methyl cytosine and 0.75-1% dUTP. In yet further embodiments, the population of dUTPs with respect to dTTPs and the population of 5-methyl cytosine with respect to cytosine comprises about 0.1%-0.5%, 0.5%-0.8%, 1%-25%, 5%-20%, 10%-15% dUTPs. In still further embodiments, the population of dUTPs with respect to dTTPs and the population of 5-methyl cytosine with respect to cytosine comprises at least about 0.5%, 0.75% 1%, 2%, 3%, 4%, 5%, 6%, 7%, 8%, 9%, 10%, 11%, 12%, 13%, 14%, 15% dUTPs. As will be appreciated, the same proportion or different proportions of dUTP to dTTP as compared to the proportions of 5-methyl cytosine to cytosine can be used in this embodiment of the invention. If different proportions are used when different nucleotide analogs are used, then any combination of the above listed proportions can be used to generate amplicons in which at least a portion of the naturally occurring nucleotides are replaced by nucleotide analogs.

An exemplary CoRE fragmentation method is illustrated in FIG. 1. First, a nucleic acid 101 is subjected to an enzyme catalyzed multiple displacement amplification (MDA) in the presence of dNTPs doped with dUTP or UTP in a defined ration to the dTTP. This results in the substitution of deoxyuracil ("dU") or uracil ("U") at defined and controllable proportions of the T positions in both strands of the amplification product (103). The U moieties are then excised (104), usually through use of one or more enzymes, including without limitation UDG, EndoIV, EndoVIII, and T4PNK, to create single base gaps (also referred to herein as "nicks") with functional 5' phosphate and 3' hydroxyl ends (105). The single base gaps will be created at an average spacing defined by the frequency of U of dU in the MDA product. Treatment of the gapped nucleic acid (105) with a polymerase with exonuclease activity results in "translation" or "translocation" of the nicks or gaps along the length of the nucleic acid until nicks on opposite strands converge, thereby creating double strand breaks, resulting a relatively population of double stranded fragments of a relatively homogenous size (107). The exonuclease activity of the polymerase (such as Taq polymerase) will excise the short DNA strand that abuts the nick while the polymerase activity will "fill in" the nick and subsequent nucleotides in that strand (essentially, the Taq moves along the strand, excising bases using the exonuclease activity and adding the same bases, with the result being that the nick or gap is translocated along the strand until the enzyme reaches the end). The size distribution of the double stranded fragments (107) is a result of the ratio of dTTP to dUTP or UTP used in the MDA reaction, rather than by the duration or degree of enzymatic treatment. That is, the higher the amount of dUTP, the shorter the resulting fragments. Thus, CoRE fragmentation methods produce high degrees of fragmentation reproducibility as compared to other enzymatic or mechanical fragmentation methods.

As will be appreciated, in the above exemplary embodiment and in any embodiment of the CoRE method, a number of amplification methods can be used in the step to replace nucleotides with modified nucleotides or nucleotide analogs. Such amplification methods are described in further detail below and can include without limitation polymerase chain reaction (PCR), multiple displacement amplification (MDA), rolling circle amplification (RCA) (for circularized fragments), as well as any other applicable amplification methods known in the art. As will also be discussed in further detail below, in certain embodiments the methods and compositions of the amplification reactions used in this step of the CoRE method can also reduce bias and increase coverage of the resultant fragments.

Figure 2:
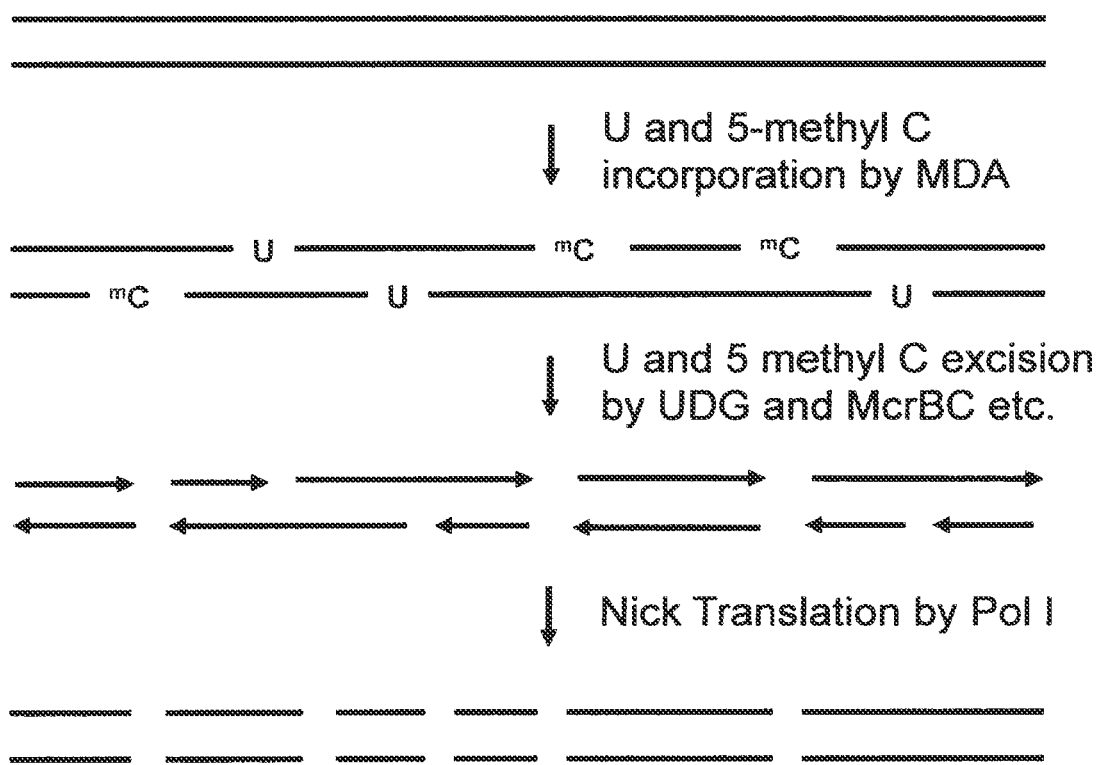
FIG. 2 a schematic illustration of an embodiment of a method for fragmenting nucleic acids.

A further exemplary embodiment of a CoRE fragmentation method is illustrated in FIG. 2. In this exemplary embodiment, two different nucleotides are replaced by nucleotide analogs: thymines are replaced by uracil and cytosines are replaced by 5-methyl cytosine. As illustrated in FIG. 2, a nucleic acid 201 is subjected to an enzyme catalyzed multiple displacement amplification (MDA) in the presence of dNTPs doped with dUTP or UTP in a defined ratio to dTTP. The dNTPs are also doped with 5-methyl-dCTP at a defined proportion of the dCTP. This results in the substitution of dU and 5-methyl dC at a defined (and controllable) proportion of T and C positions in both strands of the DNA product (203). Next, the U and regions near 5-methyl C moieties are excised—in one non-limiting example, the excision (204) is accomplished by a combination of McrBC, UDG and EndoIV or EndoVIII and T4PNK, to create single base gaps with functional 5'PO$_4$ and 3'OH ends (or in the case of McrBC double strand cuts), at a mean spacing defined by the frequency of uracil and 5-methyl cytosine in the MDA product (203). The single base gaps will be created at an average spacing defined by the frequency of U of dU in the MDA product. Treatment of the gapped nucleic acid (205) with a polymerase such as Taq polymerase or *E. coli* DNA pol I (206) results in translation of the gaps until gaps on opposite strands converge, thereby creating double strand breaks (207). Treatment with *E. coli* DNA pol I also fills in or removes any overhangs created from double strand excision by McrBC. As in the method illustrated in FIG. 1, this exemplary embodiment of CoRE results in double stranded fragments whose length can be reproducibly controlled by altering the proportion of nucleotide analogs included in the population of dNTPs during amplification. The introduction of the additional nucleotide analog (5-methyl cytosine) in this embodiment of CoRE improves fragmenting in GC-rich regions of the genome as compared to methods in which only a single species of nucleotide analog is introduced into the target nucleic acid. For example, the embodiment of CoRE illustrated in FIG. 1 can show a bias towards higher fragmenting in AT rich regions of the genome. Embodiments of CoRE in which more than one nucleotide analog is introduced, such as the embodiment illustrated in FIG. 2, reduce coverage biases that can be observed in embodiments in which only a single species of nucleotide analog is used or in other enzymatic and/or mechanical fragmentation methods.

As will be appreciated, any nucleotide analogs and modified nucleotides known in the art can be used to produce nucleic acid fragments in accordance with the CoRE methods described above. In addition to the uracil and 5-methyl cytosine nucleotide analogs discussed above, further exemplary modified nucleotides and nucleotide analogs that can be of use in the CoRE methods of the present invention include without limitation peptide nucleotides, modified peptide nucleotides, modified phosphate-sugar backbone nucleotides, N-7-methylguanine, deoxyuridine and deoxy-3'-methyladenosine.

II.B. Further Enzymatic and Chemical Treatment of Fragments

In some embodiments, after fragmenting, target nucleic acids are further modified to prepare them for later applications, such as in the preparation of nucleic acid constructs as discussed in further detail below. Such modifications can be necessary because the process of fragmentation may result in target nucleic acids with termini that are not amenable to certain reactions, particularly the use of enzymes such as ligases and polymerases. As for all the steps outlined herein, this step of further modification is optional and can be combined with any other step in any order.

In an exemplary embodiment, after fragmenting, target nucleic acids frequently have a combination of blunt and overhang ends as well as combinations of phosphate and hydroxyl chemistries at the termini. Such fragments can be treated with several enzymes to create blunt ends with particular chemistries. In one embodiment, a polymerase and dNTPs is used to fill in any 5' single strands of an overhang to create a blunt end. Polymerase with 3' exonuclease activity (generally but not always the same enzyme as the 5' active one, such as T4 polymerase) is used to remove 3' overhangs. Suitable polymerases include, but are not limited to, T4 polymerase, Taq polymerases, E. coli DNA Polymerase 1, Klenow fragment, reverse transcriptases, φ29 related polymerases including wild type φ29 polymerase and derivatives of such polymerases, T7 DNA Polymerase, T5 DNA Polymerase, RNA polymerases. These techniques can be used to generate blunt ends, which are useful in a variety of applications.

In further optional embodiments, the chemistry at the termini is altered to avoid target nucleic acids from ligating to each other. For example, in addition to a polymerase, a protein kinase can also be used in the process of creating blunt ends by utilizing its 3' phosphatase activity to convert 3' phosphate groups to hydroxyl groups. Such kinases can include without limitation commercially available kinases such as T4 kinase, as well as kinases that are not commercially available but have the desired activity.

Similarly, a phosphatase can be used to convert terminal phosphate groups to hydroxyl groups. Suitable phosphatases include, but are not limited to, Alkaline Phosphatase (including Calf Intestinal (CIP)), Antarctic Phosphatase, Apyrase, Pyrophosphatase, Inorganic (yeast) thermostable inorganic pyrophosphatase, and the like, which are known in the art and commercially available, for example from New England Biolabs.

As will be appreciated by those in the art, and as for all the steps outlined herein, any combination of these steps and enzymes may be used. For example, some enzymatic fragmentation techniques, such as the use of restriction endonucleases, may render one or more of these enzymatic "end repair" steps superfluous.

The modifications described above can prevent the creation of nucleic acid templates containing different fragments ligated in an unknown conformation, thus reducing and/or removing the errors in sequence identification and assembly that can result from templates generated from such undesirable configurations.

In further embodiments, DNA fragments are denatured after fragmentation to produce single stranded fragments.

II.C. Amplification

In one embodiment, after fragmenting, (and in fact before or after any step outlined herein) an amplification step can be applied to the population of fragmented nucleic acids to ensure that a large enough concentration of all the fragments is available for subsequent applications. Such amplification methods are well known in the art and include without limitation: polymerase chain reaction (PCR), ligation chain reaction (sometimes referred to as oligonucleotide ligase amplification OLA), cycling probe technology (CPT), multiple displacement amplification (MDA), transcription mediated amplification (TMA), nucleic acid sequence based amplification (NASBA), rolling circle amplification (RCA) (for circularized fragments), and invasive cleavage technology. As used herein, MDA encompasses and is used interchangeably with the term "strand displacement amplification (SDA)".

II.C.1. Multiple Displacement Amplification (MDA)

In one aspect of the invention, MDA is used to amplify fragments or nucleic acid constructs generated according to methods described herein. MDA generally involves bringing into contact at least one primer, DNA polymerase, and a target sample, and incubating the target sample under conditions that promote replication of the target sequence. If one primer is used (e.g. a "Watson" primer, complementary to the "Crick" target), multiple copies of one strand (e.g. "Crick") of the double stranded target are generated; if a second primer (e.g. "Crick"), which is complementary to the second strand (e.g. "Watson") of the target, then amplification of both strands occurs. Replication of the target sequence results in replicated strands such that, during replication, the replicated strands are displaced from the target sequence by strand displacement replication of another replicated strand. In some embodiments of MDA, a random set of primers is used to randomly prime a sample of genomic nucleic acid (or another sample of nucleic acid of high complexity). By choosing a sufficiently large set of primers of random or partially random sequence, the primers in the set will be collectively, and randomly, complementary to nucleic acid sequences distributed throughout nucleic acids in the sample. Amplification proceeds by replication with a highly processive polymerase initiating at each primer and continuing until spontaneous termination. A key feature of this method is the displacement of intervening primers during replication by the polymerase. In this way, multiple overlapping copies of the entire genome can be synthesized in a short time. General methods for MDA are known in the art and disclosed for example in U.S. Pat. No. 7,074,600, which is hereby incorporated by reference in its entirety for all purposes and in particular for all teachings related to MDA.

One weakness of conventional MDA methods, particularly when used for whole genome amplification, is that a bias is often introduced into the amplification products. In many cases, this bias is a GC bias in which a greater number of copies are generated of regions of the genomic sequence that are GC-rich. In some cases, an AT bias is seen in which AT-rich regions of the genome are amplified in greater quantities than other sequences. The present invention provides compositions and methods that ameliorate or prevent bias that can result in amplification reactions, particularly MDA reactions.

Figure 3:
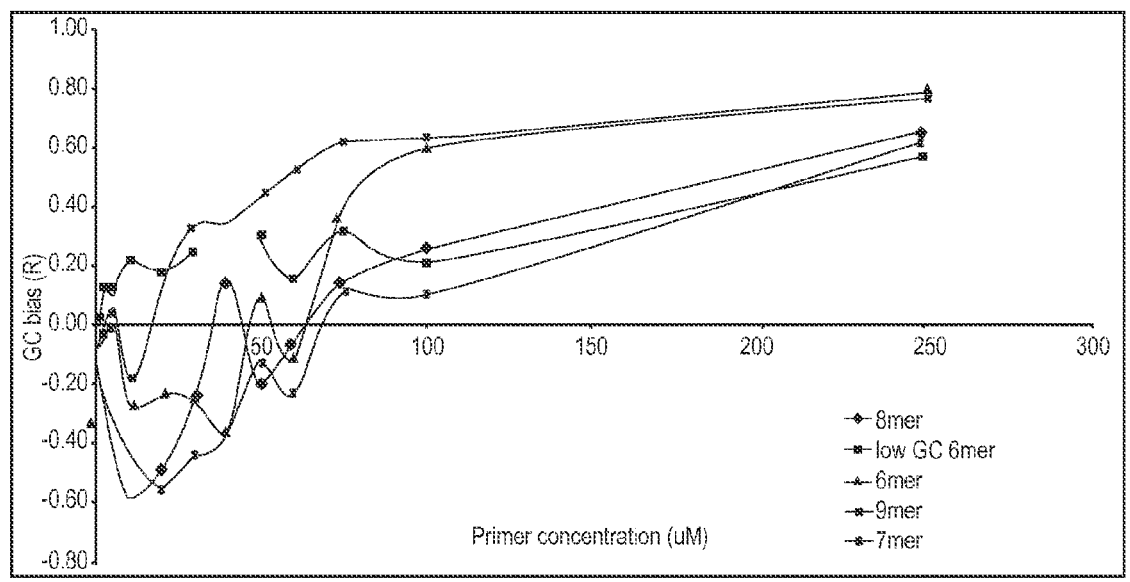
FIG. 3 is a graph of the effect of primer concentration on GC bias in MDA reactions.

In some embodiments, rather than the random hexamers conventionally used in MDA reactions, random 8-mer primers are used to reduce amplification bias in the population of fragments. In addition, the primers used in MDA reactions can be designed to have a lower GC content, which also has the effect of lowering the GC bias. For example, FIG. 3 shows the effect of primer concentration on GC bias. In FIG. 3, points above the x-axis represent bias towards AT rich sequences and points below the x-axis show bias toward GC rich sequences. Low GC content 6-mers (squares in FIG. 3) show relatively low bias across a wide range of concentrations in MDA reactions conducted at 30° C. for 90 minutes.

In further embodiments, certain enzymes can be added to the MDA reaction to reduce the bias of the amplification. For example, low concentrations of non-processive 5' exonucleases can reduce GC-bias.

In still further embodiments, additives are included in the MDA reactions to prevent or ameliorate GC bias. Such additives include without limitation single-stranded binding proteins, betaine, DMSO, trehalose, glycerol.

FIG. 4 demonstrates that DMSO reduces the GC bias caused in MDA reactions by higher concentrations of primers (see FIG. 4B). As will be appreciate, a wide range of concentrations of DMSO can be used in accordance with the invention. In exemplary non-limiting embodiments, about 0.5% to about 10% DMSO are used as an additive in MDA reactions of the invention. In still further embodiments, about 1%, 2%, 3%, 4%, 5%, 6%, 7%, 8%, 10% DMSO is used in methods of the invention. In yet further embodiments, about 1%-2%, 2%-4%, 5%-8%, and 3%-6% DMSO is used.

Figure 5A:
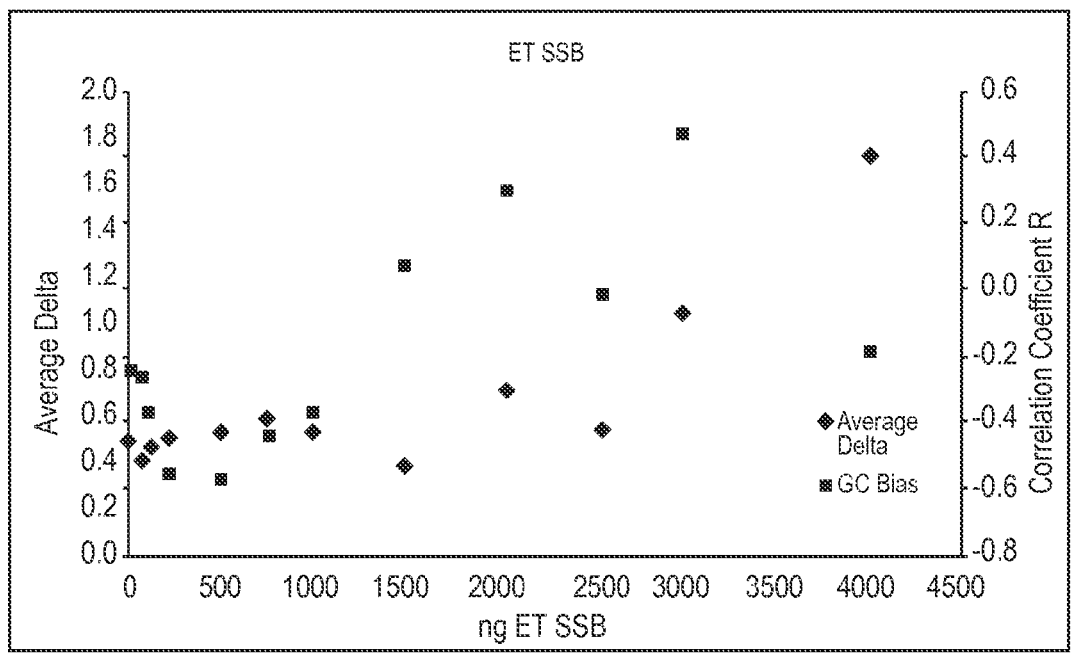
FIG. 5 shows the effect of SSB (FIG. 5A) and betaine (FIG. 5B) on GC bias in MDA reactions.
Figure 5B:
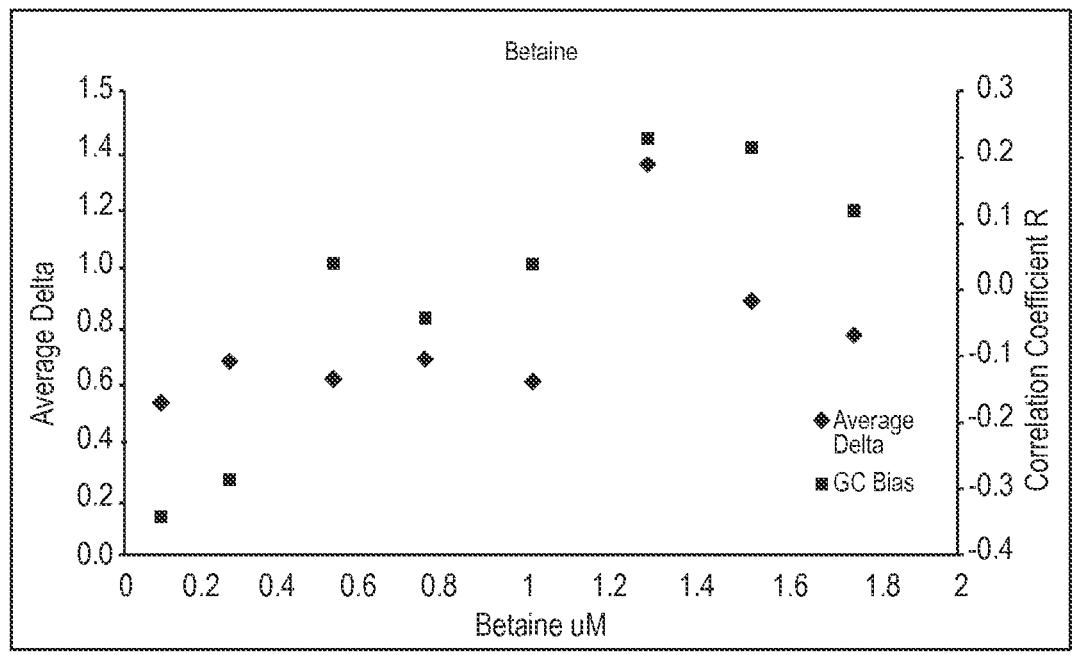

FIG. 5 shows that both SSB (FIG. 5A) and betaine (FIG. 5B) can reduce GC bias across a wide range of concentrations. The experiments for FIGS. 4 and 5 were conducted at 30° C. for 90 minutes. As will be appreciated, a wide range of concentrations of SSB and betaine can be used in accordance with the invention. In some embodiments, about 1 to about 5000 ng of SSB are used in accordance with the invention. In further embodiments, about 1-10, 20-4000, 30-3000, 40-2000, 50-1000, 60-500, 70-400, 80-300, 90-200, 10-100, 15-90, 20-80, 30-70, 40-60 ng of SSB are used. In some embodiments, about 0.1 to about 5 µM betaine is used in accordance with the present invention. In further embodiments, about 0.2-4, 0.5-3, and 1-2 µM betaine is used. In still further embodiments, about 0.2, 0.3, 0.4, 0.5, 0.6, 0.7, 0.8, 0.9, 1.0, 1.1, 1.2, 1.3, 1.4 and 1.5 µM betaine is used.

In certain embodiments, nucleic acid fragments are combined with spermidine prior to amplification with MDA in order to protect from shearing during pipetting or other physical manipulations. However, high concentrations of spermidine can interfere with MDA. In certain embodiments, prior to MDA, nucleic acid fragments are denatured in the presence of a high concentration (~100 mM) spermidine. The mixture is then diluted to result in a 1 mM final concentration of spermidine and then amplified using MDA or other amplification methods known in the art.

As will be appreciated, methods for preventing or ameliorating bias in MDA reactions can be used with any of the methods for fragmenting nucleic acids or generating nucleic acid constructs for production of DNA nanoballs where those methods include one or more amplification steps.

II.D. Preparation of Circular Constructs

In one aspect, nucleic acid fragments produced as described above can be used to produce circular nucleic acid template constructs. These circular constructs can serve as templates for the generation of DNA nanoballs, which are described in further detail below. The present invention provides circular nucleic acid template constructs comprising target nucleic acids and multiple interspersed adaptors. The nucleic acid template constructs are assembled by inserting adaptors molecules at a multiplicity of sites throughout each target nucleic acid fragment. The interspersed adaptors permit acquisition of sequence information from multiple sites in the target nucleic acid consecutively or simultaneously.

Although the embodiments of the invention described herein are generally described in terms of circular nucleic acid template constructs, it will be appreciated that nucleic acid template constructs may also be linear. Furthermore, nucleic acid template constructs of the invention may be single- or double-stranded, with the latter being preferred in some embodiments. As used herein, unless otherwise noted, the term "target nucleic acid" and "target nucleic acid fragments" and all grammatical equivalents are used interchangeably.

The nucleic acid templates (also referred to herein as "nucleic acid constructs" and "library constructs") of the invention comprise target nucleic acids and adaptors. As used herein, the term "adaptor" refers to an oligonucleotide of known sequence. Adaptors of use in the present invention may include a number of elements. The types and numbers of elements (also referred to herein as "features") included in an adaptor will depend on the intended use of the adaptor. Adaptors of use in the present invention will generally include without limitation sites for restriction endonuclease recognition and/or cutting, particularly Type IIs recognition sites that allow for endonuclease binding at a recognition site within the adaptor and cutting outside the adaptor as described below, sites for primer binding (for amplifying the nucleic acid constructs) or anchor primer (sometimes also referred to herein as "anchor probes") binding (for sequencing the target nucleic acids in the nucleic acid constructs), nickase sites, and the like. In some embodiments, adaptors will comprise a single recognition site for a restriction endonuclease, whereas in other embodiments, adaptors will comprise two or more recognition sites for one or more restriction endonucleases. As outlined herein, the recognition sites are frequently (but not exclusively) found at the termini of the adaptors, to allow cleavage of the double stranded constructs at the farthest possible position from the end of the adaptor.

In some embodiments, adaptors will not include any recognition sites for restriction endonucleases.

In some embodiments, adaptors of the invention have a length of about 10 to about 250 nucleotides, depending on the number and size of the features included in the adaptors. In certain embodiments, adaptors of the invention have a length of about 50 nucleotides. In further embodiments, adaptors of use in the present invention have a length of about 20 to about 225, about 30 to about 200, about 40 to about 175, about 50 to about 150, about 60 to about 125, about 70 to about 100, and about 80 to about 90 nucleotides.

In further embodiments, adaptors may optionally include elements such that they can be ligated to a target nucleic acid as two "arms". One or both of these arms may comprise an intact recognition site for a restriction endonuclease, or both arms may comprise part of a recognition site for a restriction endonuclease. In the latter case, circularization of a construct comprising a target nucleic acid bounded at each termini by an adaptor arm will reconstitute the entire recognition site.

In still further embodiments, adaptors of use in the invention will comprise different anchor binding sites at their 5' and the 3' ends of the adaptor. As described further herein, such anchor binding sites can be used in sequencing applications, including the combinatorial probe anchor ligation (cPAL) method of sequencing, described herein and in U.S. Application Nos. 60/992,485; 61/026,337; 61/035,914; 61/061,134; 61/116,193; 61/102,586; Ser. No. 12/265,593; and Ser. Nos. 12/266,385 11/938,106; 11/938,096; 11/982, 467; 11/981,804; 11/981,797; 11/981,793; 11/981,767; 11/981,761; 11/981,730; 11/981,685; 11/981,661; 11/981, 607; 11/981,605; 11/927,388; 11/927,356; 11/679,124; 11/541,225; 10/547,214; and 11/451,691, all of which are hereby incorporated by reference in their entirety, and particularly for disclosure relating to sequencing by ligation.

In one aspect, adaptors of the invention are interspersed adaptors. By "interspersed adaptors" is meant herein oligonucleotides that are inserted at spaced locations within the interior region of a target nucleic acid. In one aspect, "interior" in reference to a target nucleic acid means a site internal to a target nucleic acid prior to processing, such as circularization and cleavage, that may introduce sequence inversions, or like transformations, which disrupt the ordering of nucleotides within a target nucleic acid.

II.D.1. Overview of Template Construction Process

The nucleic acid template constructs of the invention contain multiple interspersed adaptors inserted into a target nucleic acid, and in a particular orientation. As discussed further herein, the target nucleic acids are produced from nucleic acids isolated from one or more cells, including one to several million cells. These nucleic acids are then fragmented using mechanical or enzymatic methods. In specific embodiments, nucleic acid fragments produced using CoRE methods described herein are used to produce nucleic acid template constructs of the invention.

The target nucleic acid that becomes part of a nucleic acid template construct of the invention may have interspersed adaptors inserted at intervals within a contiguous region of the target nucleic acids at predetermined positions. The intervals may or may not be equal. In some aspects, the accuracy of the spacing between interspersed adaptors may be known only to an accuracy of one to a few nucleotides. In other aspects, the spacing of the adaptors is known, and the orientation of each adaptor relative to other adaptors in the library constructs is known. That is, in many embodiments, the adaptors are inserted at known distances, such that the target sequence on one termini is contiguous in the naturally occurring genomic sequence with the target sequence on the other termini. For example, in the case of a Type IIs restriction endonuclease that cuts 16 bases from the recognition site, located 3 bases into the adaptor, the endonuclease cuts 13 bases from the end of the adaptor. Upon the insertion of a second adaptor, the target sequence "upstream" of the adaptor and the target sequence "downstream" of the adaptor are actually contiguous sequences in the original target sequence.

The present invention provides nucleic acid templates comprising a target nucleic acid containing one or more interspersed adaptors. In a further embodiment, nucleic acid templates formed from a plurality of genomic fragments can be used to create a library of nucleic acid templates. Such libraries of nucleic acid templates will in some embodiments encompass target nucleic acids that together encompass all or part of an entire genome. That is, by using a sufficient number of starting genomes (e.g. cells), combined with random fragmentation, the resulting target nucleic acids of a particular size that are used to create the circular templates of the invention sufficiently "cover" the genome, although as will be appreciated, on occasion, bias may be introduced inadvertently to prevent the entire genome from being represented.

The nucleic acid template constructs of the invention comprise multiple interspersed adaptors, and in some aspects, these interspersed adaptors comprise one or more recognition sites for restriction endonucleases. In a further aspect, the adaptors comprise recognition sites for nicking endonucleases, Type I endonucleases, Type II endonucleases, and/or Type III endonucleases such as EcoP1 and EcoP15). In further aspect, the adaptors comprise recognition sites for Type IIs endonucleases. Type-IIs and Type III endonucleases are generally commercially available and are well known in the art. Such endonucleases recognize specific sequences of nucleotide base pairs within a double stranded polynucleotide sequence. Upon recognizing that sequence, the Type IIs endonucleases will cleave the polynucleotide sequence, generally leaving an overhang of one strand of the sequence, or "sticky end." Type-IIs and Type III endonucleases generally cleave outside of their recognition sites; the distance may be anywhere from about 2 to 30 nucleotides away from the recognition site depending on the particular endonuclease. Some Type-IIs endonucleases are "exact cutters" that cut a known number of bases away from their recognition sites. In some embodiments, Type IIs endonucleases are used that are not "exact cutters" but rather cut within a particular range (e.g. 6 to 8 nucleotides). Generally, Type IIs restriction endonucleases of use in the present invention have cleavage sites that are separated from their recognition sites by at least six nucleotides (i.e. the number of nucleotides between the end of the recognition site and the closest cleavage point). Exemplary Type IIs restriction endonucleases include, but are not limited to, Eco57M I, Mme I, Acu I, Bpm I, BceA I, Bbv I, BciV I, BpuE I, BseM II, BseR I, Bsg I, BsmF I, BtgZ I, Eci I, Eco57M I, Fok I, Hga I, Hph I, Mbo II, Mnl I, SfaN I, TspDT I, TspDW I, Taq II, and the like. In some exemplary embodiments, the Type IIs restriction endonucleases used in the present invention are AcuI, which has a cut length of about 16 bases with a 2-base 3' overhang and the Type III endonuclease EcoP15, which has a cut length of about 25 bases with a 2-base 5' overhang. As will be discussed further below, the inclusion of a Type IIs and Type III sites in the adaptors of the nucleic acid template constructs of the invention is one tool for inserting multiple adaptors in a target nucleic acid at a defined location.

As will be appreciated, adaptors may also comprise other elements, including recognition sites for other (non-Type IIs) restriction endonucleases, primer binding sites for amplification as well as binding sites for probes used in sequencing reactions ("anchor probes"), described further herein. Adaptors of use in the invention may in addition contain palindromic sequences, which can serve to promote intramolecular binding once nucleic acid templates comprising such adaptors are used to generate concatemers, as is discussed in more detail below.

Control over the spacing and orientation of insertion of each subsequent adaptor provides a number of advantages over random insertion of interspersed adaptors. In particular, the methods described herein improve the efficiency of the adaptor insertion process, thus reducing the need to introduce amplification steps as each subsequent adaptor is inserted. In addition, controlling the spacing and orientation of each added adaptor ensures that the restriction endonuclease recognition sites that are generally included in each adaptor are positioned to allow subsequent cleavage and ligation steps to occur at the proper point in the nucleic acid construct, thus further increasing efficiency of the process by reducing or eliminating the formation of nucleic acid templates that have adaptors in the improper location or orientation. In addition, control over location and orientation of each subsequently added adaptor can be beneficial to certain uses of the resultant nucleic acid construct, because the adaptors serve a variety of functions in sequencing applications, including serving as a reference point of known sequence to aid in identifying the relative spatial location of bases identified at certain positions within the target nucleic acid. Such uses of adaptors in sequencing applications are described further herein.

The 5' and 3' ends of the double stranded fragments can optionally be adjusted, as described above. For example, many techniques used to fractionate nucleic acids result in a combination of lengths and chemistries on the termini of the fragments. For example, the termini may contain overlaps, and for many purposes, blunt ends of the double stranded fragments are preferred. This can be done using known techniques such as a polymerase and dNTPs. Similarly, the fractionation techniques may also result in a variety of termini, such as 3' and 5' hydroxyl groups and/or 3' and 5' phosphate groups. In some embodiments, as described below, it is desirable to enzymatically alter these termini. For example, to prevent the ligation of multiple fragments without the adaptors, it can be desirable to alter the chemistry of the termini such that the correct orientation of phosphate and hydroxyl groups is not present, thus preventing "polymerization" of the target sequences. The control over the chemistry of the termini can be provided using methods known in the art. For example, in some circumstances, the use of phosphatase eliminates all the phosphate groups, such that all ends contain hydroxyl groups. Each end can then be selectively altered to allow ligation between the desired components.

In addition, as needed, amplification can also optionally be conducted using a wide variety of known techniques to increase the number of genomic fragments for further manipulation, although in many embodiments, an amplification step is not needed at this step.

In some embodiments, if amplification is used to increase the number of fragments before or after any steps of constructing the nucleic acid template, that amplification is an MDA reaction using one or more of the additives described above to reduce bias that could otherwise result from the amplification.

Figure 6:
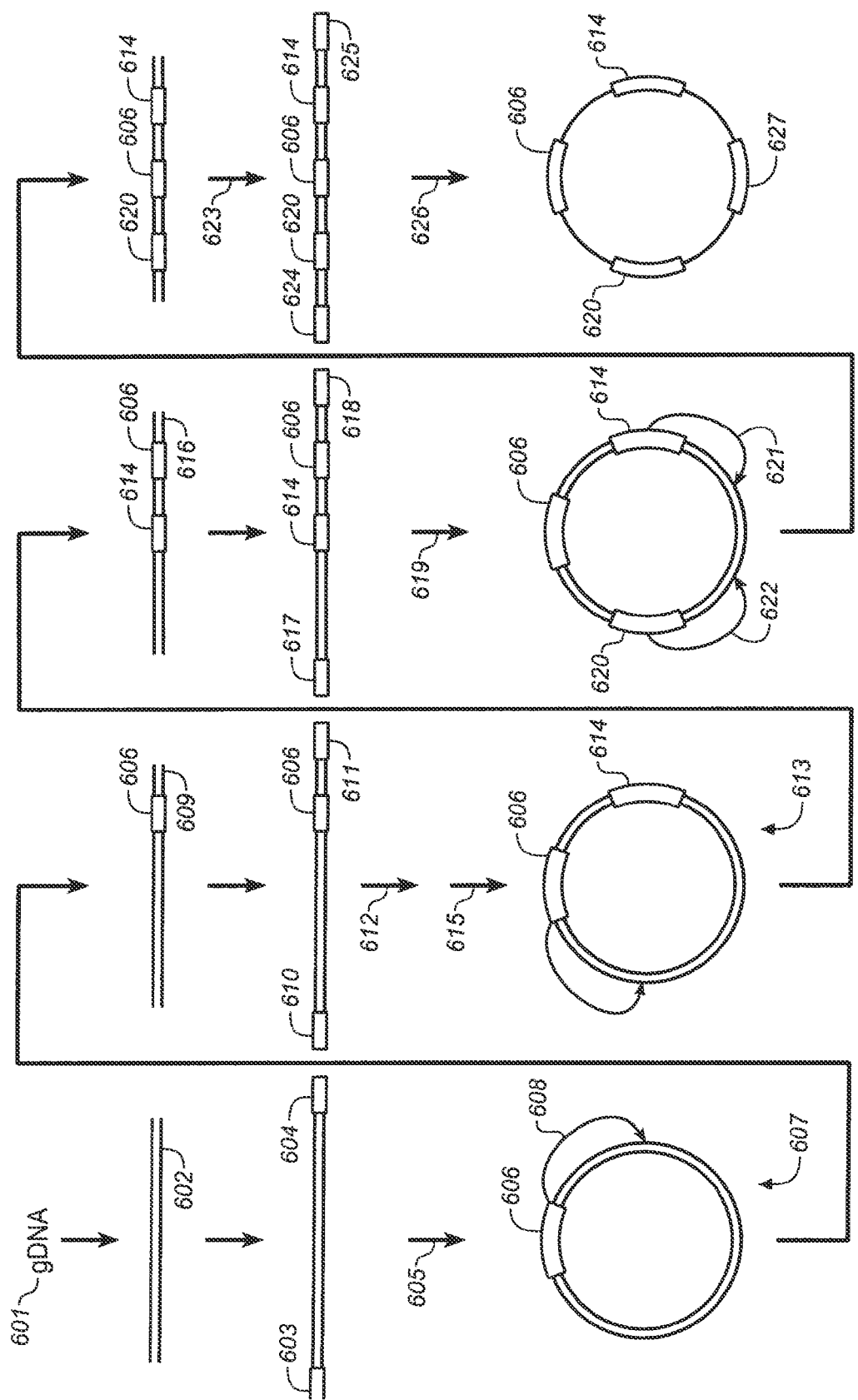
FIG. 6 is a schematic illustration of an embodiment of the invention for making circular nucleic acid templates comprising multiple adaptors.

After fractionation and optional termini adjustment, a set of adaptor "arms" are added to the termini of the genomic fragments. The two adaptor arms, when ligated together, form the first adaptor. For example, as depicted in FIG. 6, circularization (605) of a linear construct with an adaptor arm on each end of the construct ligates the two arms together to form the full adaptor (606) as well as the circular construct (607). Thus, a first adaptor arm (603) of a first adaptor is added to one terminus of the genomic fragment, and a second adaptor arm (604) of a first adaptor is added to the other terminus of the genomic fragment. Generally, and as more fully described below, either or both of the adaptor arms will include a recognition site for a Type IIs endonuclease, depending on the desired system. Alternatively, the adaptor arms can each contain a partial recognition site that is reconstituted upon ligation of the arms.

In order to ligate subsequent adaptors in a desired position and orientation for sequencing, the present invention provides a method in which a Type IIs restriction endonuclease binds to a recognition site within the first adaptor of a circular nucleic acid construct and then cleaves at a point outside the first adaptor and in the genomic fragment (also referred to herein as the "target nucleic acid"). A second adaptor can then be ligated into the point at which cleavage occurs (again, usually by adding two adaptor arms of the second adaptor). In order to cleave the target nucleic acid at a known point, it can be desirable to block any other recognition sites for that same enzyme that may randomly be encompassed in the target nucleic acid, such that the only point at which that restriction endonuclease can bind is within the first adaptor, thus avoiding undesired cleavage of the constructs. Generally, the recognition site in the first adaptor is first protected from inactivation, and then any other unprotected recognition sites in the construct are inactivated, generally through methylation. That is, methylated recognition sites will not bind the enzyme, and thus no cleavage will occur. Only the unmethylated recognition site within the adaptor will allow binding of the enzyme with subsequent cleaving.

One method of protecting the recognition site in the first adaptor from inactivation is to make the site single stranded, as the methylation enzyme will not bind to a single strand. Thus, one method of protecting the recognition site of the first adaptor is by amplifying the linear genomic fragments ligated to the two first adaptor arms using primers modified with uracil. The primers are complementary to the adaptor arms and are modified with uracil such that, upon amplification (generally using PCR), the resultant linear constructs contain uracil embedded in the recognition site of one of the first adaptor arms. Digestion of the uracil using known techniques renders that first adaptor arm (or whatever contains the uracil) single stranded. A sequence specific methylase is then applied to the linear constructs that will methylate all of the double-stranded recognition sites for the same endonuclease as that contained in the first adaptor. Such a sequence-specific methylase will not be able to methylate the single stranded recognition site in the first adaptor arm, and thus the recognition site in the first adaptor arm will be protected from inactivation by methylation. As described below, if a restriction site is methylated, it will not be cleaved by the restriction endonuclease enzyme.

Figure 7:
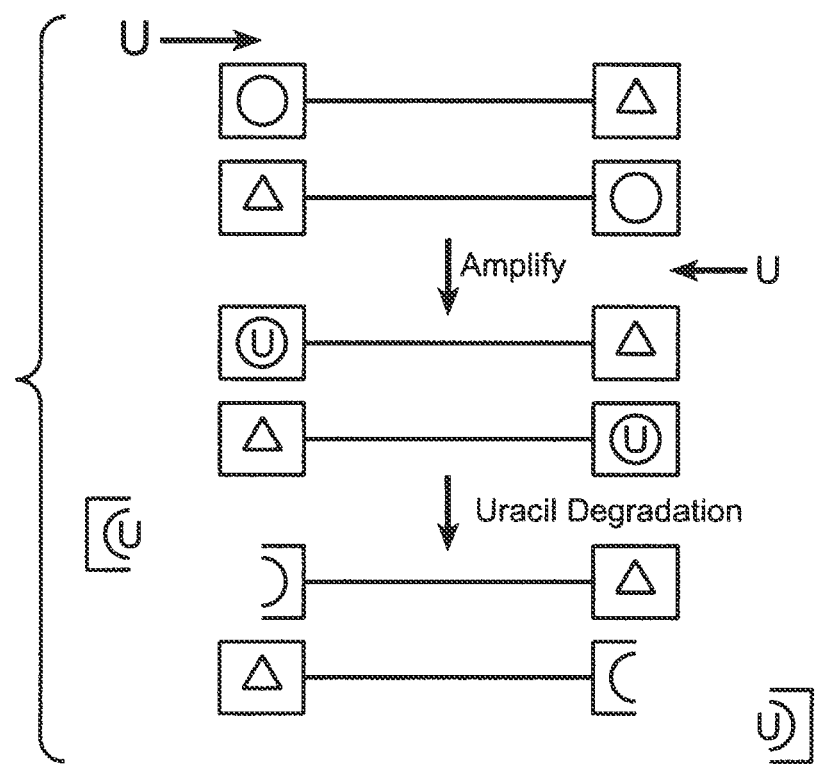
FIG. 7 is a schematic illustration of an embodiment of the invention for controlling the orientation of adaptors inserted into target nucleic acids.

In some cases, as more fully described below, a single adaptor may have two of the same recognition sites, to allow cleavage both "upstream" and "downstream" from the same adaptor. In this embodiment, as depicted in FIG. 7, the primers and uracil positions are chosen appropriately, such that either the "upstream" or "downstream" recognition site may be selectively protected from inactivation or inactivated. For example, in FIG. 7, the two different adaptor arms (represented as rectangles) each comprise a recognition site for a restriction endonuclease (represented by the circle in one adaptor arm and by a triangle in the other). If the adaptor arm with the recognition site represented by the circle needs to be protected using the above-described uracil degradation method, then the uracil-modified amplification primers are designed to incorporate uracils into that recognition site. Then upon uracil degradation, that adaptor arm is rendered single stranded (represented by the half-rectangles), thus protecting that recognition site from inactivation.

After protecting the recognition site in the first adaptor arm from methylation, the linear construct is circularized, for example, by using a bridge oligonucleotide and T4 ligase. The circularization reconstitutes the double stranded restriction endonuclease recognition site in the first adaptor arm. In some embodiments, the bridge oligonucleotide has a blocked end, which results in the bridging oligonucleotide serving to allow circularization, ligating the non-blocked end, and leaving a nick near the recognition site. This nick can be further exploited as discussed below. Application of the restriction endonuclease produces a second linear construct that comprises the first adaptor in the interior of the target nucleic acid and termini comprising (depending on the enzyme) a two base overhang.

A second set of adaptor arms for a second adaptor is ligated to the second linear construct. In some cases, when a nick is utilized, in order to ensure that the adaptors are ligated in the proper orientation, the nick in the first adaptor is "translated" (or "translocated") by using a polymerase with exonuclease activity. The exonuclease activity of the polymerase (such as Taq polymerase) will excise the short DNA strand that abuts the nick while the polymerase activity will "fill in" the nick and subsequent nucleotides in that strand (essentially, the Taq moves along the strand, excising bases using the exonuclease activity and adding the same bases, with the result being that the nick is translocated along the strand until the enzyme reaches the end).

In addition, to create an asymmetry of the template, one termini of the construct is modified with a single base. For example, certain polymerases, such as Taq, will undergo untemplated nucleotide addition to result in addition of a single nucleotide to the 3' end of the blunt DNA duplex, resulting in a 3' overhang. As will be appreciated by those in the art, any base can be added, depending on the dNTP concentration in the solution. In certain embodiments, the polymerase utilized will only be able to add a single nucleotide. For example, Taq polymerase will be able to add a single G or A. Other polymerases may also be used to add other nucleotides to produce the overhang. In one embodiment, an excess of dGTP is used, resulting in the untemplated addition of a guanosine at the 3' end of one of the strands. This "G-tail" on the 3' end of the second linear construct results in an asymmetry of the termini, and thus will ligate to a second adaptor arm, which will have a C-tail that will allow the second adaptor arm to anneal to the 3' end of the second linear construct. The adaptor arm meant to ligate to the 5' end will have a C-tail positioned such that it will ligate to the 5' G-tail. After ligation of the second adaptor arms, the construct is circularized to produce a second circular construct comprising two adaptors. The second adaptor will generally contain a recognition site for a Type IIs endonuclease, and this recognition site may be the same or different than the recognition site contained in the first adaptor, with the latter finding use in a variety of applications A third adaptor can be inserted on the other side of the first adaptor by cutting with a restriction endonuclease bound to a recognition site in the second arm of the first adaptor (the recognition site that was originally inactivated by methylation). In order to make this recognition site available, uracil-modified primers complementary to the second recognition site in the first adaptor are used to amplify the circular constructs to produce third linear constructs in which the first adaptor comprises uracils embedded in the second restriction recognition site. The uracils are degraded to render the first adaptor single stranded, which protects the recognition site in the adaptor from methylation. Applying a sequence-specific methylase will then inactivate all unprotected recognition sites. Upon circularization the recognition site in the first adaptor is reconstituted, and applying the restriction endonuclease will cleave the circle, producing a position at which the third adaptor can be inserted in a third linear construct. Ligating third adaptor arms to the third linear construct will follow the same general procedure described above—the third linear construct will be A- or G-tailed, the third adaptor arms will be T- or C-tailed, allowing the adaptor arms to anneal to the third linear construct and be ligated. The linear construct comprising the third adaptor arms is then circularized to form a third circular construct. Like the second adaptor, the third adaptor will generally comprise a recognition site for a restriction endonuclease that is different than the recognition site contained in the first adaptor.

A fourth adaptor can be added by utilizing Type IIs restriction endonucleases that have recognition sites in the second and third adaptors. Cleavage with these restriction endonucleases will result in a fourth linear construct that can then be ligated to fourth adaptor arms. Circularization of the fourth linear construct ligated to the fourth adaptor arms will produce the nucleic acid template constructs of the invention. As will be appreciated by those in the art, other adaptors can be added. Thus, the methods described herein allow two or more adaptors to be added in an orientation and sometimes distance dependent manner.

Figure 8:
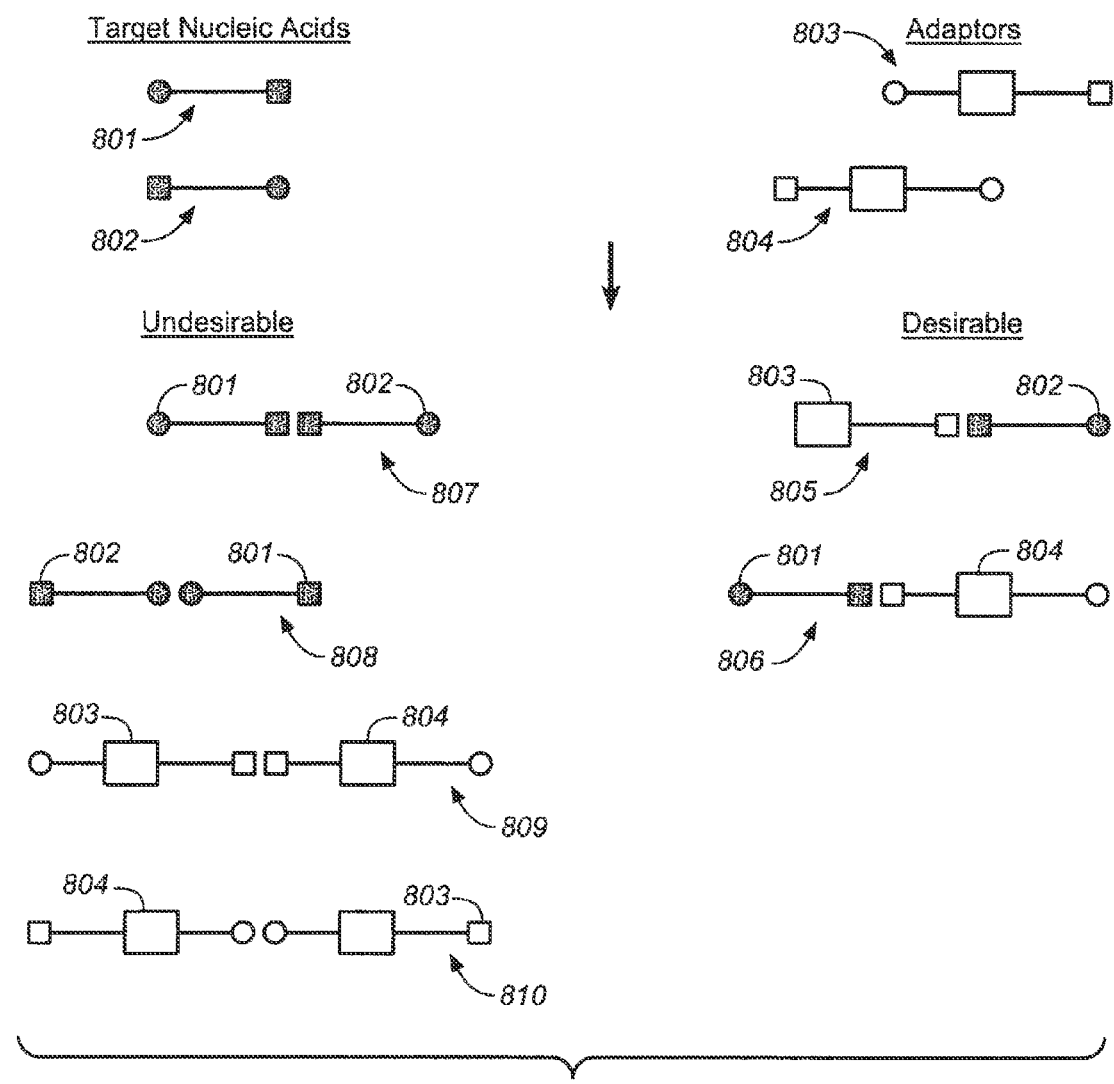
FIG. 8 is a schematic illustration of exemplary embodiments of different orientations in which adaptors and target nucleic acid molecules can be ligated to each other.

The present invention also provides methods for controlling the orientation in which each subsequently added adaptor is inserted. Such "nick translation" methods provide a way to control the way target nucleic acids and adaptors ligate to each other. These methods also prevent artifacts in the nucleic acid constructs by preventing ligation of adaptors to other adaptors and target nucleic acid molecules to other target nucleic acid molecules (essentially avoiding the "polymerization" of adaptors and target nucleic acid molecules). Examples of different orientations in which adaptors and target nucleic acid molecules can be ligated are schematically illustrated in FIG. 8. Target nucleic acids 801 and 802 are preferably ligated to adaptors 803 and 804 in a desired orientation (as illustrated in this FIG., the desired orientation is one in which the ends with the same shape—circle or square—ligates to each other). Modifying the ends of the molecules avoids the undesired configurations 807, 808, 809 and 810, in which the target nucleic acids ligate to each other and the adaptors ligate to each other. In addition, as will be discussed in further detail below, the orientation of each adaptor-target nucleic acid ligation can also be controlled through control of the chemistry of the termini of both the adaptors and the target nucleic acids. The control over the chemistry of the termini can be provided using methods known in the art. For example, in some circumstances, the use of phosphatase eliminates all the phosphate groups, such that all ends contain hydroxyl groups. Each end can then be selectively altered to allow ligation between the desired components. These and other methods for modifying ends and controlling insertion of adaptors in the nick translation methods of the invention are described in further detail below.

These nucleic acid template constructs ("monomers" comprising target sequences interspersed with these adaptors) can then be used in the generation of concatemers, which in turn form the nucleic acid nanoballs that can be used in downstream applications, such as sequencing and detection of specific target sequences.

The present invention provides methods for forming nucleic acid template constructs comprising multiple interspersed adaptors inserted into a target nucleic acid. As discussed further herein, methods of the invention allow insertion of each subsequent adaptor by utilizing recognition sites for Type IIs restriction endonucleases that are included in the adaptors. In order to insert multiple adaptors in a desired order and/or orientation, it can be necessary to block restriction endonuclease recognition sites contained within the target nucleic acids, such that only the recognition site in the adaptor is available for binding the enzyme and the subsequent cleavage. Among the advantages of such methods is that the same restriction endonuclease site can be used in each adaptor, which simplifies production of circular templates that will eventually be used to generate concatemers, adaptors can be inserted using a previously inserted adaptor as a "stepping stone" for the next, such that addition can occur in effect by "walking" down the length of the fragment with each new adaptor. Controlling the recognition sites available for restriction enzymes also avoids the excision of certain sequences, thereby obtaining only limited sequence representation (which could result if sites within the target nucleic acid were accessible).

II.D.2. Addition of First Adaptor

As a first step in the creation of nucleic acid templates of the invention, a first adaptor is ligated to a target nucleic acid. The entire first adaptor may be added to one terminus, or two portions of the first adaptor, referred to herein as "adaptor arms", can be ligated to each terminus of the target nucleic acid. The first adaptor arms are designed such that upon ligation they reconstitute the entire first adaptor. As described further above, the first adaptor will generally comprise one or more recognition sites for a Type IIs restriction endonuclease. In some embodiments, a Type IIs restriction endonuclease recognition site will be split between the two adaptor arms, such that the site is only available for binding to a restriction endonuclease upon ligation of the two adaptor arms.

FIG. 6 is a schematic representation of one aspect of a method for assembling adaptor/target nucleic acid templates (also referred to herein as "target library constructs", "library constructs" and all grammatical equivalents). DNA, such as genomic DNA 601, is isolated and fragmented into target nucleic acids 602 using standard techniques as described above. The fragmented target nucleic acids 602 are then repaired so that the 5' and 3' ends of each strand are flush or blunt ended. Following this reaction, each fragment is "A-tailed" with a single A added to the 3' end of each strand of the fragmented target nucleic acids using a non-proofreading polymerase. The A-tailing is generally accomplished by using a polymerase (such as Taq polymerase) and providing only adenosine nucleotides, such that the polymerase is forced to add one or more A's to the end of the target nucleic acid in a template-sequence-independent manner.

In the exemplary method illustrated in FIG. 6, a first (603) and second arm (603) of a first adaptor is then ligated to each target nucleic acid, producing a target nucleic acid with adaptor arms ligated to each end. In one embodiment, the adaptor arms are "T tailed" to be complementary to the A tails of the target nucleic acid, facilitating ligation of the adaptor arms to the target nucleic acid by providing a way for the adaptor arms to first anneal to the target nucleic acids and then applying a ligase to join the adaptor arms to the target nucleic acid.

In a further embodiment, the invention provides adaptor ligation to each fragment in a manner that minimizes the creation of intra- or intermolecular ligation artifacts. This is desirable because random fragments of target nucleic acids forming ligation artifacts with one another create false proximal genomic relationships between target nucleic acid fragments, complicating the sequence alignment process. Using both A tailing and T tailing to attach the adaptor to the DNA fragments prevents random intra- or inter-molecular associations of adaptors and fragments, which reduces artifacts that would be created from self-ligation, adaptor-adaptor or fragment-fragment ligation.

As an alternative to A/T tailing (or G/C tailing), various other methods can be implemented to prevent formation of ligation artifacts of the target nucleic acids and the adaptors, as well as orient the adaptor arms with respect to the target nucleic acids, including using complementary NN overhangs in the target nucleic acids and the adaptor arms, or employing blunt end ligation with an appropriate target nucleic acid to adaptor ratio to optimize single fragment nucleic acid/adaptor arm ligation ratios.

After creating a linear construct comprising a target nucleic acid and with an adaptor arm on each terminus, the linear target nucleic acid is circularized (605), a process that will be discussed in further detail herein, resulting in a circular construct 607 comprising target nucleic acid and an adaptor. Note that the circularization process results in bringing the first and second arms of the first adaptor together to form a contiguous first adaptor (606) in the circular construct. In some embodiments, the circular construct 607 is amplified, such as by circle dependent amplification, using, e.g., random hexamers and φ29 or helicase. Alternatively, target nucleic acid/adaptor structure may remain linear, and amplification may be accomplished by PCR primed from sites in the adaptor arms. The amplification preferably is a controlled amplification process and uses a high fidelity, proof-reading polymerase, resulting in a sequence-accurate library of amplified target nucleic acid/adaptor constructs where there is sufficient representation of the genome or one or more portions of the genome being queried.

II.D.3. Addition of Multiple Adaptors

As discussed above, FIG. 6 is a schematic representation of one aspect of a method for assembling adaptor/target nucleic acid templates (also referred to herein as "target library constructs", "library constructs" and all grammatical equivalents). DNA, such as genomic DNA 601, is isolated and fragmented into target nucleic acids 102 using standard techniques. The fragmented target nucleic acids 602 are then in some embodiments (as described herein) repaired so that the 5' and 3' ends of each strand are flush or blunt ended.

In the exemplary method illustrated in FIG. 6, a first (603) and second arm (604) of a first adaptor is ligated to each target nucleic acid, producing a target nucleic acid with adaptor arms ligated to each end.

After creating a linear construct comprising a target nucleic acid and with an adaptor arm on each terminus, the linear target nucleic acid is circularized (605), a process that will be discussed in further detail herein, resulting in a circular construct 607 comprising target nucleic acid and an adaptor. Note that the circularization process results in bringing the first and second arms of the first adaptor together to form a contiguous first adaptor (606) in the circular construct. In some embodiments, the circular construct 607 is amplified, such as by circle dependent amplification, using, e.g., random hexamers and φ29 or helicase. Alternatively, target nucleic acid/adaptor structure may remain linear, and amplification may be accomplished by PCR primed from sites in the adaptor arms. The amplification preferably is a controlled amplification process and uses a high fidelity, proof-reading polymerase, resulting in a sequence-accurate library of amplified target nucleic acid/adaptor constructs where there is sufficient representation of the genome or one or more portions of the genome being queried.

Similar to the process for adding the first adaptor, a second set of adaptor arms (610) and (611) can be added to each end of the linear molecule (609) and then ligated (612) to form the full adaptor (614) and circular molecule (613). Again, a third adaptor can be added to the other side of adaptor (609) by utilizing a Type IIs endonuclease that cleaves on the other side of adaptor (609) and then ligating a third set of adaptor arms (617) and (618) to each terminus of the linearized molecule. Finally, a fourth adaptor can be added by again cleaving the circular construct and adding a fourth set of adaptor arms to the linearized construct. The embodiment pictured in FIG. 6 is a method in which Type IIs endonucleases with recognition sites in adaptors (620) and (614) are applied to cleave the circular construct. The recognition sites in adaptors (620) and (614) may be identical or different. Similarly, the recognition sites in all of the adaptors illustrated in FIG. 6 may be identical or different.

Figure 9:
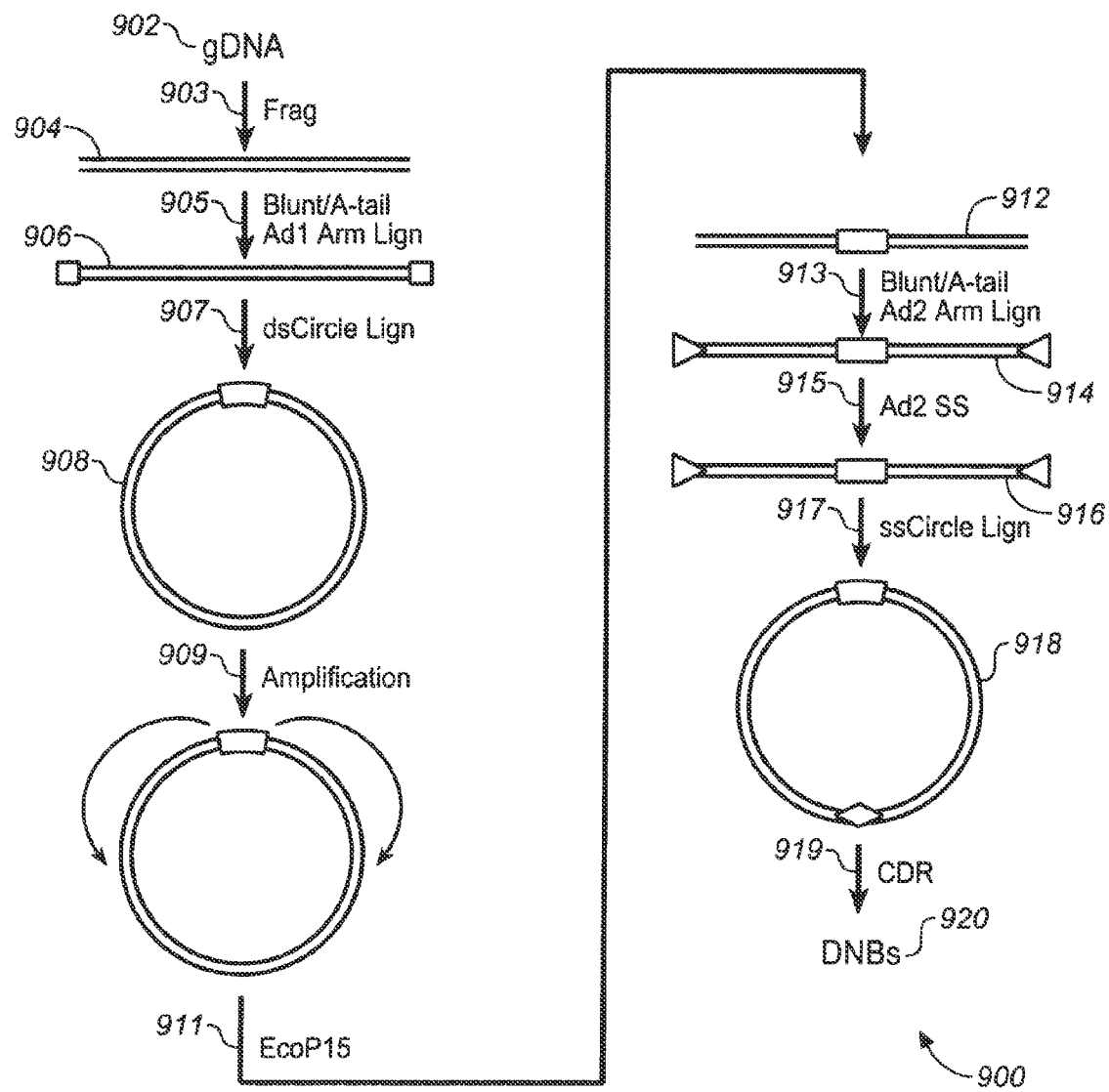
FIG. 9 is a schematic illustration of one aspect of a method for assembling nucleic acid templates of the invention.

As generally illustrated in FIG. 9, a circular construct comprising a first adaptor may contain two Type IIs restriction endonuclease recognition sites in that adaptor, positioned such that the target nucleic acid outside the recognition sequence (and outside of the adaptor) is cut (910). The arrows around structure 510 indicate the recognition sites and the site of restriction. In process 911, EcoP15, a Type IIs restriction endonuclease, is used to cut the circular construct. Note that in the aspect shown in FIG. 9, a portion of each library construct mapping to a portion of the target nucleic acid will be cut away from the construct (the portion of the target nucleic acid between the arrow heads in structure 910). Restriction of the library constructs with EcoP15 in process 911 results in a library of linear constructs containing the first adaptor, with the first adaptor "interior" to the ends of the linear construct 912. The resulting linear library construct will have a size defined by the distance between the endonuclease recognition sites and the endonuclease restriction site plus the size of the adaptor. In process 913, the linear construct 912, like the fragmented target nucleic acid 904, is treated by conventional methods to become blunt or flush ended, A tails comprising a single A are added to the 3' ends of the linear library construct using a non-proofreading polymerase and first and second arms of a second adaptor are ligated to ends of the linearized library construct by A-T tailing and ligation 913. The resulting library construct comprises the structure seen at 914, with the first adaptor interior to the ends of the linear construct, with target nucleic acid flanked on one end by the first adaptor, and on the other end by either the first or second arm of the second adaptor.

In process 915, the double-stranded linear library constructs are treated so as to become single-stranded 916, and the single-stranded library constructs 916 are then ligated 917 to form single-stranded circles of target nucleic acid interspersed with two adaptors 918. The ligation/circularization process of 917 is performed under conditions that optimize intramolecular ligation. At certain concentrations and reaction conditions, the local intramolecular ligation of the ends of each nucleic acid construct is favored over ligation between molecules.

II.D.4. Controlling Orientation of Ligation Between Target Nucleic Acids and Adaptors In one aspect, the present invention provides methods in which ligation of adaptors to target nucleic acids, as described above, is accomplished in a desired orientation. Such control over orientation is advantageous, because random fragments of target nucleic acids forming ligation artifacts with one another create false proximal genomic relationships between target nucleic acid fragments, complicating the sequence alignment process.

There are several methods that find use in controlling orientation of the adaptor insertion. As described above, altering the chemistry of the termini of the targets and the adaptors can be done, such that ligation can only occur when the correct orientation is present. Alternatively, "nick translation methods" can be done, which also rely on the termini chemistries, as outlined below. Finally, methods involving amplification with specific choices of primers can be done as described below.

Figure 12:
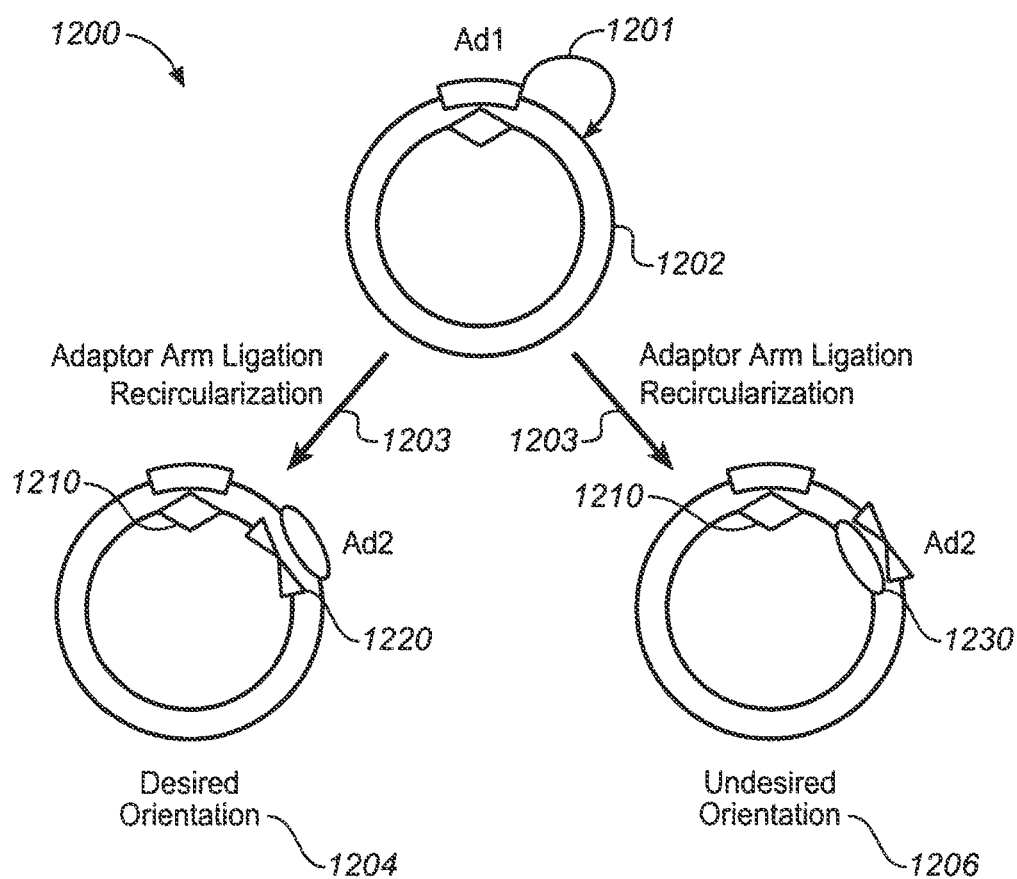
FIG. 12 is a schematic illustration of possible orientations of adaptor insertion.

FIG. 12 is a schematic illustration of the different orientations in which a second adaptor may be added to a nucleic acid construct. Again, process 1200 begins with circular library construct 1202, having an inserted first adaptor 1210. First adaptor 1210 has a specific orientation, with a rectangle identifying the "outer strand" of the first adaptor and a diamond identifying the "inner strand" of the first adaptor (Ad1 orientation 1210). A Type IIs restriction endonuclease site in the first adaptor 1210 is indicated by the tail of arrow 1201, and the site of cutting is indicated by the arrow head. Process 1203 comprises cutting with the Type IIs restriction endonuclease, ligating first and second adaptor arms of a second adaptor, and recircularization. As can be seen in the resulting library constructs 1204 and 1206, the second adaptor can be inserted in two different ways relative to the first adaptor. In the desired orientation 1204, the oval is inserted into the outer strand with the rectangle, and the bowtie is inserted into the inner strand with the diamond (Ad2 orientation 1220). In the undesired orientation the oval is inserted into the inner strand with the diamond and the bowtie is inserted into the outer strand with the rectangle (Ad2 orientation 1230).

Although much of the following discussion and referenced illustrative figures discuss for clarity's sake insertion of a second adaptor in relation to a first, it will be appreciated that the processes discussed herein are applicable to adaptors added subsequently to the second adaptor, creating library constructs with three, four, five, six, seven, eight, nine, ten or more inserted adaptors.

In one embodiment, both A tailing and T tailing are used to attach an adaptor to a nucleic acid fragment. For example, following the modifications described above to repair the ends of fragments, each fragment can be "A-tailed" with a single A added to the 3' end of each strand of the fragmented target nucleic acids using a non-proofreading polymerase. The A-tailing is generally accomplished by using a polymerase (such as Taq polymerase) and providing either only adenosine nucleotides (or an excess thereof), such that the polymerase is forced to add one or more A's to the end of the target nucleic acid in a template-sequence-independent manner. In embodiments in which "A-tailing" is used, ligation to adaptor (or adaptor arms) can be accomplished by adding a "T-tail" to the 5' end of the adaptor/adaptor arms to be complementary to the A tails of the target nucleic acid, facilitating ligation of the adaptor arms to the target nucleic acid by providing a way for the adaptor arms to first anneal to the target nucleic acids and then applying a ligase to join the adaptor arms to the target nucleic acid.

Because the aspects of the claimed invention work optimally when nucleic acid templates are of a desired size and comprise target nucleic acid derived from a single fragment, it can be beneficial to ensure that throughout the process of producing nucleic acid templates that the circularization reactions occur intramolecularly. That is, it can be beneficial to ensure that target nucleic acids in the process of being ligated to a first, second, third, etc. adaptor do not ligate to one another. One embodiment of controlling the circularization process is illustrated in FIG. 10. As shown in FIG. 10, blocking oligos 1017 and 1027 are used to block the binding regions 1012 and 1022 regions, respectively. Blocker oligonucleotide 1017 is complementary to binding sequence 1016, and blocker oligonucleotide 1027 is complementary to binding sequence 1026. In the schematic illustrations of the 5' adaptor arm and the 3' adaptor arm, the underlined bases are dideoxycytosine (ddC) and the bolded font bases are phosphorylated. Blocker oligonucleotides 1017 and 1027 are not covalently bound to the adaptor arms, and can be "melted off" after ligation of the adaptor arms to the library construct and before circularization; further, the dideoxy nucleotide (here, ddC or alternatively a different non-ligatable nucleotide) prevents ligation of blocker to adaptor. In addition or as an alternative, in some aspects, the blocker oligo-adaptor arm hybrids contain a one or more base gap between the adaptor arm and the blocker to reduce ligation of blocker to adaptor. In some aspects, the blocker/binding region hybrids have $T_m$s of about 37° C. to enable easy melting of the blocker sequences prior ligation of the adaptor arms (circularization).

II.D.5. Controlling Orientation of Ligation: Arm-by-Arm Ligation

Figure 11A:
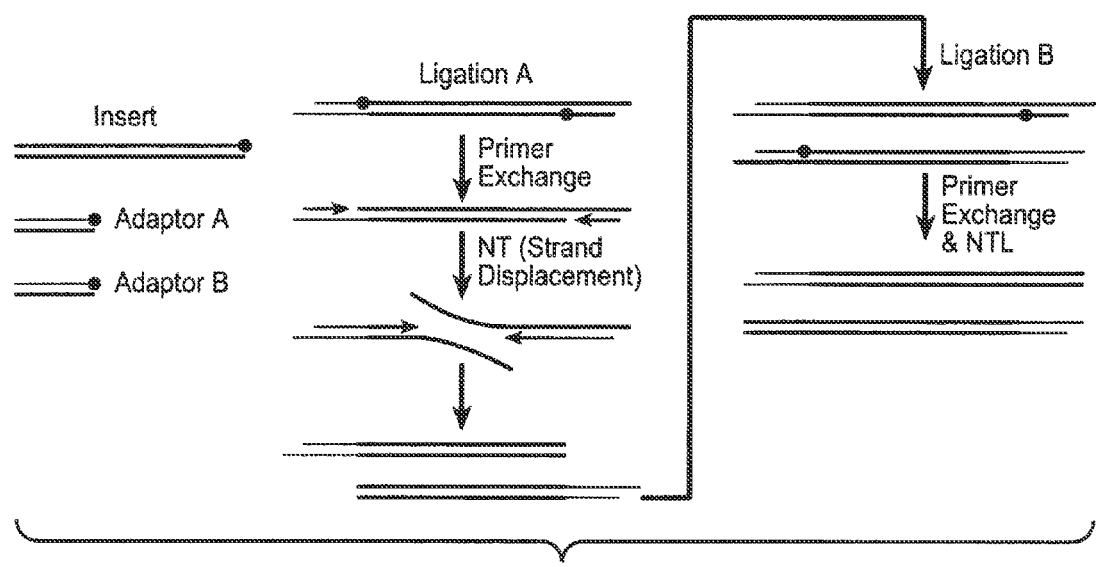
FIG. 11A illustrates an exemplary embodiment of the arm-by-arm ligation process and FIG. 11B illustrates exemplary components of adaptor arms of use in this process.

In one aspect, the directional insertion of adaptors can be controlled without modifying the termini of the target nucleic acid using an "arm-by-arm" ligation method. In general, this is a two-step ligation process in which an adaptor arm is added to a target nucleic acid and primer extension with strand displacement produces two double stranded molecules each with an adaptor arm on one end—a second adaptor arm can then be ligated to the terminus without an adaptor arm. This process can prevent the creation of nucleic acid molecules that comprise the same adaptor arm on both termini—for example, as depicted in FIG. 11A, the arm-by-arm ligation process can prevent the formation of nucleic acid molecules that have both termini occupied by Adaptor A or Adaptor B. In many embodiments it is preferred that each terminus of a target nucleic acid is ligated to a different adaptor arm, such that when the two arms are ligated they are able to form a complete whole adaptor. This can be particularly useful for minimizing the number of amplification steps that are needed after addition of each adaptor arm, because the arm-by-arm ligation reduces the number of non-useful molecules produced in each ligation reaction.

Figure 11B:
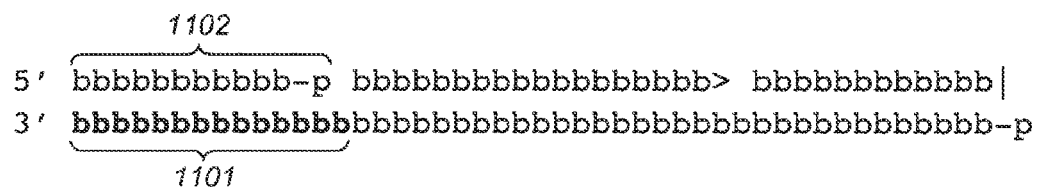

FIG. 11 illustrates one embodiment of the arm-by-arm ligation method. In this embodiment, one strand of the first adaptor arm A is added to both strands of a dephosphorylated target nucleic acid. This adaptor arm is blocked on one end (depicted as the closed circle), generally by using alkaline phosphatase. Primer exchange can be used to replace the strand with the blocked end. Primer extension with strand displacement (which can be accomplished, in one exemplary embodiment, through the use of φ29 or Pfu polymerase) will prime from both ends and extend through the whole insert, resulting in two double-stranded nucleic acid molecules, each with an adaptor arm A on one terminus and a blunt end on the other. In an alternative embodiment, adaptor arm A can be used pre-hybridized with a primer upstream of the blocked strand to initiate primer extension without requiring a primer exchange reaction. After the strand-displacing polymerase reaction, a second adaptor arm B can then be ligated, generally to the blunt end of the target nucleic acid rather than to the terminus with the adaptor arm. This arm-by-arm ligation process can prevent the formation of target nucleic acids that comprise the same adaptor arm on both termini.

II.D.6. Controlling Orientation of Ligation: Nick Translation Methods

In one embodiment, the present invention provides "nick translation methods" for constructing nucleic acid molecules. In one embodiment, nick translation methods are used to ligate nucleic acid molecules in a desired orientation. In a further embodiment, nick translation methods are used for inserting adaptors in a desired orientation. Such methods generally involve modifying one or both termini of one or both of the nucleic acid molecules to be ligated together. For example, when ligating an adaptor to a target nucleic acid, one or both termini of either or both the target nucleic acid and adaptor to be ligated are modified. Following such modification, a "translocation" or "translation" of a nick inserted into one strand of a construct provides the ability to control the final orientation of the ligated adaptor-target nucleic acid construct. "Nick translation methods" as described herein may also include primer extension or gap-fill-in methods, as is described in further detail below. Although the following discussion is provided in terms of controlling ligation of adaptors to target nucleic acids, it will be appreciated that these methods are not limited to ligation of adaptors and target nucleic acids, and that these methods can also be used to control ligation of any two nucleic acid molecules. For example, nick translation methods and any other controlled ligation methods described herein can be used as part of genetic and/or DNA engineering methods, such as the construction of new plasmids or other DNA vectors, gene or genome synthesis or modifications, as well as in constructing building blocks for nanotechnology constructs.

Figure 13:
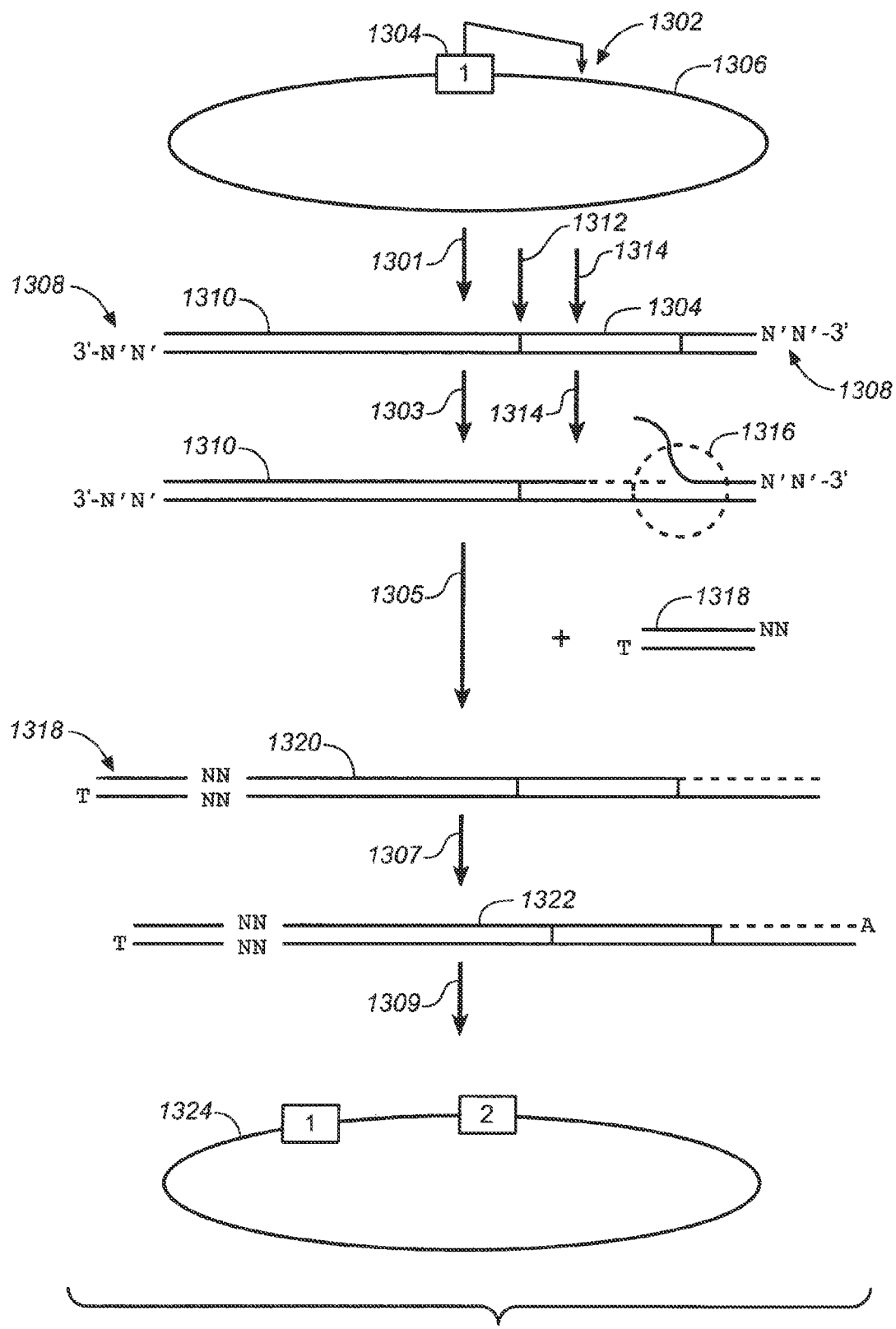
FIG. 13 is a schematic illustration of one embodiment of a nick translation ligation method.
Figure 14:
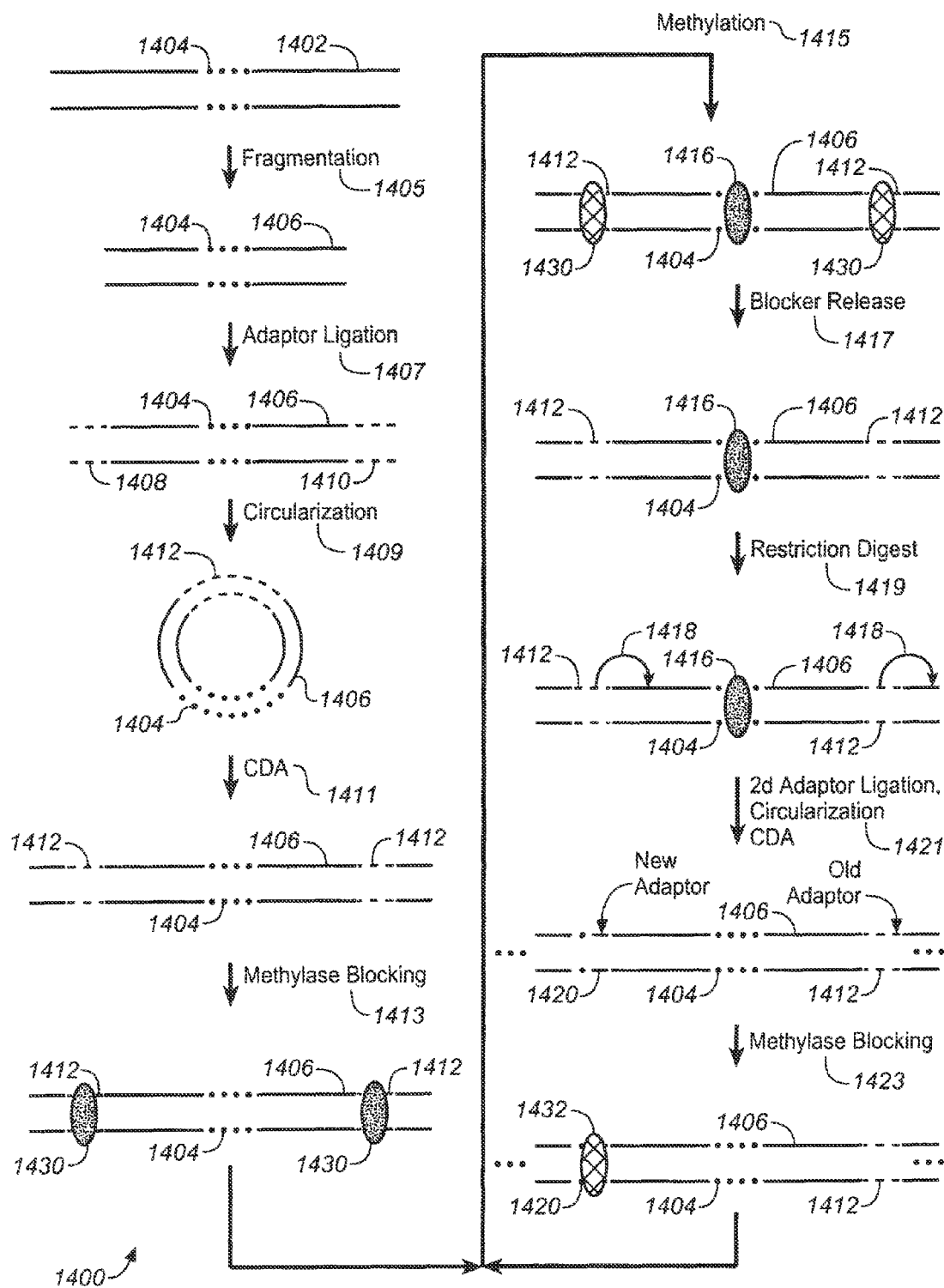
FIG. 14 is a schematic illustration of one embodiment of a method for inserting multiple adaptors.

FIG. 13 is a schematic illustration of such a "nick translation" type of process. Construct 1306 in FIG. 13 is formed using methods discussed herein, and has an interspersed adaptor 1304, with a restriction endonuclease recognition site (tail of the arrow in FIG. 13), and a cleavage site. In FIG. 14, the library construct is not circularized, but is a branched concatemer of alternating target nucleic acid fragments 1406 (with restriction endonuclease recognition sites 1404) and adaptors 1412; however, the nick translation type process shown in FIG. 13 may be performed on such a library construct configuration as well. The term "library construct" as used herein refers to nucleic acid constructs comprising one or more adaptors, and is interchangeable with the term "nucleic acid template".

The library constructs with an inserted first adaptor are digested by a restriction endonuclease (process 1301)—in certain aspects, a Type IIs restriction endonuclease—that cuts the target nucleic acid to render 3' nucleotide overhangs 1308. In FIG. 13, two nucleotides (NN-3') 1308 are shown, though the number of overhanging nucleotides varies in alternative aspects depending at least in part on the identify of the restriction endonuclease used. The library construct 1310 is linearized, with the first inserted adaptor shown at 1304. The first inserted adaptor 1304 is engineered such that it comprises either a nick 1312 at the boundary of the adaptor fragment or it comprises the recognition site for a nicking endonuclease that permits the introduction of a nick 1314 at the interior of the adaptor. In either case, library construct 1310 is treated 1303 with a polymerase 1316 that can extend the upper strand from nick 1312 or 1314 to the end of the lower strand of library construct 1310 to form a strand having a 3' overhang at one end and a blunt end at the other. To this library construct 1310, a second adaptor 1318 is ligated in process 1305, where the second adaptor 1318 has a degenerate nucleotide overhang at one end and a single 3' nucleotide (e.g., dT) overhang at the other end to form library construct 1320. Library construct 1320 is then treated (e.g., with Taq polymerase) in process 1307 to add a 3' dA to the blunt end. Library construct 1322 may then be amplified by PCR, with, e.g., uracil-containing primers. Alternatively, library construct 1322 may then be circularized in process 1309 in which case CDA may be performed (such as in step 1421 of FIG. 14). Combining the processes discussed herein with the nick translation type process shown in FIG. 13 allows for selecting both the relative position and relative orientation of subsequently-added adaptors to any adaptors previously inserted into the library constructs.

In order to utilize a nick translation type of procedure, it may be beneficial to modify one or both of the termini of the target nucleic acid and/or the adaptor as discussed above. In one exemplary embodiment, a first arm of an adaptor that is meant to ligate to the 3' end of a target nucleic acid may be designed such that its 3' terminus is blocked, such that only the 5' end of the adaptor arm is available to ligate to only the 3' end of the target nucleic acid. Similarly, the second arm that is meant to ligate to the 5' end of the target nucleic acid may be designed such that its 5' end is blocked, such that only the 3' end of the second arm can ligate to the 5' end of the target nucleic acid. Methods for blocking one terminus of the adaptor arm and/or the target nucleic acid are well known in the art. For example, the target nucleic acid (which is also referred to herein as a "nucleic acid insert" or a "DNA insert" or an "insert") is treated with enzymes that generate defined functional ends and remove phosphates from both the 3' and 5' ends as discussed above. Removing all of the phosphate groups renders the target nucleic acid molecules unable to ligate to each other. Adaptors in this embodiment are also designed to have one strand capable of ligation (for example by creating or maintaining a 5' phosphate group) and a complementary strand that has a 3' end that is protected from ligation. Generally, this protection of the 3' end is accomplished using a dideoxy nucleotide to inactivate the 3' end. Thus, when the modified target nucleic acids lacking phosphate groups on both ends and modified adaptors comprising only a phosphate group on one 5' end with a 3' block (for example, a dideoxy) on the complementary strand, the only ligation product that will form is that of target nucleic acid ligated to the 5' end of the adaptor that has a phosphate group. Subsequent to this ligation step, the protected 3' end of the adaptor can be exchanged with a strand containing a functional 3' end. This exchange is generally accomplished by taking advantage of the fact that the strand with 3' protection is generally short and easy to denature. The exchange strand with a functional 3' end is longer and will thus bind more efficiently to the complementary strand—in further embodiments, the strand with the functional end is also added in higher concentrations to further influence the reaction toward exchanging the protected strand with the strand with the functional end. This strand with the functional 3' end is then primed by adding a DNA polymerase with nick translation activity, such that the polymerase exonucleolytically removes bases from the 5' end of the target nucleic acid, thereby exposing a functional 5' phosphate. This newly generated 5' phosphate can be ligated to the extension product by a ligase, (If ligase is absent during the extension reaction, two polymerase molecules will nick translate from each end of the target nucleic acid until they meet each other, resulting in a broken molecule). For example, as illustrated in FIG. 2, the target nucleic acid (insert) is first end-repaired to form defined functional ends, preferentially blunt-ends. Next, to avoid concatemerization of inserts, 5'-end phosphates are removed. The insert is then mixed with DNA ligase and DNA adaptors. The DNA adaptor contains two oligonucleotides, and has one blunt-end and one sticky-end when the two oligonucleotides are hybridized together. The blunt-end side contains one "top-strand" with a protected/inactivated 3'-end, and one "bottom-strand" with a functional 5'-end phosphate, and are thus also unable to self-ligate. The only possible ligation combination is therefore one insert with one "bottom-strand" blunt-ligated to each end. The "top-strand" with 3'-end protection is then exchanged with an oligonucleotide containing a functional 3'-end that can act as a primer in a polymerase extension reaction. Upon addition of polymerase and ligase, the second oligonucleotide can be built-in through a nick translation and ligation reaction. When the polymerase is extending into the insert, it introduces a nick with a functional 5'-end phosphate that can be recognized and sealed by DNA ligase. The resulting insert with an adaptor or adaptor arm on each side of each strand can now be subjected to PCR using primers specific to the adaptor.

Generally in a nick translation reaction such as the one described above, an active ligase is present or added in the mixture before addition of the polymerase or simultaneously with the polymerase. In some embodiments, it can be beneficial to use low activity polymerase (slow nick translation) conditions. Both addition of the ligase before or simultaneously with the polymerase and low activity conditions can help assure that the translating nick is sealed before reached the opposite end of the DNA fragment. In some embodiments, this can achieved by incubating the Taq polymerase with T4 ligase at 37° C., a temperature that will usually result in low polymerase activity and high ligase activity. The reaction may then be further incubated at a higher temperature (such as 50-60° C.) to further assure nick-translation-ligation occurs to completion across most/all constructs in the reaction.

In further embodiments, the present invention provides methods for forming nucleic acid template constructs comprising multiple interspersed adaptors. Methods of the present invention include methods of inserting multiple adaptors such that each subsequent adaptor is inserted in a defined position with respect to one or more previously added adaptors. Certain methods of inserting multiple interspersed adaptors are known in the art, for example, as discussed in U.S. application Ser. Nos. 60/992,485; 61/026,337; 61/035,914; 61/061,134; 61/116,193; 61/102,586; 12/265,593; 12/266,385; 11/679,124; 11/981,761; 11/981,661; 11/981,605; 11/981,793 and 11/981,804, each of which is herein incorporated by reference in its entirety for all purposes and in particular for all teachings related to methods and compositions for creating nucleic acid templates comprising multiple interspersed adaptors as well as all methods for using such nucleic acid templates. Insertion of known adaptor sequences into target sequences, such that there is an interruption of contiguous target sequence with the multiple interspersed adaptors, provides the ability to sequence both "upstream" and "downstream" of each adaptor, thus increasing the amount of sequence information that can be generated from each nucleic acid template. The present invention provides further methods for inserting each subsequent adaptor in a defined position with respect to one or more previously added adaptors.

Nick translation ligation is usually performed after ligating the first strand by adding at least polymerase to the reaction. In some embodiments, the nick translation reaction may be performed as a one-step reaction by adding all components at once, while in some embodiments the steps of the reaction are performed sequentially. There are multiple possible embodiments of a "one-step" approach of the nick translation reaction. For example, a single mix with a primer can be used in which Taq is added at the beginning of the reaction. Use of a thermo-stable ligase provides the ability of performing primer exchange and nick translation ligation (and PCR if necessary) by simply increasing the temperature. In another exemplary embodiment, the reaction mixture will contain a minimal concentration of non-processive nick-translating polymerase with a weak 3' exonuclease that activates the 3' blocked strand.

Figure 16:
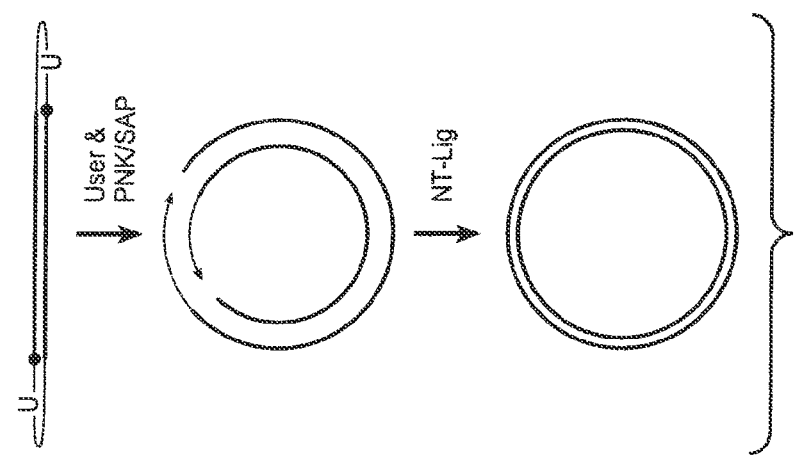
FIG. 16 is a schematic illustration of one embodiment of a nick translation ligation method.

In a further embodiment, T4 polynucleotide kinase (PNK) or alkaline phosphatase is used to alter 3' ends of adaptors and/or target nucleic acids to prepare them for a nick translation process. For example, adaptors can be inserted as part of a circularization reaction. End-repaired and alkaline phosphatase treated target nucleic acids are ligated to adaptors, and in this exemplary embodiment are designed to form self-complementary hairpin shaped units (FIG. 16). The hairpins are designed to contain modifications at a given position that can be recognized and cleaved by enzymes or chemicals. For example, if the hairpins contain deoxyuridines, the deoxyuridiines can be recognized and cut by UDG/EndoVIII. After cutting, the two hairpins become single-stranded with phosphates on their respective 3-end. These 3' phosphates can then be removed by either T4 Polynucleotide Kinase (PNK) or alkaline phosphatase (SAP) to enable nick-translation methods as described further herein. In an exemplary embodiment such as the one illustrated in FIG. 4A, the two hairpins are designed to be partly complementary to each other and can thus form, by intra-molecular hybridization, circularized molecules. Finally, the circularized molecules are subjected to a nick-translation process in which a polymerase extends into the insert and introduces a nick with a functional 5'-end phosphate that can be recognized and sealed by DNA ligase.

Instead of using hairpins as described above, a pair of double stranded adaptors that are partly complementary to each other can be used for circularization. One pair has deoxyuridines on one strand that can be recognized and cut by UDG/EndoVIII. Other methods of nicking one strand can also be used, including without limitation: nicking enzymes, incorporating inosine modified DNA that can be recognized by endonucleolytic enzymes, and incorporating DNA with RNA modifications that can be recognized by RNA-endonucleases. The target nucleic acid and adaptors can be prepared for controlled ligation as described above, for example by treating the target nucleic acid with alkaline phosphatase to create blunt ends that are unable to ligate to other target nucleic acid. Circularization is activated by denaturing the short 3'-protected strand in the adaptor from the strand ligated to the target nucleic acid, leaving two partly complementary single stranded ends on each end of the target nucleic acid insert. The ends are then joined by intra-molecular hybridization and subjected to nick-translation and ligation, forming a covalently closed circle. The circles are then treated with UDG/EndoVIII to prepare the circle for directional insertion of the next adaptor.

Figure 15:
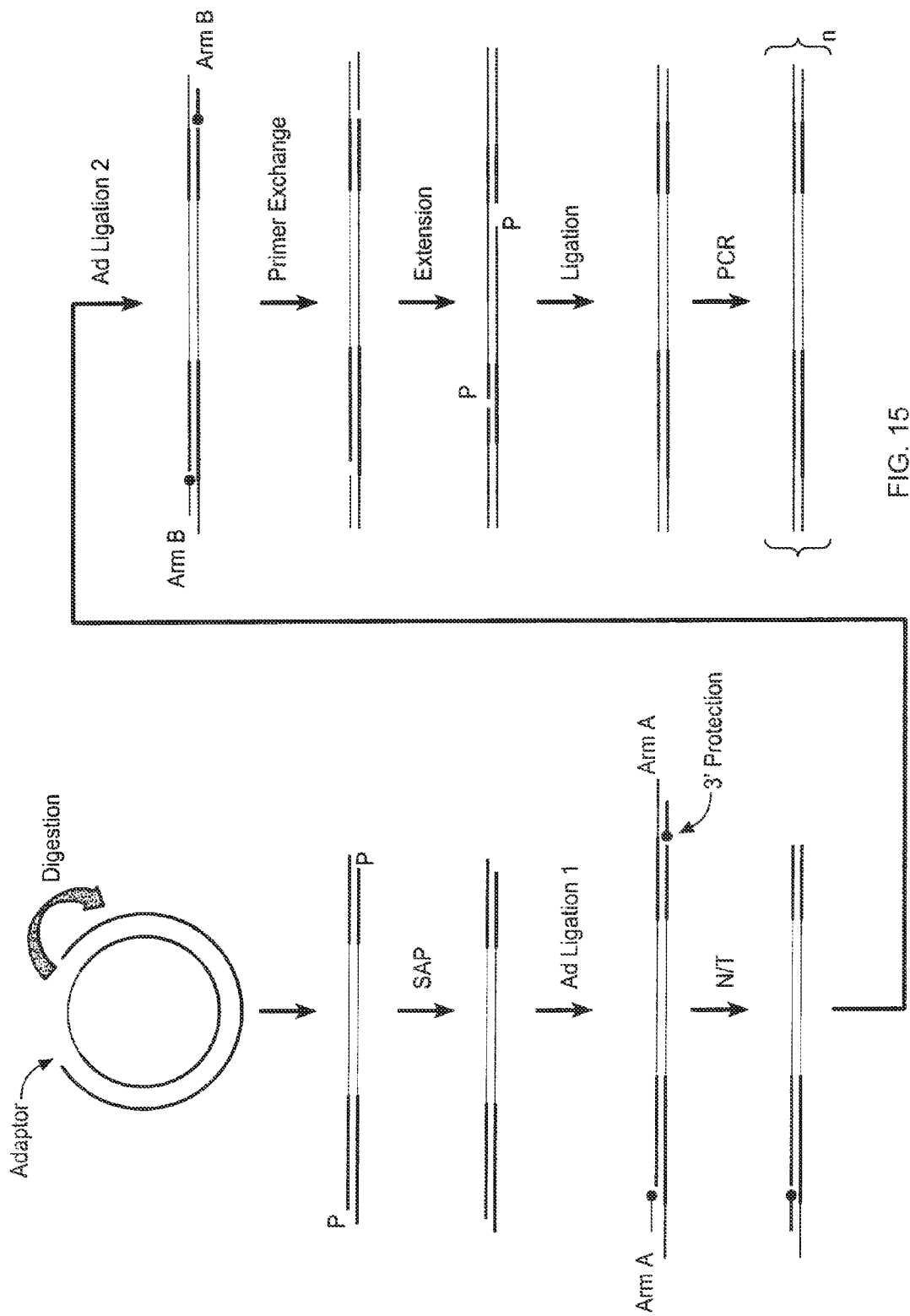
FIG. 15 is a schematic illustration of one embodiment of a nick translation ligation method.

In a still further embodiment illustrated in FIG. 15, a linear target nucleic acid is treated with shrimp alkaline phosphatase (SAP) to remove 5' phosphates. Next, the target nucleic acid is ligated to one arm of the adaptor (arm A), containing a strand with a 5' phosphate, and a complementary shorter strand with a protected 3' end. The ligation product is then subjected to nick-translation. The nick generated in the circularization reaction is located on the top strand of the first adaptor, and acts as a primer for the polymerase used in the nick-translation reaction. The polymerase extends the top-strand to the nick at the adaptor-insert junction, releasing one of the adaptor A arms and generating blunt end or A or G overhang. Next, the resulting polymerase-generated insert end is ligated to the second adaptor arm (arm B). By designing the first adaptor to generate a nick in the circularization reaction, the subsequent adaptor can be added in a predetermined orientation. This strategy is applicable for all type IIs restriction enzymes or other enzymatic or non-enzymatic fragmenting methods regardless of whether they generate a digested product that has blunt ends, 3' overhangs, or 5' overhangs. A non-amplification option may also be used to close the circle comprising melting off the blocked oligonucleotides followed by DNA circularization via nick translation ligation reaction.

Both proofreading polymerases (which have 3'-5' exonuclease activity), such as Pfu polymerase, and non-proofreading polymerases (which lack 3'-5' exonuclease activity), such as Taq polymerase, can be used in the nick translation and strand synthesis with strand displacement processes described herein. Proofreading polymerases can efficiently generate blunt-ends in the nick translation process but have the disadvantage of also degrading non-protected 3' overhangs. The resulting nick translation product will therefore have two blunt ends and will thus be unable to ligate subsequent adaptors in defined orientation. One solution is to protect the 3' end of the ligated adaptor (arm A in FIG. 15 for example) from degradation, using e.g. dideoxyribonucleoside triphosphates (ddNTP) on the 3' ends. However, ddNTP protection also protects the 3' end from subsequent extension, thus limiting the adaptors to be carried forward in a direct circularization procedure. Another potential solution is to protect the 3' ends from polymerase degradation using modifications on the 3' end (e.g. 3' phosphate) that can be removed prior to nick translation circularization (e.g. using alkaline phosphatase). Another approach is to use hairpin shaped adaptors (as described in FIG. 16) in combination with proofreading polymerase in nick translation reactions. These adaptors will be protected from degradation but have the disadvantage of requiring an extra UDG/EndoVIII step. Furthermore, the inventors have found that one of the proofreading polymerases, Pfu polymerase, is able to efficiently generate blunt ends without degrading the non-protected 3' overhang, indicating a low 3'-5' exonuclease activity.

Non-proofreading polymerases, such as Taq polymerase, can generate both blunt ends and single base overhangs in the nick translation process (Taq can generate non-templated A- and G-tails in addition to blunt ends). An advantage of using polymerases without 3'-5' exonuclease activity in the nick translation process is that non-protected 3' overhangs remain intact. This enables ligation of subsequent adaptors in defined orientation without protecting 3' overhangs from degradation. A potential disadvantage with many proofreading polymerases is that they have a function of adding single nucleotides on 3' ends in a non-templated process. This process can be hard to control, and will often generate a mixed population of 3' ends, resulting in a low adaptor-to-insert ligation yield. In general, methods utilizing blunt end ligation are more efficient than one base overhang ligation.

Figure 17B:
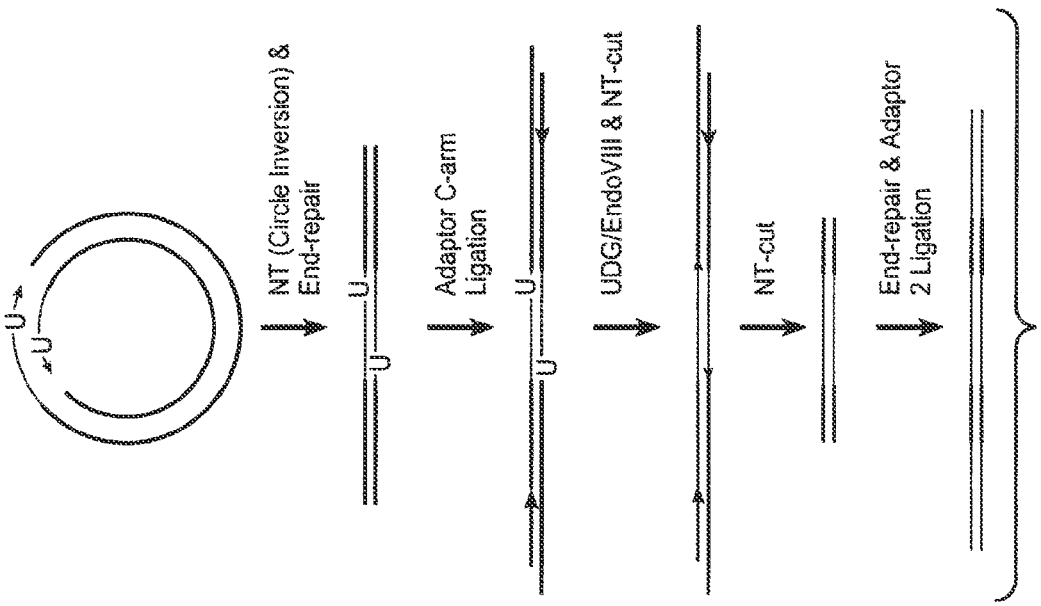
FIG. 17 is a schematic illustration of one embodiment of a nick translation ligation method utilizing nick translation circle inversion (FIG. 17A) and nick translation circle inversion combined with uracil degradation (FIG. 17B).
Figure 17A:
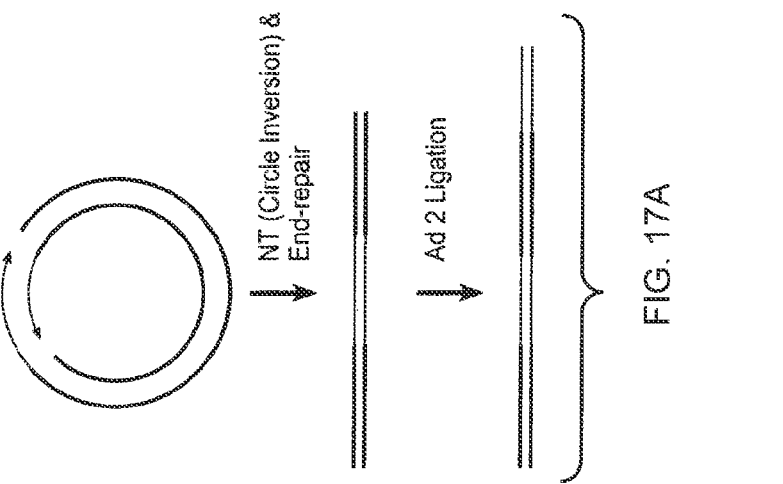

In one embodiment, after ligation of a first adaptor, rather than forming a circle and then cleaving with a type IIs endonuclease that has a recognition site in the first adaptor (which is a step in some embodiments of producing nucleic acid templates of the invention, such as embodiments schematically illustrated in FIGS. 6 and 9), a second adaptor can be added using a variation of the nick translation method. Exemplary embodiments of this variation are schematically illustrated in FIG. 17. In general, these embodiments begin with addition of a first adaptor to a target nucleic acid and then circularization, as is described in detail above and illustrated in FIGS. 6 and 9. In the embodiment illustrated in FIG. 17A, a nick translation is carried out using a polymerase with 5'-3' exonuclease activity (such as Taq polymerase), which generates an inverted circle with the first adaptor located in the interior of the target nucleic acid. This product can then be end-repaired and subjected to ligation to adaptor 2 (using methods described in further detail above). One disadvantage of this embodiment is that the target nucleic acid may be longer than is required for sequencing application, and such longer templates might be prone to generating secondary structures in any nucleic acid concatemer products generated from the templates (the generation of concatemers from nucleic acid templates of the invention is discussed in greater detail below). Such secondary structures may result in a decreased signal when these concatemers are used in sequencing applications, such as the cPAL methods discussed below. One way to overcome this disadvantage is by shortening the target nucleic acid—one exemplary embodiment of this approach is pictured in FIG. 17B. In this embodiment, the first adaptor is modified with uracils using methods described herein. Following the nick translation-inversion of the circle comprising the first adaptor, an adaptor C-arm is added to both ends of the end-repaired molecule. The uracil-modified adaptor 1 is treated to remove the uracils, creating gaps, and also treated to generate activated 3' ends. Generally, the uracils are removed by application of an UDG/EndoVIII enzyme mix and PNK and/or alkaline phosphatase is used to remove the 3' phosphates and generate activated 3' ends. The activated 3' ends of the adaptor 1 and the 3' ends of adaptor arm C are recognized by a nick translation polymerase (i.e., a polymerase with 5'-3' exonuclease activity) resulting in a product with adaptor 1 surrounded by a target nucleic acid that has been trimmed to approximately half of its original length. This polymerase cutting procedure can be repeated to decrease the size of the target nucleic acid even further if adaptor 1 is modified with additional nicking modifications (including without limitation incorporation of inosine, RNA-modifications, and the like).

In a further embodiment, the nick translation methods illustrated in FIGS. 17A and 17B can be expanded to insert multiple adaptors. By modifying adaptors, nicks or gaps and functional 3' ends can be generated to prime nick translation reactions from multiple adaptors simultaneously. As illustrated in FIG. 17B, a nucleic acid construct comprising target nucleic acid and two adaptors, each containing a uracil modification on one strand, is circularized. Next, the circle is treated with an enzyme mix, such as UDG/EndoVIII, to remove the uracils and introduce gaps. These gaps can be simultaneously nick translated to invert the circle, making the construct available for ligation to additional adaptors. By adding multiple modifications on the same adaptors, subsequent nicking/gapping and nick translation inversion can be carried out to introduce multiple adaptors. In some embodiments, uracils can be added back to the same positions in the adaptors, making the adaptors suitable for further nick translation reactions. Adding the uracils back can be accomplished, for example, by incubating the nick translation reaction with uracil only to "build back" the modification in the adaptor, followed by addition of non-modified nucleotides in higher concentration to fill in the rest of the construct.

In a still further embodiment, illustrated in FIG. 17B, the target nucleic acid may be trimmed by controlling the speed of the nick translation enzyme. For example, the nick translation enzyme can be slowed by altering the temperature or limiting reagents, which can result in two nicks being introduced into the circularized insert that are shifted from the initial sites in the adaptor using a nick translation process. Similarly, using a strand displacement polymerase (such as .phi.29) will result in a nick being shifted, producing a branching point due to a displaced segment of the nucleic acid. These nick or branch points can be recognized by various enzymes (including without limitation S1 endonuclease, Bal31, T7 endonuclease, Mung Bean endonuclease, as well as combinations of enzymes, such as a 5' to 3' exonuclease such as T7 exonuclease and S1 or Mung Bean endonuclease) that will cut the opposite strand of the nick, resulting in a linear product. This product can then be end-repaired (if needed) and then ligated to the next adaptor. The size of the target nucleic acid remaining will be controlled by the speed of the nick translation reaction, again for example by lowering the concentration of reagents such as dNTPs or by conducting the reaction at a less than optimal temperature. The size of the target nucleic acid may also be controlled by the incubation time of the nick translation reaction.

Figure 18:
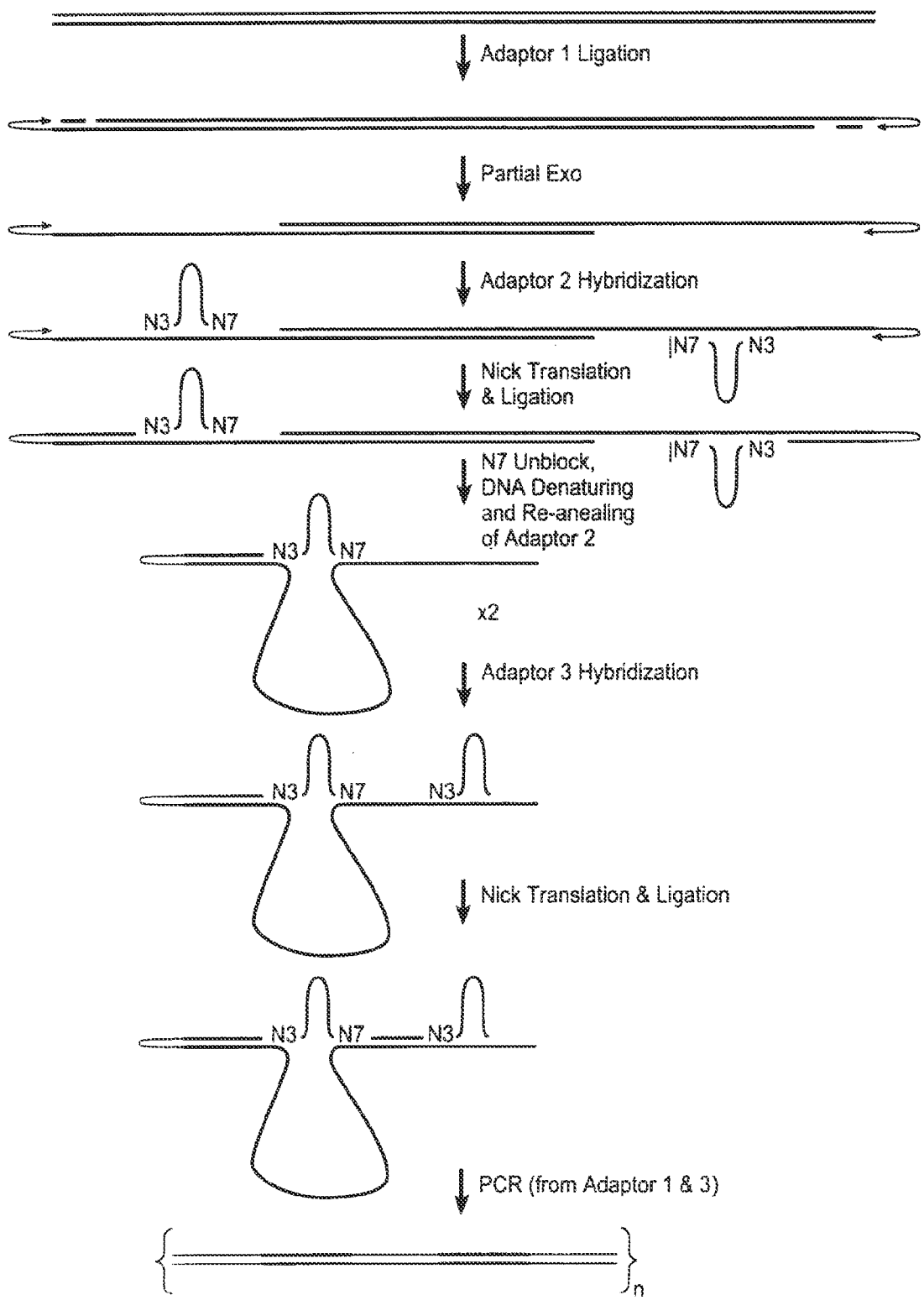
FIG. 18 is a schematic illustration of an embodiment of a nick translation ligation method.

In a further embodiment, nick translation methods can be used to form nucleic acid templates without transitioning through any circularizing steps. An exemplary embodiment of such methods is illustrated in FIG. 18, which shows that the first adaptor 1801, which is shaped as a hairpin, is ligated to target nucleic acid 1802 using ligation methods described above, such as by treating the target nucleic acid with shrimp alkaline phosphate to remove phosphate groups and thereby control the ends of the target nucleic acid that are available to ligate to the first adaptor. After ligation of the first adaptor, a controlled double-strand specific 5'-3' exonuclease reaction is carried out to generate single stranded 3' ends. In some embodiments, the exonuclease reaction is carried out using a T7 exonuclease, although it will be appreciated that other double-strand specific exonucleases can be used in this embodiment of the invention. In further embodiments, the exonuclease reaction generates single stranded 3' ends of about 100 to about 3000 bases in length. In still further embodiments, the exonuclease reaction generates single stranded 3' ends of about 150 to about 2500, about 200 to about 2000, about 250 to about 1500, about 300 to about 1000, about 350 to about 900, about 400 to about 800, about 450 to about 700, and about 500 to about 600 bases in length.

It will be appreciated that the nick translation processes described herein can be used in combination with any of the other methods of adding adaptors described herein. For example, the arm-by-arm ligation process described above and schematically illustrated in FIG. 11A can be used in combination with a nick translation process to prepare a construct for PCR amplification.

In a further embodiment, adaptor arm A used in an arm-by-arm ligation reaction can be designed for direct circularization without PCR, followed by nick translation ligation to seal the circle. In an exemplary embodiment, for direct circularization, adaptor arm A can be designed as pictured in FIG. 11B. Segment 1101 is designed to be complementary to adaptor arm B. The construct in FIG. 11B allows for direct primer extension by a strand displacing polymerase (such as φ29) without a need for a primer exchange reaction to remove a blocked end (the polymerase will not extend past the 3' phosphate on segment 1102). This construct also provides a 3' overhang for circularization. Segment 1102 prevents hybridization of adaptor arm A to adaptor arm B before circularization. In some embodiments, segment 1102 may not be necessary for preventing hybridization to arm B (such as when adaptor arm B is provided in very high concentrations) or segment 1102 may be part of the design of adaptor arm B rather than adaptor arm A.

After generating the single stranded 3' ends, a second adaptor 1803 is hybridized to the single stranded 3' end of the target nucleic acid and connected to the first adaptor through a nick translation ligation reaction (in one embodiment, the nick translation ligation is a "primer extension" or "gap fill-in" reaction). The second adaptor has a 5' phosphate and a 3' block (identified as the vertical line 1804). The 3' block can in some embodiments be a removable block such as a 3' phosphate, which can be removed in some exemplary embodiments using polynucleotide kinase (PNK) and/or shrimp alkaline phosphate. The second adaptor may in some embodiments have degenerated bases at the 3' and/or the 5' ends. In some exemplary embodiments, the second adaptor has about 2-6 degenerated bases at the 5' end and 4-9 degenerated bases at the 3' end, although it will be appreciated that any combination of numbers of degenerated bases at one or both ends of the second adaptor are encompassed by the present invention. In the embodiment pictured in FIG. 18, the second adaptor comprises 3 degenerate bases at the 5' end ("N3") and 7 degenerate bases at its 3' end ("N7"). The joining of the first adaptor to the second adaptor may in some embodiments be accomplished under reaction conditions at which hybridization of the adaptors to the target nucleic acid are favored. In some exemplary embodiments, such reaction conditions may include temperatures of from about 20 to about 40° C. Polymerases that can be used under such reaction conditions include without limitations φ29, Klenow, T4 polymerases and Pol I.

The ligation product 1805 is then denatured and/or further processed with a 5'-3' exonucleases followed by a re-annealing step to form two single stranded nucleic acid molecules (denoted by the "×2" in FIG. 18). During re-annealing, the N7 part of the second adaptor may hybridize to a segment at a random distance from the first hybridization sequence motif, thereby forming a single stranded loop 1806. In some embodiments, the N7 end of the second adaptor may not hybridize until denaturation produces long single stranded regions of the nucleic acid 1807. The average distance between two captured genomic segments (which are generally from about 20 to about 200 bases in length) will in many embodiments be between about 0.5 to about 20 kilobases. This average distance will depend in part on the number of degenerate bases ("Ns") of the adaptors and the stringency of hybridization conditions. The re-annealing step can then be followed by another round of adaptor hybridization and nick translation ligation. A final adaptor (in FIG. 18, this final adaptor is pictured as a third adaptor 1808, but it will be appreciated that the final adaptor may be the fourth, fifth, sixth, seventh or more adaptor inserted according to any of the methods described herein) is similar to the second adaptor but will in many embodiments lack the degenerate bases at the 3' end. In further embodiments, the final adaptor may comprise a binding site for a primer for an amplification reaction, for example a PCR primer.

In still further embodiments, amplification reactions, such as PCR reactions (see 1809 in FIG. 18), can be carried out, for example, by using primer binding sites included in the first and final adaptors. In still further embodiments, the first and final adaptors may be two arms of the same adaptor and more than one adaptor may be inserted prior to the addition of the final adaptor. In a yet further embodiment, the amplification products may be used to form circular double stranded nucleic acid molecules for further adaptor insertion using any of the process described herein or known in the art.

II.D.7. Controlled Insertion of Subsequent Adaptors: Protection of Restriction Endonuclease Recognition Sites In addition to controlling the orientation of adaptors inserted into a target nucleic acid as described above, multiple adaptors can also be inserted into a target nucleic acid at specified locations relative to previously inserted adaptors. Such methods include embodiments in which certain restriction endonuclease recognition sites, particularly recognition sites contained in a previously inserted adaptor, are protected from inactivation. In order to ligate subsequent adaptors in a desired position and orientation, the present invention provides methods in which a Type IIs restriction endonuclease binds to a recognition site within the first adaptor of a circular nucleic acid construct and then cleaves at a point outside the first adaptor and in the genomic fragment (also referred to herein as the "target nucleic acid"). A second adaptor can then be ligated into the point at which cleavage occurs (again, usually by adding two adaptor arms of the second adaptor). In order to cleave the target nucleic acid at a known point, it is necessary to block any other recognition sites for that same enzyme that may randomly be encompassed in the target nucleic acid, such that the only point at which that restriction endonuclease can bind is within the first adaptor, thus avoiding undesired cleavage of the constructs. Generally, the recognition site in the first adaptor is first protected from inactivation, and then any other unprotected recognition sites in the construct are inactivated, generally through methylation. By "inactivation" of a restriction endonuclease recognition site herein is meant that the recognition site is somehow rendered unavailable for binding by a restriction endonuclease, thus preventing the downstream step of cleavage by that enzyme. For example, methylated recognition sites will not bind the restriction endonuclease, and thus no cleavage will occur. Once all recognition sites in a nucleic acid construct that are unprotected have been methylated, only the unmethylated recognition site within the adaptor will allow binding of the enzyme with subsequent cleaving. Other methods of inactivating recognition sites include without limitation applying a methylase block to the recognition site, using a blocking oligonucleotide to block the recognition site, using some other blocking molecule, such as a zinc finger protein, to block the recognition site, and nicking the recognition site to prevent methylation. Such methods for protecting the desired recognition site are described in U.S. application Ser. No. 12/265,593, filed Nov. 5, 2008 and Ser. No. 12/266,385, filed Nov. 6, 2008, which are both herein incorporated by reference in their entirety and for all purposes and in particular for all teachings related to inserting multiple interspersed adaptors into a target nucleic acid.

It will be appreciated that the methods described above for controlling the orientation in which adaptors and target nucleic acids ligate to each other may also be used in combination with the methods described below for controlling the spacing of each subsequently added adaptor.

In one aspect, the present invention provides a method of protecting the recognition site in the first adaptor from inactivation by rendering the recognition site in the first adaptor single-stranded, such that a methylase that is only able to methylate double-stranded molecules will be unable to methylate the recognition site being protected. One method of rendering the recognition site in the first adaptor single-stranded is by amplifying the linear genomic fragments ligated to the two first adaptor arms using primers modified with uracil. The primers are complementary to the adaptor arms and are modified with uracil such that, upon amplification (generally using PCR), the resultant linear constructs contain uracil embedded in the recognition site of one of the first adaptor arms. The primers generate a PCR product with uracils close to the Type IIs restriction endonuclease recognition site in the first and/or second arms of the first adaptor. Digestion of the uracil renders the region(s) of the adaptor arm that include the Type IIs recognition site to be protected single stranded. A sequence specific methylase is then applied to the linear constructs that will methylate all of the double-stranded recognition sites for the same endonuclease as that contained in the first adaptor.

Such a sequence-specific methylase will not be able to methylate the single stranded recognition site in the first adaptor arm(s), and thus the recognition site in the first adaptor arm(s) will be protected from inactivation by methylation.

In some cases, as more fully described below, a single adaptor may have two of the same recognition sites, to allow cleavage both "upstream" and "downstream" from the same adaptor. In this embodiment, as depicted in FIG. 7, the primers and uracil positions are chosen appropriately, such that either the "upstream" or "downstream" recognition site may be selectively protected from inactivation or inactivated.

A third adaptor can be inserted on the other side of the first adaptor by cutting with a restriction endonuclease bound to a recognition site in the second arm of the first adaptor (the recognition site that was originally inactivated by methylation). In order to make this recognition site available, uracil-modified primers complementary to the second recognition site in the first adaptor are used to amplify the circular constructs to produce third linear constructs in which the first adaptor comprises uracils embedded in the second restriction recognition site. The uracils are degraded to render the first adaptor single stranded, which protects the recognition site in the adaptor from methylation. Applying a sequence-specific methylase will then inactivate all unprotected recognition sites. Upon circularization the recognition site in the first adaptor is reconstituted, and applying the restriction endonuclease will cleave the circle, producing a position at which the third adaptor can be inserted in a third linear construct. Ligating third adaptor arms to the third linear construct will follow the same general procedure described above—the third linear construct will be A- or G-tailed, the third adaptor arms will be T- or C-tailed, allowing the adaptor arms to anneal to the third linear construct and be ligated. The linear construct comprising the third adaptor arms is then circularized to form a third circular construct. Like the second adaptor, the third adaptor will generally comprise a recognition site for a restriction endonuclease that is different than the recognition site contained in the first adaptor.

A fourth adaptor can be added by utilizing Type IIs restriction endonucleases that have recognition sites in the second and third adaptors. Cleavage with these restriction endonucleases will result in a fourth linear construct that can then be ligated to fourth adaptor arms. Circularization of the fourth linear construct ligated to the fourth adaptor arms will produce the nucleic acid template constructs of the invention.

In general, methods of the invention provide a way to specifically protect a Type IIs endonuclease recognition site from inactivation such that, once all remaining unprotected recognition sites in a construct are inactivated, application of the Type IIs endonuclease will result in binding only to the protected site, thus providing control over where the subsequent cleavage occurs in the construct. The method described above provides one embodiment of how to protect the desired recognition site from inactivation. It will be appreciated that the above-described method can be modified using techniques known in the art, and that such modified methods are encompassed by the present invention.

Figure 19:
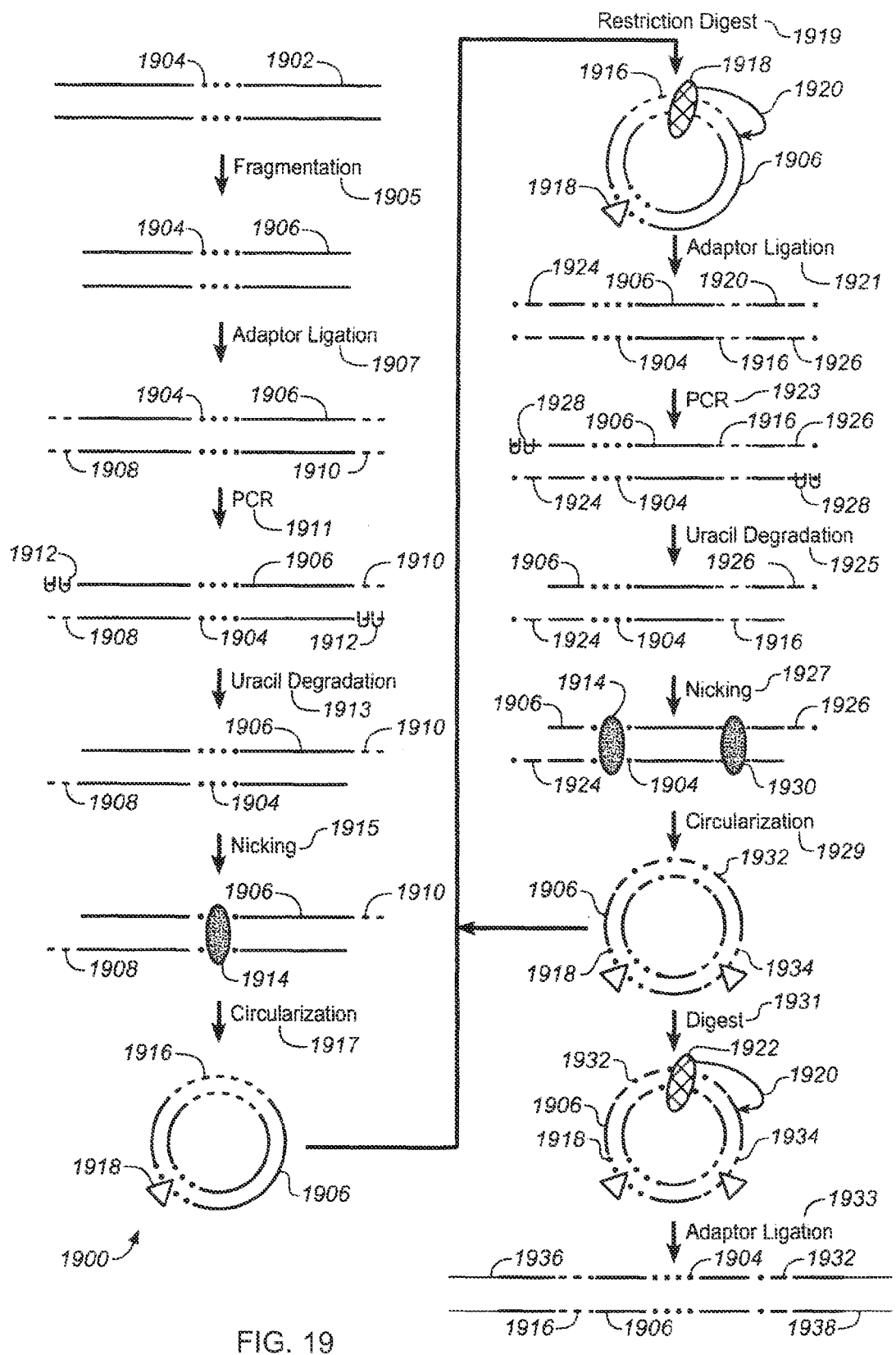
FIG. 19 is a schematic illustration of one embodiment of a method for inserting multiple adaptors.

In one exemplary embodiment, each subsequently inserted adaptor is inserted using a method in which a recognition site is protected from inactivation using a combination of methods. FIG. 19 is a schematic illustration of an embodiment in which a second adaptor is inserted at a desired position relative to a first adaptor by employing a process that is a combination of methylation and protection from methylation using a combination of uracil degradation and nickase. FIG. 19 shows genomic DNA of interest 1902 having a Type IIs restriction endonuclease recognition site at 1904. The genomic DNA is fractionated or fragmented in process 1905 to produce fragment 1906 having a Type IIs restriction endonuclease recognition site 1904. Adaptor arms 1908 and 1910 are ligated to fragment 1906 in process 1907. Fragment 1906 with first and second adaptor arms 1908 and 1910 (a library construct) are amplified by PCR in process 1911, using uracil-modified primers 1912 complementary to adaptor arms 1908 and 1910. The primers generate a PCR product with uracils close to the Type IIs restriction endonuclease recognition site. In process 1913, the uracils are specifically degraded using, e.g., uracil-DNA glycosylase enzyme (Krokan, et al., (1997) *Biochem. J.* 325:1-16), leaving a PCR product that is single-stranded in the Type IIs restriction endonuclease recognition site region. As shown, uracil incorporation and degradation may be used to render the Type IIs restriction endonuclease recognition site single-stranded; however, as described further herein, other methods may be employed to render these regions single-stranded including use of 3' or 5' exonucleases in a limited digest.

In process 1915, a sequence-specific nickase is used to nick bases in each double-stranded Type IIs restriction endonuclease recognition site to protect these sites from Type IIs restriction endonuclease recognition. However, the single-stranded Type IIs restriction endonuclease recognition site portions in first and second adaptor arms 1908 and 1910 will not be nicked, and, once circularized and ligated 1917, the Type IIs restriction endonuclease recognition site in the first and second adaptor arms re-forms such that this Type IIs restriction endonuclease recognition site is available for restriction. When selecting the nickase and the Type IIs restriction endonucleases for this process, it is preferred that the two enzymes recognize the same sequence or that one enzyme recognizes a subsequence (sequence within the sequence) of the other enzyme. Alternatively, the nickase may recognize a different sequence, but is positioned within the adaptor so that it nicks in the Type IIs restriction endonuclease recognition site. Use of uracil or 3' or 5' degradation permits the use of one nickase enzyme throughout the process; alternatively, more than one sequence-specific nickase may be employed. The circularized construct is then cut with the Type IIs restriction endonuclease in process 1919 where the Type IIs restriction endonuclease recognition site is indicated at 1922, the construct is cut at 1920, and the nick is indicated at 1918, resulting in a linearized construct available for ligation of a second set of adaptor arms to be added to the construct in process 1921

Ligation process 1921 adds first 1924 and second 1926 adaptor arms of the second adaptor to the linearized construct, and a second amplification is performed by PCR at process 1923, again using uracil-modified primers 1928 complementary to adaptor arms 1924 and 1926. As before, the primers generate a PCR product with uracils close to the Type IIs restriction endonuclease recognition site. In process 1925, the uracils are specifically degraded leaving a PCR product that is single-stranded in the Type IIs restriction endonuclease recognition site region of the first and second adaptor arms 1924 and 1926 of the second adaptor. Ligation process 1921 also serves to repair the nick 1918 in the Type IIs restriction site 1904 in the target nucleic acid fragment 1906. In process 1927, the sequence-specific nickase again is used to nick bases in the double-stranded Type IIs restriction endonuclease recognition sites in the target nucleic acid fragment (there is nicking 1914 of the Type IIs restriction endonuclease recognition site 1904) and in the Type IIs restriction endonuclease recognition site of the first adaptor 1930 protecting these sites from Type IIs restriction endonuclease recognition.

The nicked construct is then circularized and ligated at process 1929, where the Type IIs restriction endonuclease recognition site in the first and second arms 1924 and 1926 of the second adaptor is re-formed 1932 and the process is repeated where the circularized construct is cut again with the Type IIs restriction endonuclease in process 1931 to generate another linearized construct (this one with first and second adaptors already added) available for ligation of a third pair of adaptor arms 1936 and 1938 to the construct. The Type IIs restriction endonuclease recognition site is shown at 1922, the site of restriction is shown at 1920, the nick Type IIs restriction endonuclease recognition site in the target nucleic acid fragment is shown at 1918 and the nick in the first adaptor is shown at 1934. The process can be repeated to add as many adaptors as are desired. As shown here, the first added adaptor had one Type IIs restriction endonuclease recognition site; however, in other aspects, the first added adaptor may have two Type IIs restriction endonuclease recognition sites to allow for precise selection of target nucleic acid size for the construct.

In one aspect, adaptors can be designed to have sequence-specific nickase sites surrounding or partially overlapping the Type IIs restriction endonuclease recognition site. By utilizing the nickase, the Type IIs restriction endonuclease recognition site(s) of each adaptor can be selectively protected from methylation. In further embodiments, the nickase may recognize another sequence or site, but will cut at the Type IIs restriction endonuclease recognition site. Nickases are endonucleases recognize a specific recognition sequence in double-stranded DNA, and cut one strand at a specific location relative to the recognition sequence, thereby giving rise to single-stranded breaks in duplex DNA and include but are not limited to Nb.BsrDI, Nb.BsmI, Nt.BbvCI, Nb.Bbv.Nb.BtsI and Nt.BstNBI. By employing a combination of sequence-specific nickase and Type IIs restriction endonuclease, all Type IIs restriction endonuclease recognition sites in the target nucleic acid as well as the Type IIs restriction endonuclease recognition sites in any previously-inserted adaptor can be protected from digestion (assuming, of course, the Type IIs restriction endonuclease is nick sensitive, i.e., will not bind at a recognition site that has been nicked).

Figure 20:
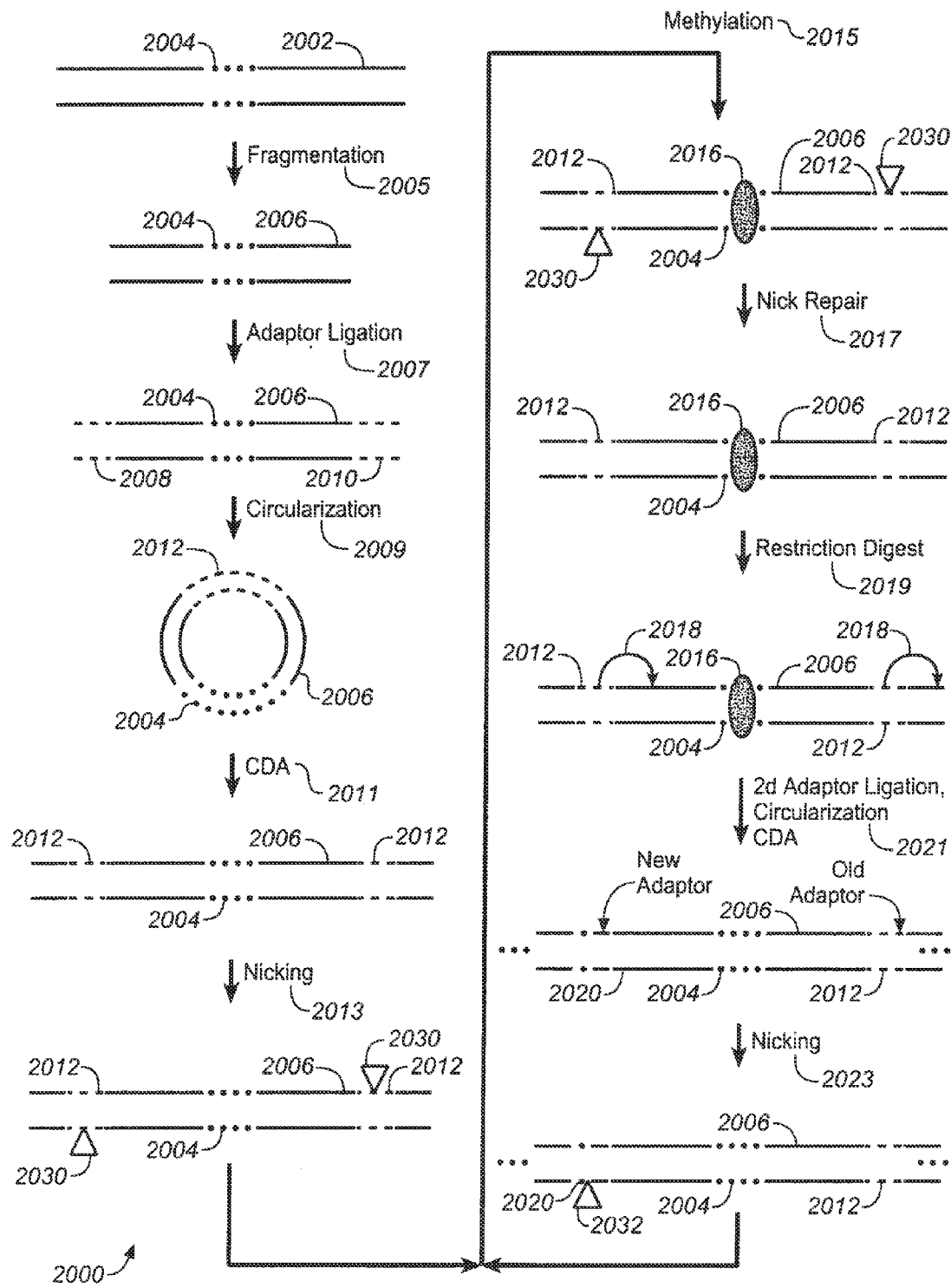
FIG. 20 is a schematic illustration of one embodiment of a method for inserting multiple adaptors.

FIG. 20 is a schematic representation of an embodiment of methods of the invention where a desired position of a second adaptor relative to a first adaptor is selected using methylation and sequence-specific nickases. FIG. 20 shows genomic DNA of interest (target nucleic acid) 2002 having a Type IIs restriction endonuclease recognition site at 2004. The genomic DNA is fractionated or fragmented in process 2005 to produce fragments 2006 having a Type IIs restriction endonuclease recognition site 2004. Adaptor arms 2008 and 2010 are ligated to fragment 2006 in process 2007. Fragment 2006 with adaptor arms 2008 and 2010 (a library construct) is circularized in process 2009 and amplified by circle dependent amplification in process 2011, resulting in a highly-branched concatemer of alternating target nucleic acid fragments 2006 (with the Type IIs restriction endonuclease recognition site at 2004) and first adaptors 2012.

In process 2013, a sequence-specific nickase 2030 is used to nick the nucleic acid in or near specific Type IIs restriction endonuclease recognition sites in the adaptor in the library construct thereby blocking methylation of these sites. Here, the Type IIs restriction endonuclease recognition sites in adaptor arms 2012 and 2014 are nicked by sequence-specific nickase 2030. In process 2015, un-nicked Type IIs restriction endonuclease recognition sites in the construct are methylated—here, methylation 2016 of the Type IIs restriction endonuclease recognition site 2004)—protecting these sites from Type IIs restriction endonuclease recognition. However, the Type IIs restriction endonuclease recognition sites in adaptors 2012 and 2014 are not methylated due to the presence of the nicks.

At process 2017, the nicks are repaired in the library construct, resulting in a library construct where the Type IIs restriction endonuclease recognition site in adaptors 2012 are available for recognition and restriction 2018, and the Type IIs restriction endonuclease recognition site in the genomic fragment 2004, is not. The methylated construct is then ligated to an second pair of adaptor arms, circularized, and amplified via circle dependent amplification at process 2021, resulting in a concatemer of alternating target nucleic acid fragments 2006 (with the Type IIs restriction endonuclease recognition site at 2004), first adaptors 2012 and second adaptors 2020. Next, in process 2023, sequence-specific nicking is performed again, this time with a sequence-specific nickase that recognizes a site in the second adaptor 2020 to block methylation of the Type IIs restriction endonuclease recognition site in the second adaptor 2020, but not the other Type IIs restriction endonuclease recognition sites in the construct (i.e., the Type IIs restriction endonuclease recognition site 2004 in the fragment and the Type IIs restriction endonuclease recognition site in first adaptor 2012). The process then continues with methylation 2015, and further adaptor arms are added, if desired. Different sequence-specific nickase sites are used in each different adaptor, allowing for sequence-specific nicking throughout the process.

Figure 21:
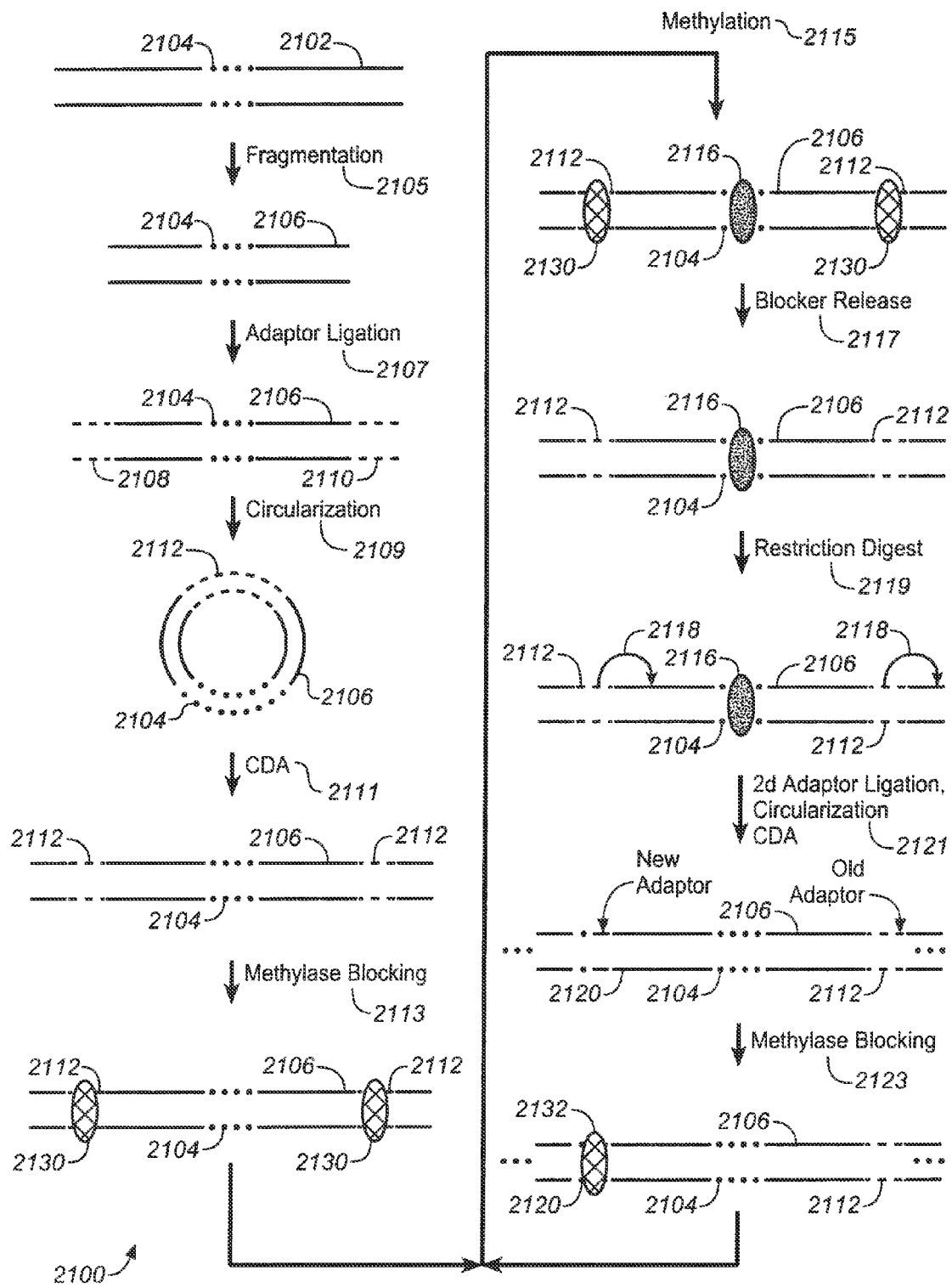
FIG. 21 is a schematic illustration of one embodiment of a method for inserting multiple adaptors.

FIG. 21 is a schematic representation of a process where a desired position of a second adaptor relative to a first adaptor is selected using methylation and sequence-specific methylase blockers. FIG. 21 shows genomic DNA of interest (target nucleic acid) 2212 having a Type IIs restriction endonuclease recognition site at 2214. The genomic DNA is fractionated or fragmented in process 2105 to produce fragment 2106 having a Type IIs restriction endonuclease recognition site 2104. Adaptor arms 2108 and 2110 are ligated to fragment 2106 in process 2107. Fragment 2106 with adaptor arms 2108 and 2110 (a library construct) is circularized in process 2109 and amplified by circle dependent amplification in process 2111, resulting in a highly-branched concatemer of alternating target nucleic acid fragments 2106 (with the Type IIs restriction endonuclease recognition site at 2104) and first adaptors 2112.

In process 2113, a sequence-specific methylase blocker 2130 such as a zinc finger is used to block methylation in specific Type IIs restriction endonuclease recognition sites in the library construct. Here, the Type IIs restriction endonuclease recognition sites in adaptor arms 2112 and 2114 are blocked by methylase blocker 2130. When selecting the methylase blocker and the Type IIs restriction endonucleases for this process, it is not necessary that the two entities recognize the same site sequence or that one entity recognizes a subsequence of the other entity. The blocker sequences may be up- or downstream from the Type IIs restriction endonuclease recognition site, but are of a configuration that the methylase blocker blocks the site (such as with a zinc finger or other nucleic acid binding protein or other entity). In process 2115, unprotected Type IIs restriction endonuclease recognition sites in the construct are methylated—here, methylation 2116 of the Type IIs restriction endonuclease recognition site 2104)—protecting these sites from Type IIs restriction endonuclease recognition. However, the Type IIs restriction endonuclease recognition sites in adaptors 2112 and 2114 are not methylated due to the presence of the methylase blocker.

At process 2117, the methylase blocker is released from the library construct, resulting in a library construct where the Type IIs restriction endonuclease recognition site in adaptors 2112 are available for recognition and restriction 2118, and the Type IIs restriction endonuclease recognition site in the genomic fragment 2104, is not. The methylated construct is then ligated to an second pair of adaptor arms, circularized, and amplified via circle dependent amplification at process 2121, resulting in a concatemer of alternating target nucleic acid fragments 2106 (with the Type IIs restriction endonuclease recognition site at 2104), first adaptors 2112 and second adaptors 2120. Next, in process 2123, methylase blocking is performed again, this time with a methylase blocker that recognizes a site in the second adaptor 2120 to block methylation of the Type IIs restriction endonuclease recognition site in the second adaptor 2120, but not the other Type IIs restriction endonuclease recognition sites in the construct (i.e., the Type IIs restriction endonuclease recognition site 2104 in the fragment and the Type IIs restriction endonuclease recognition site in first adaptor 2112). The process then continues with methylation 2115, and further adaptor arms are added, if desired. Different methylase blocker sites are used in each different adaptor, allowing for sequence-specific methylase blocking throughout the process. Though FIGS. 9 and 21 show insertion of a second adaptor in relation to a first, it should be understood that the process is applicable to adaptors added subsequently to the second adaptor, creating library constructs with up to four, six, eight, ten or more inserted adaptors.

Figure 22:
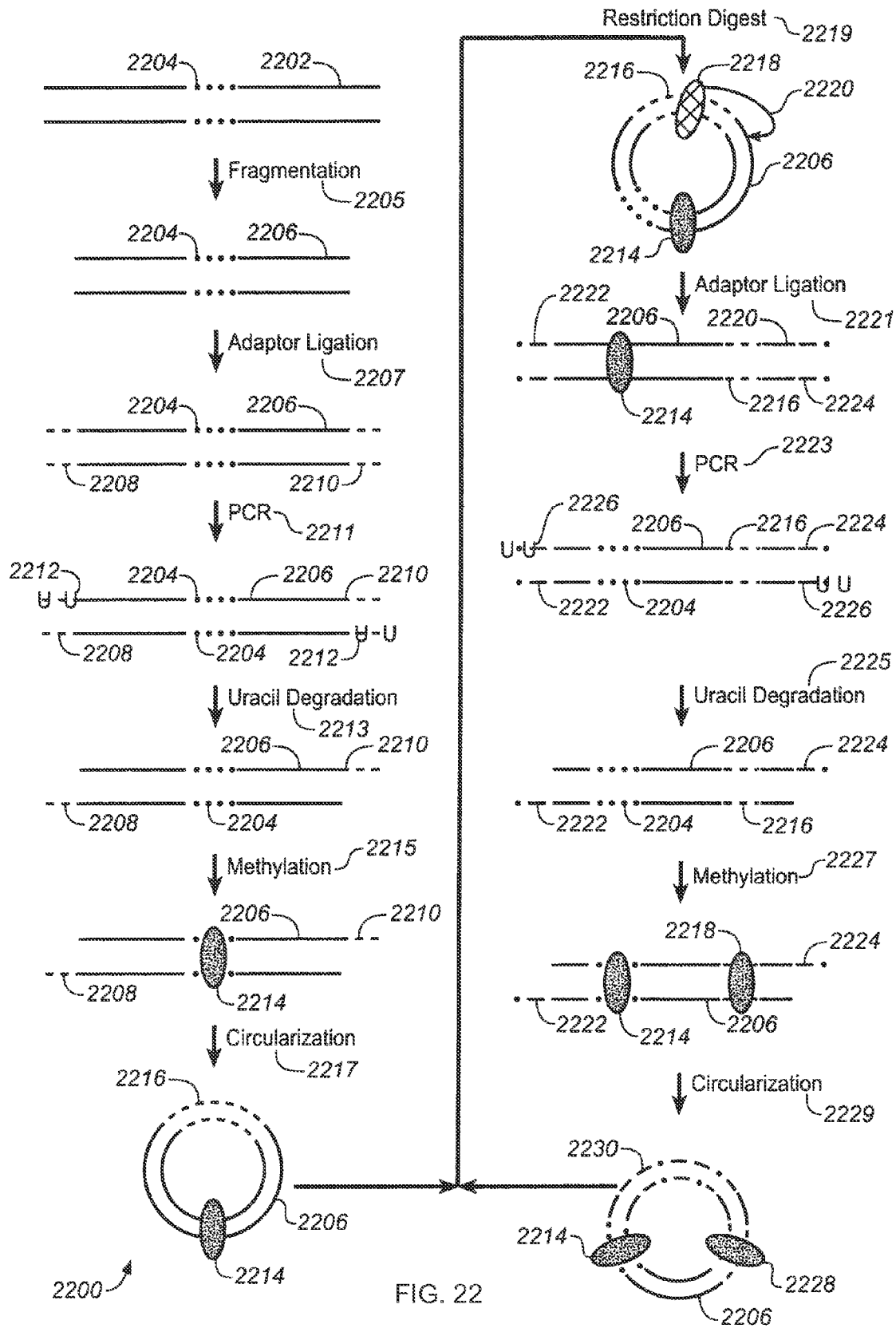
FIG. 22 is a schematic illustration of one embodiment of a method for inserting multiple adaptors.

FIG. 22 is a schematic illustration of a process where a desired position of a second adaptor relative to a first adaptor is selected using methylation and uracil degradation. FIG. 22 shows genomic DNA of interest 2202 having a Type IIs restriction endonuclease recognition site at 2204. The genomic DNA is fractionated or fragmented in process 2205 to produce fragments 2206 having a Type IIs restriction endonuclease recognition site 2204. Adaptor arms 2208 and 2210 are ligated to fragment 2206 in process 2207. Fragment 2206 with first and second adaptor arms 2208 and 2210 (a library construct) are amplified by PCR in process 2211, using uracil-modified primers 2212 complementary to adaptor arms 2208 and 2210. The primers generate a PCR product with uracils at or close to the Type IIs restriction endonuclease recognition site. In process 2213, the uracils are specifically degraded using, e.g., uracil-DNA glycosylase enzyme (Krokan, et al., (1997) Biochem. J. 325:1-16), leaving a PCR product that is single-stranded in the Type IIs restriction endonuclease recognition site region. As shown, uracil incorporation and degradation may be used to render the Type IIs restriction endonuclease recognition site single-stranded; however, as described further herein, other methods may be employed to render these regions single-stranded including use of 3' or 5' exonucleases in a limited digest.

In process 2215, a sequence-specific methylase is used to methylate bases in each double-stranded Type IIs restriction endonuclease recognition site (here, there is methylation 2214 of the Type IIs restriction endonuclease recognition site 2204), to protect these sites from Type IIs restriction endonuclease recognition. However, the single-stranded Type IIs restriction endonuclease recognition sites in first and second adaptor arms 2208 and 2210 are not methylated, and, once circularized and ligated 2217, the Type IIs restriction endonuclease recognition site re-forms 2216 such that this Type IIs restriction endonuclease recognition site is available for restriction. When selecting the methylase and the Type IIs restriction endonucleases for this process, it is necessary that the two enzymes recognize the same sequence or that one enzyme recognizes a subsequence (sequence within the sequence) of the other enzyme. The circularized construct is then cut with the Type IIs restriction endonuclease in process 2219 where the Type IIs restriction endonuclease recognition site is indicated at 2218 and the construct is cut at 2220, resulting in a linearized construct available for ligation of a second set of adaptor arms to be added to the construct in process 2221.

Ligation process 2221 adds first 2222 and second 2224 adaptor arms of the second adaptor to the linearized construct, and a second amplification is performed by PCR at process 2223, again using uracil-modified primers 2226 complementary to adaptor arms 2222 and 2224. As before, the primers generate a PCR product with uracils close to the Type IIs restriction endonuclease recognition site. In process 2225, the uracils are specifically degraded leaving a PCR product that is single-stranded in the Type IIs restriction endonuclease recognition site region of the first and second adaptor arms 2222 and 2224 of the second adaptor. In process 2227, the sequence-specific methylase again is used to methylate bases in the double-stranded Type IIs restriction endonuclease recognition sites in the target nucleic acid fragment (again, there is methylation 2214 of the Type IIs restriction endonuclease recognition site 2204) and in the Type IIs restriction endonuclease recognition site of the first adaptor 2228 protecting these sites from Type IIs restriction endonuclease recognition. The methylated construct is then circularized at process 2229, where the Type IIs restriction endonuclease recognition site in the first and second arms 2222 and 2224 of the second adaptor is re-formed 2230 and the process is repeated where the circularized construct is cut again with the Type IIs restriction endonuclease in process 2219 to generate another linearized construct (this one with first and second adaptors already added) available for ligation of a third pair of adaptor arms to the construct. The process can be repeated to add as many adaptors as are desired. As shown here, the first added adaptor had one Type IIs restriction endonuclease recognition site; however, in other aspects, the first added adaptor may have two Type IIs restriction endonuclease recognition sites to allow for precise selection of target nucleic acid size for the construct.

In addition to the above methods for controlled insertion of multiple interspersed adaptors, constructs comprising adaptors in specific orientations may further be selected by enriching a population of constructs for those with adaptors in the desired orientations. Such enrichment methods are described in U.S. Ser. Nos. 60/864,992 filed Nov. 9, 2006; 11/943,703, filed Nov. 2, 2007; 11/943,697, filed Nov. 2, 2007; 11/943,695, filed Nov. 2, 2007; and PCT/US07/835,540; filed Nov. 2, 2007, all of which are incorporated by reference in their entirety for all purposes and in particular for all teachings related to methods and compositions for selecting for specific orientations of adaptors.

II.E. Making DNBs

Any of the nucleic acid templates of the invention described above can be used to generate nucleic acid nanoballs, which are also referred to herein as "DNA nanoballs," "DNBs", and "amplicons". These nucleic acid nanoballs are generally concatemers comprising multiple copies of a nucleic acid template of the invention, although nucleic acid nanoballs of the invention may be formed from any nucleic acid molecule using the methods described herein. In certain aspects, DNBs comprise repeating monomeric units, each monomeric unit comprising one or more adaptors and a target nucleic acid. In further embodiments, populations of DNBs are formed using methods described herein, such that population includes DNBs with different target sequences, such that together the population of DNBs comprise one or more genome equivalents of one or more entire genomes.

In one aspect, rolling circle replication (RCR) is used to create concatemers of the invention. The RCR process has been shown to generate multiple continuous copies of the M13 genome, (Blanco, et al., (1989) *J Biol Chem* 264:8935-8940). In such a method, a nucleic acid is replicated by linear concatemerization. Guidance for selecting conditions and reagents for RCR reactions is available in many references available to those of ordinary skill, including U.S. Pat. Nos. 5,426,180; 5,854,033; 6,143,495; and 5,871,921, each of which is hereby incorporated by reference in its entirety for all purposes and in particular for all teachings related to generating concatemers using RCR or other methods.

Generally, RCR reaction components include single stranded DNA circles, one or more primers that anneal to DNA circles, a DNA polymerase having strand displacement activity to extend the 3' ends of primers annealed to DNA circles, nucleoside triphosphates, and a conventional polymerase reaction buffer. Such components are combined under conditions that permit primers to anneal to DNA circle. Extension of these primers by the DNA polymerase forms concatemers of DNA circle complements. In some embodiments, nucleic acid templates of the invention are double stranded circles that are denatured to form single stranded circles that can be used in RCR reactions. In some embodiments, amplification of circular nucleic acids may be implemented by successive ligation of short oligonucleotides, e.g., 6-mers, from a mixture containing all possible sequences, or if circles are synthetic, a limited mixture of these short oligonucleotides having selected sequences for circle replication, a process known as "circle dependent amplification" (CDA). "Circle dependant amplification" or "CDA" refers to multiple displacement amplification of a double-stranded circular template using primers annealing to both strands of the circular template to generate products representing both strands of the template, resulting in a cascade of multiple-hybridization, primer-extension and strand-displacement events. This leads to an exponential increase in the number of primer binding sites, with a consequent exponential increase in the amount of product generated over time. The primers used may be of a random sequence (e.g., random hexamers) or may have a specific sequence to select for amplification of a desired product. CDA results in a set of concatemeric double-stranded fragments being formed.

Concatemers may also be generated by ligation of target DNA in the presence of a bridging template DNA complementary to both beginning and end of the target molecule. A population of different target DNA may be converted in concatemers by a mixture of corresponding bridging templates.

In some embodiments, a subset of a population of nucleic acid templates may be isolated based on a particular feature, such as a desired number or type of adaptor. This population can be isolated or otherwise processed (e.g., size selected) using conventional techniques, e.g., a conventional spin column, or the like, to form a population from which a population of concatemers can be created using techniques such as RCR.

Methods for forming DNBs of the invention are described in Published Patent Application Nos. WO2007120208, WO2006073504, WO2007133831, and US2007099208, and U.S. Patent Application Nos. 60/992,485; 61/026,337; 61/035,914; 61/061,134; 61/116,193; 61/102,586; Ser. Nos. 12/265,593; 12/266,385; 11/938,096; 11/981,804; Ser. Nos. 11/981,797; 11/981,793; 11/981,767; 11/981,761; 11/981,730, filed Oct. 31, 2007; Ser. Nos. 11/981,685; 11/981,661; 11/981,607; 11/981,605; 11/927,388; 11/927,356; 11/679,124; 11/541,225; 10/547,214; 11/451,692; and 11/451,691, all of which are incorporated herein by reference in their entirety for all purposes and in particular for all teachings related to forming DNBs.

III. Methods of Obtaining Sequence Information

Nucleic acids, nucleic acid fragments, and template nucleic acid constructs isolated and generated in accordance with any of the methods described herein can be used in applications for obtaining sequence information. Such methods include sequencing and detecting specific sequences in target nucleic acids (e.g., detecting particular target sequences (e.g. specific genes) and/or identifying and/or detecting SNPs). The methods described herein can also be used to detect nucleic acid rearrangements and copy number variation. Nucleic acid quantification, such as digital gene expression (i.e., analysis of an entire transcriptome—all mRNA present in a sample) and detection of the number of specific sequences or groups of sequences in a sample, can also be accomplished using the methods described herein.

In one aspect, the fragments and nucleic acid constructs generated in accordance with the present invention provide the advantage of allowing short sequence reads to be combined and assembled to provide sequence information on longer contiguous regions of the target nucleic acid (contiguous segments of nucleic acids comprising two or more nucleotides in a row are also referred to herein as "contigs"). As used herein, "sequence reads" refers to identifying or determining the identity of one or more nucleotides in a region of a target nucleic acid. Generally sequence reads provide information on the sequence of a segment of a nucleic acid comprising two or more contiguous nucleotides. In certain aspects, unchained base reads are used to generate sequence information, as described in Drmanac et al., (2010), *Science,* 327: 78-81 and supplementary online material, which is hereby incorporated by reference in its entirety and in particular for all teachings related to methods and compositions for sequencing nucleic acids.

III.A. LFR

In one aspect, Long Fragment Read (LFR) sequencing methods are used with any of the fragments or nucleic acid template constructs or DNA nanoballs described herein. Although the following is described primarily in terms of genomic nucleic acid fragments, it will be appreciated that any nucleic acid molecules would be amenable to be the methods described below. General LFR methods are described in U.S. patent application Ser. No. 11/451,692, filed Jun. 13, 2006, now U.S. Pat. No. 7,709,197, and in U.S. patent application Ser. No. 12/329,365, filed Dec. 5, 2008, each of which is hereby incorporated by reference in its entirety and in particular for all teachings related to LFR and sequencing using LFR methods.

In general, LFR methods include physical separation of long genomic DNA fragments across many different aliquots such that the probability of any given region of the genome of both the maternal and paternal component in the same aliquot is very rare. By placing a unique identifier in each aliquot and analyzing many aliquot in the aggregate, long fragments of DNA can be assembled into a diploid genome, e.g. the sequence of each parental chromosome can be obtained.

Aliquots of LFR fragments are also referred to herein as "LFR libraries" and "LFR aliquot libraries". These LFR libraries may include tagged and non-tagged fragments.

LFR provides a novel and inexpensive way of DNA preparation and tagging with related algorithms and software to enable an accurate assembly of separate sequences of parental chromosomes (i.e., complete haplotyping) in diploid genomes (such as in human embryonic or adult somatic cells) at significantly reduced experimental and computational costs (below $1000). This process, universally applicable with any existing genome or metagenome sequencing technology including future longer read (~1 kb) methods, is in many ways equivalent to sequencing single DNA molecules of greater than 100 kb in length, a technically challenging proposition. The proposed long fragment read (LFR) process does not require expensive, less accurate and lower yield single molecule detection. The LFR process is based upon the stochastic physical separation of a genome in long fragments (100-1000 kb) into many aliquots in such a way that each aliquot contains 10% or less of a haploid genome.

LFR methods as described herein find particular use when the starting amount of DNA to be analyzed is low. In some embodiments, LFR methods of the invention are used to analyze the genome of an individual cell. In further embodiments, LFR methods of the invention are used to analyze the genomes from 1-100 cells. In still further embodiments, LFR methods of the invention are used to analyze the genomes from 1-5, 5-10, 2-90, 3-80, 4-70, 5-60, 6-50, 7-40, 8-30, 9-20, and 10-15 cells. The process for isolating DNA when small numbers of cells are used is similar to the methods described above, but occurs in a smaller volume. As will be appreciated, LFR methods of the present invention can also be used when the starting amount of DNA is high (i.e., greater than the equivalent from 50-100 cells).

In some embodiments after the DNA is isolated and before it is divided into separate aliquots (such as into individual wells of a multiwell plate or into different emulsion droplets, as described in further detail below), the genomic DNA is carefully fragmented to avoid loss of material, particularly to avoid loss of sequence from the ends of each fragment, since loss of such material will result in gaps in the final genome assembly. In some cases, sequence loss is avoided through use of an infrequent nicking enzyme, which creates starting sites for a polymerase, such as $\phi 29$ polymerase, at distances of approximately 100 kb from each other. As the polymerase creates the new DNA strand, it displaces the old strand, with the end result being that there are overlapping sequences near the sites of polymerase initiation, resulting in very few deletions of sequence.

In specific embodiments, fragments produced according to one or more embodiments of CoRE as described above are used in the LFR methods described herein. In general, the process of isolating DNA from a sample will result in 100 kb fragments. These fragments may then be further fragmented or used to generate shorter fragments using the methods described herein (including CoRE) either before or after or both before and after being divided into separate aliquots.

In some embodiments, DNA is isolated from a sample and then aliquoted into a number of different separate mixtures (such separate mixtures are also referred to interchangeably herein as "aliquots"). After aliquoting, the DNA in the separate mixtures is then fragmented, using any of the methods described herein, including any of the embodiments of CoRE fragmentation discussed above. The DNA in the separate mixtures may also be used to generate shorter fragments by using a controlled DNA synthesis or amplification using the DNA in the separate mixtures as templates. Such synthesis and amplification methods are known in the art and in general use multiple spaced-apart primers corresponding to different regions of the DNA in the separate mixtures to replicate and/or amplify the DNA. In such embodiments, a second population of DNA fragments is formed that are of shorter length than the longer fragments from which they are derived. In further embodiments, the DNA in the separate mixtures is fragmented (or used as a template to produce shorter fragments) multiple times. In still further embodiments, after one or more rounds of fragmenting, the DNA in each aliquot is tagged with adaptor tags in accordance with the methods described herein.

In one embodiment, genomic fragments (either before or after fragmentation) are aliquoted such that the nucleic acids are diluted to a concentration of approximately 10% of a haploid genome per aliquot. At such a level of dilution, approximately 95% of the base pairs in a particular aliquot are non-overlapping. This method of aliquoting, also referred to herein as a long fragment read (LFR) fragmentation method, can in particular embodiments be used on large molecular weight fragments isolated according to the methods described above and further herein. LFR usually begins with a short treatment of genomic nucleic acids, usually genomic DNA, with a 5' exonuclease to create 3' single-stranded overhangs. Such single stranded overhangs serve as multiple displacement amplification (MDA) initiation sites. The 5' exonuclease treated DNA is then diluted to sub-genome concentrations and dispersed across a number of aliquots. In some embodiments, these aliquots are dispersed across a number of wells in a multiwell plate. In other embodiments, the aliquots are contained in different emulsion droplets, as described in further detail below. The fragments in each aliquot are amplified, usually using an MDA method that includes one or more of the additives described above for reducing or preventing bias.

As discussed above, to achieve an appropriate separation of fragments, in general the DNA is aliquoted/diluted to a concentration of approximately 1-15% of a haploid genome per aliquot. In further embodiments, the DNA is aliquoted to a concentration of approximately 10% of a haploid genome per aliquot. At this concentration, 95% of the base pairs in an aliquot are non-overlapping. Dilution to sub-genome aliquots results in a statistical separation such that maternal and paternal fragments will usually land in different aliquots. It should be appreciated that the dilution factor can depend on the original size of the fragments. Techniques that allow larger fragments result in a need for fewer aliquots, and those that result in shorter fragments may require a larger number of aliquots.

In further embodiments, the DNA is diluted (i.e., aliquoted) to a concentration of approximately 1, 2, 3, 4, 5, 6, 7, 8, 9, 10, 11, 12, 13, 14, and 15% of a haploid genome per aliquot. In still further embodiments, the DNA is diluted to a concentration of less than 1% of a haploid genome per aliquot. In yet further embodiments, the DNA is diluted to about 0.1-1%, 0.2-0.9%, 0.3-0.8%, 0.4-0.7%, and 0.5-0.6% of a haploid genome per aliquot.

In some embodiments, the fragments are amplified before, after or both before and after aliquoting. In further embodiments, the fragments in each aliquot are further fragmented and then tagged with an adaptor tag such that fragments from the same aliquot will all comprise the same tag adaptor; see for example US 2007/0072208, hereby incorporated by reference in its entirety, and in particular for the discussions of additional aliquoting and coverage. In certain embodiments, fragments are not amplified after aliquoting, but are further fragmented using any of the methods discussed herein and known in the art. In certain embodiments, DNA is not amplified prior to aliquoting, but is both fragmented and amplified after aliquoting. DNA in separate aliquots may also in further embodiments be fragmented and amplified multiple times.

In still further embodiments, multiple tiers of aliquoting are used in LFR methods of the invention. Aliquots in one or more tiers may be tagged such that aliquots in each subsequent tier can be identified by their aliquot of origin in the previous tier. The fragments in each round of aliquot may or may not be amplified and/or further fragmented prior to the next round of aliquoting.

In further embodiments, sequence information obtained from LFR aliquots are assembled using bioinformatics techniques that fully utilize information from a large number of ~10 Mb aliquots, which reduces the computation effort (i.e., capital cost of computers) by about 100 fold. The added cost of reading 10-base tags (10% in sequencing reagents and instrument time for 2×50-base mate-pair reads) is offset multiple times by this savings in computation and increased sequence accuracy.

In a further embodiment, methods of the present invention are integrated with high throughput low cost short read DNA sequencing technology, such as those described in published patent application numbers WO2007120208, WO2006073504, WO2007133831, and US2007099208, and U.S. patent application Ser. Nos. 11/679,124; 11/981,761; 11/981,661; 11/981,605; 11/981,793; 11/981,804; 11/451,691; 11/981,607; 11/981,767; 11/982,467; 11/451,692; 11/541,225; 11/927,356; 11/927,388; 11/938,096; 11/938,106; 10/547,214; 11/981,730; 11/981,685; 11/981,797; 11/934,695; 11/934,697; 11/934,703; 12/265,593; 11/938,213; 11/938,221; 12/325,922; 12/252,280; 12/266,385; 12/329,365; 12/335,168; 12/335,188; and 12/361,507 all of which are incorporated herein by reference in their entirety for all purposes and in particular for all teachings related to DNA sequencing.

III.A.1. Tagging

Fragments in different aliquots can be tagged with one or more adaptor tags in order to identify fragments that were contained in the same aliquot. In some embodiments, fragments in different aliquots can be tagged with one or more "adaptor tags" (sometimes referred to as "tagging sequences", "tags" or "barcodes" (note these were also referred to as "adaptors" in U.S. Provisional App. No. 61/187,162, filed Jun. 15, 2009). Adaptor tags are in general oligonucleotides that are ligated to nucleic acid fragments to serve as an identifier during LFR methods described herein. Although adaptor tags are in general sequenced along with the target fragments to which they are attached, adaptor tags do not generally (but in some embodiments can) serve the same functions as adaptors as described herein for constructing nucleic acid constructs or in cPAL sequencing methods. In general, the sequence of an adaptor tag is used to identify the aliquot of origin of the fragment to which that tag is attached.

As outlined above, some embodiments of LFR do not require adaptor tags; in these embodiments, the LFR aliquots are put in different vessels, such as the microtiter plate embodiments discussed herein. In these embodiments, the LFR fragments can again be additionally fragmented, without the addition of adaptor tags, as long as the source of each aliquot is traced.

Alternatively, as described in detail below, the aliquots are tagged with adaptor tags to identify fragments that were contained in the same aliquot. Adaptor tags can be added in a variety of ways, as outlined below. In some cases, adaptor tags can be added (as for other adaptor additions described herein) in such a manner as to prevent "polymerization" of the adaptor tags.

Figure 27:
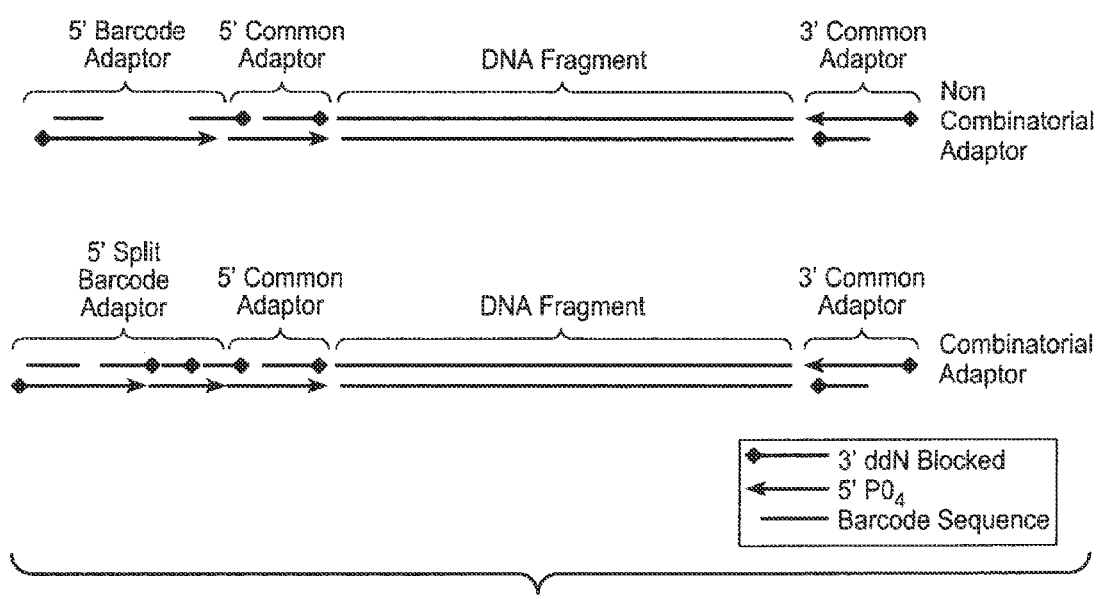
FIG. 27 is a schematic illustration of one embodiment of a method for tagging nucleic acid fragments.

In embodiments that utilize tagging, fragments in each aliquot are tagged with one or more adaptor tags. In some embodiments, the adaptor tag is designed in two segments—one segment is common to all wells and blunt end ligates directly to the fragments using methods described further herein. The second segment is unique to each well and may also contain a "barcode" sequence such that when the contents of each well are combined, the fragments from each well can be identified. FIG. 27 illustrates some exemplary barcode adaptor tags that can be added to the fragments for this aspect of the invention.

In many aspects of the present invention, it is useful to have fragments that are repaired to have blunt ends, and in some cases, it can be desirable to alter the chemistry of the termini such that the correct orientation of phosphate and hydroxyl groups is not present, thus preventing "polymerization" of the target sequences. The control over the chemistry of the termini can be provided using methods known in the art and described in further detail above in relation to further treatment of fragments and in relation to ligation of adaptors to target nucleic acids. Such methods are also applicable to controlling the directionality of ligating adaptor tags to fragments in the methods described herein. Further methods for controlling the orientation of adaptor tag orientation are illustrated in FIG. 7, in which the primers and uracil positions are chosen such that either the "upstream" or "downstream" recognition site may be selectively protected from inactivation or inactivated. For example, in FIG. 7, the two different adaptor tag arms (represented as rectangles) each comprise a recognition site for a restriction endonuclease (represented by the circle in one adaptor tag arm and by a triangle in the other). If the adaptor tag arm with the recognition site represented by the circle needs to be protected using the above-described uracil degradation method, then the uracil-modified amplification primers are designed to incorporate uracils into that recognition site. Then upon uracil degradation, that adaptor tag arm is rendered single stranded (represented by the half-rectangles), thus protecting that recognition site from inactivation.

In some circumstances, the use of phosphatase eliminates all the phosphate groups, such that all ends contain hydroxyl groups. Each end can then be selectively altered to allow ligation between the desired components. One end of the fragments can then be "activated", in some embodiments by treatment with alkaline phosphatase.

FIG. 27 provides a schematic illustration of some embodiments of adaptor tag design for use as a tag in accordance with the LFR methods described herein. Generally, the adaptor tag is designed in two segments—one segment is common to all aliquots and blunt end ligates directly to the fragments using methods described further herein. The "common adaptor tag" can be used as a control for any potential concentration differences between aliquots. In the embodiment pictured in FIG. 27, the "common" adaptor tag is added as two adaptor tag arms—one arm is blunt end ligated to the 5' end of the fragment and the other arm is blunt end ligated to the 3' end of the fragment. The second segment of the adaptor tag is a "barcode" segment that is unique to each well. This barcode is generally a unique sequence of nucleotides, and each fragment in a particular well is given the same barcode. Thus, when the tagged fragments from all the aliquots are re-combined for sequencing applications, fragments from the same aliquot can be identified through identification of the barcode adaptor tag. In the embodiment illustrated in FIG. 27, the barcode is ligated to the 5' end of the common adaptor tag arm. The common adaptor tag and the barcode adaptor tag can be ligated to the fragment sequentially or simultaneously. As is described in further detail herein, the ends of the common adaptor tag and the barcode adaptor tag can be modified such that each adaptor tag segment will ligate in the correct orientation and to the proper molecule. Such modifications prevent "polymerization" of the adaptor tag segments or of the fragments by ensuring that the fragments are unable to ligate to each other and that the adaptor tag segments are only able to ligate to the fragment in the desired orientation. Such modifications are also discussed in detail in the sections above regarding controlling adaptor ligation to target nucleic acids for producing nucleic acid template constructs of the invention.

In further embodiments, a three segment design is utilized for the adaptor tags used to tag fragments in each well. This embodiment is similar to the barcode adaptor tag design described above, except that the barcode adaptor tag segment is itself split into two segments (see FIG. 27). This design allows for a wider range of possible barcodes by allowing combinatorial barcode adaptor tag segments to be generated by ligating different barcode segments together to form the full barcode segment. This combinatorial design provides a larger repertoire of possible barcode adaptor tags while reducing the number of full size barcode adaptor tags that need to be generated.

In one embodiment, construction of an LFR library of multiple aliquots of tagged fragments involves using different adaptor tag sets. A and B adaptor tags are easily modified to each contain a different half-barcode sequence to yield thousands of combinations. In certain embodiments, the half-barcode sequences are incorporated into the same adaptor tag. This can be achieved by breaking the B adaptor tag into two parts, each with a half barcode sequence separated by a common overlapping sequence used for ligation (FIG. 28E). The two tag components have 4-6 bases each. An 8-base (2×4 bases) tag set is capable of uniquely tagging 65,000 aliquots. One extra base (2×5 bases) will allow error detection and 12 base tags (2×6 bases, 12 million unique barcode sequences) can be designed to allow substantial error detection and correction in 10,000 or more aliquots using Reed-Solomon design. Methods for designing adaptor tags are further disclosed in U.S. patent application Ser. No. 12/697,995, filed Feb. 1, 2010, which is hereby incorporated by reference in its entirety for all purposes and in particular for all teachings related to Reed-Solomon algorithms and their use in designing adaptor tags (which are also referred to as "adaptors" in that application).

In still further embodiments, the ligation of the adaptor tag is controlled for orientation, that is, the present invention provides for directional ligation of the adaptor tag. Such directional ligation may utilize any of the methods described herein for ligating adaptors to target nucleic acids. In an exemplary embodiment, half-adaptor tags (also referred to herein as tag components and adaptor tag segments) are ligated on each side of DNA fragments in two separate steps. The first half-adaptor tag is blocked on its 3' end by incorporation of a dideoxy nucleotide on one strand, thus allowing ligation only to the 3' ends of DNA fragments. Thus, a double-stranded fragment has a half-adaptor tag ligated to the 3' terminus of each strand of the fragment (i.e., there is a half-adaptor tag ligated to the 3' end of the "Watson" strand and to the "Crick" strand). These "half-tagged" fragments are then denatured and combined with primers complementary to the ligated adaptor tag and polymerase to produce double-stranded DNA from each DNA fragment strand ligated to a first half adaptor tag. In certain embodiments, the first half-adaptor tag comprises a barcode or half-barcode as discussed in further detail herein. The second half-adaptor tag (which in some embodiments does not contain a barcode) can then be ligated to the newly created 3' end of the replicated fragment comprising the first half-adaptor tag. An advantage of this sequential method of adding each half-adaptor tag to the fragments is that only those fragments ligated to the first half-adaptor tag will then undergo ligation with the second half-adaptor tag. As will be appreciated, multiple "half-adaptor tags" can be added during each cycle—in other words, 1 or more tag components can be directionally ligated to a chosen terminus of each fragment, and then upon denaturation and replication, 1 or more additional tag components can be added to the newly created 3' ends. Thus, different sets of tag components can be used in a variety of combinations to produce combinatorial tags for tagging fragments.

In still further embodiments, the first half-adaptor tag is blocked on the 5' end, allowing ligation only to the 5' end of the DNA fragments, and the second half-adaptor tag is blocked on the 3' end, allowing ligation only to the 3' end of the DNA fragments. Thus, both halves of the adaptor tag can be ligated to the fragments simultaneously in this embodiment.

In further embodiments, methods of adding adaptor tags or other tags to fragments are conducted in accordance with the disclosure of adding adaptors in WO2007120208, WO2006073504, WO2007133831, and US2007099208, and U.S. patent application Ser. Nos. 11/679,124; 11/981, 761; 11/981,661; 11/981,605; 11/981,793; 11/981,804; 11/451,691; 11/981,607; 11/981,767; 11/982,467; 11/451, 692; 11/541,225; 11/927,356; 11/927,388; 11/938,096; 11/938,106; 10/547,214; 11/981,730; 11/981,685; 11/981, 797; 11/934,695; 11/934,697; 11/934,703; 12/265,593; 11/938,213; 11/938,221; 12/325,922; 12/252,280; 12/266, 385; 12/329,365; 12/335,168; 12/335,188; and 12/361,507, each of which is hereby incorporated by reference in its entirety for all purposes and in particular for all teachings related to adaptors.

After the fragments in each well are tagged, all of the aliquots can in some embodiments be combined to form a single population. Sequence information obtained from these tagged fragments will be identifiable as belonging to a particular aliquot by the barcode tag adaptor tags attached to each fragment.

III.A.2. Multi-Well Format LFR

In many embodiments, each aliquot is contained in a separate well of a multi-well plate (for example, a 384 or 1536 well microtiter plate). It will be appreciated that although the following discussion of LFR is provided in terms of a multi-well plate, that any number of different types of containers and systems can be used to hold the different aliquots generated in this method. Such containers and systems are well known in the art and it would be apparent to one of skill in the art what types of containers and systems would be appropriate to use in accordance with this aspect of the invention.

In some embodiments, a 10% genome equivalent is aliquoted into each well of a multiwell plate. If a 384 well plate is used, a 10% genome equivalent aliquot into each well results in each plate comprising 38 genomes in total. In further embodiments, a 5-50% genome equivalent is aliquoted into each well. As noted above, the number of aliquots and genome equivalents used in LFR methods of the present invention can depend on the original fragment size.

After separation across multiple wells, the fragments in each well can be amplified, usually using an MDA method. In certain embodiments, the MDA reaction is a modified $1)_{29}$ polymerase-based amplification reaction. Although much of the discussion herein is in terms of an MDA reaction, it will be appreciated by those of skill in the art that many different kinds of amplification reactions can be used in accordance with the present invention, and that such amplification reactions are well known in the art and described generally in Maniatis et al., Molecular Cloning: A Laboratory Manual, 2d Edition, 1989, and Short Protocols in Molecular Biology, ed. Ausubel, et al, hereby incorporated by reference. In certain embodiments, MDA methods used before or after each step of aliquoting can include additives to reduce amplification bias, as is discussed in further detail above.

After amplification of the fragments in each well, the amplification products may be subjected to another round of fragmentation. In some embodiments the above-described CoRE method is used to further fragment the fragments in each well following amplification. As discussed above, in order to use the CoRE method, the MDA reaction used to amplify the fragments in each well is designed to incorporate uracils or other nucleotide analogs into the MDA products.

III.A.3. Emulsion Droplets

In certain LFR applications, emulsion droplets are used in the aliquoting and tagging methods. Methods for producing emulsion droplets containing nucleic acids and/or reagents for enzymatic reactions are known in the art—see for example, Weizmann et al., (2006), *Nature Methods*, Vol. 3 No. 7, pages 545-550, which is hereby incorporated by reference in its entirety for all purposes and in particular for all teachings related to forming emulsions and conducting enzymatic reactions within emulsion droplets.

In some embodiments, nucleic acids isolated from a sample or nucleic acid fragments, including fragments generated using CoRE fragmentation methods described herein, are contained within emulsion droplets. In such embodiments, each droplet generally contains a small number of fragments. In LFR methods used for whole genome sequencing, the population of emulsion droplets together will contain fragments representing one or more genome equivalents. In further embodiments, the population of emulsion droplets together will contain fragments representing 5-15 genome equivalents. In still further embodiments, the population of emulsion droplets together will contain fragments representing 1, 2, 3, 4, 5, 6, 7, 8, 9, 10, 11, 12, 13, 14, 15, 16, 17, 18, 19 or 20 genome equivalents.

In further embodiments, two or more adaptor tag components are also contained in emulsion droplets. For clarity's sake, emulsion droplets containing target nucleic acid fragments are referred to as "target nucleic acid droplets", and emulsion droplets containing adaptor tags are referred to as "adaptor tag droplets".

In certain embodiments, enzymes such as ligase and other reagents such as buffers and cofactors are also contained within the target nucleic acid droplets and/or in the adaptor tag droplets. "Chaining" of the fragments or the adaptor tags within the same droplet can be prevented by altering the termini as described in further detail above, such that ligation only occurs between fragments and adaptors in the preferred orientation. Ligase and other reagents may also be included in a separate set of emulsion droplets.

In still further embodiments, individual target nucleic acid droplets are combined with individual adaptor tag droplets, such that the droplets merge. In embodiments in which either the target nucleic acid droplets or the adaptor tag droplets contain ligase and/or other reagents for ligation reactions, upon merging of the adaptor tag and nucleic acid droplets, the nucleic acid fragments will ligate to one or more adaptor tags. In embodiments in which ligase and other reagents are included in a separate set of emulsion droplets, ligation will occur upon merging of the individual target nucleic acid droplets, the individual adaptor tag droplets and the ligase/reagent droplets.

Figure 28:
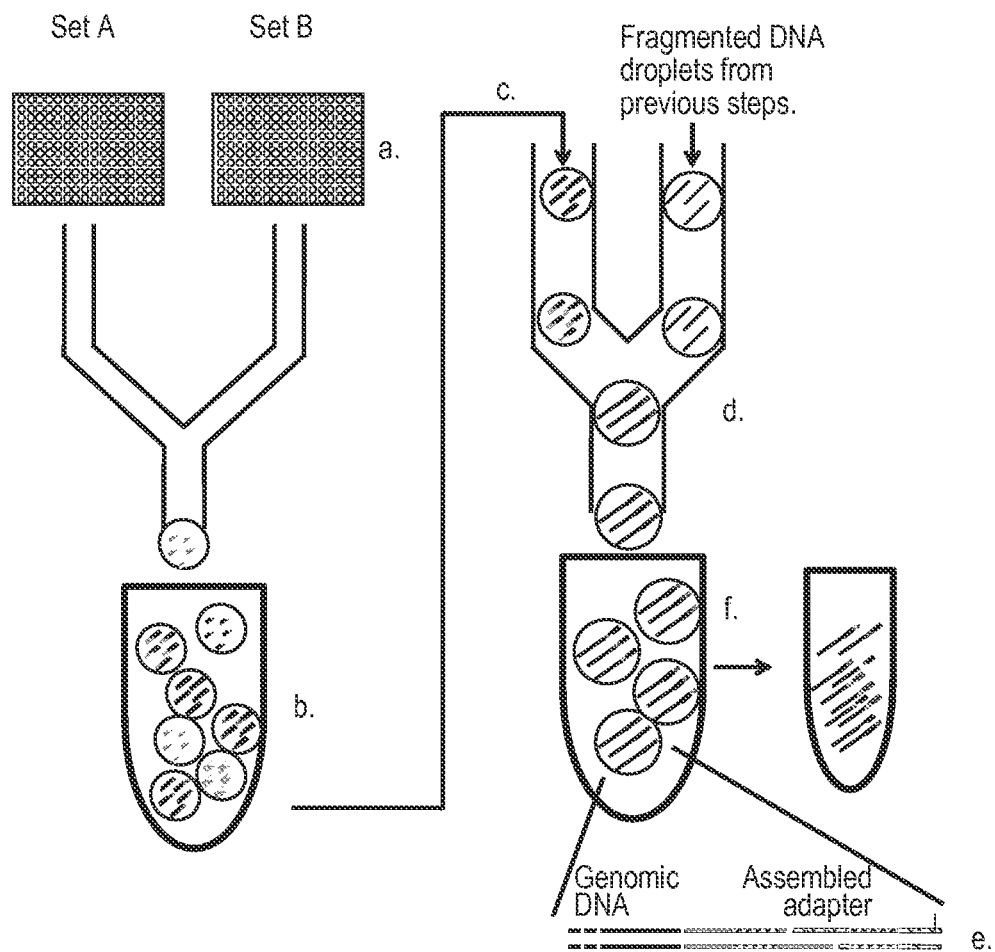
FIG. 28(A)-(F) is a schematic overview of steps of an embodiment of the long fragment read method of the present invention.

In embodiments in which the adaptor tag droplets contain two or more "half-adaptors" (also referred to herein as "tag components"), merging of the droplets results in the target nucleic acid fragments in each droplet being ligated to unique combinatorial adaptor tags. (FIG. 28 steps a and b). Two sets of 100 half barcodes is sufficient to uniquely identify 10,000 aliquots (FIG. 28 step e). However, increasing the number of half barcode adapters to over 300 can allow for a random addition of barcode droplets to be combined with the sample DNA with a low likelihood of any two aliquots containing the same combination of barcodes. An advantage of this is that tens of thousands of distinct combinatorial barcode adaptor tag droplets can be made in large quantities and stored in a single tube to be used as a reagent for thousands of different LFR libraries.

In some embodiments, 10,000 to 100,000 or more aliquot libraries (i.e., emulsion droplets) are used in methods of the invention. In further embodiments, the emulsion LFR methods are scaled up by increasing the number of initial half barcode adaptor tags. These combinatorial adaptor tag droplets are then fused one-to-one with droplets containing ligation ready DNA representing less than 1% of the haploid genome (FIG. 28D). Using a conservative estimate of 1 nl per droplet and 10,000 drops this represents a total volume of 10 μl for an entire LFR library; a volume reduction and thus a cost reduction of approximately 400 fold can be possible. In such embodiments, the emulsion droplets provide the ability to miniaturize LFR aliquots from microliters to nanoliters and increase the number of aliquots generally used in such methods from hundreds to thousands (reducing DNA per aliquot from 10% to less than 1%). Such a system with 10,000 or more emulsion droplets opens the possibility to conduct complete genome sequencing starting with just one cell.

In further embodiments, 1,000 to 500,000 droplets of fragments and adaptor tags are used in methods of the invention. In still further embodiments, 10,000-400,000; 20,000-300,000; 30,000-200,000; 40-000-150,000; 50,000-100,000; 60,000-75,000 droplets of fragments and adaptor tags are used in methods of the invention. In yet further embodiments, at least 1,000, at least 10,000, at least 30,000, and at least 100,000 droplets of fragments and adaptor tags are used in methods of the invention.

In further embodiments in which droplets of adaptor tags contain at least 2, 3, 4, 5, 6, 7, 8, 9, 10 different sets or components of adaptor tags, combining these adaptor tag droplets with droplets of nucleic acid fragments results in at least a portion of the resultant combined droplets having fragments that are tagged with different combinations of tag components. In yet further embodiments, at least 1,000, at least 10,000, at least 30,000, and at least 100,000 different droplets contain fragments tagged with different combinations of tag components. In still further embodiments, 1,000 to 500,000 droplets contain fragments tagged with different combinations of tag components. In still further embodiments, 10,000-400,000; 20,000-300,000; 30,000-200,000; 40-000-150,000; 50,000-100,000; 60,000-75,000 droplets contain fragments tagged with different combinations of tag components.

In some embodiments, nucleic acids from a sample or nucleic acid fragments generated using any of the methods described herein are contained within emulsion droplets, as discussed above. Prior to combining with adaptor tag droplets and tagging, the nucleic acids or fragments within each nucleic acid droplet are fragmented using any of the methods described herein. Such fragmentation and then subsequent tagging allows identification of fragments that are contained in the same droplet and that may also be contiguous segments of the same region of the genome. Thus, sequence information of the tagged target nucleic acid fragments can be assembled and ordered using the identification of the attached tags. In certain embodiments, sequencing of the fragments includes obtaining information about their attached adaptor tags.

In certain embodiments, the size of emulsion droplets is controlled using methods known in the art in order to prevent shearing and thus further fragmentation of the target nucleic acid fragments as they are contained within the droplets. In some embodiments, 1 nL droplets (that is, droplets of 100 $\mu m^3$ volume) are used. It has been shown that 50 kb lambda dsDNA forms 1 $\mu m^3$ balls, and thus 200 kb human genomic dsDNA would be expected to form ~2 $\mu m^3$ cubed balls, which would easily be contained in a 1 nl droplet with minimal shearing due to the containment (emulsion) process. Single stranded DNA, which is the starting step for MDA and is the material generally used to form droplets of the invention in embodiments in which DNA is amplified prior to or after aliquoting, are even more compact or flexible because it has about a tenth of the persistence length of dsDNA. In addition, and as discussed in further detail above, adding elements such as spermidine to DNA during the pipetting processes also helps protect DNA from shearing, which is (without being bound by theory) is likely due to the ability of substances such as spermidine to compact DNA.

There are currently several types of microfluidics (e.g., Advanced Liquid Logic) or pico/nano-droplet (e.g., RainDance Technologies) devices that could be modified to accept LFR reagents and processes. These instruments have pico/nano-drop making, fusing (3000/second) and collecting functions that are currently fully operational. Such small volumes may also help prevent bias introduced by amplification methods and may also reduce background amplification.

An advantage of using emulsion droplets is that reduction of reaction volumes to microliter, nanoliter and picoliter levels provides a reduction in the costs and time associated with producing LFR libraries.

III.A.4. Advantages and Exemplary Applications of LFR

In one aspect, fragments from LFR aliquot libraries are used to generate DNBs in accordance with the methods described above. These DNBs may then be used in sequencing methods known in the art and described in further detail herein.

In a further aspect, initial long DNA fragments are aliquoted and then fragmented and tagged in each aliquot. These tagged fragments are then pooled together and at least a portion of the fragments are subsequently sequenced without amplification. In certain embodiments, about 30%-80% of the fragments are sequenced. In further embodiments, about 35%-70%, 40%-65%, 45%-60%, and 50%-55% of the fragments are sequenced. In a still further embodiment, at least 30%, 40%, 50%, 60%, 70%, 80%, 90%, 95% of the aliquoted and tagged fragments are sequenced without amplification.

In other embodiments, the fragments are amplified, and then about 35%-70%, 40%-65%, 45%-60%, and 50%-55% of the amplified fragments are sequenced. In a further embodiment, at least 30%, 40%, 50%, 60%, 70%, 80%, 90%, 95% of the aliquoted and tagged fragments are sequenced after amplification.

In one aspect, sequence reads from LFR fragments are assembled to provide sequence information for a contiguous region of the original target nucleic acid that is longer than the individual sequence reads. Sequence reads can be on the order of 20-200 bases or in some methods 200-2,000 bases or longer. As discussed in further detail herein, aliquoted fragments are generally about 20-200 kb or even longer than 1 Mb. In a further aspect, this assembly relies on the identity of the tags for each fragment to identify fragments that were contained in the same aliquot. In still further aspects, the tags are oligonucleotide adaptor tags and individual tags are identified by determining at least part of the tag sequence. The identities of the tags serve to identify the aliquot of origin of the attached fragments and can also be used to order the sequence reads from individual fragments and to differentiate between haplotypes. For example, as discussed above, the process of aliquoting the long fragments in LFR generally results in separating corresponding parental DNA fragments into separate aliquots, such that with an increasing number of aliquots, the number of aliquots with both maternal and paternal haplotypes becomes negligibly small. Thus, sequence reads from fragments in the same aliquot can be assembled and ordered. The longer fragments used in this method also help bridge over segments lacking heterozygous loci or resolve long segmental duplications.

A further advantage LFR is that sequence information obtained from the longer fragments can be used to assemble sequences for genomic regions that contain repetitive sequences whose length is greater than the individual sequence reads obtained from whatever sequencing methodology is used. Such advantages and applications of LFR are also discussed in U.S. patent application Ser. No. 11/451, 692, filed Jun. 13, 2006, now U.S. Pat. No. 7,709,197, and in U.S. patent application Ser. No. 12/329,365, filed Dec. 5, 2008, each of which is hereby incorporated by reference in its entirety and in particular for all teachings related to LFR and sequencing using LFR methods.

It is recognized that the advancement of biosciences (including for agriculture and bio-fuel production) and medicine is critically dependant on accurate low cost and high throughput genome and transcriptome sequencing. To achieve these benefits the cost of accurately sequencing an individual's genome should be very low, such as less than $1000. This cost should include all components of the process such as DNA preparation, reagents, sequencing instrument depreciation, and computing.

The present LFR invention can also be used for a fast full de novo assembly without reference sequence (e.g., metagenomics). First, partial assembles can be achieved within each aliquot. A limited alignment of assembled contigs is then used to find aliquots with overlapping fragments to do full assembly of a shared DNA segment. The assembly of segments is then propagated in both directions. A large number of LFR aliquots with less than 0.1% of the genome ensures uniqueness of shorter overlaps of short reads in de novo assembly (i.e. 12 bases is sufficient for unique read overlapping in 0.1% of the genome verses the 17 bases required for the complete genome) leading to longer sequence contigs at lower read coverage. Read coverage generally refers to the fraction or fold-coverage of a genome.

In one aspect, the present invention encompasses software and algorithms that executes protocols in accordance with the above exemplary method with high efficiency.

In a further aspect, methods and compositions of the present invention are used for genomic methylation analysis. There are several methods currently available for global genomic methylation analysis. The most economically accessible method involves bisulfate treatment of genomic DNA and sequencing of repetitive elements or a fraction of the genome obtained by methylation specific restriction enzyme fragmenting. This technique yields information on total methylation, but provides no locus specific data. The next higher level of resolution uses DNA arrays and is limited by the number of features on the chip. Finally, the highest resolution and the most expensive approach requires bisulfate treatment and then sequencing of the entire genome. Using LFR techniques of the present invention, it is possible to sequence all bases of the genome and assemble a complete diploid genome with digital information on levels of methylation for every cytosine position in the human genome (i.e., 5 base sequencing). Further, LFR allow blocks of methylated sequence of 100 kb or greater to be linked to sequence haplotypes, providing methylation haplotyping, information that is impossible to achieve with any currently available method.

In one non-limiting exemplary embodiment, methylation status is obtained in a method in which genomic DNA is first aliquoted and denatured for MDA. Next the DNA is treated with bisulfite (a step that requires denatured DNA). The remaining preparation follows those methods described for example in U.S. application Ser. No. 11/451,692, filed on Jun. 13, 2006 and Ser. No. 12/335,168, filed on Dec. 15, 2008, each of which is hereby incorporated by reference in its entirety for all purposes and in particular for all teachings related to nucleic acid analysis of mixtures of fragments according to long fragment read techniques.

In one aspect, MDA will amplify each strand of a specific fragment independently yielding for any given cytosine position 50% of the reads as unaffected by bisulfite (i.e., the base opposite of cytosine, a guanine is unaffected by bisulfate) and 50% providing methylation status. Reduced DNA complexity per aliquot helps with accurate mapping and assembly of the less informative, mostly 3-base (A, T, G) reads.

Bisulfite treatment has historically been found to fragment DNA. However, careful titration of denaturation and bisulfate buffers can avoid excessive fragmenting of genomic DNA. A 50% conversion of cytosine to uracil can be tolerated in LFR allowing a reduction in exposure of the DNA to bisulfite to minimize fragmenting. In some embodiments, some degree of fragmenting after aliquoting is acceptable as it would not affect haplotyping.

In one aspect, methods of the present invention produce quality genomic data from single cells. The ability to sequence single cells will open up many new avenues in genome research and diagnostics. Assuming no loss of DNA, there is a benefit to starting with a low number of cells (10 or less) instead of using an equivalent amount of DNA from a large prep. Starting with less than 10 cells and faithfully aliquoting all DNA ensures uniform coverage in long fragments of any given region of the genome. Starting with five or fewer cells allows four times or greater coverage per each 100 kb DNA fragment in each aliquot without increasing the total number of reads above 120 Gb (20 times coverage of a 6 Gb diploid genome). However, a large number of aliquots (10,000 or more) and longer DNA fragments (>200 kb) can be of use when sequencing samples obtained from a small number of cells, because for any given sequence there are only as many overlapping fragments as the number of starting cells and the occurrence of overlapping fragments from both parental chromosomes in an aliquot can be a devastating loss of information.

The LFR technology of the present invention is adapted to the problem of small input DNA amounts, because it is effective with only about 10 cells worth of starting input genomic DNA. In further embodiments, LFR is conducted on nucleic acids obtained from about 1-20, 2-18, 3-16, 4-14, 5-12, 6-10, and 7-8 cells. In still further embodiments, LFR also can be used with nucleic acids obtained from a single cell, because the first step in LFR is generally a low bias whole genome amplification which can be of particular use in single cell genomic analysis. Due to DNA strand breaks and DNA losses in handling, even single molecule sequencing methods would likely require some level of DNA amplification from the single cell. The difficulty in sequencing single cells comes from trying to faithfully amplify the entire genome. Studies performed on bacteria using MDA have suffered from loss of approximately half of the genome in the final assembled sequence with a fairly high amount of variation in coverage across those sequenced regions. This can partially be explained as a result of the initial genomic DNA having nicks and strand breaks which cannot be replicated at the ends and are thus lost during the MDA process. In certain aspects, LFR provides a solution to this problem, because it includes a step of generating long overlapping fragments of the genome prior to whole genome amplification methods such as MDA. As is discussed in further detail above, these long fragments are in some embodiments generated using a gentle process for isolating the genomic DNA from the cell is used. The largely intact genomic DNA is then lightly treated with a frequent nickase, resulting is a semi randomly nicked genome. The strand displacing ability of φ29 is then used to polymerize from the nicks creating very long (>200 kb) overlapping fragments. These fragments are then be used as starting template for the LFR process. In other embodiments, CoRE fragmentation techniques as discussed above are used to generate long fragments prior to MDA. As will be appreciated, combinations of CoRE and other methods known in the art for generating fragments can also be utilized to provide the materials for the steps of the LFR process described herein.

There are two basic approaches in advanced genome sequencing: using amplified DNA or relying on single molecule detection. In general, the first group is expected to have lower costs of detection (higher throughput) and the second group is expected to have lower cost in DNA preparation and reagents. To achieve accurate measurements, single molecule sequencing may require 100 times more measurements than using amplified DNA due to nonsynchronized base reads and/or longer detection times. Alternatively, amplified DNA arrays have already demonstrated reduced reagent costs through miniaturization while still maintaining high quality low cost detection and further reagent reduction through microfluidic devices is well within reach. As a result advanced miniaturized approaches that use amplified DNA are likely to be the first systems to provide low-cost medical genome sequencing.

For diagnostic medical applications low cost cannot compromise the accuracy and completeness of the sequence. In addition to high per base accuracy, an important component of accuracy and completeness for human genome sequencing is assembly of independent and accurate sequences of both parental chromosomes from diploid cells (including haplotype state of methylation). This can be of importance for accurate predictions of the primary structure of synthesized protein or RNA alleles and their corresponding levels of expression. Consensus sequence information is unable to make these predictions because enhancers and other sequences responsible for allelic expression levels can be over 100 kb upstream of the gene of interest or because two neighboring SNPs affecting the amino acid sequence of a protein might reside on different alleles of the gene of interest.

To achieve chromosome level haplotyping, simulation experiments show that allele linkage information across a range of at least 70-100 kb is needed. This is impossible to achieve with technologies using amplified DNA. These technologies most likely would be limited to reads less than 1000 bases due to difficulties in uniform amplification of long DNA molecules and loss of linkage information in sequencing. Mate-pair technologies can provide an equivalent to the extended read length but are limited to less than 10 kb due to inefficiencies in making such DNA libraries (i.e., circularization of DNA longer than a few kb is very difficult). This approach also needs extreme read coverage to link all heterozygotes. An ideal technology for this would be single molecule sequencing of greater than 100 kb DNA fragments if processing such long molecules were feasible and if the accuracy of single molecule sequencing were high and detection/instrument costs were low. This is very difficult to achieve on short molecules with high yield let alone on 100 kb fragments.

LFR provides a universal solution equivalent to inexpensive long single DNA molecule sequencing that will make both current shorter read amplified DNA technologies and potential future longer read single molecule technologies less expensive to obtain and accurately assemble genomic sequence data. At the same time this process will provide complete haplotype resolution in complex diploid genomes and allows the assembly of metagenomic mixtures.

In one aspect, the present invention is based on virtual read lengths of approximately 100-1000 kb in length. In addition, LFR can also dramatically reduce the computational demands and associated costs of any short read technology. Importantly, LFR removes the need for extending sequencing read length if that reduces the overall yield. Combined with a low cost short read technology, such as DNA nanoarray based cPAL (combinatorial probe anchor ligation) chemistry (described for example in published patent application numbers WO2007120208, WO2006073504, WO2007133831, and US2007099208, and U.S. patent application Ser. Nos. 11/679,124; 11/981,761; 11/981,661; 11/981,605; 11/981,793; 11/981,804; 11/451,691; 11/981,607; 11/981,767; 11/982,467; 11/451,692; 11/541,225; 11/927,356; 11/927,388; 11/938,096; 11/938,106; 10/547,214; 11/981,730; 11/981,685; 11/981,797; 11/934,695; 11/934,697; 11/934,703; 12/265,593; 11/938,213; 11/938,221; 12/325,922; 12/252,280; 12/266,385; 12/329,365; 12/335,168; 12/335,188; and 12/361,507 all of which are incorporated herein by reference in their entirety for all purposes and in particular for all teachings related to sequencing technologies), LFR provides a complete solution for human genome sequencing at an affordable cost for medical and research applications.

LFR provides the ability to obtain actual sequences of individual chromosomes as opposed to just the consensus sequences of parental or related chromosomes (in spite of their high similarities and presence of long repeats and segmental duplications). To generate this type of data the continuity of sequence is in general established over long DNA ranges such as 100 kb to 1 Mb. Traditionally such information was obtained by BAC cloning, an expensive and unreliable process (e.g., unclonable sequences). Most sequencing technologies generate relatively short DNA reads (100 to a few thousand bases). Furthermore, it is very difficult to maintain long fragments in multiple processing steps. Thus, one advantage of LFR is that it provides a universal in-vitro process to obtain such information at a low cost.

LFR with 10,000 or more aliquots provides a large reduction in the cost of computation incurred through short read length sequencing technologies and the complexity of genome assembly. This may be of particular importance for reducing the total cost of human genome sequencing below $1000.

LFR provides a reduction in the relatively high rate of errors or questionable base calls, usually one in 100 kb or 30,000 false positive calls and a similar number of undetected variants per human genome, that plaque current genome sequencing technologies. To minimize follow up confirmation of detected variants and to allow for adoption of human genome sequencing for diagnostic applications such error rates can be 10-1000 fold using methods of the present invention.

LFR using emulsion droplets is of particular use in reducing cost and increasing efficiency. By reducing the total reaction volume of the LFR process by over 1000 fold, increasing the number of aliquots to approximately 10,000, and improving the quality of data the total cost of a complete genome processed via methods such as those described herein and in published patent application numbers WO2007120208, WO2006073504, WO2007133831, and US2007099208, and U.S. patent application Ser. Nos. 11/679,124; 11/981,761; 11/981,661; 11/981,605; 11/981,793; 11/981,804; 11/451,691; 11/981,607; 11/981,767; 11/982,467; 11/451,692; 11/541,225; 11/927,356; 11/927,388; 11/938,096; 11/938,106; 10/547,214; 11/981,730; 11/981,685; 11/981,797; 11/934,695; 11/934,697; 11/934,703; 12/265,593; 11/938,213; 11/938,221; 12/325,922; 12/252,280; 12/266,385; 12/329,365; 12/335,168; 12/335,188; and 12/361,507 all of which are incorporated herein by reference in their entirety for all purposes and in particular for all teachings related to sequencing and nucleic acid preparation, would be less than the 1,000 dollar mark.

In addition to being universal for all sequencing platforms, LFR based sequencing can be applied beyond just standard personal genome analysis to all major applications of low cost-high throughput sequencing (e.g., structural rearrangements in cancer genomes, full methylome analysis including the haplotypes of methylated sites, and de novo assembly applications for metagenomics or novel genome sequencing, even of complex polyploid genomes like those found in plants).

Due to the universal nature and cost-effectiveness in providing linked information for sequences separated by 100-1000 kb, this novel DNA processing and bar-coding technology is expected to have a broad and highly beneficial impact on biosciences, medical genetics, and the development of new diagnostics and drugs; including novel treatments for cancer. One of the critical goals in various genomic applications is to generate enough genome sequence data of high accuracy and completeness to be able to develop knowledge about various genome codes driving complex genetic regulatory networks. The present invention encompasses LFR kits, tools and software for application to all genomics and sequencing platforms LFR provides the ability to understand the genetic basis of thousands of diseases, especially for the large number of sporadic genetic diseases (with novel or combinatorial genetic defects) where only a few patients are available to study. In these cases, the completeness of genome sequences (including complete haplotyping of all sequence variants and methylation states) allows discovery of the actual genetic defects that result in such rare diseases.

In some embodiments, the present invention is of use in genetic medical diagnostics in cancer genomes and individual genomic sequencing. Complete sequencing of cancer genomes, in addition to helping to better understand tumor development, will be critical for selecting optimal personalized cancer therapies. Accurate and complete sequence data at a low cost from a small number of cells may be of use in this important health application. Second, individual genome sequencing for the purpose of personalized disease diagnoses, preventions, and treatments has to be complete (full chromosomal haplotypes included), accurate and affordable to be effective. The present invention significantly improves all three measures of success. Such a low cost universal genetic test can be performed as part of the in vitro fertilization process where only one or two cells are available, as a prenatal diagnostic or a newborn screen and as part of routine health care for adults. Once implemented at an impact-achieving scale (over 10 million genomes sequenced per year) this genetic test could significantly reduce health care cost via preventive measures and appropriate drug use.

The present invention can yield haplotype reads in excess of 100 kb. In some aspects, a cost reduction of approximately 10 fold can be achieved by reducing volumes to sub-microliter levels. This is achievable due to methods, compositions and reaction conditions of the present invention which allow the performance of all six enzymatic steps in the same well without DNA purification. In some embodiments, the present invention includes the use of commercially available automated pipetting approaches in 1536 well formats. Nanoliter (nl) dispensing tools (e.g., Hamilton Robotics Nano Pipetting head, TTP LabTech Mosquito, and others) that provide non-contact pipetting of 50-100 nl can be used for fast and low cost pipetting to make tens of genome libraries in parallel. The four fold increase in aliquots results in a large reduction in the complexity of the genome within each well reducing the overall cost of computing over 10 fold and increasing data quality. Additionally, the automation of this process increases the throughput and lower the hands on cost of producing libraries.

In further embodiments, and as is discussed in further detail above, unique identification of each aliquot is achieved with barcode adaptor tags. In embodiments utilizing multiwell plates, the same number of adaptor tags as wells (384 and 1536 in two non-limiting examples) is used. In further embodiments, the costs associated with generating adaptor tags is reduced through a novel combinatorial tagging approach based on two sets of 40 half-barcode adapter tags.

A reduction of volumes down to picoliter levels in 10,000 aliquots can achieve an even greater cost reduction, possibly by as much as 30-400 fold in reagent costs and an additional 10 fold (over 100 fold in total) in computational costs. In some embodiments, this level of cost reduction and extensive aliquoting is accomplished through the combination of the LFR process with combinatorial tagging to emulsion or microfluidic type devices. Again, one development in the present invention of conditions to perform all six enzymatic steps in the same reaction without DNA purification provides the ability of miniaturization and automation, as well as adaptability to a wide variety of platforms and sample preparation methods.

Another advantage of LFR is that whole genome amplification can be much more efficient and show significantly less bias as a result of the small volumes and the long fragments used in LFR. Numerous studies have examined the range of unwanted amplification biases, background product formation, and chimeric artifacts introduced via $\phi 29$ based MDA, but many of these shortcomings have occurred under extreme conditions of amplification (greater than 1 million fold). LFR only needs a hundredth of that level of amplification. In addition, LFR starts with long DNA fragments (~100 kb) which are critical for efficient MDA.

In one aspect, the present invention provides diploid genome sequencing techniques that allow for calling parental haplotypes. LFR solves the problem of determining parental haplotypes by separating corresponding parental DNA fragments of >100 kb in length into physically separated sub-genome aliquots. As the number of aliquots increase, for instance to 1536, and the percent of the genome decreases down to approximately 1% of a haploid genome, the statistical support for haplotypes increases dramatically, because the sporadic presence of both maternal and paternal haplotypes in the same well diminishes. Consequently, a large number of small aliquots with a negligent frequency of mixed haplotypes per aliquot allow the use of fewer cells. Similarly, longer fragments (e.g., 300 kb or longer) help bridge over segments lacking heterozygous loci.

Figure 29:
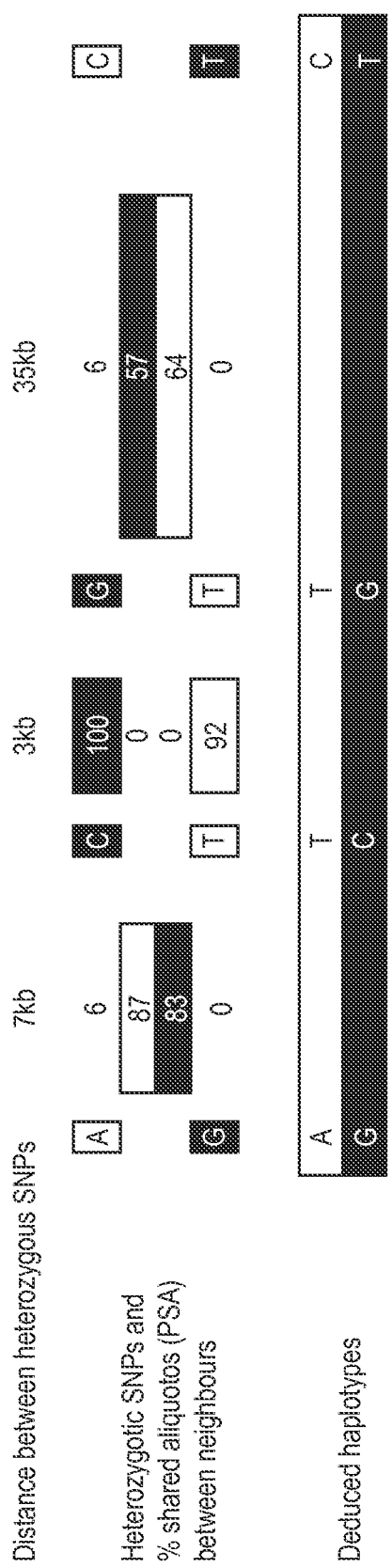
FIG. 29 is a schematic overview of using an embodiment of long fragment read technology of the present invention to define haplotypes.

An efficient algorithm for haplotyping can be made by calculating the percent of shared aliquots (PSA) for a pair of neighboring alleles (FIG. 29). This process resolves aliquots with mixed haplotypes or cases of uncalled alleles in some aliquots. For 100 kb fragments from 20 cells aliquoted in a 1536-well plate, the average PSA for pairs representing actual haplotypes reduces from close to 100% to 21% when the distance between neighboring heterozygous sites increases from 0 to 80 kb. The PSA of the false haplotype pairs in rare cases (<1%) can represent 5-10% (1-2 out of 20 aliquots; approaching the PSA of 80 kb separated alleles in true haplotypes) due the random chance of two haplotypes existing in the same aliquot. Thus, fragments even longer than 100 kb are required for haplotyping neighboring heterozygous loci separated over 80 kb.

In one aspect, the methods and compositions of the present invention provide complete diploid genome sequencing technologies that allow for calling polymorphic loci as homozygous. As a result of random sampling, there is a significant probability that at any given region of the genome only one of the parental chromosomes has been sequenced. An expensive solution, and the one commonly employed in conventional sequencing technologies, is to provide high average read coverage across the entire genome. The present invention dramatically reduces this problem, because it requires much less sequence coverage than is required in conventional technologies. As one non-limiting example, consider a homozygous position in the human genome detected with five overlapping reads (the reference in 99.9% of cases). If such positions are declared homozygous the LFR method would be incorrect in one out of 32 (each read provides a 0.5 probability of being correct, the probability of being erroneous in all five cases is $0.5^5$ or 1/32) cases (~3%), that is in 1/32 cases all 5 reads come from the same chromosome and none from the other. Because of this it is usually preferred to declare all of these positions as "no-call" or "half-call". That leads to millions of half-call positions per genome. If methods of the present invention (1536 or more aliquots) are used, 32/33 cases can be recognized as actual homozygous positions (some of the five reads come from aliquots of each parent) and only the remaining 3% would be declared half-calls (all reads come from aliquots of one parent). To achieve this improvement the homozygous reference or SNP positions are called after haplotype phasing.

A similar advantage can be realized for reducing the false positive call rate. Most false calls have lower, but still sufficient coverage from the real second allele. Using LFR data, false positive cases can be recognized by determining that the better supported allele is present in aliquots from both parents. For example, a common situation encountered in sequencing is a region covered by seven reads, five which correspond to A at a particular loci and two that correspond to G. If the two reads of G are false (e.g., mutations during DNA processing) they would most likely come from the same aliquot and five reads of A would come from multiple aliquots belonging to both parents. This would indicate homozygous A at the loci in question.

Mapping short reads to a reference genome, while less computationally complex than de novo sequencing, requires substantial computation, especially in cases where there are divergent or novel sequences created by multiple mutations, insertions, and/or deletions. Such genome segments require local or general de novo assembly of short sequence reads. Couple this with the reduction in reagent and imaging costs on new generation DNA arrays having 3-6 billion spots per microscope slide (1-4 genomes per slide) and the computation effort for sequence assembly rapidly becomes the dominate cost of genome sequencing. One way to reduce the costs associated with whole genome sequencing is to reduce these computation requirements.

The present invention provides LFR methods (>1500 aliquots) that provide solutions to the computational problem of short read sequencing at multiple levels: (a) fast read mapping to the reference sequence, (b) minimizing number of loci that require extensive local assembly, and (c) orders of magnitude faster local and global de-novo assembly. This is achieved in part because by local assembly of less than 1% of the genome at a time. In essence, the human genome assembly is reduced to the equivalent of 1000 bacterial genome assemblies. In one aspect, the following sequence assembly process is used:

1. Map <1% of reads to entire genome reference.
2. Define 3-10 Mb (for 10,000 aliquots) of reference sequence for each aliquot.
3. Map all reads from each aliquot to short aliquot reference.
4. Call ~80% of the obvious heterozygous positions.
5. Establish parental chromosome haplotypes by phasing heterozygous loci.
6. Call all homozygous reference (no variation) or SNPs and short indels as well as low coverage heterozygous positions.
7. Define the sequences for the remaining ~40K regions (1 in ~1 million bases) that need extensive (including de novo) assembly.

By way of example for reducing mapping cost (a), consider the sequencing and mapping of DNA from five cells that has been divided into 10,000 aliquots consisting of 0.1% of a haploid human genome per aliquot (3 Mb or thirty 100 kb fragments). If each aliquot was sequenced to four times coverage with 120 base pair reads then there would be approximately 100,000 reads per aliquot (3 Mb×4/120). Each 100 kb fragment within an aliquot would be covered by 3,300 reads. By mapping 500 (or 0.5%) of all reads in an aliquot against the entire human reference (step 1), amounting to approximately 15 reads per fragment, the reference segments corresponding to fragments in each aliquot will be defined (step 2). The remaining reads would then be mapped to the 0.1-0.2% of the composite reference (3-6 Mb) uniquely defined for each aliquot (step 3). This process uses only 1% of the total mapping effort required without LFR or a 100 fold reduction in computation cost for mapping. In one embodiment, the present invention includes software for fast gathering and indexing of aliquot reference sequence.

The present invention improves the efficiency of diploid genome sequencing by first defining haplotypes (steps 4 and 5) and then using aliquot-haplotype pairing to achieve accurate and computationally efficient base (variant) calling for the majority of remaining cases (step 6). For example, for over almost 3 billion base positions in a personal human genome there is a reference/reference homozygous state. Without LFR haplotype information on over 100 million positions cannot be called at both chromosomes without extensive evaluation of novel sequences. With advanced LFR most of these positions can accurately be determined to be reference/reference without any de novo type sequence assembly. This yields a computation reduction of approximately 1000 fold for this genome assembly step. Furthermore, 99.9% of all variants in a genome (e.g., SNPs and 1-2 base indels) would be accurately called at this step and the remaining 0.1% (forty thousand out of four million variants found per individual human genome), representing more complex changes, would be solved in step 7.

Assuming a standard forty times coverage of a haploid genome (one billion 120-base reads), a de novo assembly of sequence comprising an unresolved site in a parental chromosome (step 7), could be achieved using approximately 100,000 reads (in about 10 of the 10,000 aliquots). This is much more efficient than using over 100 million (>10%) of the expected unused reads in standard assembly without LFR. Additionally, false assembly is minimized even in the case of shorter overlap between consecutive reads. Thus, a cost reduction in excess of 100 fold can be achieved per de novo assembly site.

The ability of LFR techniques of the present invention to sequence and assemble very long (>100 kb) fragments of the genome make it well suited for the sequencing of complete cancer genomes. It is has been suggested that more than 90% of cancers, in some manner, harbor significant losses or gains in regions of the human genome, termed aneuploidy, with some individual cancers having been observed to contain in excess of four copies of some chromosomes. This increased complexity in copy number of chromosomes and regions within chromosomes can make sequencing using methods other than LFR untenable.

In further embodiments, the present invention utilizes automation to further reduce costs associated with whole genome sequencing. The methods and compositions of the present invention also include miniaturization, which can be achieved by a number of techniques, including the use of nanoliter-drops. In further embodiments, ~10-20 nanoliter drops are deposited in plates or on glass slides in 3072-6144 format (still a cost effective total MDA volume of 60 µl without losing the computational cost savings or the ability to sequence from four cells) or higher using improved nano-pipetting or acoustic droplet ejection technology (e.g., LabCyte Inc.) or using microfluidic devices capable of handling up to 9216 individual reaction wells.

In one aspect, the present invention encompasses software with the capability of handling data from in excess of 10,000 aliquots. Because aliquot mapping is performed on a reference that is just a few megabases, a Smith-Waterman algorithm can be used instead of fast indexing that does not map reads with indels. This allows an accurate alignment of reads even to reference sequences with multiple changes or indels in a cost effective way.

III.B. Further Sequencing Methods

As will be appreciated, nucleic acids of the invention, including fragments in LFR aliquot libraries and DNBs, can be used in any sequencing methods known in the art, including without limitation sequencing by ligation, sequencing by hybridization, sequencing by synthesis (including sequencing by primer extension), chained sequencing by ligation of cleavable probes, and the like.

Methods similar to those described herein for sequencing can also be used to detect specific sequences in a target nucleic acid, including detection of single nucleotide polymorphisms (SNPs). In such methods, sequencing probes that will hybridize to a particular sequence, such as a sequence containing a SNP, can be used. Such sequencing probes can be differentially labeled to identify which SNP is present in the target nucleic acid. Anchor probes can also be used in combination with such sequencing probes to provide further stability and specificity.

In one aspect, methods and compositions of the present invention are used in combination with techniques such as those described in WO2007120208, WO2006073504, WO2007133831, and US2007099208, and U.S. Patent Application Nos. 60/992,485; 61/026,337; 61/035,914; 61/061,134; 61/116,193; 61/102,586; Ser. Nos. 12/265,593; 12/266,385; 11/938,096; 11/981,804; Nos. 11/981,797; 11/981,793; 11/981,767; 11/981,761; 11/981,730; 11/981,685; 11/981,661; 11/981,607; 11/981,605; 11/927,388; 11/927,356; 11/679,124; 11/541,225; 10/547,214; 11/451,692; and 11/451,691, all of which are incorporated herein by reference in their entirety for all purposes and in particular for all teachings related to sequencing, particularly sequencing of nucleic acids.

In a further aspect, sequences of nucleic acids are identified using sequencing methods known in the art, including, but not limited to, hybridization-based methods, such as disclosed in Drmanac, U.S. Pat. Nos. 6,864,052; 6,309,824; and 6,401,267; and Drmanac et al, U.S. patent publication 2005/0191656, and sequencing by synthesis methods, e.g. Nyren et al, U.S. Pat. No. 6,210,891; Ronaghi, U.S. Pat. No. 6,828,100; Ronaghi et al (1998), Science, 281: 363-365; Balasubramanian, U.S. Pat. No. 6,833,246; Quake, U.S. Pat. No. 6,911,345; Li et al, Proc. Natl. Acad. Sci. 100: 414-419 (2003); Smith et al, PCT publication WO 2006/074351; and ligation-based methods, e.g. Shendure et al (2005), Science, 309: 1728-1739, Macevicz, U.S. Pat. No. 6,306,597, wherein each of these references is herein incorporated by reference in its entirety for all purposes and in particular teachings regarding the figures, legends and accompanying text describing the compositions, methods of using the compositions and methods of making the compositions, particularly with respect to sequencing.

III.B.1. cPAL

Although the following is described in terms of sequencing DNBs, any of the sequencing methods described herein are also applicable to target nucleic acid fragments, such as those generated for LFR sequencing methods described above. As will be further appreciated, combinations of sequencing methods are also encompassed by the present invention.

In one aspect, sequences of DNBs are identified using methods referred to herein as combinatorial probe anchor ligation ("cPAL") and variations thereof, as described below. In brief, cPAL involves identifying a nucleotide at a particular detection position in a target nucleic acid by detecting a probe ligation product formed by ligation of at least one anchor probe that hybridizes to all or part of an adaptor and a sequencing probe that contains a particular nucleotide at an "interrogation position" that corresponds to (e.g. will hybridize to) the detection position. The sequencing probe contains a unique identifying label. If the nucleotide at the interrogation position is complementary to the nucleotide at the detection position, ligation can occur, resulting in a ligation product containing the unique label which is then detected. Descriptions of different exemplary embodiments of cPAL methods are provided below. It will be appreciated that the following descriptions are not meant to be limiting and that variations of the following embodiments are encompassed by the present invention.

"Complementary" or "substantially complementary" refers to the hybridization or base pairing or the formation of a duplex between nucleotides or nucleic acids, such as, for instance, between the two strands of a double-stranded DNA molecule or between an oligonucleotide primer and a primer binding site on a single-stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the other strand, usually at least about 90% to about 95%, and even about 98% to about 100%.

As used herein, "hybridization" refers to the process in which two single-stranded polynucleotides bind non-covalently to form a stable double-stranded polynucleotide. The resulting (usually) double-stranded polynucleotide is a "hybrid" or "duplex." "Hybridization conditions" will typically include salt concentrations of less than about 1M, more usually less than about 500 mM and may be less than about 200 mM. A "hybridization buffer" is a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are usually performed under stringent conditions, i.e., conditions under which a probe will hybridize to its target subsequence but will not hybridize to the other, uncomplimentary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. Exemplary stringent conditions include a salt concentration of at least 0.01M to no more than 1M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of 30° C. are suitable for allele-specific probe hybridizations. Further examples of stringent conditions are well known in the art, see for example Sambrook J et al. (2001), *Molecular Cloning, A Laboratory Manual*, (3rd Ed., Cold Spring Harbor Laboratory Press.

As used herein, the term "$T_m$" generally refers to the temperature at which half of the population of double-stranded nucleic acid molecules becomes dissociated into single strands. The equation for calculating the Tm of nucleic acids is well known in the art. As indicated by standard references, a simple estimate of the $T_m$ value may be calculated by the equation: $T_m=81.5+16.6(\log 10[Na+]) 0.41(\%[G+C])-675/n-$ 1.0 m, when a nucleic acid is in aqueous solution having cation concentrations of 0.5 M, or less, the (G+C) content is between 30% and 70%, n is the number of bases, and m is the percentage of base pair mismatches (see e.g., Sambrook J et al. (2001), *Molecular Cloning, A Laboratory Manual*, (3rd Ed., Cold Spring Harbor Laboratory Press). Other references include more sophisticated computations, which take structural as well as sequence characteristics into account for the calculation of $T_m$ (see also, Anderson and Young (1985), Quantitative Filter Hybridization, *Nucleic Acid Hybridization*, and Allawi and SantaLucia (1997), *Biochemistry* 36:10581-94).

Figure 23:
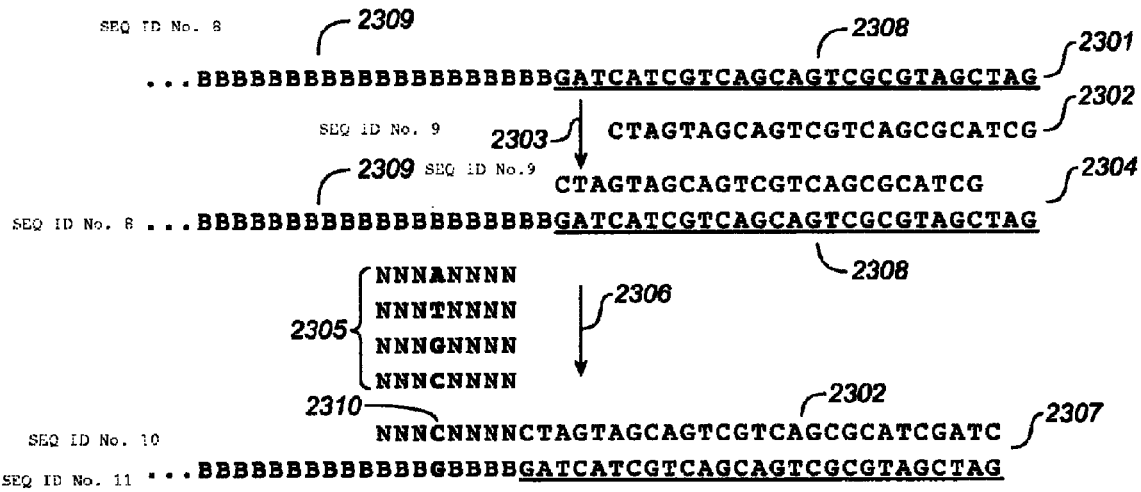
FIG. 23 is a schematic illustration of one embodiment of a combinatorial probe anchor ligation method.
Figure 24:
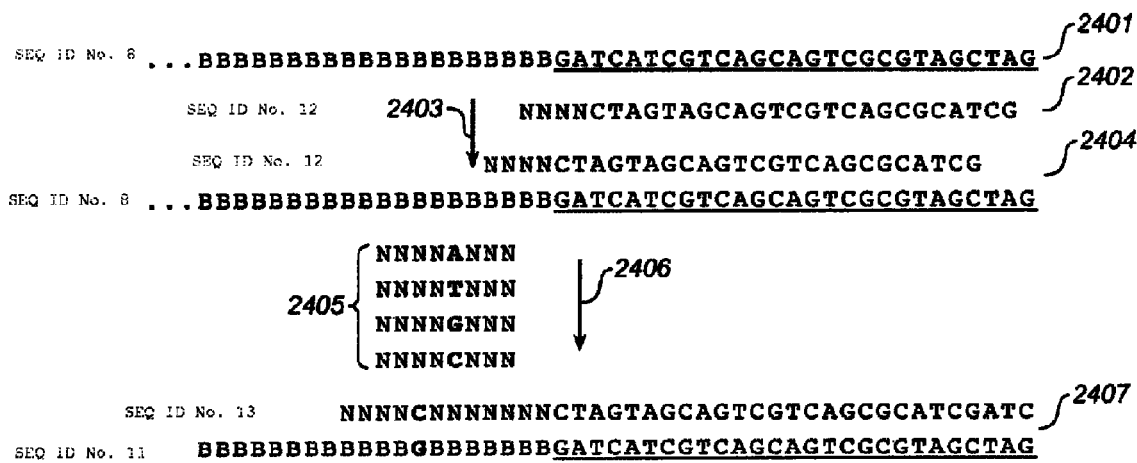
FIG. 24 is a schematic illustration of one embodiment of a combinatorial probe anchor ligation method.

In one example of a cPAL method, referred to herein as "single cPAL", as illustrated in FIG. 23, anchor probe 2302 hybridizes to a complementary region on adaptor 2308 of the DNB 2301. Anchor probe 2302 hybridizes to the adaptor region directly adjacent to target nucleic acid 2309, but in some cases, anchor probes can be designed to "reach into" the target nucleic acid by incorporating a desired number of degenerate bases at the terminus of the anchor probe, as is schematically illustrated in FIG. 24 and described further below. A pool of differentially labeled sequencing probes 2305 will hybridize to complementary regions of the target nucleic acid, and sequencing probes that hybridize adjacent to anchor probes are ligated to form a probe ligation product, usually by application of a ligase. The sequencing probes are generally sets or pools of oligonucleotides comprising two parts: different nucleotides at the interrogation position, and then all possible bases (or a universal base) at the other positions; thus, each probe represents each base type at a specific position. The sequencing probes are labeled with a detectable label that differentiates each sequencing probe from the sequencing probes with other nucleotides at that position. Thus, in the example illustrated in FIG. 23, a sequencing probe 2310 that hybridizes adjacent to anchor probe 2302 and is ligated to the anchor probe will identify the base at a position in the target nucleic acid 5 bases from the adaptor as a "G". FIG. 23 depicts a situation where the interrogation base is 5 bases in from the ligation site, but as more fully described below, the interrogation base can also be "closer" to the ligation site, and in some cases at the point of ligation. Once ligated, non-ligated anchor and sequencing probes are washed away, and the presence of the ligation product on the array is detected using the label. Multiple cycles of anchor probe and sequencing probe hybridization and ligation can be used to identify a desired number of bases of the target nucleic acid on each side of each adaptor in a DNB. Hybridization of the anchor probe and the sequencing probe may occur sequentially or simultaneously. The fidelity of the base call relies in part on the fidelity of the ligase, which generally will not ligate if there is a mismatch close to the ligation site.

The present invention also provides methods in which two or more anchor probes are used in every hybridization-ligation cycle. FIG. 25 illustrate an additional example of a "double cPAL with overhang" method in which a first anchor probe 2502 and a second anchor probe 2505 each hybridize to complimentary regions of an adaptor. In the example illustrated in FIG. 25, the first anchor probe 2502 is fully complementary to a first region of the adaptor 2511, and the second anchor probe 2505 is complementary to a second adaptor region adjacent to the hybridization position of the first anchor probe. The second anchor probe also comprises degenerate bases at the terminus that is not adjacent to the first anchor probe. As a result, the second anchor probe is able to hybridize to a region of the target nucleic acid 2512 adjacent to adaptor 2511 (the "overhang" portion). The second anchor probe is generally too short to be maintained alone in its duplex hybridization state, but upon ligation to the first anchor probe it forms a longer anchor probe that is stably hybridized for subsequent methods. As discussed above for the "single cPAL" method, a pool of sequencing probes 2508 that represents each base type at a detection position of the target nucleic acid and labeled with a detectable label that differentiates each sequencing probe from the sequencing probes with other nucleotides at that position is hybridized 2509 to the adaptor-anchor probe duplex and ligated to the terminal 5' or 3' base of the ligated anchor probes. In the example illustrated in FIG. 25, the sequencing probes are designed to interrogate the base that is five positions 5' of the ligation point between the sequencing probe 2514 and the ligated anchor probes 2513. Since the second adaptor probe 2505 has five degenerate bases at its 5' end, it reaches five bases into the target nucleic acid 2512, allowing interrogation with the sequencing probe at a full ten bases from the interface between the target nucleic acid 2512 and the adaptor 2511.

In variations of the above described examples of a double cPAL method, if the first anchor probe terminates closer to the end of the adaptor, the second adaptor probe will be proportionately more degenerate and therefore will have a greater potential to not only ligate to the end of the first adaptor probe but also to ligate to other second adaptor probes at multiple sites on the DNB. To prevent such ligation artifacts, the second anchor probes can be selectively activated to engage in ligation to a first anchor probe or to a sequencing probe. Such activation methods are described in further detail below, and include methods such as selectively modifying the termini of the anchor probes such that they are able to ligate only to a particular anchor probe or sequencing probe in a particular orientation with respect to the adaptor.

Similar to the double cPAL method described above, it will be appreciated that cPAL methods utilizing three or more anchor probes are also encompassed by the present invention.

In addition, sequencing reactions can be done at one or both of the termini of each adaptor, e.g., the sequencing reactions can be "unidirectional" with detection occurring 3' or 5' of the adaptor or the other or the reactions can be "bidirectional" in which bases are detected at detection positions 3' and 5' of the adaptor. Bidirectional sequencing reactions can occur simultaneously—i.e., bases on both sides of the adaptor are detected at the same time—or sequentially in any order.

Multiple cycles of cPAL (whether single, double, triple, etc.) will identify multiple bases in the regions of the target nucleic acid adjacent to the adaptors. In brief, the cPAL methods are repeated for interrogation of multiple adjacent bases within a target nucleic acid by cycling anchor probe hybridization and enzymatic ligation reactions with sequencing probe pools designed to detect nucleotides at varying positions removed from the interface between the adaptor and target nucleic acid. In any given cycle, the sequencing probes used are designed such that the identity of one or more of bases at one or more positions is correlated with the identity of the label attached to that sequencing probe. Once the ligated sequencing probe (and hence the base(s) at the interrogation position(s) is detected, the ligated complex is stripped off of the DNB and a new cycle of adaptor and sequencing probe hybridization and ligation is conducted.

As will be appreciated, DNBs of the invention can be used in other sequencing methods in addition to the cPAL methods described above, including other sequencing by ligation methods as well as other sequencing methods, including without limitation sequencing by hybridization, sequencing by synthesis (including sequencing by primer extension), chained sequencing by ligation of cleavable probes, and the like.

Methods similar to those described above for sequencing can also be used to detect specific sequences in a target nucleic acid, including detection of single nucleotide polymorphisms (SNPs). In such methods, sequencing probes that will hybridize to a particular sequence, such as a sequence containing a SNP, will be applied. Such sequencing probes can be differentially labeled to identify which SNP is present in the target nucleic acid. Anchor probes can also be used in combination with such sequencing probes to provide further stability and specificity.

Target nucleic acids of use in sequencing methods of the present invention comprise target sequences with a plurality of detection positions. The term "detection position" refers to a position in a target sequence for which sequence information is desired. As will be appreciated by those in the art, generally a target sequence has multiple detection positions for which sequence information is required, for example in the sequencing of complete genomes as described herein. In some cases, for example in SNP analysis, it may be desirable to just read a single SNP in a particular area.

As discussed above, the present invention provides methods of sequencing that utilize a combination of anchor probes and sequencing probes. By "sequencing probe" as used herein is meant an oligonucleotide that is designed to provide the identity of a nucleotide at a particular detection position of a target nucleic acid. Sequencing probes hybridize to domains within target sequences, e.g. a first sequencing probe may hybridize to a first target domain, and a second sequencing probe may hybridize to a second target domain. The terms "first target domain" and "second target domain" or grammatical equivalents herein means two portions of a target sequence within a nucleic acid which is under examination. The first target domain may be directly adjacent to the second target domain, or the first and second target domains may be separated by an intervening sequence, for example an adaptor. The terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain. Sequencing probes can overlap, e.g. a first sequencing probe can hybridize to the first 6 bases adjacent to one terminus of an adaptor, and a second sequencing probe can hybridize to the 3rd-9th bases from the terminus of the adaptor (for example when an anchor probe has three degenerate bases). Alternatively, a first sequencing probe can hybridize to the 6 bases adjacent to the "upstream" terminus of an adaptor and a second sequencing probe can hybridize to the 6 bases adjacent to the "downstream" terminus of an adaptor.

Sequencing probes will generally comprise a number of degenerate bases and a specific nucleotide at a specific location within the probe to query the detection position (also referred to herein as an "interrogation position").

In general, pools of sequencing probes are used when degenerate bases are used. That is, a probe having the sequence "NNNANN" is actually a set of probes of having all possible combinations of the four nucleotide bases at five positions (i.e., 1024 sequences) with an adenosine at the 6th position, (As noted herein, this terminology is also applicable to adaptor probes: for example, when an adaptor probe has "three degenerate bases", for example, it is actually a set of adaptor probes comprising the sequence corresponding to the anchor site, and all possible combinations at 3 positions, so it is a pool of 64 probes).

In some embodiments, for each interrogation position, four differently labeled pools can be combined in a single pool and used in a sequencing step. Thus, in any particular sequencing step, 4 pools are used, each with a different specific base at the interrogation position and with a different label corresponding to the base at the interrogation position. That is, sequencing probes are also generally labeled such that a particular nucleotide at a particular interrogation position is associated with a label that is different from the labels of sequencing probes with a different nucleotide at the same interrogation position. For example, four pools can be used: NNNANN-dye1, NNNTNN-dye2, NNNCNN-dye3 and NNNGNN-dye4 in a single step, as long as the dyes are optically resolvable. In some embodiments, for example for SNP detection, it may only be necessary to include two pools, as the SNP call will be either a C or an A, etc. Similarly, some SNPs have three possibilities. Alternatively, in some embodiments, if the reactions are done sequentially rather than simultaneously, the same dye can be done, just in different steps: e.g. the NNNANN-dye1 probe can be used alone in a reaction, and either a signal is detected or not, and the probes washed away; then a second pool, NNNTNN-dye1 can be introduced.

In any of the sequencing methods described herein, sequencing probes may have a wide range of lengths, including about 3 to about 25 bases. In further embodiments, sequencing probes may have lengths in the range of about 5 to about 20, about 6 to about 18, about 7 to about 16, about 8 to about 14, about 9 to about 12, and about 10 to about 11 bases.

Sequencing probes of the present invention are designed to be complementary, and in general, perfectly complementary, to a sequence of the target sequence such that hybridization of a portion target sequence and probes of the present invention occurs. In particular, it is important that the interrogation position base and the detection position base be perfectly complementary and that the methods of the invention do not result in signals unless this is true.

In many embodiments, sequencing probes are perfectly complementary to the target sequence to which they hybridize; that is, the experiments are run under conditions that favor the formation of perfect base pairing, as is known in the art. As will be appreciated by those in the art, a sequencing probe that is perfectly complementary to a first domain of the target sequence could be only substantially complementary to a second domain of the same target sequence; that is, the present invention relies in many cases on the use of sets of probes, for example, sets of hexamers, that will be perfectly complementary to some target sequences and not to others.

In some embodiments, depending on the application, the complementarity between the sequencing probe and the target need not be perfect; there may be any number of base pair mismatches, which will interfere with hybridization between the target sequence and the single stranded nucleic acids of the present invention. However, if the number of mismatches is so great that no hybridization can occur under even the least stringent of hybridization conditions, the sequence is not a complementary target sequence. Thus, by "substantially complementary" herein is meant that the sequencing probes are sufficiently complementary to the target sequences to hybridize under normal reaction conditions. However, for most applications, the conditions are set to favor probe hybridization only if perfectly complementarity exists. Alternatively, sufficient complementarity is required to allow the ligase reaction to occur; that is, there may be mismatches in some part of the sequence but the interrogation position base should allow ligation only if perfect complementarity at that position occurs.

In some cases, in addition to or instead of using degenerate bases in probes of the invention, universal bases which hybridize to more than one base can be used. For example, inosine can be used. Any combination of these systems and probe components can be utilized.

Sequencing probes of use in methods of the present invention are usually detectably labeled. By "label" or "labeled" herein is meant that a compound has at least one element, isotope or chemical compound attached to enable the detection of the compound. In general, labels of use in the invention include without limitation isotopic labels, which may be radioactive or heavy isotopes, magnetic labels, electrical labels, thermal labels, colored and luminescent dyes, enzymes and magnetic particles as well. Dyes of use in the invention may be chromophores, phosphors or fluorescent dyes, which due to their strong signals provide a good signal-to-noise ratio for decoding. Sequencing probes may also be labeled with quantum dots, fluorescent nanobeads or other constructs that comprise more than one molecule of the same fluorophore. Labels comprising multiple molecules of the same fluorophore will generally provide a stronger signal and will be less sensitive to quenching than labels comprising a single molecule of a fluorophore. It will be understood that any discussion herein of a label comprising a fluorophore will apply to labels comprising single and multiple fluorophore molecules.

Many embodiments of the invention include the use of fluorescent labels. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue™, Texas Red, and others described in the 6th Edition of the Molecular Probes Handbook by Richard P. Haugland, hereby expressly incorporated by reference in its entirety for all purposes and in particular for its teachings regarding labels of use in accordance with the present invention. Commercially available fluorescent dyes for use with any nucleotide for incorporation into nucleic acids include, but are not limited to: Cy3, Cy5, (Amersham Biosciences, Piscataway, N.J., USA), fluorescein, tetramethylrhodamine-, Texas Red®, Cascade Blue®, BODIPY® FL-14, BODIPY®R, BODIPY® TR-14, Rhodamine Green™, Oregon Green® 488, BODIPY® 630/650, BODIPY® 650/665-, Alexa Fluor® 488, Alexa Fluor® 532, Alexa Fluor® 568, Alexa Fluor® 594, Alexa Fluor® 546 (Molecular Probes, Inc. Eugene, Oreg., USA), Quasar 570, Quasar 670, Cal Red 610 (BioSearch Technologies, Novato, Ca). Other fluorophores available for post-synthetic attachment include, inter alia, Alexa Fluor® 350, Alexa Fluor® 532, Alexa Fluor® 546, Alexa Fluor® 568, Alexa Fluor® 594, Alexa Fluor® 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3.5, Cy5.5, and Cy7 (Amersham Biosciences, Piscataway, N.J. USA, and others). In some embodiments, the labels used include fluoroscein, Cy3, Texas Red, Cy5, Quasar 570, Quasar 670 and Cal Red 610 are used in methods of the present invention.

Labels can be attached to nucleic acids to form the labeled sequencing probes of the present invention using methods known in the art, and to a variety of locations of the nucleosides. For example, attachment can be at either or both termini of the nucleic acid, or at an internal position, or both. For example, attachment of the label may be done on a ribose of the ribose-phosphate backbone at the 2' or 3' position (the latter for use with terminal labeling), in one embodiment through an amide or amine linkage. Attachment may also be made via a phosphate of the ribose-phosphate backbone, or to the base of a nucleotide. Labels can be attached to one or both ends of a probe or to any one of the nucleotides along the length of a probe.

Sequencing probes are structured differently depending on the interrogation position desired. For example, in the case of sequencing probes labeled with fluorophores, a single position within each sequencing probe will be correlated with the identity of the fluorophore with which it is labeled. Generally, the fluorophore molecule will be attached to the end of the sequencing probe that is opposite to the end targeted for ligation to the anchor probe.

By "anchor probe" as used herein is meant an oligonucleotide designed to be complementary to at least a portion of an adaptor, referred to herein as "an anchor site". Adaptors can contain multiple anchor sites for hybridization with multiple anchor probes, as described herein. As discussed further herein, anchor probes of use in the present invention can be designed to hybridize to an adaptor such that at least one end of the anchor probe is flush with one terminus of the adaptor (either "upstream" or "downstream", or both). In further embodiments, anchor probes can be designed to hybridize to at least a portion of an adaptor (a first adaptor site) and also at least one nucleotide of the target nucleic acid adjacent to the adaptor ("overhangs"). As illustrated in FIG. 24, anchor probe 2402 comprises a sequence complementary to a portion of the adaptor. Anchor probe 2402 also comprises four degenerate bases at one terminus. This degeneracy allows for a portion of the anchor probe population to fully or partially match the sequence of the target nucleic acid adjacent to the adaptor and allows the anchor probe to hybridize to the adaptor and reach into the target nucleic acid adjacent to the adaptor regardless of the identity of the nucleotides of the target nucleic acid adjacent to the adaptor. This shift of the terminal base of the anchor probe into the target nucleic acid shifts the position of the base to be called closer to the ligation point, thus allowing the fidelity of the ligase to be maintained. In general, ligases ligate probes with higher efficiency if the probes are perfectly complementary to the regions of the target nucleic acid to which they are hybridized, but the fidelity of ligases decreases with distance away from the ligation point. Thus, in order to minimize and/or prevent errors due to incorrect pairing between a sequencing probe and the target nucleic acid, it can be useful to maintain the distance between the nucleotide to be detected and the ligation point of the sequencing and anchor probes. By designing the anchor probe to reach into the target nucleic acid, the fidelity of the ligase is maintained while still allowing a greater number of nucleotides adjacent to each adaptor to be identified. Although the embodiment illustrated in FIG. 24 is one in which the sequencing probe hybridizes to a region of the target nucleic acid on one side of the adaptor, it will be appreciated that embodiments in which the sequencing probe hybridizes on the other side of the adaptor are also encompassed by the invention. In FIG. 24, "N" represents a degenerate base and "B" represents nucleotides of undetermined sequence. As will be appreciated, in some embodiments, rather than degenerate bases, universal bases may be used.

Anchor probes of the invention may comprise any sequence that allows the anchor probe to hybridize to a DNB, generally to an adaptor of a DNB. Such anchor probes may comprise a sequence such that when the anchor probe is hybridized to an adaptor, the entire length of the anchor probe is contained within the adaptor. In some embodiments, anchor probes may comprise a sequence that is complementary to at least a portion of an adaptor and also comprise degenerate bases that are able to hybridize to target nucleic acid regions adjacent to the adaptor. In some exemplary embodiments, anchor probes are hexamers that comprise 3 bases that are complementary to an adaptor and 3 degenerate bases. In some exemplary embodiments, anchor probes are 8-mers that comprise 3 bases that are complementary to an adaptor and 5 degenerate bases. In further exemplary embodiments, particularly when multiple anchor probes are used, a first anchor probe comprises a number of bases complementary to an adaptor at one end and degenerate bases at another end, whereas a second anchor probe comprises all degenerate bases and is designed to ligate to the end of the first anchor probe that comprises degenerate bases. It will be appreciated that these are exemplary embodiments, and that a wide range of combinations of known and degenerate bases can be used to produce anchor probes of use in accordance with the present invention.

In certain aspects, the sequencing by ligation methods of the invention include providing different combinations of anchor probes and sequencing probes, which, when hybridized to adjacent regions on a DNB, can be ligated to form probe ligation products. The probe ligation products are then detected, which provides the identity of one or more nucleotides in the target nucleic acid. By "ligation" as used herein is meant any method of joining two or more nucleotides to each other. Ligation can include chemical as well as enzymatic ligation. In general, the sequencing by ligation methods discussed herein utilize enzymatic ligation by ligases. Such ligases invention can be the same or different than ligases discussed above for creation of the nucleic acid templates. Such ligases include without limitation DNA ligase 1, DNA ligase II, DNA ligase III, DNA ligase IV, E. coli DNA ligase, T4 DNA ligase, T4 RNA ligase 1, T4 RNA ligase 2, T7 ligase, T3 DNA ligase, and thermostable ligases (including without limitation Taq ligase) and the like. As discussed above, sequencing by ligation methods often rely on the fidelity of ligases to only join probes that are perfectly complementary to the nucleic acid to which they are hybridized. This fidelity will decrease with increasing distance between a base at a particular position in a probe and the ligation point between the two probes. As such, conventional sequencing by ligation methods can be limited in the number of bases that can be identified. The present invention increases the number of bases that can be identified by using multiple probe pools, as is described further herein.

A variety of hybridization conditions may be used in the sequencing by ligation methods of sequencing as well as other methods of sequencing described herein. These conditions include high, moderate and low stringency conditions; see for example Maniatis et al., Molecular Cloning: A Laboratory Manual, 2d Edition, 1989, and Short Protocols in Molecular Biology, ed. Ausubel, et al, which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays," (1993). Generally, stringent conditions are selected to be about 5-10° C. lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions can be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of helix destabilizing agents such as formamide. The hybridization conditions may also vary when a non-ionic backbone, i.e. PNA is used, as is known in the art. In addition, cross-linking agents may be added after target binding to cross-link, i.e. covalently attach, the two strands of the hybridization complex.

For any of sequencing methods known in the art and described herein using nucleic acids of the invention (including LFR aliquot fragments and DNBs), the present invention provides methods for determining at least about 10 to about 200 bases in target nucleic acids. In further embodiments, the present invention provides methods for determining at least about 20 to about 180, about 30 to about 160, about 40 to about 140, about 50 to about 120, about 60 to about 100, and about 70 to about 80 bases in target nucleic acids. In still further embodiments, sequencing methods are used to identify at least 5, 10, 15, 20, 25, 30 or more bases adjacent to one or both ends of each adaptor in a nucleic acid template of the invention.

Any of the sequencing methods described herein and known in the art can be applied to nucleic acids in solution or on a surface and/or in an array.

III.B.1(a) Single cPAL

In one aspect, the present invention provides methods for identifying sequences of DNBs by using combinations of sequencing and anchor probes that hybridize to adjacent regions of a DNB and are ligated, usually by application of a ligase. Such methods are generally referred to herein as cPAL (combinatorial probe anchor ligation) methods. In one aspect, cPAL methods of the invention produce probe ligation products comprising a single anchor probe and a single sequencing probe. Such cPAL methods in which only a single anchor probe is used are referred to herein as "single cPAL".

One embodiment of single cPAL is illustrated in FIG. 23. A monomeric unit 2301 of a DNB comprises a target nucleic acid 2309 and an adaptor 2308. An anchor probe 2302 hybridizes to a complementary region on adaptor 2308. In the example illustrated in FIG. 23, anchor probe 2302 hybridizes to the adaptor region directly adjacent to target nucleic acid 2309, although, as is discussed further herein, anchor probes can also be designed to reach into the target nucleic acid adjacent to an adaptor by incorporating a desired number of degenerate bases at the terminus of the anchor probe. A pool of differentially labeled sequencing probes 2306 will hybridize to complementary regions of the target nucleic acid. A sequencing probe 2310 that hybridizes to the region of target nucleic acid 2309 adjacent to anchor probe 2302 will be ligated to the anchor probe form a probe ligation product. The efficiency of hybridization and ligation is increased when the base in the interrogation position of the probe is complementary to the unknown base in the detection position of the target nucleic acid. This increased efficiency favors ligation of perfectly complementary sequencing probes to anchor probes over mismatch sequencing probes. As discussed above, ligation is generally accomplished enzymatically using a ligase, but other ligation methods can also be utilized in accordance with the invention. In FIG. 23, "N" represents a degenerate base and "B" represents nucleotides of undetermined sequence. As will be appreciated, in some embodiments, rather than degenerate bases, universal bases may be used.

As also discussed above, the sequencing probes can be oligonucleotides representing each base type at a specific position and labeled with a detectable label that differentiates each sequencing probe from the sequencing probes with other nucleotides at that position. Thus, in the example illustrated in FIG. 23, a sequencing probe 2310 that hybridizes adjacent to anchor probe 2302 and is ligated to the anchor probe will identify the base at a position in the target nucleic acid 5 bases from the adaptor as a "G". Multiple cycles of anchor probe and sequencing probe hybridization and ligation can be used to identify a desired number of bases of the target nucleic acid on each side of each adaptor in a DNB.

As will be appreciated, hybridization of the anchor probe and the sequencing probe can be sequential or simultaneous in any of the cPAL methods described herein.

In the embodiment illustrated in FIG. 23, sequencing probe 2310 hybridizes to a region "upstream" of the adaptor, however it will be appreciated that sequencing probes may also hybridize "downstream" of the adaptor. The terms "upstream" and "downstream" refer to the regions 5' and 3' of the adaptor, depending on the orientation of the system. In general, "upstream" and "downstream" are relative terms and are not meant to be limiting; rather they are used for ease of understanding. As illustrated in FIG. 6, a sequencing probe 607 can hybridize downstream of adaptor 604 to identify a nucleotide 4 bases away from the interface between the adaptor and the target nucleic acid 603. In further embodiments, sequencing probes can hybridize both upstream and downstream of the adaptor to identify nucleotides at positions in the nucleic acid on both sides of the adaptor. Such embodiments allow generation of multiple points of data from each adaptor for each hybridization-ligation-detection cycle of the single cPAL method.

In some embodiments, probes used in a single cPAL method may have from about 3 to about 20 bases corresponding to an adaptor and from about 1 to about 20 degenerate bases (i.e., in a pool of anchor probes). Such anchor probes may also include universal bases, as well as combinations of degenerate and universal bases.

In some embodiments, anchor probes with degenerated bases may have about 1-5 mismatches with respect to the adaptor sequence to increase the stability of full match hybridization at the degenerated bases. Such a design provides an additional way to control the stability of the ligated anchor and sequencing probes to favor those probes that are perfectly matched to the target (unknown) sequence. In further embodiments, a number of bases in the degenerate portion of the anchor probes may be replaced with abasic sites (i.e., sites which do not have a base on the sugar) or other nucleotide analogs to influence the stability of the hybridized probe to favor the full match hybrid at the distal end of the degenerate part of the anchor probe that will participate in the ligation reactions with the sequencing probes, as described herein. Such modifications may be incorporated, for example, at interior bases, particularly for anchor probes that comprise a large number (i.e., greater than 5) of degenerated bases. In addition, some of the degenerated or universal bases at the distal end of the anchor probe may be designed to be cleavable after hybridization (for example by incorporation of a uracil) to generate a ligation site to the sequencing probe or to a second anchor probe, as described further below.

In further embodiments, the hybridization of the anchor probes can be controlled through manipulation of the reaction conditions, for example the stringency of hybridization. In an exemplary embodiment, the anchor hybridization process may start with conditions of high stringency (higher temperature, lower salt, higher pH, higher concentration of formamide, and the like), and these conditions may be gradually or stepwise relaxed. This may require consecutive hybridization cycles in which different pools of anchor probes are removed and then added in subsequent cycles. Such methods provide a higher percentage of target nucleic acid occupied with perfectly complementary anchor probes, particularly anchor probes perfectly complementary at positions at the distal end that will be ligated to the sequencing probe. Hybridization time at each stringency condition may also be controlled to obtain greater numbers of full match hybrids.

III.B.1(b) Double cPAL (and Beyond)

In still further embodiments, the present invention provides cPAL methods utilizing two ligated anchor probes in every hybridization-ligation cycle. See for example U.S. Patent Application Ser. Nos. 60/992,485; 61/026,337; 61/035,914 and 61/061,134, which are hereby expressly incorporated by reference in their entirety, and especially the examples and claims. FIG. 25 illustrates an example of a "double cPAL" method in which a first anchor probe 2502 and a second anchor probe 2505 hybridize to complimentary regions of an adaptor; that is, the first anchor probe hybridizes to the first anchor site and the second anchor probe hybridizes to the second adaptor site. In the example illustrated in FIG. 25, the first anchor probe 2502 is fully complementary to a region of the adaptor 2511 (the first anchor site), and the second anchor probe 2505 is complementary to the adaptor region adjacent to the hybridization position of the first anchor probe (the second anchor site). In general, the first and second anchor sites are adjacent.

The second anchor probe may optionally also comprises degenerate bases at the terminus that is not adjacent to the first anchor probe such that it will hybridize to a region of the target nucleic acid 2512 adjacent to adaptor 2511. This allows sequence information to be generated for target nucleic acid bases farther away from the adaptor/target interface. Again, as outlined herein, when a probe is said to have "degenerate bases", it means that the probe actually comprises a set of probes, with all possible combinations of sequences at the degenerate positions. For example, if an anchor probe is 9 bases long with 6 known bases and three degenerate bases, the anchor probe is actually a pool of 64 probes.

The second anchor probe is generally too short to be maintained alone in its duplex hybridization state, but upon ligation to the first anchor probe it forms a longer anchor probe that is stable for subsequent methods. In the some embodiments, the second anchor probe has about 1 to about 5 bases that are complementary to the adaptor and about 5 to about 10 bases of degenerate sequence. As discussed above for the "single cPAL" method, a pool of sequencing probes 2508 representing each base type at a detection position of the target nucleic acid and labeled with a detectable label that differentiates each sequencing probe from the sequencing probes with other nucleotides at that position is hybridized 2509 to the adaptor-anchor probe duplex and ligated to the terminal 5' or 3' base of the ligated anchor probes. In the example illustrated in FIG. 25, the sequencing probes are designed to interrogate the base that is five positions 5' of the ligation point between the sequencing probe 2514 and the ligated anchor probes 2513. Since the second anchor probe 2505 has five degenerate bases at its 5' end, it reaches 5 bases into the target nucleic acid 2512, allowing interrogation with the sequencing probe at a full 10 bases from the interface between the target nucleic acid 2512 and the adaptor 2511. In FIG. 25, "N" represents a degenerate base and "B" represents nucleotides of undetermined sequence. As will be appreciated, in some embodiments, rather than degenerate bases, universal bases may be used.

In some embodiments, the second anchor probe may have about 5-10 bases corresponding to an adaptor and about 5-15 bases, which are generally degenerated, corresponding to the target nucleic acid. This second anchor probe may be hybridized first under optimal conditions to favor high percentages of target occupied with full match at a few bases around the ligation point between the two anchor probes. The first adaptor probe and/or the sequencing probe may be hybridized and ligated to the second anchor probe in a single step or sequentially. In some embodiments, the first and second anchor probes may have at their ligation point from about 5 to about 50 complementary bases that are not complementary to the adaptor, thus forming a "branching-out" hybrid. This design allows an adaptor-specific stabilization of the hybridized second anchor probe. In some embodiments, the second anchor probe is ligated to the sequencing probe before hybridization of the first anchor probe; in some embodiments the second anchor probe is ligated to the first anchor probe prior to hybridization of the sequencing probe; in some embodiments the first and second anchor probes and the sequencing probe hybridize simultaneously and ligation occurs between the first and second anchor probe and between the second anchor probe and the sequencing probe simultaneously or essentially simultaneously, while in other embodiments the ligation between the first and second anchor probe and between the second anchor probe and the sequencing probe occurs sequentially in any order. Stringent washing conditions can be used to remove unligated probes; (e.g., using temperature, pH, salt, a buffer with an optimal concentration of formamide can all be used, with optimal conditions and/or concentrations being determined using methods known in the art). Such methods can be particularly useful in methods utilizing second anchor probes with large numbers of degenerated bases that are hybridized outside of the corresponding junction point between the anchor probe and the target nucleic acid.

In certain embodiments, double cPAL methods utilize ligation of two anchor probes in which one anchor probe is fully complementary to an adaptor and the second anchor probe is fully degenerate (again, actually a pool of probes). An example of such a double cPAL method is illustrated in FIG. 26, in which the first anchor probe 2602 is hybridized to adaptor 2611 of DNB 2601. The second anchor probe 2605 is fully degenerate and is thus able to hybridize to the unknown nucleotides of the region of the target nucleic acid 2612 adjacent to adaptor 2611. The second anchor probe is designed to be too short to be maintained alone in its duplex hybridization state, but upon ligation to the first anchor probe the formation of the longer ligated anchor probe construct provides the stability needed for subsequent steps of the cPAL process. The second fully degenerate anchor probe may in some embodiments be from about 5 to about 20 bases in length. For longer lengths (i.e., above 10 bases), alterations to hybridization and ligation conditions may be introduced to lower the effective Tm of the degenerate anchor probe. The shorter second anchor probe will generally bind non-specifically to target nucleic acid and adaptors, but its shorter length will affect hybridization kinetics such that in general only those second anchor probes that are perfectly complementary to regions adjacent to the adaptors and the first anchor probes will have the stability to allow the ligase to join the first and second anchor probes, generating the longer ligated anchor probe construct. Non-specifically hybridized second anchor probes will not have the stability to remain hybridized to the DNB long enough to subsequently be ligated to any adjacently hybridized sequencing probes. In some embodiments, after ligation of the second and first anchor probes, any unligated anchor probes will be removed, usually by a wash step. In FIG. 26, "N" represents a degenerate base and "B" represents nucleotides of undetermined sequence. As will be appreciated, in some embodiments, rather than degenerate bases, universal bases may be used.

In further exemplary embodiments, the first anchor probe will be a hexamer comprising 3 bases complementary to the adaptor and 3 degenerate bases, whereas the second anchor probe comprises only degenerate bases and the first and second anchor probes are designed such that only the end of the first anchor probe with the degenerate bases will ligate to the second anchor probe. In further exemplary embodiments, the first anchor probe is an 8-mer comprising 3 bases complementary to an adaptor and 5 degenerate bases, and again the first and second anchor probes are designed such that only the end of the first anchor probe with the degenerate bases will ligate to the second anchor probe. It will be appreciated that these are exemplary embodiments and that a wide range of combinations of known and degenerate bases can be used in the design of both the first and second (and in some embodiments the third and/or fourth) anchor probes.

In variations of the above described examples of a double cPAL method, if the first anchor probe terminates closer to the end of the adaptor, the second anchor probe will be proportionately more degenerate and therefore will have a greater potential to not only ligate to the end of the first anchor probe but also to ligate to other second anchor probes at multiple sites on the DNB. To prevent such ligation artifacts, the second anchor probes can be selectively activated to engage in ligation to a first anchor probe or to a sequencing probe. Such activation include selectively modifying the termini of the anchor probes such that they are able to ligate only to a particular anchor probe or sequencing probe in a particular orientation with respect to the adaptor. For example, 5' and 3' phosphate groups can be introduced to the second anchor probe, with the result that the modified second anchor probe would be able to ligate to the 3' end of a first anchor probe hybridized to an adaptor, but two second anchor probes would not be able to ligate to each other (because the 3' ends are phosphorylated, which would prevent enzymatic ligation). Once the first and second anchor probes are ligated, the 3' ends of the second anchor probe can be activated by removing the 3' phosphate group (for example with T4 polynucleotide kinase or phosphatases such as shrimp alkaline phosphatase and calf intestinal phosphatase).

If it is desired that ligation occur between the 3' end of the second anchor probe and the 5' end of the first anchor probe, the first anchor probe can be designed and/or modified to be phosphorylated on its 5' end and the second anchor probe can be designed and/or modified to have no 5' or 3' phosphorylation. Again, the second anchor probe would be able to ligate to the first anchor probe, but not to other second anchor probes. Following ligation of the first and second anchor probes, a 5' phosphate group can be produced on the free terminus of the second anchor probe (for example, by using T4 polynucleotide kinase) to make it available for ligation to sequencing probes in subsequent steps of the cPAL process.

In some embodiments, the two anchor probes are applied to the DNBs simultaneously. In some embodiments, the two anchor probes are applied to the DNBs sequentially, allowing one of the anchor probes to hybridize to the DNBs before the other. In some embodiments, the two anchor probes are ligated to each other before the second adaptor is ligated to the sequencing probe. In some embodiments, the anchor probes and the sequencing probe are ligated in a single step. In embodiments in which two anchor probes and the sequencing probe are ligated in a single step, the second adaptor can be designed to have enough stability to maintain its position until all three probes (the two anchor probes and the sequencing probe) are in place for ligation. For example, a second anchor probe comprising five bases complementary to the adaptor and five degenerate bases for hybridization to the region of the target nucleic acid adjacent to the adaptor can be used. Such a second anchor probe may have sufficient stability to be maintained with low stringency washing, and thus a ligation step would not be necessary between the steps of hybridization of the second anchor probe and hybridization of a sequencing probe. In the subsequent ligation of the sequencing probe to the second anchor probe, the second anchor probe would also be ligated to the first anchor probe, resulting in a duplex with increased stability over any of the anchor probes or sequencing probes alone.

Similar to the double cPAL method described above, it will be appreciated that cPAL with three or more anchor probes is also encompassed by the present invention. Such anchor probes can be designed in accordance with methods described herein and known in the art to hybridize to regions of adaptors such that one terminus of one of the anchor probes is available for ligation to sequencing probes hybridized adjacent to the terminal anchor probe. In an exemplary embodiment, three anchor probes are provided—two are complementary to different sequences within an adaptor and the third comprises degenerate bases to hybridize to sequences within the target nucleic acid. In a further embodiment, one of the two anchors complementary to sequences within the adaptor may also comprise one or more degenerate bases at on terminus, allowing that anchor probe to reach into the target nucleic acid for ligation with the third anchor probe. In further embodiments, one of the anchor probes may be fully or partially complementary to the adaptor and the second and third anchor probes will be fully degenerate for hybridization to the target nucleic acid. Four or more fully degenerate anchor probes can in further embodiments be ligated sequentially to the three ligated anchor probes to achieve extension of reads further into the target nucleic acid sequence. In an exemplary embodiment, a first anchor probe comprising twelve bases complementary to an adaptor may ligate with a second hexameric anchor probe in which all six bases are degenerate. A third anchor, also a fully degenerate hexamer, can also ligate to the second anchor probe to further extend into the unknown sequence of the target nucleic acid. A fourth, fifth, sixth, etc. anchor probe may also be added to extend even further into the unknown sequence. In still further embodiments and in accordance with any of the cPAL methods described herein, one or more of the anchor probes may comprise one or more labels that serve to "tag" the anchor probe and/or identify the particular anchor probe hybridized to an adaptor of a DNB.

III.B.1(c) Detecting Fluorescently Labeled Sequencing Probes

As discussed above, sequencing probes used in accordance with the present invention may be detectably labeled with a wide variety of labels. Although the following description is primarily directed to embodiments in which the sequencing probes are labeled with fluorophores, it will be appreciated that similar embodiments utilizing sequencing probes comprising other kinds of labels are encompassed by the present invention.

Multiple cycles of cPAL (whether single, double, triple, etc.) will identify multiple bases in the regions of the target nucleic acid adjacent to the adaptors. In brief, the cPAL methods are repeated for interrogation of multiple bases within a target nucleic acid by cycling anchor probe hybridization and enzymatic ligation reactions with sequencing probe pools designed to detect nucleotides at varying positions removed from the interface between the adaptor and target nucleic acid. In any given cycle, the sequencing probes used are designed such that the identity of one or more of bases at one or more positions is correlated with the identity of the label attached to that sequencing probe. Once the ligated sequencing probe (and hence the base(s) at the interrogation position(s) is detected, the ligated complex is stripped off of the DNB and a new cycle of adaptor and sequencing probe hybridization and ligation is conducted.

In general, four fluorophores are generally used to identify a base at an interrogation position within a sequencing probe, and a single base is queried per hybridization-ligation-detection cycle. However, as will be appreciated, embodiments utilizing 8, 16, 20 and 24 fluorophores or more are also encompassed by the present invention. Increasing the number of fluorophores increases the number of bases that can be identified during any one cycle.

In one exemplary embodiment, a set of 7-mer pools of sequencing probes is employed having the following structures:

```
3'-F1-NNNNNNAp
3'-F2-NNNNNNGp
3'-F3-NNNNNNCp
3'-F4-NNNNNNTp
```

The "p" represents a phosphate available for ligation and "N" represents degenerate bases. F1-F4 represent four different fluorophores—each fluorophore is thus associated with a particular base. This exemplary set of probes would allow detection of the base immediately adjacent to the adaptor upon ligation of the sequencing probe to an anchor probe hybridized to the adaptor. To the extent that the ligase used to ligate the sequencing probe to the anchor probe discriminates for complementarity between the base at the interrogation position of the probe and the base at the detection position of the target nucleic acid, the fluorescent signal that would be detected upon hybridization and ligation of the sequencing probe provides the identity of the base at the detection position of the target nucleic acid.

In some embodiments, a set of sequencing probes will comprise three differentially labeled sequencing probes, with a fourth optional sequencing probe left unlabeled.

After performing a hybridization-ligation-detection cycle, the anchor probe-sequencing probe ligation products are stripped and a new cycle is begun. In some embodiments, accurate sequence information can be obtained as far as six bases or more from the ligation point between the anchor and sequencing probes and as far as twelve bases or more from the interface between the target nucleic acid and the adaptor. The number of bases that can be identified can be increased using methods described herein, including the use of anchor probes with degenerate ends that are able to reach further into the target nucleic acid.

Imaging acquisition may be performed using methods known in the art, including the use of commercial imaging packages such as Metamorph (Molecular Devices, Sunnyvale, Calif.). Data extraction may be performed by a series of binaries written in, e.g., C/C++ and base-calling and read-mapping may be performed by a series of Matlab and Perl scripts.

In an exemplary embodiment, DNBs disposed on a surface undergo a cycle of cPAL as described herein in which the sequencing probes utilized are labeled with four different fluorophores (each corresponding to a particular base at an interrogation position within the probe). To determine the identity of a base of each DNB disposed on the surface, each field of view ("frame") is imaged with four different wavelengths corresponding the to the four fluorescently labeled sequencing probes. All images from each cycle are saved in a cycle directory, where the number of images is four times the number of frames (when four fluorophores are used). Cycle image data can then be saved into a directory structure organized for downstream processing.

In some embodiments, data extraction will rely on two types of image data: bright-field images to demarcate the positions of all DNBs on a surface, and sets of fluorescence images acquired during each sequencing cycle. Data extraction software can be used to identify all objects with the bright-field images and then for each such object, the software can be used to compute an average fluorescence value for each sequencing cycle. For any given cycle, there are four data points, corresponding to the four images taken at different wavelengths to query whether that base is an A, G, C or T. These raw data points (also referred to herein as "base calls") are consolidated, yielding a discontinuous sequencing read for each DNB.

The population of identified bases can then be assembled to provide sequence information for the target nucleic acid and/or identify the presence of particular sequences in the target nucleic acid. In some embodiments, the identified bases are assembled into a complete sequence through alignment of overlapping sequences obtained from multiple sequencing cycles performed on multiple DNBs. As used herein, the term "complete sequence" refers to the sequence of partial or whole genomes as well as partial or whole target nucleic acids. In further embodiments, assembly methods utilize algorithms that can be used to "piece together" overlapping sequences to provide a complete sequence. In still further embodiments, reference tables are used to assist in assembling the identified sequences into a complete sequence. A reference table may be compiled using existing sequencing data on the organism of choice. For example human genome data can be accessed through the website of the National Center for Biotechnology Information, or the website of the J. Craig Venter Institute. All or a subset of human genome information can be used to create a reference table for particular sequencing queries. In addition, specific reference tables can be constructed from empirical data derived from specific populations, including genetic sequence from humans with specific ethnicities, geographic heritage, religious or culturally-defined populations, as the variation within the human genome may slant the reference data depending upon the origin of the information contained therein.

In any of the embodiments of the invention discussed herein, a population of nucleic acid templates and/or DNBs may comprise a number of target nucleic acids to substantially cover a whole genome or a whole target polynucleotide. As used herein, "substantially covers" means that the amount of nucleotides (i.e., target sequences) analyzed contains an equivalent of at least two copies of the target polynucleotide, or in another aspect, at least ten copies, or in another aspect, at least twenty copies, or in another aspect, at least 100 copies. Target polynucleotides may include DNA fragments, including genomic DNA fragments and cDNA fragments, and RNA fragments. Guidance for the step of reconstructing target polynucleotide sequences can be found in the following references, which are incorporated by reference: Lander et al, Genomics, 2: 231-239 (1988); Vingron et al, J. Mol. Biol., 235: 1-12 (1994); and like references.

III.B.1(d) Sets of Probes

As will be appreciated, different combinations of sequencing and anchor probes can be used in accordance with the various cPAL methods described above. The following descriptions of sets of probes (also referred to herein as "pools of probes") of use in the present invention are exemplary embodiments and it will be appreciated that the present invention is not limited to these combinations.

In one aspect, sets of probes are designed for identification of nucleotides at positions at a specific distance from an adaptor. For example, certain sets of probes can be used to identify bases up to 3, 4, 5, 6, 7, 8, 9, 10, 11, 12, 13, 14, 15, 16, 17, 18, 19, 20, 21, 22, 23, 24, 25, 26, 27, 28, 29, 30 and more positions away from the adaptor. As discussed above, anchor probes with degenerate bases at one terminus can be designed to reach into the target nucleic acid adjacent to an adaptor, allowing sequencing probes to ligate further away from the adaptor and thus provide the identity of a base further away from the adaptor.

In an exemplary embodiment, a set of probes comprises at least two anchor probes designed to hybridize to adjacent regions of an adaptor. In one embodiment, the first anchor probe is fully complementary to a region of the adaptor, while the second anchor probe is complementary to the adjacent region of the adaptor. In some embodiments, the second anchor probe will comprise one or more degenerate nucleotides that extend into and hybridize to nucleotides of the target nucleic acid adjacent to the adaptor. In an exemplary embodiment, the second anchor probe comprises at least 1-10 degenerate bases. In a further exemplary embodiment, the second anchor probe comprises 2-9, 3-8, 4-7, and 5-6 degenerate bases. In a still further exemplary embodiment, the second anchor probe comprises one or more degenerate bases at one or both termini and/or within an interior region of its sequence.

In a further embodiment, a set of probes will also comprise one or more groups of sequencing probes for base determination in one or more detection positions with a target nucleic acid. In one embodiment, the set comprises enough different groups of sequencing probes to identify about 1 to about 20 positions within a target nucleic acid. In a further exemplary embodiment, the set comprises enough groups of sequencing probes to identify about 2 to about 18, about 3 to about 16, about 4 to about 14, about 5 to about 12, about 6 to about 10, and about 7 to about 8 positions within a target nucleic acid.

In further exemplary embodiments, 10 pools of labeled or tagged probes will be used in accordance with the invention. In still further embodiments, sets of probes will include two or more anchor probes with different sequences. In yet further embodiments, sets of probes will include 3, 4, 5, 6, 7, 8, 9, 10, 11, 12, 13, 14, 15 or more anchor probes with different sequences.

In a further exemplary embodiment, a set of probes is provided comprising one or more groups of sequencing probes and three anchor probes. The first anchor probe is complementary to a first region of an adaptor, the second anchor probe is complementary to a second region of an adaptor, and the second region and the first region are adjacent to each other. The third anchor probe comprises three or more degenerate nucleotides and is able to hybridize to nucleotides in the target nucleic acid adjacent to the adaptor. The third anchor probe may also in some embodiments be complementary to a third region of the adaptor, and that third region may be adjacent to the second region, such that the second anchor probe is flanked by the first and third anchor probes.

In some embodiments, sets of anchor and/or sequencing probes will comprise variable concentrations of each type of probe, and the variable concentrations may in part depend on the degenerate bases that may be contained in the anchor probes. For example, probes that will have lower hybridization stability, such as probes with greater numbers of A's and/or T's, can be present in higher relative concentrations as a way to offset their lower stabilities. In further embodiments, these differences in relative concentrations are established by preparing smaller pools of probes independently and then mixing those independently generated pools of probes in the proper amounts.

III.B.1(e) Two-Phase Sequencing

In one aspect, the present invention provides methods for "two-phase" sequencing, which is also referred to herein as "shotgun sequencing". Such methods are described in U.S. patent application Ser. No. 12/325,922, filed Dec. 1, 2008, which is hereby incorporated by reference in its entirety for all purposes and in particular for all teachings related to two-phase or shotgun sequencing.

Generally, two phase-sequencing methods of use in the present invention comprise the following steps: (a) sequencing the target nucleic acid to produce a primary target nucleic acid sequence that comprises one or more sequences of interest; (b) synthesizing a plurality of target-specific oligonucleotides, wherein each of said plurality of target-specific oligonucleotides corresponds to at least one of the sequences of interest; (c) providing a library of fragments of the target nucleic acid (or constructs that comprise such fragments and that may further comprise, for example, adaptors and other sequences as described herein) that hybridize to the plurality of target-specific oligonucleotides; and (d) sequencing the library of fragments (or constructs that comprise such fragments) to produce a secondary target nucleic acid sequence. In order to close gaps due to missing sequence or resolve low confidence base calls in a primary sequence of genomic DNA, such as human genomic DNA, the number of target-specific oligonucleotides that are synthesized for these methods may be from about ten thousand to about one million; thus the present invention contemplates the use of at least about 10,000 target-specific oligonucleotides, or about 25,000, or about 50,000, or about 100,000, or about 20,000, or about 50,000, or about 100,000, or about 200,000 or more.

In saying that the plurality of target-specific oligonucleotides "corresponds to" at least one of the sequences of interest, it is meant that such target-specific oligonucleotides are designed to hybridize to the target nucleic acid in proximity to, including but not limited to, adjacent to, the sequence of interest such that there is a high likelihood that a fragment of the target nucleic acid that hybridizes to such an oligonucleotides will include the sequence of interest. Such target-specific oligonucleotides are therefore useful for hybrid capture methods to produce a library of fragments enriched for such sequences of interest, as sequencing primers for sequencing the sequence of interest, as amplification primers for amplifying the sequence of interest, or for other purposes.

In shotgun sequencing and other sequencing methods according to the present invention, after assembly of sequencing reads, to the skilled person it is apparent from the assembled sequence that gaps exist or that there is low confidence in one or more bases or stretches of bases at a particular site in the sequence. Sequences of interest, which may include such gaps, low confidence sequence, or simply different sequences at a particular location (i.e., a change of one or more nucleotides in target sequence), can also be identified by comparing the primary target nucleic acid sequence to a reference sequence.

According to one embodiment of such methods sequencing the target nucleic acid to produce a primary target nucleic acid sequence comprises computerized input of sequence readings and computerized assembly of the sequence readings to produce the primary target nucleic acid sequence. In addition, design of the target-specific oligonucleotides can be computerized, and such computerized synthesis of the target-specific oligonucleotides can be integrated with the computerized input and assembly of the sequence readings and design of the target-specific oligonucleotides. This is especially helpful since the number of target-specific oligonucleotides to be synthesized can be in the tens of thousands or hundreds of thousands for genomes of higher organisms such as humans, for example. Thus the invention provides automated integration of the process of creating the oligonucleotide pool from the determined sequences and the regions identified for further processing. In some embodiments, a computer-driven program uses the identified regions and determined sequence near or adjacent to such identified regions to design oligonucleotides to isolate and/or create new fragments that cover these regions. The oligonucleotides can then be used as described herein to isolate fragments, either from the first sequencing library, from a precursor of the first sequencing library, from a different sequencing library created from the same target nucleic acid, directly from target nucleic acids, and the like. In further embodiments, this automated integration of identifying regions for further analysis and isolating/creating the second library defines the sequence of the oligonucleotides within the oligonucleotide pool and directs synthesis of these oligonucleotides.

In some embodiments of the two phase sequencing methods of the invention, a releasing process is performed after the hybrid capture process, and in other aspects of the technology, an amplification process is performed before the second sequencing process.

In still further embodiments, some or all regions are identified in the identifying step by comparison of determined sequences with a reference sequence. In some aspects, the second shotgun sequencing library is isolated using a pool of oligonucleotides comprising oligonucleotides based on a reference sequence. Also, in some aspects, the pool of oligonucleotides comprises at least 1000 oligonucleotides of different sequence, in other aspects, the pool of oligonucleotides comprises at least 10,000, 25,000, 50,000, 75,000, or 100,000 or more oligonucleotides of different sequence In some aspects of the invention, one or more of the sequencing processes used in this two-phase sequencing method is performed by sequencing-by-ligation, and in other aspects, one or more of the sequencing processes is performed by sequencing-by-hybridization or sequencing-by-synthesis.

In certain aspects of the invention, between about 1 to about 30% of the complex target nucleic acid is identified as having to be re-sequenced in Phase II of the methods, and in other aspects, between about 1 to about 10% of the complex target nucleic acid is identified as having to be re-sequenced in Phase II of the methods. In some aspects, coverage for the identified percentage of complex target nucleic acid is between about 25× to about 100×.

In further aspects, 1 to about 10 target-specific selection oligonucleotides are defined and synthesized for each target nucleic acid region that is re-sequenced in Phase II of the methods; in other aspects, about 3 to about 6 target-specific selection oligonucleotides are defined for each target nucleic acid region that is re-sequenced in Phase II of the methods.

In still further aspects of the technology, the target-specific selection oligonucleotides are identified and synthesized by an automated process, wherein the process that identifies regions of the complex nucleic acid missing nucleic acid sequence or having low confidence nucleic acid sequence and defines sequences for the target-specific selection oligonucleotides communicates with oligonucleotide synthesis software and hardware to synthesize the target-specific selection oligonucleotides. In other aspects of the technology, the target-specific selection oligonucleotides are between about 20 and about 30 bases in length, and in some aspects are unmodified.

Not all regions identified for further analysis may actually exist in the complex target nucleic acid. One reason for predicted lack of coverage in a region may be that a region expected to be in the complex target nucleic acid may actually not be present (e.g., a region may be deleted or re-arranged in the target nucleic acid), and thus not all oligonucleotides produced from the pool may isolate a fragment for inclusion in the second shotgun sequencing library. In some embodiments, at least one oligonucleotide will be designed and created for each region identified for further analysis. In further embodiments, an average of three or more oligonucleotides will be provided for each region identified for further analysis. It is a feature of the invention that the pool of oligonucleotides can be used directly to create the second shotgun sequencing library by polymerase extension of the oligonucleotides using templates derived from a target nucleic acid. It is another feature of the invention that the pool of oligonucleotides can be used directly to create amplicons via circle dependent replication using the oligonucleotide pools and circle dependent replication. It is another feature of the invention that the methods will provide sequencing information to identify absent regions of interest, e.g. predicted regions that were identified for analysis but which do not exist, e.g., due to a deletion or rearrangement.

The above described embodiments of the two-phase sequencing method can be used in combination with any of the nucleic acid constructs and sequencing methods described herein and known in the art.

III.B.1(f) SNP Detection

Methods and compositions discussed above can in further embodiments be used to detect specific sequences in nucleic acid constructs such as DNBs. In particular, cPAL methods utilizing sequencing and anchor probes can be used to detect polymorphisms or sequences associated with a genetic mutation, including single nucleotide polymorphisms (SNPs). For example, to detect the presence of a SNP, two sets of differentially labeled sequencing probes can be used, such that detection of one probe over the other indicates whether a polymorphism present in the sample. Such sequencing probes can be used in conjunction with anchor probes in methods similar to the cPAL methods described above to further improve the specificity and efficiency of detection of the SNP.

IV. Arrays

In one aspect, nucleic acids, including LFR aliquot fragments and DNBs, are disposed on a surface to form a random array of single molecules. Nucleic acids can be fixed to surface by a variety of techniques, including covalent attachment and non-covalent attachment. Non-covalent attachment includes hydrogen bonding, van der Waals forces, electrostatic attraction and the like.

Methods for forming arrays of the invention are described in Published Patent Application Nos. WO2007120208, WO2006073504, WO2007133831, and US2007099208, and U.S. Patent Application Nos. 60/992,485; 61/026,337; 61/035,914; 61/061,134; 61/116,193; 61/102,586; Ser. Nos. 12/265,593; 12/266,385; 11/938,096; 11/981,804; Ser. Nos. 11/981,797; 11/981,793; 11/981,767; 11/981,761; 11/981,730; 11/981,685; 11/981,661; 11/981,607; 11/981,605; 11/927,388; 11/927,356; 11/679,124; 11/541,225; 10/547,214; 11/451,692; and 11/451,691, all of which are incorporated herein by reference in their entirety for all purposes and in particular for all teachings related to forming arrays.

In some embodiments, patterned substrates are formed by growing a layer of silicon dioxide on the surface of a standard silicon wafer. A layer of metal, such as titanium, is deposited over silicon dioxide, and the titanium layer is patterned with fiducial markings with conventional photolithography and dry etching techniques. A layer of hexamethyldisilazane (HMDS) (Gelest Inc., Morrisville, Pa.) can then be added to the substrate surface by vapor deposition, and a deep-UV, positive-tone photoresist material is coated to the surface by centrifugal force. The photoresist surface can then be exposed with the array pattern with a 248 nm lithography tool, and the resist developed to produce arrays having discrete regions of exposed HMDS. The HMDS layer in the holes can be removed, in some embodiments with a plasma-etch process, and functional moieties can be vapor-deposited in the holes to provide attachment sites for nucleic acids. In certain embodiments, these functional moieties are aminosilane moieties, which provide a positive charge that can be used to non-covalently immobilize nucleic acids through electrostatic attraction. Surfaces can in some embodiments be further coated with a layer of photoresist after deposition of aminosilane moieties and cut into substrates of a predetermined size. For example, in some embodiments substrates of 75 mm×25 mm area are of use in aspects of the present invention. In further embodiments, photoresist material can be stripped from individual substrates using methods known in the art, including ultrasonication. In still further embodiments, regions between the discrete aminosilane features are inert to prevent nucleic acid binding to the spaces between discrete regions. For example, the aminosilane features patterned onto the substrate in accordance with the embodiments described herein serve as nucleic acid binding sites, whereas the remaining HMDS inhibits nucleic acid binding between features. In yet further embodiments, a mixture of polystyrene beads and polyurethane glue is applied in a series of parallel lines to each diced substrate, and a coverslip pressed into the flue lines to form a six-lane gravity/capillary-driven flow slide. In certain embodiments, the polystyrene beads are 50 µm beads. Nucleic acids can be loaded into flow slide lanes by pipetting nucleic acids onto the slide. In certain embodiments, a larger quantity of nucleic acids is applied to the slide than the number of binding sites present on the slide. In further exemplary embodiments, 2-20 fold more nucleic acid single molecules than binding sites are applied to the slide. In still further embodiments, 2, 3, 4, 5, 6, 7, 8, 9, 10, 11, 12, 13, 14, 15, 16, 17, 18, 19, and 20 fold more nucleic acid single molecules than binding sites are applied to the slide.

As will be appreciated, a wide range of densities of nucleic acids of the invention can be placed on a surface comprising discrete regions to form an array. Nucleic acids are generally immobilized to the discrete regions by a variety of methods known in the art and described in further detail below. In specific embodiments, nucleic acids are immobilized to discrete regions on an array through non-covalent electrostatic interactions.

In preferred embodiments, at least a majority of the discrete regions comprises a single molecule attached thereto, and the discrete regions and/or the single molecules are distributed such that at least a majority of the single molecules immobilized to the discrete regions are optically resolvable. In further embodiments, at least 50%-100% of the discrete regions have a single molecule attached thereto. In still further embodiments, at least 55%-95%, 60%-90%, 65%-85%, and 70%-80% of the discrete regions on an array have a single molecule attached thereto. In yet further embodiments, at least 60%, 65%, 70%, 75%, 80%, 85%, 90%, 95%, 96%, 97%, 98%, and 99% of discrete regions on an array have a single molecule attached thereto.

In further embodiments, at least at least 50%-100% of the single molecules on a random array of the invention are optically resolvable. In still further embodiments, at least 55%-95%, 60%-90%, 65%-85%, and 70%-80% of the single molecules on a random array of the invention are optically resolvable. In yet further embodiments, at least 60%, 65%, 70%, 75%, 80%, 85%, 90%, 95%, 96%, 97%, 98%, and 99% of the single molecules on a random array of the invention are optically resolvable.

In some embodiments, the area of discrete regions is less than 1 µm$^2$; and in some embodiments, the area of discrete regions is in the range of from 0.04 µm$^2$ to 1 µm$^2$; and in some embodiments, the area of discrete regions is in the range of from 0.2 µm$^2$ to 1 µm$^2$. In still further embodiments, the area of the discrete regions is about 0.1, 0.2, 0.3, 0.4, 0.5, 0.6, 0.7, 0.8, 0.9, 1, 1.5, 2, 2.5 µm$^2$. In embodiments in which discrete regions are approximately circular or square in shape so that their sizes can be indicated by a single linear dimension, the size of such regions are in the range of from 125 nm to 250 nm, or in the range of from 200 nm to 500 nm. In some embodiments, center-to-center distances of nearest neighbors of discrete regions are in the range of from 0.25 µm to 20 µm; and in some embodiments, such distances are in the range of from 1 µm to 10 µm, or in the range from 50 to 1000 nm. In still further embodiments, center-to-center distances of nearest neighbors of discrete regions are in the range of from about 100-900, 200-800, 300-700, 400-500 nm. In yet further embodiments, center-to-center distances of nearest neighbors of discrete regions are in the range of from about 650-750, 660-740, 650-730, 660-720, 670-710, 680-700, 700-710 nm. In certain embodiments, center-to-center distances of nearest neighbors of discrete regions are 707 nm. Generally, discrete regions are designed such that a majority of the discrete regions on a surface are optically resolvable. In some embodiments, regions may be arranged on a surface in virtually any pattern in which regions have defined locations. As discussed in further detail above, in certain embodiments, a single nucleic acid is attached to each of at least a majority of discrete regions on a surface.

In some embodiments, an array of the invention comprises 1, 2, 3, 4, 5, 6, 7, 8, 9, or 10 single molecules per square micron.

In some embodiments, arrays of nucleic acids are provided in densities of at least 0.5, 1, 2, 3, 4, 5, 6, 7, 8, 9, or 10 million molecules per square millimeter.

In some embodiments, nucleic acids are randomly disposed on substrates described herein and known in the art at a density such that each discrete region comprises a single nucleic acid molecule immobilized thereto. In further embodiments, nucleic acids are disposed on substrates at a density of 100, 200, 500, 750, 1000, 2000, 3000, 4000, 5000, 10,000, 50,000, 100,000, 250,000, 500,000, 750,000, 1,000,000 molecules per square micron.

In some embodiments, a surface may have reactive functionalities that react with complementary functionalities on the polynucleotide molecules to form a covalent linkage, e.g., by way of the same techniques used to attach cDNAs to microarrays, e.g., Smirnov et al (2004), Genes, Chromosomes & Cancer, 40: 72-77; Beaucage (2001), Current Medicinal Chemistry, 8: 1213-1244, which are incorporated herein by reference. Nucleic acids may also be efficiently attached to hydrophobic surfaces, such as a clean glass surface that has a low concentration of various reactive functionalities, such as —OH groups. Attachment through covalent bonds formed between the polynucleotide molecules and reactive functionalities on the surface is also referred to herein as "chemical attachment".

In one aspect, nucleic acids on a surface are confined to an area of a discrete region. Discrete regions may be incorporated into a surface using methods known in the art and described further below. As will be appreciated, nucleic acids of the invention can be immobilized to discrete regions through non-specific interactions, or through non-covalent interactions such as hydrogen bonding, van der Waals forces, electrostatic attraction and the like. Nucleic acids may also be attached to discrete regions through the use of capture probes or through covalent interaction with reactive functionalities, as is known in the art and described in further detail herein. As will be appreciated, attachment may also include wash steps of varying stringencies to remove incompletely attached single molecules or other reagents present from earlier preparation steps whose presence is undesirable or that are nonspecifically bound to surface.

The discrete regions may have defined locations in a regular array, which may correspond to a rectilinear pattern, hexagonal pattern, or the like. A regular array of such regions is advantageous for detection and data analysis of signals collected from the arrays during an analysis. Also, first- and/or second-stage amplicons confined to the restricted area of a discrete region provide a more concentrated or intense signal, particularly when fluorescent probes are used in analytical operations, thereby providing higher signal-to-noise values. In some embodiments, nucleic acids are randomly distributed on the discrete regions so that a given region is equally likely to receive any of the different single molecules. In other words, the resulting arrays are not spatially addressable immediately upon fabrication, but may be made so by carrying out an identification, sequencing and/or decoding operation. As such, the identities of the polynucleotide molecules of the invention disposed on a surface are discernable, but not initially known upon their disposition on the surface. In some embodiments, the area of discrete is selected, along with attachment chemistries, macromolecular structures employed, and the like, to correspond to the size of single molecules of the invention so that when single molecules are applied to surface substantially every region is occupied by no more than one single molecule. In some embodiments, nucleic acids are disposed on a surface comprising discrete regions in a patterned manner, such that specific nucleic acids (identified, in an exemplary embodiment, by tag adaptors or other labels) are disposed on specific discrete regions or groups of discrete regions.

In further embodiments, molecules are directed to the discrete regions of a surface, because the areas between the discrete regions, referred to herein as "inter-regional areas," are inert, in the sense that concatemers, or other macromolecular structures, do not bind to such regions. In some embodiments, such inter-regional areas may be treated with blocking agents, e.g., DNAs unrelated to concatemer DNA, other polymers, and the like.

A wide variety of supports may be used with the compositions and methods of the invention to form random arrays. In one aspect, supports are rigid solids that have a surface, preferably a substantially planar surface so that single molecules to be interrogated are in the same plane. The latter feature permits efficient signal collection by detection optics, for example. In another aspect, the support comprises beads, wherein the surface of the beads comprise reactive functionalities or capture probes that can be used to immobilize polynucleotide molecules.

In still another aspect, solid supports of the invention are nonporous, particularly when random arrays of single molecules are analyzed by hybridization reactions requiring small volumes. Suitable solid support materials include materials such as glass, polyacrylamide-coated glass, ceramics, silica, silicon, quartz, various plastics, and the like. In one aspect, the area of a planar surface may be in the range of from 0.5 to 4 $cm^2$. In one aspect, the solid support is glass or quartz, such as a microscope slide, having a surface that is uniformly silanized. This may be accomplished using conventional protocols, e.g., acid treatment followed by immersion in a solution of 3-glycidoxypropyl trimethoxysilane, N,N-diisopropylethylamine, and anhydrous xylene (8:1:24 v/v) at 80° C., which forms an epoxysilanized surface. e.g., Beattie et al (1995), Molecular Biotechnology, 4: 213. Such a surface is readily treated to permit end-attachment of capture oligonucleotides, e.g., by providing capture oligonucleotides with a 3' or 5' triethylene glycol phosphoryl spacer (see Beattie et al, cited above) prior to application to the surface. Further embodiments for functionalizing and further preparing surfaces for use in the present invention are described for example in U.S. Patent Application Ser. Nos. 60/992,485; 61/026,337; 61/035,914; 61/061,134; 61/116,193; 61/102,586; 12/265,593; 12/266,385; 11/938,096; 11/981,804; Ser. Nos. 11/981,797; 11/981,793; 11/981,767; 11/981,761; 11/981,730; 11/981,685; 11/981,661; 11/981,607; 11/981,605; 11/927,388; 11/927,356; 11/679,124; 11/541,225; 10/547,214; 11/451,692; and 11/451,691, each of which is herein incorporated by reference in its entirety for all purposes and in particular for all teachings related to preparing surfaces for forming arrays and for all teachings related to forming arrays, particularly arrays of nucleic acids.

In embodiments of the invention in which patterns of discrete regions are required, photolithography, electron beam lithography, nano imprint lithography, and nano printing may be used to generate such patterns on a wide variety of surfaces, e.g., Pirrung et al, U.S. Pat. No. 5,143,854; Fodor et al, U.S. Pat. No. 5,774,305; Guo, (2004) Journal of Physics D: Applied Physics, 37: R123-141; which are incorporated herein by reference.

In one aspect, surfaces containing a plurality of discrete regions are fabricated by photolithography. A commercially available, optically flat, quartz substrate is spin coated with a 100-500 nm thick layer of photo-resist. The photo-resist is then baked on to the quartz substrate. An image of a reticle with a pattern of regions to be activated is projected onto the surface of the photo-resist, using a stepper. After exposure, the photo-resist is developed, removing the areas of the projected pattern which were exposed to the UV source. This is accomplished by plasma etching, a dry developing technique capable of producing very fine detail. The substrate is then baked to strengthen the remaining photo-resist. After baking, the quartz wafer is ready for functionalization. The wafer is then subjected to vapor-deposition of 3-aminopropyldimethylethoxysilane. The density of the amino functionalized monomer can be tightly controlled by varying the concentration of the monomer and the time of exposure of the substrate. Only areas of quartz exposed by the plasma etching process may react with and capture the monomer. The substrate is then baked again to cure the monolayer of amino-functionalized monomer to the exposed quartz. After baking, the remaining photo-resist may be removed using acetone. Because of the difference in attachment chemistry between the resist and silane, aminosilane-functionalized areas on the substrate may remain intact through the acetone rinse. These areas can be further functionalized by reacting them with p-phenylenediisothiocyanate in a solution of pyridine and N—N-dimethlyformamide. The substrate is then capable of reacting with amine-modified oligonucleotides. Alternatively, oligonucleotides can be prepared with a 5'-carboxy-modifier-c10 linker (Glen Research). This technique allows the oligonucleotide to be attached directly to the amine modified support, thereby avoiding additional functionalization steps.

In another aspect, surfaces containing a plurality of discrete regions are fabricated by nano-imprint lithography (NIL). For DNA array production, a quartz substrate is spin coated with a layer of resist, commonly called the transfer layer. A second type of resist is then applied over the transfer layer, commonly called the imprint layer. The master imprint tool then makes an impression on the imprint layer. The overall thickness of the imprint layer is then reduced by plasma etching until the low areas of the imprint reach the transfer layer. Because the transfer layer is harder to remove than the imprint layer, it remains largely untouched. The imprint and transfer layers are then hardened by heating. The substrate is then put into a plasma etcher until the low areas of the imprint reach the quartz. The substrate is then derivatized by vapor deposition as described above.

In another aspect, surfaces containing a plurality of discrete regions are fabricated by nano printing. This process uses photo, imprint, or e-beam lithography to create a master mold, which is a negative image of the features required on the print head. Print heads are usually made of a soft, flexible polymer such as polydimethylsiloxane (PDMS). This material, or layers of materials having different properties, are spin coated onto a quartz substrate. The mold is then used to emboss the features onto the top layer of resist material under controlled temperature and pressure conditions. The print head is then subjected to a plasma based etching process to improve the aspect ratio of the print head, and eliminate distortion of the print head due to relaxation over time of the embossed material. Random array substrates are manufactured using nano-printing by depositing a pattern of amine modified oligonucleotides onto a homogenously derivatized surface. These oligonucleotides would serve as capture probes for nucleic acids. One potential advantage to nano-printing is the ability to print interleaved patterns of different capture probes onto the random array support. This would be accomplished by successive printing with multiple print heads, each head having a differing pattern, and all patterns fitting together to form the final structured support pattern. Such methods allow for some positional encoding of DNA elements within the random array. For example, control concatemers containing a specific sequence can be bound at regular intervals throughout a random array.

In still another aspect, a high density array of capture oligonucleotide spots of sub micron size is prepared using a printing head or imprint-master prepared from a bundle, or bundle of bundles, of about 10,000 to 100 million optical fibers with a core and cladding material. By pulling and fusing fibers a unique material is produced that has about 50-1000 nm cores separated by a similar or 2-5 fold smaller or larger size cladding material. By differential etching (dissolving) of cladding material a nano-printing head is obtained having a very large number of nano-sized posts. This printing head may be used for depositing oligonucleotides or other biological (proteins, oligopeptides, DNA, aptamers) or chemical compounds such as silane with various active groups. In one embodiment the glass fiber tool is used as a patterned support to deposit oligonucleotides or other biological or chemical compounds. In this case only posts created by etching may be contacted with material to be deposited. Also, a flat cut of the fused fiber bundle may be used to guide light through cores and allow light-induced chemistry to occur only at the tip surface of the cores, thus eliminating the need for etching. In both cases, the same support may then be used as a light guiding/collection device for imaging fluorescence labels used to tag oligonucleotides or other reactants. This device provides a large field of view with a large numerical aperture (potentially >1). Stamping or printing tools that perform active material or oligonucleotide deposition may be used to print 2 to 100 different oligonucleotides in an interleaved pattern. This process requires precise positioning of the print head to about 50-500 nm. This type of oligonucleotide array may be used for attaching 2 to 100 different DNA populations such as different source DNA. They also may be used for parallel reading from sub-light resolution spots by using DNA specific anchors or tags. Information can be accessed by DNA specific tags, e.g., 16 specific anchors for 16 DNAs and read 2 bases by a combination of 5-6 colors and using 16 ligation cycles or one ligation cycle and 16 decoding cycles. This way of making arrays is efficient if limited information (e.g., a small number of cycles) is required per fragment, thus providing more information per cycle or more cycles per surface.

In one aspect, multiple arrays of the invention may be placed on a single surface. For example, patterned array substrates may be produced to match the standard 96 or 384 well plate format. A production format can be an 8×12 pattern of 6 mm×6 mm arrays at 9 mm pitch or 16×24 of 3.33 mm×3.33 mm array at 4.5 mm pitch, on a single piece of glass or plastic and other optically compatible material. In one example each 6 mm×6 mm array consists of 36 million 250-500 nm square regions at 1 micrometer pitch. Hydrophobic or other surface or physical barriers may be used to prevent mixing different reactions between unit arrays.

Other methods of forming arrays of molecules are known in the art and are applicable to forming arrays.

V. Exemplary Embodiments

The following provide certain exemplary embodiments of the invention. It will be appreciated that these embodiments may be altered or expanded using methods well within the skills of one in the art. Since many aspects can be made without departing from the spirit and scope of the presently described technology, the appropriate scope resides in the claims hereinafter appended. Other aspects are therefore contemplated. Furthermore, it should be understood that any operations may be performed in any order, unless explicitly claimed otherwise or a specific order is inherently necessitated by the claim language.

In an exemplary embodiment, the present invention provides a method of fragmenting a double-stranded target nucleic acid. This method includes (a) providing genomic DNA; (b) dividing DNA into a number of separate aliquots; (c) amplifying the DNA in the separate aliquots in the presence of a population of dNTPs that includes dNTP analogs, such that a number of nucleotides in the DNA are replaced by dNTP analogs; (d) removing the dNTP analogs to form gapped DNA; (e) treating the gapped DNA to translate the gaps until gaps on opposite strands converge, thereby creating blunt-ended DNA fragments. In a further embodiment, substantially every fragment in a separate mixture is non-overlapping with every other fragment of the same aliquot.

In a further embodiment and in accordance with the above, the dNTP analogs are selected from a group that includes inosine, uracil and 5-methyl cytosine.

In a still further embodiment and in accordance with any of the above, the dNTP analogs include both deoxy-uracil and 5-methyl cytosine.

In a further embodiment and in accordance with any of the above, methods of the invention include a further step of obtaining a number of sequence reads from fragments of each separate mixture.

In a further embodiment and in accordance with any of the above, prior to obtaining sequence reads, the fragments are used to generate DNA nanoballs.

In a further embodiment and in accordance with any of the above, the separate mixtures comprise on average less than about 0.1%, 0.3%, 1%, or 3% of the genome.

In a further embodiment and in accordance with any of the above, the present invention provides a method for fragmenting nucleic acids that includes the steps of: (a) providing at least two genome-equivalents of DNA for at least one genome; (b) dividing the DNA into a first tier of separate mixtures; (c) amplifying the DNA in the separate mixtures, wherein the amplifying is conducted with a population of dNTPs that comprises a predetermined ratio of dUTP to dTTP, such that a number of thymines in said DNA are replaced by uracils, and a predetermined ratio of 5-methyl dCTP to dCTP, such that a number of cytosines are replaced by 5-methyl cytosines; (d) removing the uracils and the 5-methyl cytosines to form gapped DNA; (e) treating the gapped DNA to translate said gaps until gaps on opposite strands converge, thereby creating blunt-ended DNA fragments, where the blunt-ended fragments have less GC bias and less coverage bias as compared to fragments generated in the absence of 5-methyl cytosine.

In a further embodiment and in accordance with any of the above, sequence reads from fragments of each separate mixture of the first tier are obtained.

In a further embodiment and in accordance with any of the above, the separate mixtures of fragments are separated further into a second tier of separate mixtures. In a still further embodiment, sequence reads are obtained from fragments of each separate mixture in the second tier.

In a further embodiment and in accordance with any of the above, the separate mixtures in either a first, second or greater tier of aliquoting and/or fragmenting have a volume of less than 1 µl, 100 nl, 10 nl, 1 nl or 100 pl.

In a further embodiment and in accordance with any of the above, amplification is conducted in the presence of a member selected from glycogen, DMSO, ET SSB, betaine, and any combination thereof.

In a further embodiment and in accordance with any of the above, after one or more rounds of fragmenting, the fragments have lengths of about 100 kb to about 1 mb.

In a further embodiment and in accordance with any of the above, the present invention provides a method of fragmenting a double-stranded target nucleic acid that includes the steps of: (a) providing genomic DNA; (b) dividing the DNA into separate aliquots; (c) amplifying the DNA in the separate aliquots to form a plurality of amplicons, where the amplifying is conducted with a population of dNTPs that comprises dNTP analogs, such that a number of nucleotides in the amplicons are replaced by the dNTP analogs; and wherein the amplifying is conducted in the presence of an additive selected from glycogen, DMSO, ET SSB, betaine, and any combination thereof; (c) removing the dNTP analogs from the amplicons to form gapped DNA; (d) treating the gapped DNA to translate said gaps until gaps on opposite strands converge, thereby creating blunt-ended DNA fragments, wherein the blunt-ended fragments have less GC bias as compared to fragments generated in the absence of the additive.

In a further embodiment and in accordance with any of the above, a number of sequence reads are obtained from fragments of each separate mixture.

In a further embodiment and in accordance with any of the above, the fragments of each separate mixture are amplified a second time before or after the step of obtaining sequence reads.

In a further embodiment and in accordance with any of the above, the dNTP analogs are selected from a group that includes inosine, uracil and 5-methyl cytosine.

In a further embodiment and in accordance with any of the above, the dNTP analogs include both deoxy-uracil and 5-methyl cytosine.

In a further embodiment and in accordance with any of the above, the fragments have lengths of from about 10,000 to about 200,000 bp.

In a further embodiment and in accordance with any of the above, the fragments have lengths of about 100,000 bp.

In a further embodiment and in accordance with any of the above, the present invention provides a method of obtaining sequence information from a genome that includes the steps: (a) providing a population of first fragments of said genome; (b) preparing emulsion droplets of the first fragments, such that each emulsion droplet comprises a subset of the population of first fragments; (c) obtaining a population of second fragments within each emulsion droplet, such that the second fragments are shorter than the first fragments from which they are derived; (d) combining the emulsion droplets of the second fragments with emulsion droplets of adaptor tags; (e) ligating the second fragments with the adaptor tags to form tagged fragments; (f) combining the tagged fragments into a single mixture; (g) obtaining sequence reads from the tagged fragments, where the sequence reads include sequence information from the adaptor tags and the fragments to identify fragments from the same emulsion droplet, thereby providing sequence information for the genome.

In a further embodiment and in accordance with any of the above, the emulsion droplets of the adaptors include at least two sets of different tag components such that fragments in at least some of the emulsion droplets are tagged with different combinations of the tag components in the ligating step (f).

In a further embodiment and in accordance with any of the above, at least 1000 different emulsion droplets include fragments tagged with different combinations of the tag components.

In a further embodiment and in accordance with any of the above, at least 10,000; 30,000; or 100,000 different emulsion droplets include fragments tagged with different combinations of tag components.

In a further embodiment and in accordance with any of the above, the tag components are from a set of over 1000 distinct barcodes prepared as a population of liquid drops in oil.

In a further embodiment and in accordance with any of the above, the emulsion droplets of the first fragments comprise only 1-5 first fragments in each droplet.

In a further embodiment and in accordance with any of the above, the emulsion droplets of the fragments or the emulsion droplets of the adaptors further comprise ligase and/or other reagents needed for a ligation reaction.

EXAMPLES

Example 1

Overview of LFR Technology

Figure 30A:
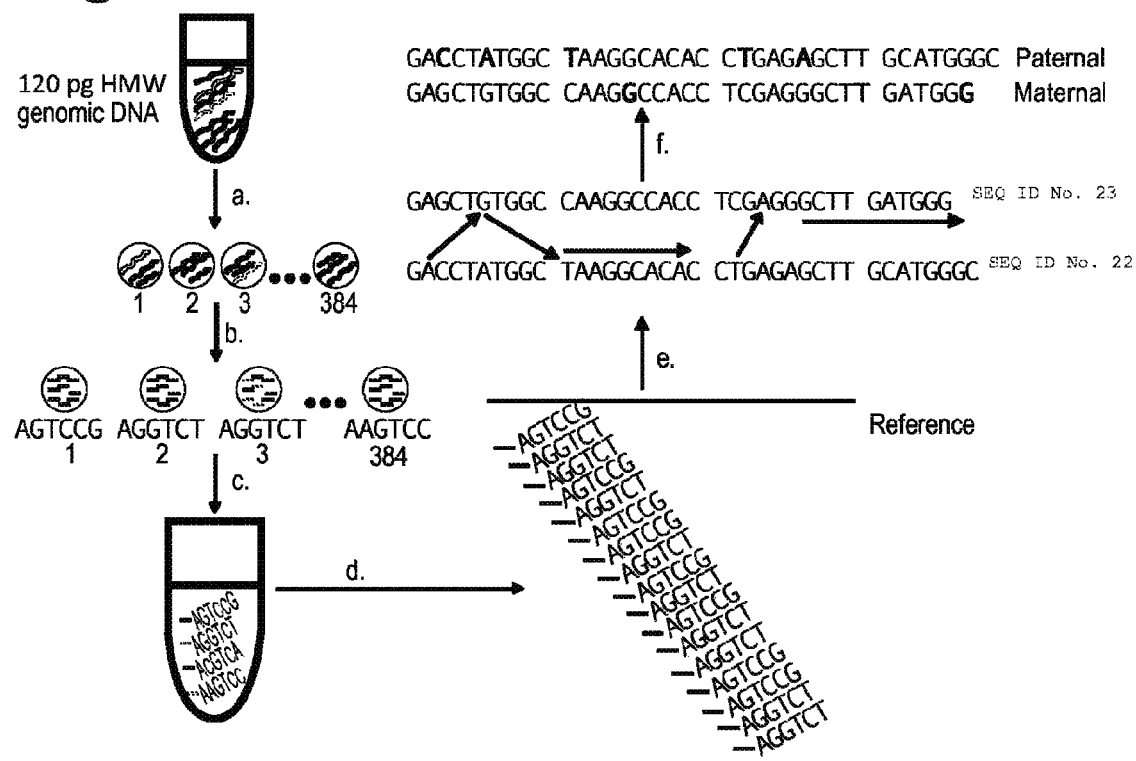
FIG. 30A is a schematic overview of an embodiment of long fragment read technology of the present invention.
Figure 30B:
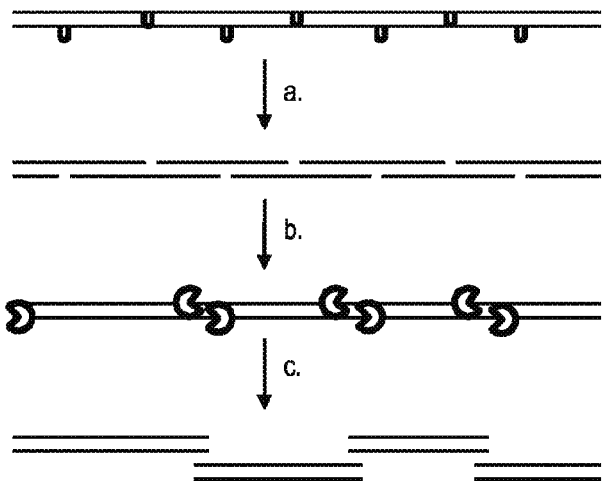
FIG. 30B is a schematic overview of an exemplary method of preparing fragments for long fragment read technology.

As illustrated in FIG. 30(A), genomic DNA is released from 1-100 cells and maintained as long fragments from 100 kb to 1 mb in size. DNA is replicated if a few cells are used. Blue represents the maternal and red the paternal fragment of a selected loci. In FIG. 30 (B), the long genomic DNA is split into 1000 to 100,000 aliquots (e.g., a 1536- or 6144-well plate or >10,000 nanoliter drops such as in RainDance or Advanced Liquid Logic systems) containing 1% or as low as 0.01% of a haploid genome (1-1,000 fragments per aliquot). In FIG. 30 (A) step c, DNA is amplified (not necessary for some platforms) by phi29 polymerase (resulting DNA can be shorter than original), enzymatically fragmented to 100-10,000 by (standard is 500 bp), and uniquely bar-coded in each aliquot via combinatorial DNA adapter ligation with unique 6- to 12-mer sequence. In FIG. 30 (A) step d, aliquots are pooled into a single reaction. In FIG. 30 (A) step e barcoded DNA is incorporated into standard library preparation and DNA and barcodes are sequenced. Minimal mapping of tagged-reads to the entire reference determines which regions of the genome to use as a short composite reference for fast read assembly in individual aliquots. Computational cost of read mapping is thus reduced 100 fold. In FIG. 30 (A) step f, tagged-reads are used to independently assemble maternal and paternal 100+ kb fragments of genome. Overlapping 100+kb fragments (e.g., from aliquots 3 and 77) are recognized by shared SNP alleles and used to independently assemble sequences of maternal and paternal chromosomes. Ten cells provide fragments that overlap over 90+kb, on average, with ~60 heterozygote variants that ensure correct parental mapping.

Example 2

Miniaturization of LFR

As shown in FIG. 28 step a, 96-384 uniquely barcoded half adapters from Set A and Set B are combined in a pair wise fashion into about 10K-150K distinct individual combinatorial adapter oil-water droplets. In FIG. 28 step b, up to 10 billion combinatorial adapter droplets in 10 ml are formed (in a few days) and stored. This amount is sufficient to process over 1000 human samples. In FIG. 28 step c, combinatorial adapter droplets from step b are fed into a microfluidic device and merged one-to-one with drops of amplified fragmented DNA generated from sub-genome aliquots of >100 kb fragments, FIG. 28 step d, fragmented DNA in 10,000 or more emulsion droplets is ligated to unique combinatorial adapters. In FIG. 28 step e is shown a magnified view of a combinatorial adapter. Yellow represents 4-6 bps components of barcode sequence; blue and red represent Set A and Set B common adapter sequence, respectively. Set A and B adapters have 2-4 bps of complementary sequence for improved directional ligation; B is blocked ("|") from ligating to genomic DNA (black). In FIG. 28 step f, after adapter ligation individual emulsion droplets are broken and DNA fragments are pooled for entry into standard library preparation.

Example 3

Using LFR Data to Define Haplotypes

An example of a consensuses chromosomal sequence with 4 heterozygote sites at variable distances of 3 to 35 kb is depicted in FIG. 29. Starting from the left, the percent of shared aliquots (PSA) is calculated for each pair of neighboring alleles. The numbers for 4 possible pairs are written in the following order: top-top, top-bottom, bottom-top, and bottom-bottom (e.g., numbers 7, 87, 83, and 0) for the 7 kb segment correspond to A-C, A-T, G-C and G-T pairs, respectively. If 20 cells are used an allele can be found in 20 or less aliquots. For A-C and A-T pairs only A aliquots lacking G are used. For G-C and G-T pairs only G aliquots lacking A are used. For A-T pair, if A without G is present in 15 aliquots, T is present in 17 aliquots and A and T are present together in 13 aliquots, the PSA is 13/15=87%.

Example 4

φ29 Mediated Overlapping Genomic Fragments

Long fragment genomic DNA can treated with a low concentration of an infrequent nicking enzyme. φ29 polymerase molecules simultaneously extend DNA from the nicks displacing proceeding DNA strands. Complete extension results in long overlapping fragments without loss of DNA at fragment ends.

Example 5

Sequencing Cancer Samples

Four cancer samples with matched normal cells are sequenced using LFR techniques discussed herein. Emulsion technology or libraries in 3072-6144 aliquots are used. Complete methylome data is also generated at the same time. Depending on the cost reduction achieved more than 120 Gb of data may be obtained per genome. The results from the experiments demonstrate the completeness and quality of sequence, and the nature of genetic and epigenetic changes in the analyzed cancer tissues.

Example 6

MDA Reaction for Inserting Uracils for CoRE

An aliquot of DNA was diluted to 1 ng/µL. Excessive pipetting is avoided to help retain long fragment lengths. No vortexing is conducted of the mixtures at any point of preparing the reaction.

A ⅕ dilution of denaturation buffer was made from concentrated frozen stock. The denaturation buffer contained:

| | |
|---|---|
| 1 mL | 1M KOH |
| 50 uL | 500 mM EDTA |
| 1.45 mL | dH2O |
| 2.5 mL of 400 mM KOH, 10 mM EDTA | |

5 ng (5 µL) of the 1 ng/µL DNA was diluted in 45 µL of 1× glycogen water.

The DNA was denatured by adding 50 µL of a ⅕ dilution of denaturation buffer (the total current volume is 100 µL). The final concentration of this mix will be 50 pg/µL.

The mixture was incubated for 5 minutes.

DNA needed for the number of wells/aliquots is removed to create a concentration of 0.025 genome equivalents per µL (i.e., 0.0825 pg/µL) and placed in a tube, well or other method of aliquot storage. In embodiments using wells, the amount is determined using the following calculation: DNA (µL)=[0.0825 pg/µL)×(2 µL)×(# aliquots/wells)]/50 pg/µL.

An appropriate amount of 1 mM 9-mer primer (0.03 µL per well) was added to the denatured DNA from the above step and incubated for 1 minute. The appropriate amount was calculated from the number of aliquots that would be used. For example, for 405 wells, this would be equal to 0.03 µL×(# aliquots)=12.2 µL.

The reaction was neutralized with an appropriate amount of a 1/45 dilution of neutralization buffer (used ½ the volume of denatured DNA from the removal step described above). The neutralization buffer contained the following:

| | |
|---|---|
| 4 mL | 1M HCl |
| 6 mL | 1M Tris-HCl buffer, pH 7.5 |
| 10 mL | final pH of the solution is 0.6 |

The reaction was then diluted to 0.025 genome equivalents in distilled water with 1× glycogen. For embodiments using multi-well formats, the calculation was [(# of wells×2 µL)−(µL of denatured DNA+µL of buffer N+µL of 9mer]— for a 405 well plate, this would be (405×2)−(1.33+0.67+12.2)=796 µL. 2 µL of the mixture was then added to each well.

A 4.0% dUTP-MDA mix was created according to the protocol set out below (an example for 405 wells is shown):

| | 1X | 405X |
|---|---|---|
| 3X master mix | 0.9625 ul | 389.8 ul |
| Φ29 (Enzymatics 10U/ul) | 0.0375 ul | 15.2 ul |
| | 1.0 ul | 405 ul |

The 3× master mix contained the following:

| | 1 well | 10000 wells |
|---|---|---|
| 10X Φ buffer | .3 µL | 3 ml |
| 25 mM dNTPs (USB) | .03 µL | 300 µL |
| 0.4% PO34 | .075 µL | 750 µL |
| 1 mM dUTP (USB) | .03 µL | 300 µL |
| dH$_2$O | 0.5275 µL | 5.275 ml |
| | 0.9625 µL | |

0.0375 µL of φ29 was added to 1 well of 3× master mix prior to MDA (i.e. for a 384 well plate added 14.4 ul of φ29 to master mix). 0.03 µL per well of 1 mM random 9-mer was added directly to DNA during the denaturation step.

1 µL of the MDA mix was added to each well and spun down briefly. The aliquots were incubated at 26° C. for approximately 120 minutes to achieve about 10-30K amplification to 3-10 ng/w2ell.

φ29 was inactivated by incubating at 45-65° C. for five minutes.

Example 7

Complete Diploid Genome Sequence of Yoruban Female Using LFR

The LFR approach eliminates some of the problems associated with short read sequencing because it is equivalent to single molecule sequencing of fragments >10 kb (up to 1 Mb is possible). This is achieved by the random separation of corresponding parental DNA fragments into physically distinct pools. As the fraction of the genome in each pool decreases to less than a haploid genome, the statistical likelihood of having a fragment from both parental chromosomes in the same pool dramatically diminishes (i.e., at 0.1 genome equivalents per well there is a 10% chance that two fragments will overlap and a 50% chance those fragments will be derived from separate parental chromosomes resulting in a 5% overall chance that a particular well will be uninformative for a given fragment). Likewise, the more individual pools interrogated the greater number of times a fragment from the maternal and paternal complements will be analyzed (i.e., a 384 well plate with 0.1 genome equivalents in each well results in a theoretical 19× coverage of both the maternal and paternal alleles of each fragment). Ultimately, the entirety of all chromosomes from one parent is expected to be separated from the corresponding chromosomes of the other parent in the majority of the aliquots sequenced.

Several steps of preparation were used to generate these physically isolated fragments for analysis by any short read sequencing platform. First, a highly uniform amplification using a modified φ29-based multiple displacement amplification (MDA) was performed to increase the number of each fragment to >1000 copies per well. This step could be omitted for single molecule sequencing methods. Next, through a process of five enzymatic steps within each well, without any intervening purification steps, DNA is fragmented and ligated with barcode adapters. Briefly, long DNA molecules were fragmented to blunt ended 300-1,300 bp segments through the novel process of Controlled Random Enzymatic fragmenting (CoRE). CoRE fragments DNA through removal of uridine bases, incorporated at a predefined frequency during MDA, by uracil DNA glycosylase and endonuclease IV. Nick translation with E. coli polymerase 1 resolved the fragments and generated blunt ends. Unique barcode adapters designed to reduce any bias caused by differences in sequence and concentration of each barcode were then ligated to fragmented DNA in each well using a high yield, low chimera formation protocol. At this point all 384 wells were combined and an unsaturated polymerase chain reaction using primers common to the ligated adapters were employed if necessary to generate sufficient template for short read sequencing platforms.

To demonstrate the ability of LFR to determine a diploid genome sequence a library was generated starting from high molecular weight genomic DNA from an immortalized B-cell line of Yoruban female HapMap sample NA19240. NA19240 was extensively interrogated as part of a trio (NA19240 is the daughter of samples NA19238 and NA19239) in the HapMap and 1,000 Genomes Projects. As a result, highly accurate haplotype information was generated based upon the sequence data for parental samples NA19238 and NA19239. A total of ~130 picograms of DNA (equivalent to ~20 cells) were aliquoted into a 384-well plate. DNA in each well was tagged with a distinct 6-base sequence and sequenced using Complete Genomics' DNA nanoarray sequencing platform. 35 base mate-paired reads were mapped to the reference genome using a custom alignment algorithm yielding 236 Gb of mapped data and an average genomic coverage of 86 fold.

Mapped reads from each well were then grouped based on unique 6 base barcode identifiers and assembled into paternal and maternal chromosomal fragments. These fragment sizes were had a median of ~90 kb and a maximum >180 kb. Using a two step custom haplotyping algorithm, overlapping heterozygous SNPs between fragments from the same parental chromosome located in different wells were used to assemble large contigs with an N50 of 373 Kb and an upper bound of 2.63 Mb. In total almost 2.7 million heterozygous SNPs were phased and approximately 86% of the genome of NA19240 was covered by LFR haplotypes.

To confirm the accuracy of LFR haplotype calls a low coverage BAC library was made and 10 clones that overlapped an average of 83 kb with LFR contigs were selected for further validation. Sequencing was performed at approximately 10 different heterozygous SNPs spread across each BAC. 128 out of 130 informative SNPs were in perfect agreement with LFR calls resulting in a discrepancy rate of only 1.5%. To further validate the LFR results, the SNP phasing data was compared to those generated from parental sequencing. In general the two sets of data were highly correlated.

To generate complete haplotypes of all NA19240 chromosomes (single contigs per parental chromosome comprising almost all heterozygous SNPs) we combined the LFR data with haplotypes derived from the sequences of the mother and of the father. To achieve this whole chromosome sparse haplotypes were established using informative variants from one or both parents and NA19240. This allowed phasing of about 1.8 million SNPs. Chromosome scaffolds were then used to phase haplotype contigs generated by LFR resulting in high density whole chromosome haplotypes encompassing 2.6 million SNPs. It is estimated that ~5% of heterozygous SNPs were detected but remained unphased and ~5% were undetected.

Example 8

Ligation of Combinatorial Adaptors to DNA Fragments

In a first step, adaptor "A" was ligated to both sides of genomic DNA fragments in a reaction using T4 ligase. Ligation was conducted at 14° C. for two hours. The DNA:adaptor ratio was ~30:1. The following concentrations of reactants were used for this first step of the process:

| Adaptor A ligation | | 1 x |
|---|---|---|
| DNA | 15.60 ng/µl | 40 µl |
| HM Lig Bfr. | 3 x | 28.4 µl |
| T4 Lig. | 600 U/µl | 2.1 µl |
| Adaptor | 5 uM | 14.8 µl |
| H2O | | µl |
| Volume | | 85.3 µl |

The partially-tagged DNA fragments were denatured and then annealed to primers complementary to Adaptor A. The polymerase extends from the primer to result in double stranded fragments, each tagged with an adaptor on one end. The following concentrations of reactants were used for this step of the process:

| PfuCx | | 1 x |
|---|---|---|
| Lig. DNA | 12.0 ng/ul | 40 µl |
| PfuCx mix3 | 2 x | 40 µl |
| ON904 | 20 uM | 2 µl |
| PfuCx | 2.5 U/µl | 1.6 µl |
| volume | | 83.6 µl |

The protocol used with the above reactants was incubation at 95° C. for 3 minutes, 55° C. for 1 minute, and 72° C. for 10 minutes, then a ramp down to 4° C.

The next step of the process ligated adaptor B to the blunt end created during primer extension. Again, the mixture was incubated at 14° C. for 2 hours. The DNA:adaptor B ratio was ~15:1. The following concentrations of reactants were used for this step of the process:

| Adaptor B ligation | | 1 x |
|---|---|---|
| PfuCx DNA | 19.00 ng/µl | 40 µl |
| HM Lig Bfr. | 3 x | 28.4 µl |
| T4 Lig. | 600 U/µl | 2.1 µl |
| Ad119_3' | 5 uM | 7.4 µl |
| H2O | | 2.1 µl |
| Volume | | 80 µl |

The present specification provides a complete description of the methodologies, systems and/or structures and uses thereof in example aspects of the presently-described technology. Although various aspects of this technology have been described above with a certain degree of particularity, or with reference to one or more individual aspects, those skilled in the art could make numerous alterations to the disclosed aspects without departing from the spirit or scope of the technology hereof. Since many aspects can be made without departing from the spirit and scope of the presently described technology, the appropriate scope resides in the claims hereinafter appended. Other aspects are therefore contemplated. Furthermore, it should be understood that any operations may be performed in any order, unless explicitly claimed otherwise or a specific order is inherently necessitated by the claim language. It is intended that all matter contained in the above description and shown in the accompanying drawings shall be interpreted as illustrative only of particular aspects and are not limiting to the embodiments shown. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes. Changes in detail or structure may be made without departing from the basic elements of the present technology as defined in the following claims.

The invention claimed is:

1. A method of analyzing genomic DNA in a sample, the method comprising:
   (a) dividing the sample into a plurality of separate aliquots;
   (b) amplifying fragments of the genomic DNA in the separate aliquots to produce a plurality of amplicons, wherein the amplifying is conducted with a population of dNTPs containing dNTP analogs, whereby a number of nucleotides in the amplicons are nucleotide analogs;
   (c) removing nucleotide analogs incorporated into the amplicons to form gapped DNA;
   (d) treating the gapped DNA such that gaps on opposite strands converge, thereby further fragmenting the genomic DNA;
   (e) tagging DNA fragments in different aliquots with different oligonucleotide tags or tag combinations to form tagged fragments;
   (f) combining the aliquots to produce a mixture of tagged fragments;
   (g) obtaining sequence reads from tagged fragments in the mixture, wherein using the nucleotide analogs to create the gapped DNA has the effect of reducing GC bias in the sequence reads; and
   (h) phasing heterozygous loci in the genomic DNA by a process that includes identifying sequence reads for DNA fragments having the same oligonucleotide tag.

2. The method of claim 1, wherein the population comprises at least two different dNTP analogs.

3. The method of claim 1, wherein the population comprises dUTP and 5-methyl dCTP.

4. The method of claim 1, wherein the separate aliquots are droplets.

5. A method of preparing genomic DNA in a sample for sequence determination, comprising:
   (a) dividing the sample into a plurality of separate aliquots;
   (b) amplifying DNA in the separate aliquots in the presence of a mixture of nucleotides and nucleotide analogs having a ratio of dUTP to dTTP and a ratio of 5-methyl dCTP to dCTP, thereby producing a plurality of amplicons in which 0.05% to 4% of the cytosines and 0.05% to 4% of the thymines are replaced by a nucleotide analog;

(c) contacting the amplicons with a reagent such that deoxyuracils incorporated into the amplicons are removed, leaving gaps;

(d) contacting the amplicons with a reagent such that 5-methyl cytosines incorporated into amplicons are removed, leaving gaps; and (e) contacting the amplicons with a reagent such that gaps on opposite strands of the DNA converge, thereby creating DNA fragments.

6. A method of sequencing a sample of DNA, comprising preparing the DNA according to claim 5, and then obtaining a number of sequence reads from DNA fragments in a plurality of the aliquots.

7. The method of claim 5, the method further comprising preselecting the ratio of dUTP to dTTP and preselecting the ratio of 5-methyl dCTP to dCTP such that the blunt-ended DNA fragments produced following step (d) are between 50,000 and 1,500,000 nucleotides in length.

8. The method of claim 5, the method further comprising preselecting the ratio of dUTP to dTTP and preselecting the ratio of 5-methyl dCTP to dCTP such that the blunt-ended DNA fragments produced following step (d) are no more than about 10,000 nucleotides in length.

9. The method of claim 5, wherein the separate aliquots have a volume of less than 100 nL.

10. The method of claim 5, wherein step (b) is conducted in the presence of an additive selected from glycogen, dimethyl sulfoxide (DMSO), Extreme Thermostable Single-Stranded DNA Binding Protein (ET SSB), trimethylglycine (TMG) (betaine), and any combination thereof.

11. A method for reducing GC bias when sequencing a sample of genomic DNA, wherein the sequencing comprises:

(i) dividing the sample into a plurality of separate aliquots;

(ii) amplifying fragments of the genomic DNA in the separate aliquots to produce amplicons, (iii) combining the amplicons from a plurality of the aliquots into a mixture;

(iv) obtaining sequence reads from amplicons in the mixture; and (v) assembling sequence information for the genomic DNA by a process that includes identifying sequence reads for fragments originating in the same aliquot;

wherein the method of reducing GC bias comprises:

(a) conducting the amplifying in step (ii) in the presence of a combination of dNTPs containing nucleotide analogs, such that some of the nucleotides incorporated into the amplicons are nucleotide analogs;

(b) removing nucleotide analogs incorporated into the amplicons to form gapped DNA; and (c) treating the gapped DNA such that gaps on opposite strands converge, thereby producing cleaved fragments for sequencing;

wherein using the nucleotide analogs to produce the cleaved fragments has the effect of reducing GC bias in the sequencing.

12. The method of claim 11, further comprising tagging the gapped DNA in the separate aliquots such that gapped DNA in different aliquots is tagged with oligonucleotide tags having different sequences.

13. The method of claim 11, wherein step (a) is conducted in the presence of at least two different dNTP analogs.

14. The method of claim 11, wherein the step (a) is conducted in the presence of both dUTP and 5-methyl dCTP.

15. The method of claim 11, wherein the separate aliquots are droplets.

16. The method of claim 11, wherein the amplifying in step (ii) is conducted in the presence of an additive selected from glycogen, dimethyl sulfoxide (DMSO), Extreme Thermostable Single-Stranded DNA Binding Protein (ET SSB), trimethylglycine (TMG) (betaine), and any combination thereof.

17. The method of claim 16, wherein the additive or additive combination includes 0.5% to 10% DMSO.

18. The method of claim 16, wherein the additive or additive combination includes ET SSB.

19. The method of claim 16, wherein the additive or additive combination includes betaine.

20. The method of claim 11, wherein GC bias is further reduced by amplifying in step (ii) using primers with a low GC content.

21. The method of claim 1, wherein the amplifying of the genomic DNA or DNA fragments in the separate aliquots is performed before the DNA fragments are tagged with the different oligonucleotide tag or tag combinations.

22. The method of claim 5, wherein the reagent used in step (c) includes at least one of UDG, EndoIV, and EndoVIII.

23. The method of claim 5, wherein the reagent used in step (d) includes McrBC.

24. The method of claim 5, wherein the reagent used in step (e) includes Taq polymerase or E. coli Pol 1.

* * * * *

SEQUENCE LISTING

<160> NUMBER OF SEQ ID NOS: 23

<210> SEQ ID NO 1
<211> LENGTH: 30
<212> TYPE: DNA
<213> ORGANISM: Artificial Sequence
<220> FEATURE:
<223> OTHER INFORMATION: Synthetic oligonucleotide referred to as an
      adaptor

<400> SEQUENCE: 1
actgctgacg cttacgatgc acgatacgtc                                           30

<210> SEQ ID NO 2
<211> LENGTH: 32
<212> TYPE: DNA
<213> ORGANISM: Artificial Sequence
<220> FEATURE:
<223> OTHER INFORMATION: Synthetic oligonucleotide referred to as an
      adaptor

<400> SEQUENCE: 2
ttgacgactg cgaatgctac gtgctatgca gt                                        32

<210> SEQ ID NO 3
<211> LENGTH: 32
<212> TYPE: DNA
<213> ORGANISM: Artificial Sequence
<220> FEATURE:
<223> OTHER INFORMATION: Synthetic oligonucleotide referred to as an
      adaptor

<400> SEQUENCE: 3
tgcacgatac gtctacgatg cgaacagcag at                                        32

<210> SEQ ID NO 4
<211> LENGTH: 30
<212> TYPE: DNA
<213> ORGANISM: Artificial Sequence
<220> FEATURE:
<223> OTHER INFORMATION: Synthetic oligonucleotide referred to as an
      adaptor

<400> SEQUENCE: 4
cgtgctatgc agatgctacg cttgtcgtct                                           30

<210> SEQ ID NO 5
<211> LENGTH: 50
<212> TYPE: DNA
<213> ORGANISM: Artificial Sequence
<220> FEATURE:
<223> OTHER INFORMATION: Synthetic oligonucleotide referred to as an
      adaptor
<220> FEATURE:
<221> NAME/KEY: misc_feature
<222> LOCATION: (10)..(19)
<223> OTHER INFORMATION: N is A, C, G or T
<220> FEATURE:
<221> NAME/KEY: misc_feature
<222> LOCATION: (21)..(30)
<223> OTHER INFORMATION: N is A, C, G or T
<220> FEATURE:
<221> NAME/KEY: misc_feature
<222> LOCATION: (32)..(41)
<223> OTHER INFORMATION: N is A, C, G or T

<400> SEQUENCE: 5
aactgctgan nnnnnnnnng nnnnnnnnnn cnnnnnnnnn nacagcagat                     50

```
<210> SEQ ID NO 6
<211> LENGTH: 49
<212> TYPE: DNA
<213> ORGANISM: Artificial Sequence
<220> FEATURE:
<223> OTHER INFORMATION: Synthetic oligonucleotide referred to as an
      adaptor

<400> SEQUENCE: 6
aactgctgac gcttacgatg cacgatacgt ctacgatgcg aacagcaga              49

<210> SEQ ID NO 7
<211> LENGTH: 49
<212> TYPE: DNA
<213> ORGANISM: Artificial Sequence
<220> FEATURE:
<223> OTHER INFORMATION: Synthetic oligonucleotide referred to as an
      adaptor

<400> SEQUENCE: 7
tgacgactgc gaatgctacg tgctatgcag atgctacgct tgtcgtcta              49

<210> SEQ ID NO 8
<211> LENGTH: 47
<212> TYPE: DNA
<213> ORGANISM: Artificial Sequence
<220> FEATURE:
<223> OTHER INFORMATION: Target sequence
<220> FEATURE:
<221> NAME/KEY: misc_feature
<222> LOCATION: (1)..(20)
<223> OTHER INFORMATION: n is a, c, g, or t

<400> SEQUENCE: 8
nnnnnnnnnn nnnnnnnnnn gatcatcgtc agcagtcgcg tagctag                47

<210> SEQ ID NO 9
<211> LENGTH: 24
<212> TYPE: DNA
<213> ORGANISM: Artificial Sequence
<220> FEATURE:
<223> OTHER INFORMATION: Probe

<400> SEQUENCE: 9
ctagtagcag tcgtcagcgc atcg                                         24

<210> SEQ ID NO 10
<211> LENGTH: 35
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(3)
<223> OTHER INFORMATION: N is A, C, T or G
<220> FEATURE:
<221> NAME/KEY: misc_feature
<222> LOCATION: (5)..(8)
<223> OTHER INFORMATION: N is A, C, T or G

<400> SEQUENCE: 10
nnncnnnnct agtagcagtc gtcagcgcat cgatc                             35

<210> SEQ ID NO 11
<211> LENGTH: 45
<212> TYPE: DNA
<213> ORGANISM: Artificial Sequence
```

```
<220> FEATURE:
<223> OTHER INFORMATION: Target Sequence
<220> FEATURE:
<221> NAME/KEY: misc_feature
<222> LOCATION: (1)..(13)
<223> OTHER INFORMATION: N is A, C, T or G
<220> FEATURE:
<221> NAME/KEY: misc_feature
<222> LOCATION: (15)..(18)
<223> OTHER INFORMATION: N is A, C, T or G

<400> SEQUENCE: 11
nnnnnnnnnn nnngnnnnga tcatcgtcag cagtcgcgta gctag          45

<210> SEQ ID NO 12
<211> LENGTH: 28
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(4)
<223> OTHER INFORMATION: N is A, C, T or G

<400> SEQUENCE: 12
nnnnctagta gcagtcgtca gcgcatcg                              28

<210> SEQ ID NO 13
<211> LENGTH: 39
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(4)
<223> OTHER INFORMATION: N is A, C, T or G
<220> FEATURE:
<221> NAME/KEY: misc_feature
<222> LOCATION: (6)..(12)
<223> OTHER INFORMATION: N is A, C, T or G

<400> SEQUENCE: 13
nnnncnnnnn nnctagtagc agtcgtcagc gcatcgatc                  39

<210> SEQ ID NO 14
<211> LENGTH: 17
<212> TYPE: DNA
<213> ORGANISM: Artificial Sequence
<220> FEATURE:
<223> OTHER INFORMATION: Probe

<400> SEQUENCE: 14
tcgtcagcgc atcgatc                                          17

<210> SEQ ID NO 15
<211> LENGTH: 15
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(5)
<223> OTHER INFORMATION: N is A, C, T or G

<400> SEQUENCE: 15
nnnnnctagt agcag                                            15
```

```
<210> SEQ ID NO 16
<211> LENGTH: 32
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(5)
<223> OTHER INFORMATION: N is A, C, T or G

<400> SEQUENCE: 16
nnnnnctagt agcagtcgtc agcgcatcga tc                                      32

<210> SEQ ID NO 17
<211> LENGTH: 40
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(3)
<223> OTHER INFORMATION: N is A, C, T or G
<220> FEATURE:
<221> NAME/KEY: misc_feature
<222> LOCATION: (5)..(13)
<223> OTHER INFORMATION: N is A, C, T or G

<400> SEQUENCE: 17
nnnannnnnn nnnctagtag cagtcgtcag cgcatcgatc                              40

<210> SEQ ID NO 18
<211> LENGTH: 47
<212> TYPE: DNA
<213> ORGANISM: Artificial Sequence
<220> FEATURE:
<223> OTHER INFORMATION: Target seqeunce
<220> FEATURE:
<221> NAME/KEY: misc_feature
<222> LOCATION: (1)..(10)
<223> OTHER INFORMATION: N is A, C, T or G
<220> FEATURE:
<221> NAME/KEY: misc_feature
<222> LOCATION: (12)..(20)
<223> OTHER INFORMATION: N is A, C, T or G

<400> SEQUENCE: 18
nnnnnnnnnn tnnnnnnnnn gatcatcgtc agcagtcgcg tagctag                      47

<210> SEQ ID NO 19
<211> LENGTH: 37
<212> TYPE: DNA
<213> ORGANISM: Artificial Sequence
<220> FEATURE:
<223> OTHER INFORMATION: Target sequence
<220> FEATURE:
<221> NAME/KEY: misc_feature
<222> LOCATION: (1)..(20)
<223> OTHER INFORMATION: N is A, C, T or G

<400> SEQUENCE: 19
nnnnnnnnnn nnnnnnnnnn agcagtcgcg tagctag                                 37

<210> SEQ ID NO 20
<211> LENGTH: 24
<212> TYPE: DNA
<213> ORGANISM: Artificial Sequence
<220> FEATURE:
<223> OTHER INFORMATION: Probe
```

```
<220> FEATURE:
<221> NAME/KEY: misc_feature
<222> LOCATION: (1)..(7)
<223> OTHER INFORMATION: N is A, C, T or G

<400> SEQUENCE: 20
nnnnnnntcg tcagcgcatc gatc                                          24

<210> SEQ ID NO 21
<211> LENGTH: 40
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(3)
<223> OTHER INFORMATION: N is A, C, T or G
<220> FEATURE:
<221> NAME/KEY: misc_feature
<222> LOCATION: (5)..(13)
<223> OTHER INFORMATION: N is A, C, T or G

<400> SEQUENCE: 21
nnnannnnnn nnnctagtag cagtcgtcag cgcatcgatc                         40

<210> SEQ ID NO 22
<211> LENGTH: 38
<212> TYPE: DNA
<213> ORGANISM: Artificial Sequence
<220> FEATURE:
<223> OTHER INFORMATION: Target

<400> SEQUENCE: 22
gacctatggc taaggcacac ctgagagctt gcatgggc                           38

<210> SEQ ID NO 23
<211> LENGTH: 36
<212> TYPE: DNA
<213> ORGANISM: Artificial Sequence
<220> FEATURE:
<223> OTHER INFORMATION: Target

<400> SEQUENCE: 23
gagctgtggc caaggccacc tcgagggctt gatggg                             36
```